(12) United States Patent
Skerlj et al.

(10) Patent No.: US 11,878,979 B2
(45) Date of Patent: *Jan. 23, 2024

(54) SUBSTITUTED IMIDAZO[1,2-B]PYRIDAZINES, SUBSTITUTED IMIDAZO[1,5-B]PYRIDAZINES, RELATED COMPOUNDS, AND THEIR USE IN THE TREATMENT OF MEDICAL DISORDERS

(71) Applicant: Bial—R&D Investments, S.A., Coronado (PT)

(72) Inventors: Renato T. Skerlj, West Newton, MA (US); Elyse Marie Josee Bourque, L'etang-du-Nord (CA); William J. Greenlee, Teaneck, NJ (US); Peter T. Lansbury, Brookline, MA (US)

(73) Assignee: Bial—R&D Investments, S.A., Coronado (PT)

( * ) Notice: Subject to any disclaimer, the term of this patent is extended or adjusted under 35 U.S.C. 154(b) by 3 days.

This patent is subject to a terminal disclaimer.

(21) Appl. No.: 17/385,269

(22) Filed: Jul. 26, 2021

(65) Prior Publication Data

US 2022/0185814 A1 Jun. 16, 2022

Related U.S. Application Data

(63) Continuation of application No. 16/097,905, filed as application No. PCT/US2017/031189 on May 5, 2017, now Pat. No. 11,168,087.

(60) Provisional application No. 62/332,151, filed on May 5, 2016.

(51) Int. Cl.
| | |
|---|---|
| *C07D 487/04* | (2006.01) |
| *C07D 495/04* | (2006.01) |
| *C07D 498/04* | (2006.01) |
| *C07D 491/048* | (2006.01) |
| *A61K 31/519* | (2006.01) |
| *A61P 25/16* | (2006.01) |
| *A61P 25/28* | (2006.01) |
| *C07D 513/04* | (2006.01) |

(52) U.S. Cl.
CPC ....... *C07D 487/04* (2013.01); *C07D 491/048* (2013.01); *C07D 495/04* (2013.01); *C07D 498/04* (2013.01); *C07D 513/04* (2013.01)

(58) Field of Classification Search
CPC .. C07D 487/04; C07D 495/04; C07D 498/04; C07D 491/048; A61K 31/519; A61P 25/16; A61P 25/28
See application file for complete search history.

(56) References Cited

U.S. PATENT DOCUMENTS

| | | | |
|---|---|---|---|
| 4,838,925 A | 6/1989 | Tseng | |
| 7,550,470 B2 | 6/2009 | Fraley | |
| 7,723,336 B2 | 5/2010 | Vaccaro et al. | |
| 7,795,273 B2 | 9/2010 | Imbach et al. | |
| 8,163,759 B2 | 4/2012 | Tanimoto et al. | |
| 8,372,851 B2 | 2/2013 | Rice et al. | |
| 8,680,159 B2 | 3/2014 | Reich et al. | |
| 9,085,560 B2 | 7/2015 | Ren et al. | |
| 9,127,000 B2 | 9/2015 | Ren et al. | |
| 9,353,117 B2 | 5/2016 | Marugan et al. | |
| 9,732,089 B2 | 8/2017 | Skerlj et al. | |
| 9,802,942 B2 | 10/2017 | Krainc et al. | |
| 9,840,510 B1 | 12/2017 | Skerlj et al. | |
| 9,868,742 B2 | 1/2018 | Skerlj et al. | |
| 9,920,061 B2 | 3/2018 | Skerlj et al. | |
| 10,040,799 B2 | 8/2018 | Krainc et al. | |
| 10,227,352 B2 | 3/2019 | Krainc et al. | |
| 10,442,812 B2 | 10/2019 | Krainc et al. | |
| 10,570,135 B2 | 2/2020 | Skerlj et al. | |
| 10,751,341 B2 | 8/2020 | Skerlj et al. | |
| 10,786,508 B2 | 9/2020 | Skerlj et al. | |
| 10,787,454 B2 | 9/2020 | Skerlj et al. | |
| 10,934,298 B2 | 3/2021 | Skerlj et al. | |
| 11,091,492 B2 | 8/2021 | Skerlj et al. | |
| 11,124,516 B2 | 9/2021 | Skerlj et al. | |
| 11,168,087 B2 | 11/2021 | Skerlj et al. | |
| 11,192,892 B2 | 12/2021 | Skerlj et al. | |
| 11,345,698 B2 | 5/2022 | Skerlj et al. | |
| 11,351,173 B2 | 6/2022 | Skerlj et al. | |
| 2006/0287324 A1 | 12/2006 | Sun et al. | |
| 2007/0082902 A1 | 4/2007 | Paruch et al. | |
| 2008/0051409 A1 | 2/2008 | Gmeiner et al. | |
| 2008/0176870 A1 | 7/2008 | Nolte et al. | |
| 2008/0255153 A1 | 10/2008 | Bremberg et al. | |
| 2008/0287463 A1 | 11/2008 | Herrmann et al. | |
| 2012/0015962 A1 | 1/2012 | Arora et al. | |
| 2012/0071461 A1 | 3/2012 | Reich et al. | |
| 2013/0095089 A1 | 4/2013 | Larsen et al. | |
| 2013/0245021 A1 | 9/2013 | Bl et al. | |

(Continued)

FOREIGN PATENT DOCUMENTS

| | | |
|---|---|---|
| DE | 102004049363 A1 | 4/2006 |
| EP | 1878727 A1 | 1/2008 |
| EP | 2269990 A1 | 1/2011 |
| EP | 2746265 B1 | 11/2015 |
| EP | 3026051 A1 | 6/2016 |
| JP | 2000-318321 A | 11/2000 |
| JP | 2000-327681 A | 11/2000 |
| JP | 2004277337 A | 10/2004 |
| KR | 20140086002 A | 7/2014 |

(Continued)

OTHER PUBLICATIONS

U.S. Appl. No. 15/523,769 U.S. Pat. No. 10,570,135, Substituted Pyrazolo[1,5-A)Pyrimidines and Their Use in the Treatment of Medical Disorders, filed May 2, 2017, Patented.

(Continued)

*Primary Examiner* — Bruck Kifle
(74) *Attorney, Agent, or Firm* — Goodwin Procter LLP

(57) ABSTRACT

The invention provides substituted imidazo[1,2-b]pyridazine compounds, substituted imidazo[1,5-b]pyridazine compounds, related compounds, compositions containing such compounds, medical kits, and methods for using such compounds and compositions to treat medical disorders, e.g., Gaucher disease, Parkinson's disease, Lewy body disease, dementia, or multiple system atrophy, in a patient. Exemplary substituted imidazo[1,2-b]pyridazine compounds described herein include substituted imidazo[1,2-b]pyridazine-3-carboxamide compounds and variants thereof.

22 Claims, No Drawings

(56) References Cited

U.S. PATENT DOCUMENTS

| | | |
|---|---|---|
| 2014/0288093 A1 | 9/2014 | Krainc et al. |
| 2014/0349993 A1 | 11/2014 | Casaubon et al. |
| 2015/0175610 A1 | 6/2015 | Bl et al. |
| 2015/0183791 A1 | 7/2015 | Bl et al. |
| 2015/0191474 A1 | 7/2015 | Takahashi et al. |
| 2016/0159808 A1 | 6/2016 | Kawasaki et al. |
| 2017/0001976 A1 | 1/2017 | Krainc et al. |
| 2017/0002013 A1 | 1/2017 | Krainc et al. |
| 2017/0183354 A1 | 6/2017 | Skerlj et al. |
| 2017/0333435 A1 | 11/2017 | Skerlj et al. |
| 2017/0334916 A1 | 11/2017 | Skerlj et al. |
| 2017/0349598 A1 | 12/2017 | Skerlj et al. |
| 2017/0355702 A1 | 12/2017 | Skerlj et al. |
| 2018/0185368 A1 | 7/2018 | Skerlj et al. |
| 2018/0325899 A1 | 11/2018 | Weinstein et al. |
| 2019/0119283 A1 | 4/2019 | Skerlj et al. |
| 2019/0216813 A1 | 7/2019 | Skerlj et al. |
| 2019/0315751 A1 | 10/2019 | Skerlj et al. |
| 2019/0330213 A1 | 10/2019 | Skerlj et al. |
| 2019/0389856 A1 | 12/2019 | Skerlj et al. |
| 2019/0389865 A1 | 12/2019 | Skerlj et al. |
| 2019/0389866 A1 | 12/2019 | Skerlj et al. |
| 2020/0017507 A1 | 1/2020 | Skerlj et al. |
| 2020/0030331 A1 | 1/2020 | Skerlj et al. |
| 2020/0339587 A1 | 10/2020 | Skerlj et al. |
| 2020/0385390 A1 | 12/2020 | Skerlj et al. |
| 2021/0169886 A1 | 6/2021 | Skerlj et al. |
| 2021/0177853 A1 | 6/2021 | Skerlj et al. |
| 2021/0309661 A1 | 10/2021 | Skerlj et al. |
| 2022/0169652 A1 | 6/2022 | Skerlj et al. |
| 2023/0098494 A1 | 3/2023 | Skerlj et al. |

FOREIGN PATENT DOCUMENTS

| | | |
|---|---|---|
| WO | WO-2001051919 A2 | 7/2001 |
| WO | WO-2002064545 A1 | 8/2002 |
| WO | WO-2003002584 A1 | 1/2003 |
| WO | WO-2003035649 A1 | 5/2003 |
| WO | WO-2003074525 A1 | 9/2003 |
| WO | WO-2004026868 A1 | 4/2004 |
| WO | WO-2004026869 A1 | 4/2004 |
| WO | WO-2004052315 A2 | 6/2004 |
| WO | WO-2004094418 A1 | 11/2004 |
| WO | WO-2005046611 A2 | 5/2005 |
| WO | WO-2005058837 A1 | 6/2005 |
| WO | WO-2005068426 A1 | 7/2005 |
| WO | WO-2005077953 A1 | 8/2005 |
| WO | WO-2005113004 A2 | 12/2005 |
| WO | WO-2005123738 A1 | 12/2005 |
| WO | WO-2006015737 A1 | 2/2006 |
| WO | WO-2006078676 A2 | 7/2006 |
| WO | WO-2006084634 A1 | 8/2006 |
| WO | WO-2006115168 A1 | 11/2006 |
| WO | WO-2007048066 A2 | 4/2007 |
| WO | WO-2007108750 A1 | 9/2007 |
| WO | WO-2007150064 A2 | 12/2007 |
| WO | WO-2008019363 A2 | 2/2008 |
| WO | WO-2008063669 A1 | 5/2008 |
| WO | WO-2008063671 A2 | 5/2008 |
| WO | WO-2008116898 A1 | 10/2008 |
| WO | WO-2008138889 A2 | 11/2008 |
| WO | WO-2008157575 A1 | 12/2008 |
| WO | WO-2009060197 A1 | 5/2009 |
| WO | WO-2009060835 A1 | 5/2009 |
| WO | WO-2009070567 A1 | 6/2009 |
| WO | WO-2009100375 A1 | 8/2009 |
| WO | WO-2009134973 A1 | 11/2009 |
| WO | WO-2010043893 A1 | 4/2010 |
| WO | WO-2010051549 A1 | 5/2010 |
| WO | WO-2010086040 A1 | 8/2010 |
| WO | WO-2011006074 A1 | 1/2011 |
| WO | WO-2011022439 A1 | 2/2011 |
| WO | WO-2012007375 A1 | 1/2012 |
| WO | WO-2012034095 A1 | 3/2012 |
| WO | WO-2012038081 A1 | 3/2012 |
| WO | WO-2012075393 A2 | 6/2012 |
| WO | WO-2012078855 A1 | 6/2012 |
| WO | WO-2012116237 A2 | 8/2012 |
| WO | WO-2012129258 A1 | 9/2012 |
| WO | WO-2012177997 A1 | 12/2012 |
| WO | WO-2013030288 A1 | 3/2013 |
| WO | WO-2013059587 A1 | 4/2013 |
| WO | WO-2013096060 A1 | 6/2013 |
| WO | WO-2013134079 A1 | 9/2013 |
| WO | WO-2013134336 A2 | 9/2013 |
| WO | WO-2013148333 A1 | 10/2013 |
| WO | WO-2013178591 A1 | 12/2013 |
| WO | WO-2014025651 A1 | 2/2014 |
| WO | WO-2014037340 A1 | 3/2014 |
| WO | WO-2014075168 A1 | 5/2014 |
| WO | WO-2014085607 A1 | 6/2014 |
| WO | WO-2014089379 A1 | 6/2014 |
| WO | WO-2014141129 A2 | 9/2014 |
| WO | WO-2014144455 A1 | 9/2014 |
| WO | WO-2015012328 A1 | 1/2015 |
| WO | WO-2015026574 A1 | 2/2015 |
| WO | WO-2015027124 A1 | 2/2015 |
| WO | WO-2015035117 A1 | 3/2015 |
| WO | WO-2015073267 A1 | 5/2015 |
| WO | WO-2015147639 A1 | 10/2015 |
| WO | WO-2016007736 A1 | 1/2016 |
| WO | WO-2016073889 A1 | 5/2016 |
| WO | WO-2016073891 A1 | 5/2016 |
| WO | WO-2016073895 A1 | 5/2016 |
| WO | WO-2017004408 A1 | 1/2017 |
| WO | WO-2017040877 A1 | 3/2017 |
| WO | WO-2017079519 A1 | 5/2017 |
| WO | WO-2017087590 A1 | 5/2017 |
| WO | WO-2017140825 A1 | 8/2017 |
| WO | WO-2017176960 A1 | 10/2017 |
| WO | WO-2017176961 A1 | 10/2017 |
| WO | WO-2017176962 A1 | 10/2017 |
| WO | WO-2017192841 A1 | 11/2017 |
| WO | WO-2017192929 A1 | 11/2017 |
| WO | WO-2017192930 A1 | 11/2017 |
| WO | WO-2017192931 A1 | 11/2017 |
| WO | WO-2019126776 A1 | 6/2019 |

OTHER PUBLICATIONS

U.S. Appl. No. 15/440,107 U.S. Pat. No. 9,732,089, Substituted Pyrazolo[1,5-A)Pyrimidines and Their Use in the Treatment of Medical Disorders, filed Feb. 23, 2017, Patented.

U.S. Appl. No. 16/733,598 U.S. Pat. No. 11,091,492, Substituted Pyrazolo[1,5-A]Pyrimidines and Their Use in the Treatment of Medical Disorders, filed Jan. 3, 2020, Patented.

U.S. Appl. No. 17/369,507, Substituted Pyrazolo[1,5-A]Pyrimidines and Their Use in the Treatment of Medical Disorders, filed Jul. 7, 2021, Pending.

U.S. Appl. No. 15/523,774 US 2017/0333435, Substituted Imidazo [1,5-A]Pyrimidines and Their Use in the Treatment of Medical Disorders, filed May 2, 2017, Abandoned.

U.S. Appl. No. 16/131,287 U.S. Pat. No. 10,786,508, Substituted Imidazo [1,5-A]Pyrimidtnes and Their Use in the Treatment of Medical Disorders, filed Sep. 14, 2018, Patented.

U.S. Appl. No. 16/934,819 US 2021/0169886, Substituted Imidazo [1,5-A]Pyrimidines and Their Use in the Treatment of Medical Disorders, filed Jul. 21, 2020, Allowed.

U.S. Appl. No. 15/523,775 US 2018/0185368, Substituted Pyrrolo[1,2-A]Pyrimidines and Their Use in the Treatment of Medical Disorders, filed May 2, 2017 Abandoned.

U.S. Appl. No. 16/453,109 U.S. Pat. No. 10,751,341, Substituted Pyrrolo [1,2-A]Pyrimidines and Their Use in the Treatment of Medical Disorders, filed Jun. 26, 2019, Patented.

U.S. Appl. No. 16/929,779 US 2021/0177853, Substituted Pyrrolo[1,2-A]Pyrimidines and Their Use in the Treatment of Medical Disorders, filed Jul. 15, 2020, Allowed.

U.S. Appl. No. 16/097,902 US 2019/0389865, Substituted Pyrrolo [1,2-A]Triazines and Related Compounds and Their Use in the Treatment of Medical Disorders, filed Oct. 31, 2018, Abandoned.

(56) References Cited

OTHER PUBLICATIONS

U.S. Appl. No. 16/097,905 U.S. Pat. No. 11,168,087, Substituted Imidazo[1,2-b]Pyridazines, Substituted Imidazo[1,5-b] Pyridazines, Related Compounds, and Their Use in the Treatment of Medical Disorders, filed Oct. 31, 2018, Patented.
U.S. Appl. No. 15/678,468 U.S. Pat. No. 9,868,742, Substitued Imidazo[1,2-b]Pyridazines, Substituted Imidazo[1,5-b]Pyridazines, Related Compounds, and Their Use in the Treatment of Medical Disorders, filed Aug. 16, 2017, Patented.
U.S. Appl. No. 16/097,907 US 2019/0389856, Substituted Imidazo[1,2-a]Pyridines, Substituted Imidazo[1,2-a] Pyrazines, Related Compounds, and Their Use in the Treatment of Medical Disorders, filed Oct. 31, 2018, Allowed.
U.S. Appl. No. 16/091,311 U.S. Pat. No. 11,192,892, Substituted Pyrazolo[1,5-a]Pyrimidines for the Treatment of Medical Disorders, filed Oct. 4, 2018, Patented.
U.S. Appl. No. 15/678,474 U.S. Pat. No. 9,840,510, Pyrazolo[1,5-A]Pyrimidinyl Carboxamide Compounds and Their Use in the Treatment of Medical Disorders, filed Aug. 16, 2017, Patented.
U.S. Appl. No. 16/356,564 U.S. Pat. No. 10,934,298, Substituted Pyrazolo[1,5-a]Pyrimidines for the Treatment of Medical Disorders, filed Mar. 18, 2019, Patented.
U.S. Appl. No. 17/509,353, Pyrazolo[1,5-a]Pyrimidinyl Pending Carboxamide Compounds and Their Use in the Treatment of Medical Disorders, filed Oct. 25, 2021, Pending.
U.S. Appl. No. 16/091,316 U.S. Pat. No. 10,787,454, Imidazo[1,5-a]Pyrimidinyl Carboxamide Compounds and Their Use in the Treatment of Medical Disorders, filed Oct. 4, 2018, Patented.
U.S. Appl. No. 15/678,476 U.S. Pat. No. 9,920,061, Imidazo[1,5-A]Pyrimidinyl Carboxamide Compounds and Their Use in the Treatment of Medical Disorders, filed Aug. 16, 2017, Patented.
U.S. Appl. No. 16/989,254, Imidazo[1,5-A]Pyrimidinyl Carboxamide Compounds and Their Use in the Treatment of Medical Disorders, filed Aug. 10, 2020, Allowed.
U.S. Appl. No. 16/091,337 U.S. Pat. No. 11,124,516, Pyrrolo[1,2-A]Pyrimidinyl Carboxamide Compounds and Their Use in the Treatment of Medical Disorders, filed Oct. 4, 2018, Patented.
U.S. Appl. No. 17/403,369, Pyrrolo[1,2-A]pyrimidinyl Carboxamide Compounds and Their Use in the Treatment of Medical Disorders, filed Aug. 16, 2021, Pending.
U.S. Appl. No. 16/955,589 US 2020/0339587, Crystalline Substituted Cyclohexyl Pyrazolo[1,5-A]Pyrimidinyl Carboxamide Compound and Therapeutic Uses Thereof, filed Dec. 22, 2020, Pending.
"Symptoms of Gaucher Disease" retrieved from the internet Apr. 17, 2017 from url: http://www.gaucherdisease.org/about-gaucher-disease/symptoms/.
Ahmetaj, S. et al. "Parallel synthesis of 7-heteroaryl-pyrazolo[1,5-a]pyrimidine-3-carboxamides" *Molecular Diversity* (2013) vol. 17, No. 4, pp. 731-743.
Almeida, MR."Glucocerebrosidase Involvement in Parkinson Disease and other Synucleinopathies," Frontiers in Neurology Apr. 27;3:65 2012.
Brogi Simone et al: 3D-QSAR using pharmacophore-based alignment and virtual screening for discovery of novel MCF-7 cell line inhibitors11 , Composites: Part A: Applied Science and Manufacturing,, vol. 67, Jul. 1, 2013 (Jul. 1, 2013), pp. 344-351, XP028710082.
Caira M. R. "Crystalline Polymorphism of Organic Compounds." Topics in Current Chemistry. Springer, Berlin, DE, vol. 198, Jan. 1, 1998, pp. 163-208.
CAS Abstract and Indexed Compounds, WO2013/059587 (2013).
CAS Registry No. 1003709-79-2; STN Entry Date Feb. 15, 2008; Thieno[3,2-b]pyridine-3-carboxamide, N-[2-(1-piperidinyl)ethyl]-6-(2-pyrazinyl)-.
CAS Registry No. 1355610-51-3; STN Entry Date Feb. 7, 2012; (2-Cyclopentyl-1-pyrrolidinyl)(5,7-dimethylpyrazolo[1,5-a]pyrimidin-3-yl)methanone.
CAS Registry No. 1355851-51-2; STN Entry Date Feb. 8, 2012; (2-Cyclohexyl-1-pyrrolidinyl)pyrazolo[1,5-a]pyrimidin-3-ylmethanone.

CAS Registry No. 1424084-03-6; STN Entry Date Mar. 15, 2013; (4-bicyclo[2.2.1]hept-2-yl-1-piperazinyl)(2-methylpyrazolo[1,5-a]pyrimidin-3-yl)methanone.
CAS Registry No. 1624709-79-0; STN Entry Date Sep. 23, 2014; 4-cyclopentyl-1-piperazinyl)(2-methylpyrazolo[1,5-a]pyrimidin-3-yl)methanone.
CAS Registry No. 1664399-83-0; STN Entry Date Mar. 18, 2015; Furo[3,2]pyridine-3-carboxamide, 2-amino-N-[4-[(1R,3S,5S)-3-amino-5-methylcyclohexyl]-3-pyridinyl]-6-(1-methylethyl)-.
CAS Registry No. 1022459-94-4, STN entry date: May 25, 2008, chemical name: 5-(2-furanyl)-N-[(4-methylphenyl)methyl]-7-(trifluoromethyl)-pyrazolo[1,5-a]pyrimidine-3-carboxamide.
CAS Registry No. 1027839-50-4, STN entry date: Jun. 13, 2008, chemical name: 8-Quinazolinecarboxamide, N-ethyl-2-(2-propoxyphenyl)-.
CAS Registry No. 1090443-11-0, STN entry date: Dec. 26, 2008, chemical name: N-(dicyclopropylmethyl)-5,7-dimethyl-pyrazolo[1,5-a]pyrimidine-3-carboxamide.
CAS Registry No. 1099976-59-6, STN entry date: Feb. 3, 2009, chemical name: N-(1-cyclopropyl-4-piperidinyl)-5,7-dimethyl-pyrazolo[1,5-a]pyrimidine-3-carboxamide.
CAS Registry No. 1121583-22-9, STN entry date: Mar. 16, 2009, chemical name: pyrrolo[1,2-a]pyrimidine-8-carboxamide, 6-chloro-N-(3-methylphenyl)-.
CAS Registry No. 1121584-90-4, STN entry date: Mar. 16, 2009, chemical name: pyrrolo[1,2-a]pyrimidine-8-carboxamide, 6-chloro-N-[2-(1-piperidinyl)ethyl]-.
CAS Registry No. 1224940-28-6, STN entry date: May 24, 2010, chemical name: N-cyclohexyl-5-methoxy-pyrazolo[1,5-a]pyrimidine-3-carboxamide.
CAS Registry No. 1224940-60-6, STN entry date: May 24, 2010, chemical name: N-cyclohexyl-5-(ethylamino)-pyrazolo[1,5-a]pyrimidine-3-carboxamide.
CAS Registry No. 1260846-47-6, STN entry date: Jan. 27, 2011, chemical name: N-(1,1-dimethylethyl)-5-[(2R)-2-(3-fluorophenyl)-4-oxo-1-pyrrolidinyl]-pyrazolo[1,5-a]pyrimidine-3-carboxamide.
CAS Registry No. 1348484-20-7, STN entry date: Dec. 4, 2011, chemical name: Imidazo[1,2-a]pyridine-8-carboxamide, N-[(1-butyl-4-piperidinyl)methyl]-6-chloro-2-ethyl-5-(methylamino)-.
CAS Registry No. 1348704-16-4, STN entry date: Dec. 4, 2011, chemical name: Imidazo[1,2-a]pyridine-8-carboxamide, N-[(1-butyl-4-piperidinyl)methyl]-6-chloro-2-methyl-5-(methylamino)-.
CAS registry No. 1477723-10-6, STN entry date: Nov. 21, 2013, chemical name: Pyrazolo[1,5-a]pyrimidine-3-carboxamide, N-[2-(aminomethyl)cyclopentyl]-5,7-dimethyl-.
CAS registry No. 1486188-70-8, STN entry date: Dec. 3, 2013, chemical name: Pyrazolo[1,5-a]pyrimidine-3-carboxamide, N-[1-(hydroxymethyl)cyclopentyl]-5,7-dimethyl-.
CAS registry No. 1487377-87-6, STN entry date: Dec. 5, 2013, chemical name: Pyrazolo[1,5-a]pyrimidine-3-carboxamide, N-[1-(aminomethyl)cyclopentyl]-5,7-dimethyl-.
CAS registry No. 1626061-70-8, STN entry date: Sep. 25, 2014, chemical name: Pyrazolo[1,5-a]pyrimidine-3-carboxamide, 2-methyl-N-[[2-(2-methylpropoxy)phenyl]methyl]-.
CAS registry No. 1626265-70-0, STN entry date: Sep. 25, 2014, chemical name: Pyrazolo[1,5-a]pyrimidine-3-carboxamide, 2-methyl-N-[[4-(2-methylpropoxy)phenyl]methyl]-.
CAS registry No. 1626915-96-5, STN entry date: Sep. 26, 2014, chemical name: Pyrazolo[1,5-a]pyrimidine-3-carboxamide, N-[1-[3-methoxy-4-(pentyloxy)phenyl]ethyl]-2-methyl.
CAS registry No. 1713613-74-1, STN entry date: May 27, 2015, chemical name: Pyrazolo[1,5-a]pyrimidine-3-carboxamide, N-[1-(hydroxymethyl)cyclopropyl]-5,7-dimethyl-.
CAS registry No. 1775586-63-4, STN entry date: Jun. 8, 2015, chemical name: Pyrazolo[1,5-a]pyrimidine-3-carboxamide, N-[1-(hydroxymethyl)cyclobutyl]-5,7-dimethyl-.
CAS registry No. 1825314-78-0, STN entry date: Dec. 8, 2015, chemical name: 4-Benzoxazolecarboxamide, 2-methyl-N-6-oxa-2-thiaspiro[4.5]dec-9-yl-.
CAS registry No. 422537-28-8, STN entry date: May 29, 2002, chemical name: Pyrazolo[1,5-a]pyrimidine-3-carboxamide, 5,7-dimethyl-N-(4-phenoxyphenyl)-.

(56) References Cited

OTHER PUBLICATIONS

CAS Registry No. 696640-82-1, STN entry date: Jun. 21, 2004, chemical name: 7-(difluoromethyl)-5-(4-methoxyphenyl)-N-(tricyclo[3.3.1.1 3,7 ]dec-1-ylmethyl)-pyrazolo[1,5-a]pyrimidine-3-carboxamide.
CAS Registry No. 765896-16-0, STN entry date: Oct. 20, 2004, chemical name: Imidazo[1,2-a]pyridine-8-carboxamide, 5-amino-2-ethyl-N-[[1-(3-methoxypropyl)-4-piperidinyl]methyl]-.
CAS Registry No. 895779-11-0, STN entry date: Jul. 25, 2006, chemical name: 5-(4-bromophenyl)-N-[(4-methoxyphenyl)methyl]-7-(trifluoromethyl)-pyrazolo[1,5-a]pyrimidine-3-carboxamide.
CAS registry No. 1050831-16-7, STN entry date: Sep. 21, 2008, chemical name: Pyrazolo[1,5-a]pyrimidine-3-carboxamide, 5,7-dimethyl-N-(1,2,3,4-tetrahydro-1-naphthalenyl)-.
CAS Registry No. 1116067-90-3, STN entry date: Mar. 5, 2009, chemical name: N-[3-(hexahydro-IH-azepin-l-yl)propyl]-6-phenyl-1,2,4-Triazolo[4,3-b]pyridazine-3-carboxamide.
CAS registry No. 1147832-58-3, STN entry date: May 20, 2009, chemical name: Pyrazolo[1,5-a]pyrimidine-3-carboxamide,N-[3-chloro-4-(2-methylpropoxy)phenyl]-.
CAS registry No. 1280061-59-7, STN entry date: Apr. 14, 2011, chemical name: Pyrazolo[1,5-a]pyrimidine-3-carboxamide, N-(2-butoxy-5-methoxyphenyl)-2,5,7-trimethyl-.
CAS registry No. 1541365-83-6, STN entry date: Feb. 11, 2014, chemical name:Cyclobutanecarboxylic acid, 1-[[(5,7-dimethylpyrazolo[1,5-a]pyrimidin-3-yl)carbonyl]amino]-.
Dalinger Igor L., Journal of Combinatorial Chemistry, 2005, 7(2), 236-245 (10 pages).
Database Registry [Online] Chemical Abstracts Service, Columbus, Ohio, US; Jan. 12, 2014 (Jan. 12, 2014), XP002794586, Database accession No. 1517327-54-6 compound with the Registry No. 1517327-54-6.
Database Registry [Online] Chemical Abstracts Service, Columbus, Ohio, US; Jan. 13, 2014 (Jan. 13, 2014), XP002794585, Database accession No. 1518103-84-8 compound with the Registry No. 1518103-84-8.
Database Registry [Online] Chemical Abstracts Service, Columbus, Ohio, US; May 14, 2013 (May 14, 2013), XP002794418, Database accession No. 1423757-47-4 Compounds with the Registry Nos. 1423757-47-4 and 1423807-67-3.
Database Registry [Online] Chemical Abstracts Service, Columbus, Ohio, US; Jan. 16, 2014 (Jan. 16, 2014), XP002794584, Database accession No. 1521766-89-1 compounds with the Registry Nos. 1521766-89-1 and 1522335-76-7.
Database Registry [Online] Chemical Abstracts Service, Columbus, Ohio, US; Jul. 16, 2013 (Jul. 16, 2013), XP002794421, Database accession No. 1444105-29-6 Compound with the Registry No. 1444105-29-6.
Database Registry [Online] Chemical Abstracts Service, Columbus, Ohio, US; Dec. 22, 2013 (Dec. 22, 2013), XP002794594, Database accession No. 1500341-69-4 compound with the registry No. 1500341-69-4.
Database Registry [Online] Chemical Abstracts Service, Columbus, Ohio, US; Dec. 23, 2013 (Dec. 23, 2013), XP002794593, Database accession No. 1502022-92-5 compound with the Registry No. 1502022-92-5.
Database Registry [Online] Chemical Abstracts Service, Columbus, Ohio, US; Jan. 24, 2014 (Jan. 24, 2014), XP002794583, Database accession No. 1529636-26-7 compound with the Registry No. 1529636-26-7.
Database Registry [Online] Chemical Abstracts Service, Columbus, Ohio, US; Dec. 27, 2013 (Dec. 27, 2013), XP002794592, Database accession No. 1505014-97-0 compound with the Registry No. 1505014-97-0.
Database Registry [Online] Chemical Abstracts Service, Columbus, Ohio, US; Dec. 29, 2013 (Dec. 29, 2013), XP002794591, Database accession No. 1506311-11-0 compound with the Registry No. 1506311-11-0.
Database Registry [Online] Chemical Abstracts Service, Columbus, Ohio, US; Sep. 29, 2015 (Sep. 29, 2015), XP002794420, Database accession No. 1808330-01-9 Compounds with the Registry Nos. 1808330-01-9, 1808808-91-4 and 1808880-93-4.
Database Registry [Online] Chemical Abstracts Service, Columbus, Ohio, US; Dec. 30, 2013 Dec. 30, (2013), XP002794590, Database accession No. 1507166-09-7 compound with the Registry No. 1507166-09-7.
Database Registry [Online] Chemical Abstracts Service, Columbus, Ohio, US; Dec. 31, 2013 (Dec. 31, 2013), XP002794589, Database accession No. 1508094-23-2 compound with the Registry No. 1508094-23-2.
Database Registry [Online] Chemical Abstracts Service, Columbus, Ohio, US; Jan. 5, 2014 (Jan. 5, 2014), XP002794588, Database accession No. 1511391-62-0 compound with the Registry Nos. 1511391-62-0 and 1510939-79-3.
Database Registry [Online] Chemical Abstracts Service, Columbus, Ohio, US; Feb. 6, 2014 (Feb. 6, 2014), XP002794582, Database accession No. 1537972-48-7 compound with the Registry No. 1537972-48-7.
Database Registry [Online] Chemical Abstracts Service, Columbus, Ohio, US; Jan. 6, 2014 (Jan. 6, 2014), XP002794587, Database accession No. 1512267-66-1 compound with the Registry No. 1512267-66-1.
Database Registry [Online] Chemical Abstracts Service, Columbus, Ohio, US; Feb. 7, 2014 (Feb. 7, 2014), XP002794581, Database accession No. 1539191-30-4 compound with the Registry No. 1539191-30-4.
Database Registry [Online] Chemical Abstracts Service, Columbus, Ohio, US; Feb. 9, 2014 (Feb. 9, 2014), XP002794580, Database accession No. 1539876-08-8 compound with the Registry No. 1539876-08-8.
Database Registry [Online] Chemical Abstracts Service, Columbus, Ohio, US; Jun. 9, 2013 (Jun. 9, 2013), XP002794419, Database accession No. 1436029-77-4 Compounds with the Registry Nos. 1436029-77-4, 1436085-73-2, 1436108-94-9, 1436139-15-9 and 1436367-43-9.
Database Registry [Online]Chemical Abstracts Service, Columbus, Ohio, US; Sep. 18, 2012 (Sep. 18, 2012), XP002794417, Database accession No. 1394732-89-8 Compounds with the Registry Nos. 1394732-89-8, 1394738-37-4, 1394760-10-1, 1394789-28-6 and 1394793-42-0.
Graeme R. Robb et al. "Design of pyrazolo-pyrimidines as 11β-HSD1 inhibitors through optimisation of molecular electrostatic potential" MedChemComm, vol. 6, No. 5, 2015, pp. 926-934, XP0555534025.
Huppatz, J. L. "Systemic Fungicides. The Synthesis of Pyrazolo[1,5-a]pyrimidine Analogues of Carboxin," Australian J. Chem. (1985) vol. 38, No. 1, pp. 221-230. (Abstract Only).
International Search Report and Writen Opinion for PCT/US2017/031189 dated Jul. 19, 2017 (25 pages).
International Search Report and Written Opinion for PCT/US2017/026280 dated Jul. 3, 2017 (20 pages).
Liu, K. C. C. et al. "Quinazolines with intra-molecular hydrogen bonding scaffold (iMHBS) as PI3K/mTOR dual inhibitors," *Bioorg. Med. Chem. Lett.* (2011) vol. 21, Issue 4, pp. 1270-1274.
Liu, K. K. C. et al. "Quinazolines with intra-molecular hydrogen bonding scaffold (iMHBS) as PI3K/mTOR dual inhibitors," *Bioorg. Med. Chem. Lett.* (2011) vol. 21, Issue 4, pp. 1270-1274.
Marugan, J. J. et al. "Evaluation of Quinazoline Analogues as Glucocerebrosidase Inhibitors with Chaperone Activity," *J. Med. Chem.* (2011) vol. 54, pp. 1033-1058.
Mata, I. F. et al. "Glucocerebrosidase Gene Mutations: A Risk Factor for Lewy Body Disorders," Arch. Neurol. (2008) vol. 65, No. 3, pp. 379-382.
Moraski Garrett C et al: "Scaffold-switching: An exploration of 5,6-fused bicyclic heteroaromatics systems to afford antituberculosis activity akin to the imidazo[l,2-a]pyridine-3-carboxylates", Bioorganic & Medicinal Chemistry Letters, Pergamon, Amsterdam, NL, vol. 24, No. 15, May 28, 2014 (May 28, 2014), pp. 3493-3498, XP028864111.

(56) References Cited

OTHER PUBLICATIONS

Ortega, R. A. et al. "Glucocerebrosidase enzyme activity in GBA mutation Parkinson's disease," *J. Clin. Neurosci.* (2016) vol. 28, p. 185-186. (Abstract Only—Retrieved from the internet on Apr. 17, 2017 from url: https://www.ncbi.nlm.nih.gov/pubmed/26857292).

Patnaik et al., "Discovery, Structure-Activity Relationship, and Biological Evaluation of Non-inhibitory Small Molecule Chaperones of Glucocerebrosidase," Journal of Medicinal Chemistry, 55(12) 5734-5748 (2012).

RN 1424311-75-0 Registry, Database Registry [Online] Retrieved from STN, Mar. 15, 2013, search date: Aug. 21, 2021.

STN Chemical Structure Search Results (dated Aug. 24, 2015). (26 pages).

STN Chemical Structure Search Results (dated Aug. 6, 2014). (61 pages).

STN Chemical Structure Search Results (dated Jul. 1, 2014). (44 pages).

STN Chemical Structure Search Results (dated Jul. 1, 2014). (8 pages).

STN Chemical Structure Search Results (dated Jul. 8, 2014). (108 pages).

STN Chemical Structure Search Results (dated Jul. 8, 2014). (38 pages).

STN Chemical Structure Search Results (dated Jun. 10, 2015). (26 pages).

STN Chemical Structure Search Results Part I (dated Aug. 18, 2016). (29 pages).

STN Chemical Structure Search Results Part I (dated Mar. 13, 2016). (39 pages).

STN Chemical Structure Search Results Part I (dated Mar. 14, 2016). (108 pages).

STN Chemical Structure Search Results Part II (dated Aug. 18, 2016). (87 pages).

STN Chemical Structure Search Results Part II (dated Mar. 13, 2016). (115 pages).

STN Chemical Structure Search Results Part II (dated Mar. 14, 2016). (28 pages).

Wang, X. et al. "Discovery of novel pyrazolo[1,5-a]pyrimidines as potent pan-Pim inhibitors by structure- and property-based drug design," Bioorg. Med. Chem. Lett. (2013) vol. 23, pp. 3149-3153.

Hackam, Daniel G., et al., "Translations of Research Evidence From Animals to Humans," JAMA, (Oct. 11, 2006), vol. 296, No. 14, pp. 1731-1732.

Jordan, V. C., "Taxmoxifen: A most unlikely Pioneering Medicine," Nature Reviews, (Mar. 2003), vol. 2, pp. 205-213.

SUBSTITUTED IMIDAZO[1,2-B]PYRIDAZINES, SUBSTITUTED IMIDAZO[1,5-B]PYRIDAZINES, RELATED COMPOUNDS, AND THEIR USE IN THE TREATMENT OF MEDICAL DISORDERS

CROSS-REFERENCE TO RELATED APPLICATIONS

This application is a continuation of U.S. patent application Ser. No. 16/097,905, filed Oct. 31, 2018, which is the national stage of International (PCT) Patent Application Serial No. PCT/US2017/031189, filed May 5, 2017, which claims the benefit of and priority to U.S. Provisional Patent Application Ser. No. 62/332,151, filed May 5, 2016, the contents of each of which are hereby incorporated by reference.

FIELD OF THE INVENTION

The invention provides substituted imidazo[1,2-b]pyridazine compounds, substituted imidazo[1,5-b]pyridazine compounds, related compounds, compositions containing such compounds, medical kits, and methods for using such compounds and compositions to treat medical disorders in a patient.

BACKGROUND

Gaucher disease is a genetic disorder associated with a deficiency of the lysosomal enzyme, glucocerebrosidase. Gaucher disease has been reported to have an incidence of approximately 1 in 20,000 live births in the general population, and it is a common lysosomal storage disorder. Current treatments for patients suffering from this disease include enzyme replacement therapy, which tends to be expensive, analgesics for bone pain relief, and medical procedures such as blood and platelet transfusions, splenectomy, and joint replacement for patients who experience bone erosion. However, new treatment options are needed having improved efficacy across a broader range of patients and/or reduced adverse side effects.

Mutations in the gene encoding glucocerebrosidase are also a risk factor for Parkinson's disease and diffuse Lewy Body Disease. Parkinson's disease is a degenerative disorder of the central nervous system associated with death of dopamine-containing cells in a region of the midbrain. Parkinson's disease afflicts millions of people, and the incidence of the disease increases with age. Treatment of Parkinson's disease frequently involves use of levodopa and dopamine agonists. However, these drugs can produce significant side effects such as hallucinations, insomnia, nausea, and constipation. Further, patients often develop tolerance to these drugs such that the drugs become ineffective at treating the symptoms of the disease, while sometimes also producing a movement disorder side effect called dyskinesia. Diffuse Lewy Body disease is a dementia that is sometimes confused with Alzheimer's disease.

Accordingly, the need exists for new therapeutic agents for treating Gaucher disease, Parkinson's disease, and related medical disorders. The present invention addresses this need and provides other related advantages.

SUMMARY

The invention provides substituted imidazo[1,2-b]pyridazine compounds, substituted imidazo[1,5-b]pyridazine compounds, related compounds, compositions containing such compounds, medical kits, and methods for using such compounds and compositions to treat medical disorders, e.g., Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, endometriosis, and multiple myeloma, in a patient. Various aspects and embodiments of the invention are described in further detail below.

Accordingly, one aspect of the invention provides a family of substituted imidazo[1,2-b]pyridazine compounds embraced by Formula I that may be used in the methods, compositions, and kits described herein, wherein Formula I is represented by:

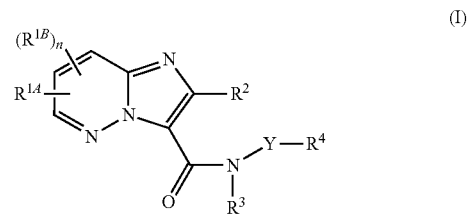

(I)

or a pharmaceutically acceptable salt thereof, wherein the variables are as defined in the detailed description.

Another aspect of the invention provides a family of substituted imidazo[1,2-b]pyridazine compounds embraced by Formula II that may be used in the methods, compositions, and kits described herein, wherein Formula II is represented by:

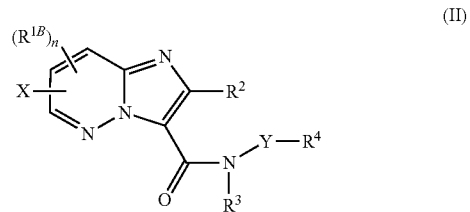

(II)

or a pharmaceutically acceptable salt thereof, wherein the variables are as defined in the detailed description.

Another aspect of the invention provides a family of substituted imidazo[1,5-b]pyridazine compounds embraced by Formula III that may be used in the methods, compositions, and kits described herein, wherein Formula III is represented by:

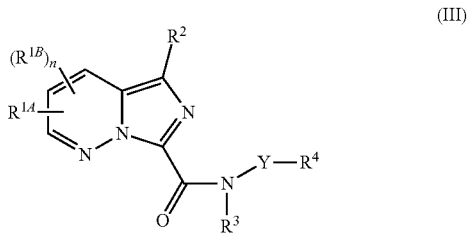

(III)

or a pharmaceutically acceptable salt thereof, wherein the variables are as defined in the detailed description.

Another aspect of the invention provides a family of compounds embraced by Formula IV that may be used in the methods, compositions, and kits described herein, wherein Formula IV is represented by:

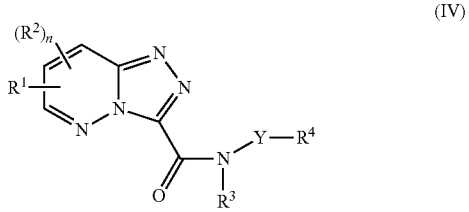

(IV)

or a pharmaceutically acceptable salt thereof, wherein the variables are as defined in the detailed description.

Another aspect of the invention provides a family of compounds embraced by Formula V that may be used in the methods, compositions, and kits described herein, wherein Formula V is represented by:

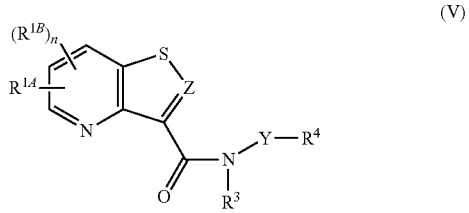

(V)

or a pharmaceutically acceptable salt thereof, wherein the variables are as defined in the detailed description.

Another aspect of the invention provides a family of compounds embraced by Formula VI that may be used in the methods, compositions, and kits described herein, wherein Formula VI is represented by:

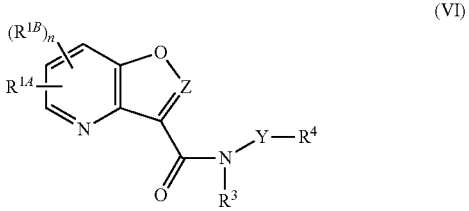

(VI)

or a pharmaceutically acceptable salt thereof, wherein the variables are as defined in the detailed description.

Another aspect of the invention provides a family of compounds embraced by Formula VII that may be used in the methods, compositions, and kits described herein, wherein Formula VII is represented by:

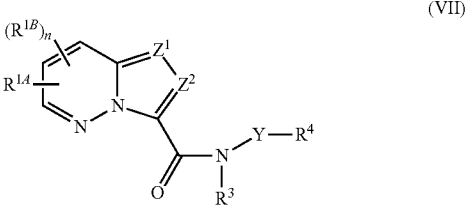

(VII)

or a pharmaceutically acceptable salt thereof, wherein the variables are as defined in the detailed description.

Another aspect of the invention provides a pharmaceutical composition, comprising a pharmaceutically acceptable carrier and a substituted imidazo[1,2-b]pyridazine compound, substituted imidazo[1,5-b]pyridazine compound, or related compound described herein, such as a compound of Formula I, II, III, IV, V, VI, or VII. In certain embodiments, the invention provides a pharmaceutical composition, comprising a pharmaceutically acceptable carrier and a substituted imidazo[1,2-b]pyridazine compound described herein, such as a compound of Formula I or II. In certain other embodiments, the invention provides a pharmaceutical composition, comprising a pharmaceutically acceptable carrier and a substituted imidazo[1,5-b]pyridazine compound described herein, such as a compound of Formula III.

Another aspect of the invention provides a method of treating a disorder, e.g., Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, endometriosis, and multiple myeloma, in a patient. The method comprises administering to a patient in need thereof a therapeutically effective amount of a substituted imidazo[1,2-b]pyridazine compound, substituted imidazo[1,5-b]pyridazine compound, or related compound described herein, such as a compound of Formula I, II, III, IV, V, VI, or VII, to treat the disorder, e.g., Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, endometriosis, or multiple myeloma.

DETAILED DESCRIPTION

The invention provides substituted imidazo[1,2-b]pyridazine compounds, substituted imidazo[1,5-b]pyridazine compounds, related compounds, compositions containing such compounds, medical kits, and methods for using such compounds and compositions to treat medical disorders in a patient. The practice of the present invention employs, unless otherwise indicated, conventional techniques of organic chemistry, pharmacology, cell biology, and biochemistry. Such techniques are explained in the literature, such as in "Comprehensive Organic Synthesis" (B. M. Trost & I. Fleming, eds., 1991-1992); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety. Various aspects of the invention are set forth below in sections; however, aspects of the invention described in one particular section are not to be limited to any particular section.

I. Definitions

To facilitate an understanding of the present invention, a number of terms and phrases are defined below.

The terms "a" and "an" as used herein mean "one or more" and include the plural unless the context is inappropriate.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1- propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkylene" refers to a diradical of an alkyl group. An exemplary alkylene group is —CH$_2$CH$_2$—.

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, and the like.

The term "haloalkylene" refers to a diradical of a haloalkyl group. Exemplary haloalkylene groups are —CH$_2$CF$_2$— and —C(H)(CF$_3$)CH$_2$—.

The term "heteroalkyl" as used herein refers to an "alkyl" group in which at least one carbon atom has been replaced with a heteroatom (e.g., an O, N, or S atom). The heteroalkyl may be, for example, an —O—C$_1$-C$_{10}$alkyl group, an —C$_1$-C$_6$alkylene-O—C$_1$-C$_6$alkyl group, or a C$_1$-C$_6$ alkylene-OH group. In certain embodiments, the "heteroalkyl" may be 2-8 membered heteroalkyl, indicating that the heteroalkyl contains from 2 to 8 atoms selected from the group consisting of carbon, oxygen, nitrogen, and sulfur. In yet other embodiments, the heteroalkyl may be a 2-6 membered, 4-8 membered, or a 5-8 membered heteroalkyl group (which may contain for example 1 or 2 heteroatoms selected from the group oxygen and nitrogen). One type of heteroalkyl group is an "alkoxyl" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C$_2$-C$_{12}$alkenyl, C$_2$-C$_{10}$alkenyl, and C$_2$-C$_6$alkenyl, respectively. Exemplary alkenyl groups include vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, and the like.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C$_2$-C$_{12}$alkynyl, C$_2$-C$_{10}$alkynyl, and C$_2$-C$_6$alkynyl, respectively. Exemplary alkynyl groups include ethynyl, prop-1-yn-1-yl, and but-1-yn-1-yl.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C$_{4-8}$cycloalkyl," derived from a cycloalkane. Unless specified otherwise, the cycloalkyl group is optionally substituted by 1 or 2 C$_1$-C$_6$ alkyl groups. In certain embodiments, the cycloalkyl group is unsubstituted. Exemplary cycloalkyl groups include, but are not limited to, cyclohexanes, cyclopentanes, cyclobutanes and cyclopropanes.

The term "cycloalkylene" refers to a diradical of an cycloalkyl group. An exemplary cycloalkylene group is

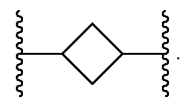

The term "cycloalkenyl" as used herein refers to a monovalent unsaturated cyclic, bicyclic, or bridged cyclic (e.g., adamantyl) hydrocarbon group of 3-12, 3-8, 4-8, or 4-6 carbons containing one carbon-carbon double bond, referred to herein, e.g., as "C$_{4-8}$cycloalkenyl," derived from a cycloalkane. Exemplary cycloalkenyl groups include, but are not limited to, cyclohexenes, cyclopentenes, and cyclobutenes. Unless specified otherwise, cycloalkenyl groups are optionally substituted at one or more ring positions with, for example, alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkenyl group is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The term "aralkyl" refers to an alkyl group substituted with an aryl group.

The term "bicyclic carbocyclyl that is partially unsaturated" refers to a bicyclic carbocyclic group containing at least one double bond between ring atoms and at least one ring in the bicyclic carbocyclic group is not aromatic. Representative examples of a bicyclic carbocyclyl that is partially unsaturated include, for example:

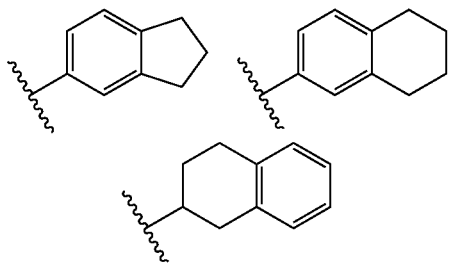

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using $C_x$-$C_x$ nomenclature where x is an integer specifying the number of ring atoms. For example, a $C_3$-$C_7$heterocyclyl group refers to a saturated or partially unsaturated 3- to 7-membered ring structure containing one to four heteroatoms, such as nitrogen, oxygen, and sulfur. The designation "$C_3$-$C_7$" indicates that the heterocyclic ring contains a total of from 3 to 7 ring atoms, inclusive of any heteroatoms that occupy a ring atom position. One example of a $C_3$heterocyclyl is aziridinyl. Heterocycles may also be mono-, bi-, or other multi-cyclic ring systems. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isooxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. Unless specified otherwise, the heterocyclic ring is optionally substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, oxo, phosphate, phosphonato, phosphinato, sulfate, sulfide, sulfonamido, sulfonyl and thiocarbonyl. In certain embodiments, the heterocyclyl group is not substituted, i.e., it is unsubstituted.

The term "oxoheterocyclyl" refers to a heterocyclyl group that is substituted with at least one oxo group (i.e., =O). In certain embodiments, the oxoheterocyclyl is substituted with 1 or 2 oxo groups. In certain embodiments, the oxoheterocyclyl is a 5-6 membered saturated heterocyclyl substituted with 1 oxo group.

The term "bicyclic heterocyclyl" refers to a heterocyclyl group that contains two rings that are fused together. Representative examples of a bicyclic heterocyclyl include, for example:

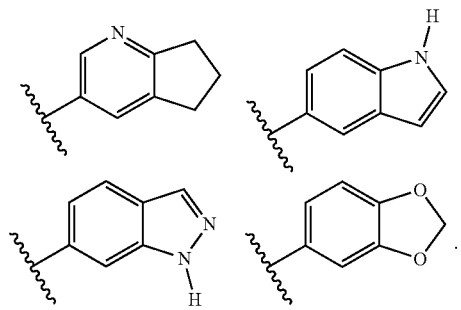

In certain embodiments, the bicyclic heterocyclyl is an carbocyclic ring fused to partially unsaturated heterocyclic ring, that together form a bicyclic ring structure having 8-10 ring atoms (e.g., where there are 1, 2, 3, or 4 heteroatoms selected from the group consisting of nitrogen, oxygen, and sulfur).

The term "heterocycloalkyl" is art-recognized and refers to a saturated heterocyclyl group as defined above. In certain embodiments, the "heterocycloalkyl" is a 3- to 10-membered ring structures, alternatively a 3- to 7-membered rings, whose ring structures include one to four heteroatoms, such as nitrogen, oxygen, and sulfur.

The term "heterocycloalkylene" refers to a diradical of a heterocycloalkyl group. An exemplary heterocycloalkylene group is

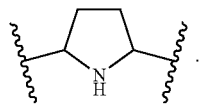

The heterocycloalkylene may contain, for example, 3-6 ring atom (i.e., a 3-6 membered heterocycloalkylene). In certain embodiments, the heterocycloalkylene is a 3-6 membered heterocycloalkylene containing 1, 2, or 3 three heteroatoms selected from the group consisting of oxygen, nitrogen, and sulfur.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls. In certain embodiments, the heteroaryl ring is substituted at one or more ring positions with halogen, alkyl, hydroxyl, or alkoxyl. In certain other embodiments, the heteroaryl ring is not substituted, i.e., it is unsubstituted. In certain embodiments, the heteroaryl group is a 5- to 10-membered ring structure, alternatively a 5- to 6-membered ring structure, whose ring structure includes 1, 2, 3, or 4 heteroatoms, such as nitrogen, oxygen, and sulfur.

The term "heteroaralkyl" refers to an alkyl group substituted with a heteroaryl group.

The terms "amine" and "amino" are art-recognized and refer to both unsubstituted and substituted amines, e.g., a moiety represented by the general formula —N($R^{50}$)($R^{51}$), wherein $R^{50}$ and $R^{51}$ each independently represent hydrogen, alkyl, cycloalkyl, heterocyclyl, alkenyl, aryl, aralkyl, or —$(CH_2)_m$—$R^{61}$; or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, $R^{50}$ and $R^{51}$ each independently represent hydrogen, alkyl, alkenyl, or —$(CH_2)_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—$(CH_2)_m$—$R_{61}$, where m and $R_{61}$ are described above.

The term "carbamate" as used herein refers to a radical of the form —$R_g$OC(O)N($R_h$)—, —$R_g$OC(O)N($R_h$)$R_i$—, or —OC(O)N$R_h R_i$, wherein $R_g$, $R_h$ and $R_i$ are each independently alkoxy, aryloxy, alkyl, alkenyl, alkynyl, amide, amino, aryl, arylalkyl, carboxy, cyano, cycloalkyl, ester, ether, formyl, halogen, haloalkyl, heteroaryl, heterocyclyl, hydroxyl, ketone, nitro, sulfide, sulfonyl, or sulfonamide. Exemplary carbamates include arylcarbamates and heteroaryl carbamates, e.g., wherein at least one of $R_g$, $R_h$ and $R_i$ are independently aryl or heteroaryl, such as phenyl and pyridinyl.

The term "carbonyl" as used herein refers to the radical —C(O)—.

The term "carboxamido" as used herein refers to the radical —C(O)NRR', where R and R' may be the same or different. R and R' may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" as used herein refers to a radical of the form —$R_a$C(O)N($R_b$)—, —$R_a$C(O)N($R_b$)$R_c$—, —C(O)N$R_b R_c$, or —C(O)N$H_2$, wherein $R_a$, $R_b$ and $R_c$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro. The amide can be attached to another group through the carbon, the nitrogen, $R_b$, $R_c$, or $R_a$. The amide also may be cyclic, for example $R_b$ and $R_c$, $R_a$ and $R_b$, or $R_a$ and $R_c$ may be joined to form a 3- to 12-membered ring, such as a 3- to 10-membered ring or a 5- to 6-membered ring.

The term "amidino" as used herein refers to a radical of the form —C(=NR)NR'R" where R, R', and R" are each independently alkyl, alkenyl, alkynyl, amide, aryl, arylalkyl, cyano, cycloalkyl, haloalkyl, heteroaryl, heterocyclyl, hydroxyl, ketone, or nitro.

The term "alkanoyl" as used herein refers to a radical —O—CO-alkyl.

The term "oxo" is art-recognized and refers to a "=O" substituent. For example, a cyclopentane substituted with an oxo group is cyclopentanone.

The term "sulfonamide" or "sulfonamido" as used herein refers to a radical having the structure —N($R_r$)—S(O)$_2$—$R_s$— or —S(O)$_2$—N($R_r$)$R_s$, where $R_r$, and $R_s$ can be, for example, hydrogen, alkyl, aryl, cycloalkyl, and heterocyclyl. Exemplary sulfonamides include alkylsulfonamides (e.g., where $R_s$ is alkyl), arylsulfonamides (e.g., where $R_s$ is aryl), cycloalkyl sulfonamides (e.g., where $R_s$ is cycloalkyl), and heterocyclyl sulfonamides (e.g., where $R_s$ is heterocyclyl), etc.

The term "sulfonyl" as used herein refers to a radical having the structure $R_u$SO$_2$—, where $R_s$ can be alkyl, aryl, cycloalkyl, and heterocyclyl, e.g., alkylsulfonyl. The term "alkylsulfonyl" as used herein refers to an alkyl group attached to a sulfonyl group.

The symbol "∼" indicates a point of attachment.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Further, enantiomers can be separated using supercritical fluid chromatographic (SFC) techniques described in the literature. Still further, stereoisomers can be obtained from stereomerically-pure intermediates, reagents, and catalysts by well-known asymmetric synthetic methods.

Geometric isomers can also exist in the compounds of the present invention. The symbol ═══ denotes a bond that may be a single, double or triple bond as described herein. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{19}F$, and $^{36}Cl$, respectively.

Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in, e.g., the Examples herein by substituting an isotopically labeled reagent for a non-isotopically labeled reagent.

As used herein, the terms "subject" and "patient" refer to organisms to be treated by the methods of the present invention. Such organisms are preferably mammals (e.g., murines, simians, equines, bovines, porcines, canines, felines, and the like), and more preferably humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see Martin, Remington's Pharmaceutical Sciences, 15th Ed., Mack Publ. Co., Easton, PA [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Abbreviations as used herein may include O-(7-azabenzotriazol-1-yl)-N,N,N',N'-tetramethyluronium hexafluorophosphate (HATU); diisopropylethylamine (DIPEA); dimethylformamide (DMF); methylene chloride (DCM); tert-butoxycarbonyl (Boc); tetrahydrofuran (THF); trifluoroacetic acid (TFA); N-methylmorpholine (NMM); triethylamine (TEA); Boc anhydride ((Boc)$_2$O); dimethylsulfoxide (DMSO); diisopropylethylamine (DIEA); N,N-Dimethylpyridin-4-amine (DMAP); flash column chromatography (FCC); and supercritical fluid chromatography (SFC).

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

II. Substituted Imidazo[1,2-b]Pyridazine, Substituted Imidazo[1,5-b]Pyridazine, and Related Compounds One aspect of the invention provides substituted imidazo [1,2-b]pyridazine compounds. The substituted imidazo[1,2-b]pyridazine compounds are contemplated to be useful in the methods, compositions, and kits described herein. In certain embodiments, the substituted imidazo[1,2-b] pyridazine compound is a compound embraced by Formula I:

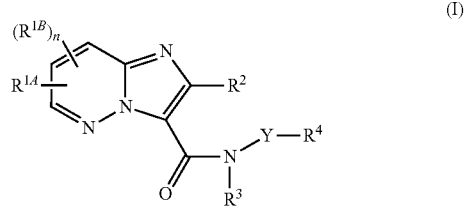

$R^{1A}$ is $C_1$-$C_6$ alkyl, $C_1$-$C_6$ haloalkyl, $C_3$-$C_6$ cycloalkyl, 3-10 membered heterocyclyl, or 6-membered aryl, wherein the cycloalkyl, heterocyclyl, and aryl are optionally substituted with 1, 2, or 3 substituents independently selected from the group consisting of halogen, hydroxyl, $C_1$-$C_6$ alkyl, $C_1$-$C_6$ haloalkyl, $C_3$-$C_6$ cycloalkyl, $C_1$-$C_6$ alkoxy, cyano, —N($R^5$)$_2$, —C(O)—($C_1$-$C_6$ alkyl), —N($R^5$)C(O)—($C_1$-$C_6$ alkyl), and —C(O)N($R^5$)$_2$;

$R^{1B}$ represents independently for each occurrence $C_1$-$C_6$ alkyl, halogen, $C_1$-$C_6$ haloalkyl, $C_3$-$C_6$ cycloalkyl, $C_1$-$C_6$ alkoxy, —($C_1$-$C_4$ alkylene)-O—($C_1$-$C_6$ alkyl), —($C_1$-$C_4$ alkylene)-O—($C_3$-$C_6$ cycloalkyl), 3-6 membered heterocyclyl, 6-membered aryl, cyano, or —N($R^5$)$_2$;

$R^2$ is hydrogen, $C_1$-$C_6$ alkyl, halogen, $C_1$-$C_6$ haloalkyl, $C_3$-$C_6$ cycloalkyl, $C_1$-$C_6$ alkoxy, —($C_1$-$C_4$ alkylene)-O—($C_1$-$C_6$ alkyl), —($C_1$-$C_4$ alkylene)-O—($C_3$-$C_6$ cycloalkyl), 3-6 membered heterocyclyl, 6-membered aryl, cyano, or —N($R^5$)$_2$;

$R^3$ is hydrogen, $C_1$-$C_6$ alkyl, or $C_3$-$C_6$ cycloalkyl;

$R^4$ is one of the following:

$C_3$-$C_8$ cycloalkyl, 3-8 membered heterocycloalkyl, 9-13 membered spiroheterocycloalkyl, —($C_2$-$C_6$ alkylene)-O-phenyl, phenyl, heteroaryl, a partially unsaturated 9-10 membered bicyclic carbocyclyl, or a partially unsaturated 8-10 membered bicyclic heterocyclyl; each of which is optionally substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, $C_2$-$C_4$ alkynyl, —($C_2$-$C_4$ alkynyl)-$C_1$-$C_6$ alkoxy, —O—($C_3$-$C_6$ cycloalkyl), aryl, —O-aryl, heteroaryl, saturated 3-8 membered heterocyclyl, amino, and —$CO_2R^5$; or $C_{1-6}$ alkyl or $C_{2-6}$ alkynyl;

$R^5$ represents independently for each occurrence hydrogen, $C_1$-$C_6$ alkyl, or $C_3$-$C_6$ cycloalkyl; or two occurrences of $R^5$ attached to the same nitrogen atom are taken together with the nitrogen atom to which they are attached to form a 3-8 membered heterocyclic ring; Y is a bond, —C(O)—, $C_1$-$C_6$ haloalkylene, $C_3$-$C_6$ cycloalkylene, or $C_1$-$C_6$ alkylene optionally substituted with $C_3$-$C_6$ cycloalkylene; and n is 0, 1, or 2;

provided that when Y—$R^4$ is —$CH_2$-phenyl, then n is 1 or 2.

Definitions of the variables in Formula I above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii), e.g., such as where $R^{1A}$ is $C_1$-$C_6$ alkyl, $R^2$ is hydrogen, and $R^4$ is $C_3$-$C_8$ cycloalkyl or phenyl; each of which is optionally substituted by 1, 2, or 3 substituents independently selected from the group consisting of $C_1$-$C_8$ alkyl, halogen, $C_1$-$C_6$ haloalkyl, and $C_3$-$C_6$ cycloalkyl.

Accordingly, in certain embodiments, $R^{1A}$ is $C_1$-$C_6$ alkyl. In certain embodiments, $R^{1A}$ is $C_1$-$C_3$ alkyl, 3-6 membered heterocyclyl, or 6-membered aryl, wherein the heterocyclyl and aryl are optionally substituted with 1, 2, or 3 substituents independently selected from the group consisting of halogen, hydroxyl, $C_1$-$C_6$ alkyl, $C_1$-$C_6$ haloalkyl, $C_3$-$C_6$ cycloalkyl, and $C_1$-$C_6$ alkoxy. In certain embodiments, $R^{1A}$ is $C_1$-$C_3$ alkyl. In certain embodiments, $R^{1A}$ is methyl. In certain embodiments, $R^{1A}$ is 6-membered aryl optionally substituted with 1, 2, or 3 substituents independently selected from the group consisting of halogen, hydroxyl, $C_1$-$C_6$ alkyl, $C_1$-$C_6$ haloalkyl, $C_3$-$C_6$ cycloalkyl, $C_1$-$C_6$ alkoxy, and cyano. In certain embodiments, $R^{1A}$ is 6-membered aryl substituted with 1, 2, or 3 substituents independently selected from the group consisting of halogen, $C_1$-$C_6$ alkyl, $C_1$-$C_6$ haloalkyl, $C_3$-$C_6$ cycloalkyl, and cyano. In certain embodiments, $R^{1A}$ is 6-membered aryl substituted with 1, 2, or 3 substituents independently selected from the group consisting of halogen, $C_1$-$C_6$ haloalkyl, and cyano. In certain embodiments, $R^{1A}$ is attached at the 6-position of the imidazo[1,2-b]pyridazinyl group of Formula I.

In certain embodiments, $R^{1B}$ represents independently for each occurrence $C_1$-$C_6$ alkyl or halogen. In certain embodiments, $R^{1B}$ represents independently for each occurrence $C_1$-$C_3$ alkyl or halogen. In certain embodiments, $R^{1B}$ is $C_1$-$C_6$ alkyl. In certain embodiments, $R^{1B}$ is $C_1$-$C_3$ alkyl. In certain embodiments, $R^{1B}$ is halogen.

In certain embodiments, $R^{1A}$ and $R^{1B}$ are $C_1$-$C_3$ alkyl. In certain embodiments, $R^{1A}$ and $R^{1B}$ are methyl. In certain embodiments, $R^{1A}$ is methyl, and $R^{1B}$ is chloro or fluoro.

In certain embodiments, $R^2$ is hydrogen.
In certain embodiments, $R^3$ is hydrogen.
In certain embodiments, Y is a bond. In certain embodiments, Y is $C_1$-$C_6$ alkylene. In certain embodiments, Y is $C_1$-$C_6$ haloalkylene.

In certain embodiments, $R^4$ is $C_3$-$C_8$ cycloalkyl optionally substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, $C_2$-$C_4$ alkynyl, —($C_2$-$C_4$ alkynyl)-$C_1$-$C_6$ alkoxy, aryl, —O-aryl, heteroaryl, saturated 3-8 membered heterocyclyl, amino, and —$CO_2R^5$. In certain embodiments, $R^4$ is $C_3$-$C_8$ cycloalkyl optionally substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, and —($C_2$-$C_4$ alkynyl)-$C_1$-$C_6$ alkoxy. In certain embodiments, $R^4$ is $C_4$-$C_6$ cycloalkyl substituted by 1, 2, or 3 substituents independently selected from the group consisting of $C_1$-$C_6$ alkyl, $C_1$-$C_6$ haloalkyl, $C_3$-$C_6$ cycloalkyl, and $C_1$-$C_6$ alkoxy. In certain embodiments, $R^4$ is $C_3$-$C_8$ cycloalkyl optionally substituted by 1, 2, or 3 substituents independently selected from the group consisting of $C_1$-$C_8$ alkyl and $C_1$-$C_6$ haloalkyl. In certain embodiments, $R^4$ is $C_3$-$C_8$ cycloalkyl.

In certain embodiments, $R^4$ is a partially unsaturated 9-10 membered bicyclic carbocyclyl optionally substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, —($C_2$-$C_4$ alkynyl)-$C_1$-$C_6$ alkoxy, aryl, heteroaryl, and saturated 3-8 membered heterocyclyl. In certain embodiments, $R^4$ is a partially unsaturated 9-10 membered bicyclic carbocyclyl optionally substituted by $C_1$-$C_6$ alkyl.

In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, —($C_2$-$C_4$ alkynyl)-$C_1$-$C_6$ alkoxy, 5-membered heteroaryl, and saturated 3-8 membered heterocyclyl. In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, and —($C_2$-$C_4$ alkynyl)-$C_1$-$C_6$ alkoxy. In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, $C_2$-$C_4$ alkynyl, and —($C_2$-$C_4$ alkynyl)-$C_1$-$C_6$ alkoxy.

In certain embodiments, $R^4$ is $C_1$-$C_6$ alkyl.

In certain embodiments, n is 2. In certain embodiments, n is 1. In certain embodiments, n is 0.

The description above describes multiple embodiments relating to compounds of Formula I. The patent application specifically contemplates all combinations of the embodiments.

In certain embodiments, the substituted imidazo[1,2-b]pyridazine compound is a compound embraced by Formula I-1:

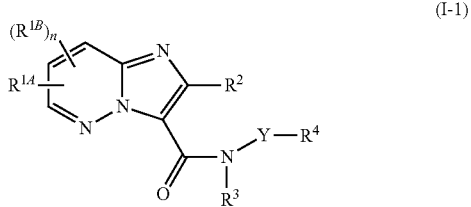

(I-1)

or a pharmaceutically acceptable salt thereof, wherein:
$R^{1A}$ is $C_1$-$C_6$ alkyl, $C_1$-$C_6$ haloalkyl, or $C_3$-$C_6$ cycloalkyl;
$R^{1B}$ represents independently for each occurrence $C_1$-$C_6$ alkyl, halogen, $C_1$-$C_6$ haloalkyl, or $C_3$-$C_6$ cycloalkyl;
$R^2$ is hydrogen, $C_1$-$C_6$ alkyl, halogen, $C_1$-$C_6$ haloalkyl, or $C_3$-$C_6$ cycloalkyl;
$R^3$ is hydrogen, $C_1$-$C_6$ alkyl, or $C_3$-$C_6$ cycloalkyl;
$R^4$ is $C_3$-$C_8$ cycloalkyl, 3-8 membered heterocycloalkyl, 9-13 membered spiroheterocycloalkyl, —($C_2$-$C_6$ alkylene)-O-phenyl, phenyl, heteroaryl, a partially unsaturated 9-10 membered bicyclic carbocyclyl, or a partially unsaturated 8-10 membered bicyclic heterocyclyl; each of which is optionally substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, $C_2$-$C_4$ alkynyl, —($C_2$-$C_4$ alkynyl)-$C_1$-$C_6$ alkoxy, aryl, —O-aryl, heteroaryl, saturated 3-8 membered heterocyclyl, amino, and —$CO_2R^5$;
$R^5$ represents independently for each occurrence hydrogen, $C_1$-$C_6$ alkyl, or $C_3$-$C_6$ cycloalkyl;
Y is a bond or $C_1$-$C_6$ alkylene; and
n is 0, 1, or 2;
provided that when Y—$R^4$ is —$CH_2$-phenyl, then n is 1 or 2.

Definitions of the variables in Formula I-1 above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii), e.g., such as where $R^{1A}$ is $C_1$-$C_6$ alkyl, $R^2$ is hydrogen, and $R^4$ is $C_3$-$C_8$ cycloalkyl or phenyl; each of which is optionally substituted by 1, 2, or 3 substituents independently selected from the group consisting of $C_1$-$C_8$ alkyl, halogen, $C_1$-$C_6$ haloalkyl, and $C_3$-$C_6$ cycloalkyl.

Accordingly, in certain embodiments, $R^{1A}$ is $C_1$-$C_6$ alkyl. In certain embodiments, R is $C_1$-$C_3$ alkyl. In certain embodiments, $R^{1A}$ is methyl.

In certain embodiments, $R^{1B}$ represents independently for each occurrence $C_1$-$C_6$ alkyl or halogen. In certain embodiments, $R^{1B}$ represents independently for each occurrence $C_1$-$C_3$ alkyl or halogen. In certain embodiments, $R^{1B}$ is $C_1$-$C_6$ alkyl. In certain embodiments, $R^{1B}$ is $C_1$-$C_3$ alkyl. In certain embodiments, $R^{1B}$ is halogen.

In certain embodiments, $R^{1A}$ and $R^{1B}$ are $C_1$-$C_3$ alkyl. In certain embodiments, $R^{1A}$ and $R^{1B}$ are methyl. In certain embodiments, $R^{1A}$ is methyl, and $R^{1B}$ is chloro or fluoro.

In certain embodiments, $R^2$ is hydrogen.

In certain embodiments, $R^3$ is hydrogen.

In certain embodiments, Y is a bond. In certain embodiments, Y is $C_1$-$C_6$ alkylene.

In certain embodiments, $R^4$ is $C_3$-$C_8$ cycloalkyl optionally substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, $C_2$-$C_4$ alkynyl, —($C_2$-$C_4$ alkynyl)-$C_1$-$C_6$ alkoxy, aryl, —O-aryl, heteroaryl, saturated 3-8 membered heterocyclyl, amino, and —$CO_2R^5$. In certain embodiments, $R^4$ is $C_3$-$C_8$ cycloalkyl optionally substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, and —($C_2$-$C_4$ alkynyl)-$C_1$-$C_6$ alkoxy. In certain embodiments, $R^4$ is $C_4$-$C_6$ cycloalkyl substituted by 1, 2, or 3 substituents independently selected from the group consisting of $C_1$-$C_6$ alkyl, $C_1$-$C_6$ haloalkyl, $C_3$-$C_6$ cycloalkyl, and $C_1$-$C_6$ alkoxy.

In certain embodiments, $R^4$ is a partially unsaturated 9-10 membered bicyclic carbocyclyl optionally substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, —($C_2$-$C_4$ alkynyl)-$C_1$-$C_6$ alkoxy, aryl, heteroaryl, and saturated 3-8 membered heterocyclyl. In certain embodiments, $R^4$ is a partially unsaturated 9-10 membered bicyclic carbocyclyl optionally substituted by $C_1$-$C_6$ alkyl.

In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, —($C_2$-$C_4$ alkynyl)-$C_1$-$C_6$ alkoxy, 5-membered heteroaryl, and saturated 3-8 membered heterocyclyl. In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, and —($C_2$-$C_4$ alkynyl)-$C_1$-$C_6$ alkoxy. In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, $C_2$-$C_4$ alkynyl, and —($C_2$-$C_4$ alkynyl)-$C_1$-$C_6$ alkoxy.

In certain embodiments, n is 2. In certain embodiments, n is 1. In certain embodiments, n is 0.

The description above describes multiple embodiments relating to compounds of Formula I-1. The patent application specifically contemplates all combinations of the embodiments.

In certain embodiments, the compound is a compound of Formula I-A:

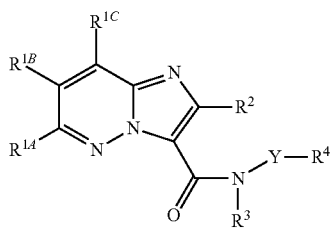

(I-A)

or a pharmaceutically acceptable salt thereof, wherein:
$R^{1A}$ is $C_1$-$C_6$ alkyl, halogen, $C_1$-$C_6$ haloalkyl, or $C_3$-$C_6$ cycloalkyl;
$R^{1B}$ and $R^2$ are independently hydrogen, $C_1$-$C_6$ alkyl, halogen, $C_1$-$C_6$ haloalkyl, or $C_3$-$C_6$ cycloalkyl;
$R^{1C}$ is $C_1$-$C_6$ alkyl, $C_1$-$C_6$ haloalkyl, or $C_3$-$C_6$ cycloalkyl;
$R^3$ is hydrogen;
$R^4$ is $C_3$-$C_8$ cycloalkyl, 3-8 membered heterocycloalkyl, 9-13 membered spiroheterocycloalkyl, —($C_2$-$C_6$ alkylene)-O-phenyl, phenyl, heteroaryl, a partially unsaturated 9-10 membered bicyclic carbocyclyl, or a partially unsaturated 8-10 membered bicyclic heterocyclyl; each of which is optionally substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, $C_2$-$C_4$ alkynyl, —($C_2$-$C_4$ alkynyl)-$C_1$-$C_6$ alkoxy, aryl, —O-aryl, heteroaryl, saturated 3-8 membered heterocyclyl, amino, and —$CO_2R^5$;
$R^5$ represents independently for each occurrence hydrogen, $C_1$-$C_6$ alkyl, or $C_3$-$C_6$ cycloalkyl; and
Y is a bond, $C_1$-$C_6$ alkylene, or $C_1$-$C_6$ haloalkylene.

Definitions of the variables in Formula I-A above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii), e.g., such as where $R^{1A}$ and $R^{1C}$ are $C_1$-$C_6$ alkyl, $R^2$ is hydrogen, and $R^4$ is $C_3$-$C_8$ cycloalkyl or phenyl; each of which is optionally substituted by 1, 2, or 3 substituents independently selected from the group consisting of $C_1$-$C_8$ alkyl, halogen, $C_1$-$C_6$ haloalkyl, and $C_3$-$C_6$ cycloalkyl.

Accordingly, in certain embodiments, $R^{1A}$ and $R^{1C}$ are methyl. In certain embodiments, $R^{1A}$ and $R^{1C}$ are $C_1$-$C_3$ alkyl. In certain embodiments, $R^{1A}$ is chloro or fluoro, and $R^{1C}$ is methyl. In certain embodiments, $R^{1A}$ and $R^{1C}$ are methyl, and $R^{1B}$ is hydrogen. In certain embodiments, $R^{1A}$ is halogen, $R^{1B}$ is hydrogen, and $R^{1C}$ is methyl.

In certain embodiments, $R^2$ is hydrogen.

In certain embodiments, Y is a bond. In certain embodiments, Y is $C_1$-$C_6$ alkylene.

In certain embodiments, $R^4$ is $C_3$-$C_8$ cycloalkyl optionally substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, and —($C_2$-$C_4$ alkynyl)-$C_1$-$C_6$ alkoxy. In certain embodiments, $R^4$ is $C_3$-$C_8$ cycloalkyl optionally substituted by 1, 2, or 3 substituents independently selected from the group consisting of $C_1$-$C_6$ alkyl, $C_1$-$C_6$ haloalkyl, $C_3$-$C_6$ cycloalkyl, $C_1$-$C_6$ alkoxy, and $C_2$-$C_4$ alkynyl. In certain embodiments, $R^4$ is $C_4$-$C_6$ cycloalkyl substituted by 1, 2, or 3 substituents independently selected from the group consisting of $C_1$-$C_6$ alkyl, $C_1$-$C_6$ haloalkyl, $C_3$-$C_6$ cycloalkyl, and $C_1$-$C_6$ alkoxy. In certain embodiments, $R^4$ is $C_4$-$C_6$ cycloalkyl optionally substituted by 1 or 2 substituents independently selected from the group consisting of $C_1$-$C_6$ alkyl, $C_1$-$C_6$ haloalkyl, $C_3$-$C_6$ cycloalkyl, and $C_1$-$C_6$ alkoxy.

In certain embodiments, $R^4$ is a partially unsaturated 9-10 membered bicyclic carbocyclyl optionally substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, and —($C_2$-$C_4$ alkynyl)-$C_1$-$C_6$ alkoxy. In certain embodiments, $R^4$ is a partially unsaturated 9-10 membered bicyclic carbocyclyl optionally substituted by $C_1$-$C_6$ alkyl.

In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, and —($C_2$-$C_4$ alkynyl)-$C_1$-$C_6$ alkoxy. In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, $C_1$-$C_6$ alkoxy, and $C_2$-$C_4$ alkynyl. In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, $C_2$-$C_4$ alkynyl, and —($C_2$-$C_4$ alkynyl)-$C_1$-$C_6$ alkoxy. In certain embodiments, $R^4$ is $C_3$-$C_8$ cycloalkyl or phenyl; each of which is optionally substituted by 1, 2, or 3 substituents independently selected from the group consisting of $C_1$-$C_8$ alkyl, halogen, $C_1$-$C_6$ haloalkyl, and $C_3$-$C_6$ cycloalkyl.

The description above describes multiple embodiments relating to compounds of Formula I-A. The patent application specifically contemplates all combinations of the embodiments.

In certain embodiments, the compound is a compound of Formula I-B:

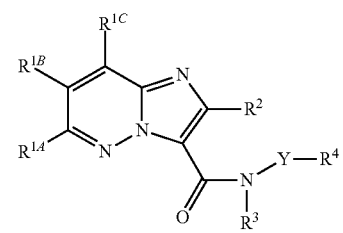

(I-B)

or a pharmaceutically acceptable salt thereof, wherein:
$R^{1A}$ is 6-membered aryl substituted with 1, 2, or 3 substituents independently selected from the group consisting of halogen, $C_1$-$C_6$ alkyl, $C_1$-$C_6$ haloalkyl, and cyano;
$R^{1B}$ and $R^2$ are hydrogen;
$R^{1C}$ is $C_1$-$C_6$ alkyl;
$R^3$ is hydrogen;
$R^4$ is (i) $C_3$-$C_8$ cycloalkyl optionally substituted by 1, 2, or 3 substituents independently selected from the group consisting of $C_1$-$C_8$ alkyl, $C_1$-$C_6$ haloalkyl, and $C_1$-$C_6$ alkoxy, or (ii) $C_1$-$C_6$ alkyl; and
Y is $C_1$-$C_6$ alkylene or $C_1$-$C_6$ haloalkylene.

Definitions of the variables in Formula I-B above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii).

Accordingly, in certain embodiments, $R^{1A}$ is 6-membered aryl substituted with 1 or 2 substituents independently selected from the group consisting of halogen, $C_1$-$C_6$ alkyl, $C_1$-$C_6$ haloalkyl, and cyano. In certain embodiments, $R^{1A}$ is 6-membered aryl substituted with 1 or 2 substituents independently selected from the group consisting of halogen, $C_1$-$C_3$ alkyl, and cyano. In certain embodiments, $R^{1A}$ is 6-membered aryl substituted with 1 or 2 substituents independently selected from fluorine and cyano. In certain embodiments, $R^{1C}$ is $C_1$-$C_3$ alkyl. In certain embodiments, $R^{1C}$ is methyl. In certain embodiments, Y is $C_1$-$C_6$ alkylene. In certain embodiments, Y is $C_1$-$C_6$ haloalkylene. In certain embodiments, $R^4$ is $C_3$-$C_8$ cycloalkyl. In certain embodiments, $R^4$ is $C_1$-$C_6$ alkyl. The description above describes multiple embodiments relating to compounds of Formula I-B. The patent application specifically contemplates all combinations of the embodiments.

Another aspect of the invention provides a family of compounds represented by Formula II:

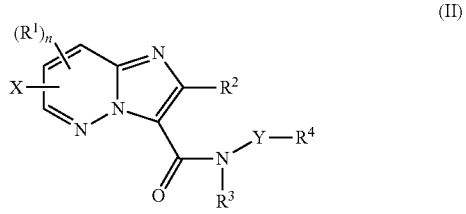

(II)

or a pharmaceutically acceptable salt thereof, wherein:
X is halogen;
$R^1$ represents independently for each occurrence $C_1$-$C_6$ alkyl, halogen, $C_1$-$C_6$ haloalkyl, $C_3$-$C_6$ cycloalkyl, $C_1$-$C_6$ alkoxy, —($C_1$-$C_4$ alkylene)-O—($C_1$-$C_6$ alkyl), —($C_1$-$C_4$ alkylene)-O—($C_3$-$C_6$ cycloalkyl), 3-6 membered heterocyclyl, 6-membered aryl, cyano, or —N($R^5$)$_2$;
$R^2$ is hydrogen, $C_1$-$C_6$ alkyl, halogen, $C_1$-$C_6$ haloalkyl, $C_3$-$C_6$ cycloalkyl, $C_1$-$C_6$ alkoxy, —($C_1$-$C_4$ alkylene)-O—($C_1$-$C_6$ alkyl), —($C_1$-$C_4$ alkylene)-O—($C_3$-$C_6$ cycloalkyl), 3-6 membered heterocyclyl, 6-membered aryl, cyano, or —N($R^5$)$_2$;
$R^3$ is hydrogen, $C_1$-$C_6$ alkyl, or $C_3$-$C_6$ cycloalkyl;
$R^4$ is one of the following:
 (a) $C_3$-$C_8$ cycloalkyl substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, —O—($C_3$-$C_6$ cycloalkyl), $C_2$-$C_4$ alkynyl, —($C_2$-$C_4$ alkynyl)-$C_1$-$C_6$ alkoxy, and saturated 3-8 membered heterocyclyl;
 (b) phenyl that is (i) substituted by $C_2$-$C_4$ alkynyl or —($C_2$-$C_4$ alkynyl)-$C_1$-$C_6$ alkoxy, and (ii) optionally substituted by 1 or 2 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, —O—($C_3$-$C_6$ cycloalkyl), heteroaryl, saturated 3-8 membered heterocyclyl, and amino; or
 (c) a partially unsaturated 9-10 membered bicyclic carbocyclyl, a partially unsaturated 8-10 membered bicyclic heterocyclyl, a 3-8 membered heterocycloalkyl, a 9-13 membered spiroheterocycloalkyl, —($C_2$-$C_6$ alkylene)-O-phenyl, or heteroaryl; each of which is optionally substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, $C_2$-$C_4$ alkynyl, —($C_2$-$C_4$ alkynyl)-$C_1$-$C_6$ alkoxy, —O—($C_3$-$C_6$ cycloalkyl), aryl, —O-aryl, heteroaryl, saturated 3-8 membered heterocyclyl, amino, and —$CO_2R^5$;
$R^5$ represents independently for each occurrence hydrogen, $C_1$-$C_6$ alkyl, or $C_3$-$C_6$ cycloalkyl; or two occurrences of $R^5$ attached to the same nitrogen atom are taken together with the nitrogen atom to which they are attached to form a 3-8 membered heterocyclic ring;
Y is a bond, —C(O)—, $C_1$-$C_6$ alkylene, $C_1$-$C_6$ haloalkylene, or $C_3$-$C_6$ cycloalkylene; and
n is 0, 1, or 2.

Definitions of the variables in Formula II above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii), e.g., such as where $R^1$ is $C_1$-$C_6$ alkyl, $R^2$ is hydrogen, and $R^4$ is $C_3$-$C_8$ cycloalkyl substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, $C_2$-$C_4$ alkynyl, —($C_2$-$C_4$ alkynyl)-$C_1$-$C_6$ alkoxy, and saturated 3-8 membered heterocyclyl.

Accordingly, in certain embodiments, $R^1$ is $C_1$-$C_6$ alkyl. In certain embodiments, $R^1$ is $C_1$-$C_3$ alkyl. In certain embodiments, $R^1$ is methyl.

In certain embodiments, X is chloro. In certain embodiments, X is chloro or fluoro.

In certain embodiments, $R^2$ is hydrogen.

In certain embodiments, $R^3$ is hydrogen.

In certain embodiments, Y is a bond. In certain embodiments, Y is $C_1$-$C_6$ alkylene.

In certain embodiments, $R^4$ is $C_3$-$C_8$ cycloalkyl substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, $C_2$-$C_4$ alkynyl, —($C_2$-$C_4$ alkynyl)-$C_1$-$C_6$ alkoxy, and saturated 3-8 membered heterocyclyl. In certain embodiments, $R^4$ is $C_3$-$C_8$ cycloalkyl substituted by 1, 2, or 3 substituents independently selected from the group consisting of $C_1$-$C_6$ alkyl, $C_1$-$C_6$ haloalkyl, $C_3$-$C_6$ cycloalkyl, $C_1$-$C_6$ alkoxy, and $C_2$-$C_4$ alkynyl. In certain embodiments, $R^4$ is $C_4$-$C_6$ cycloalkyl substituted by 1, 2, or 3 substituents independently selected from the group consisting of $C_1$-$C_6$ alkyl, $C_1$-$C_6$ haloalkyl, $C_3$-$C_6$ cycloalkyl, and $C_1$-$C_6$ alkoxy.

In certain embodiments, $R^4$ is a partially unsaturated 9-10 membered bicyclic carbocyclyl optionally substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, —($C_2$-

$C_4$ alkynyl)-$C_1$-$C_6$ alkoxy, aryl, heteroaryl, and saturated 3-8 membered heterocyclyl. In certain embodiments, $R^4$ is a partially unsaturated 9-10 membered bicyclic carbocyclyl optionally substituted by $C_1$-$C_6$ alkyl.

In certain embodiments, $R^4$ is phenyl that is (i) substituted by $C_2$-$C_4$ alkynyl or —($C_2$-$C_4$ alkynyl)-$C_1$-$C_6$ alkoxy, and (ii) optionally substituted by 1 or 2 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, and $C_1$-$C_6$ alkoxy. In certain embodiments, $R^4$ is phenyl substituted by $C_2$-$C_4$ alkynyl or —($C_2$-$C_4$ alkynyl)-$C_1$-$C_6$ alkoxy.

In certain embodiments, n is 2. In certain embodiments, n is 1. In certain embodiments, n is 0.

The description above describes multiple embodiments relating to compounds of Formula II. The patent application specifically contemplates all combinations of the embodiments.

In certain embodiments, the compound is represented by Formula IT-1:

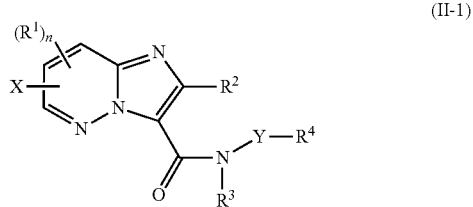

(II-1)

or a pharmaceutically acceptable salt thereof, wherein:
X is halogen;
$R^1$ represents independently for each occurrence $C_1$-$C_6$ alkyl, halogen, $C_1$-$C_6$ haloalkyl, or $C_3$-$C_6$ cycloalkyl;
$R^2$ is hydrogen, $C_1$-$C_6$ alkyl, halogen, $C_1$-$C_6$ haloalkyl, or $C_3$-$C_6$ cycloalkyl;
$R^3$ is hydrogen, $C_1$-$C_6$ alkyl, or $C_3$-$C_6$ cycloalkyl;
$R^4$ is one of the following:
  (a) $C_3$-$C_8$ cycloalkyl substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, $C_2$-$C_4$ alkynyl, —($C_2$-$C_4$ alkynyl)-$C_1$-$C_6$ alkoxy, and saturated 3-8 membered heterocyclyl;
  (b) phenyl that is (i) substituted by $C_2$-$C_4$ alkynyl or —($C_2$-$C_4$ alkynyl)-$C_1$-$C_6$ alkoxy, and (ii) optionally substituted by 1 or 2 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, heteroaryl, saturated 3-8 membered heterocyclyl, and amino; or
  (c) a partially unsaturated 9-10 membered bicyclic carbocyclyl, a partially unsaturated 8-10 membered bicyclic heterocyclyl, a 3-8 membered heterocycloalkyl, a 9-13 membered spiroheterocycloalkyl, —($C_2$-$C_6$ alkylene)-O-phenyl, or heteroaryl; each of which is optionally substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, $C_2$-$C_4$ alkynyl, —($C_2$-$C_4$ alkynyl)-$C_1$-$C_6$ alkoxy, aryl, —O-aryl, heteroaryl, saturated 3-8 membered heterocyclyl, amino, and —$CO_2R^5$;
$R^5$ represents independently for each occurrence hydrogen, $C_1$-$C_6$ alkyl, or $C_3$-$C_6$ cycloalkyl;
Y is a bond or $C_1$-$C_6$ alkylene; and
n is 0, 1, or 2.

Definitions of the variables in Formula II-1 above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii), e.g., such as where $R^1$ is $C_1$-$C_6$ alkyl, $R^2$ is hydrogen, and $R^4$ is $C_3$-$C_8$ cycloalkyl substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, $C_2$-$C_4$ alkynyl, —($C_2$-$C_4$ alkynyl)-$C_1$-$C_6$ alkoxy, and saturated 3-8 membered heterocyclyl.

Accordingly, in certain embodiments, $R^1$ is $C_1$-$C_6$ alkyl. In certain embodiments, $R^1$ is $C_1$-$C_3$ alkyl. In certain embodiments, $R^1$ is methyl.

In certain embodiments, X is chloro. In certain embodiments, X is chloro or fluoro.

In certain embodiments, $R^2$ is hydrogen.
In certain embodiments, $R^3$ is hydrogen.
In certain embodiments, Y is a bond. In certain embodiments, Y is $C_1$-$C_6$ alkylene.

In certain embodiments, $R^4$ is $C_3$-$C_8$ cycloalkyl substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, $C_2$-$C_4$ alkynyl, —($C_2$-$C_4$ alkynyl)-$C_1$-$C_6$ alkoxy, and saturated 3-8 membered heterocyclyl. In certain embodiments, $R^4$ is $C_3$-$C_8$ cycloalkyl substituted by 1, 2, or 3 substituents independently selected from the group consisting of $C_1$-$C_6$ alkyl, $C_1$-$C_6$ haloalkyl, $C_3$-$C_6$ cycloalkyl, $C_1$-$C_6$ alkoxy, and $C_2$-$C_4$ alkynyl. In certain embodiments, $R^4$ is $C_4$-$C_6$ cycloalkyl substituted by 1, 2, or 3 substituents independently selected from the group consisting of $C_1$-$C_6$ alkyl, $C_1$-$C_6$ haloalkyl, $C_3$-$C_6$ cycloalkyl, and $C_1$-$C_6$ alkoxy.

In certain embodiments, $R^4$ is a partially unsaturated 9-10 membered bicyclic carbocyclyl optionally substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, —($C_2$-$C_4$ alkynyl)-$C_1$-$C_6$ alkoxy, aryl, heteroaryl, and saturated 3-8 membered heterocyclyl. In certain embodiments, $R^4$ is a partially unsaturated 9-10 membered bicyclic carbocyclyl optionally substituted by $C_1$-$C_6$ alkyl.

In certain embodiments, $R^4$ is phenyl that is (i) substituted by $C_2$-$C_4$ alkynyl or —($C_2$-$C_4$ alkynyl)-$C_1$-$C_6$ alkoxy, and (ii) optionally substituted by 1 or 2 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, and $C_1$-$C_6$ alkoxy. In certain embodiments, $R^4$ is phenyl substituted by $C_2$-$C_4$ alkynyl or —($C_2$-$C_4$ alkynyl)-$C_1$-$C_6$ alkoxy.

In certain embodiments, n is 2. In certain embodiments, n is 1. In certain embodiments, n is 0.

The description above describes multiple embodiments relating to compounds of Formula II-1. The patent application specifically contemplates all combinations of the embodiments.

Another aspect of the invention provides substituted imidazo[1,5-b]pyridazine compounds. The substituted imidazo[1,5-b]pyridazine compounds are contemplated to be useful in the methods, compositions, and kits described herein. In certain embodiments, the substituted imidazo[1,5-b]pyridazine compound is a compound embraced by Formula III:

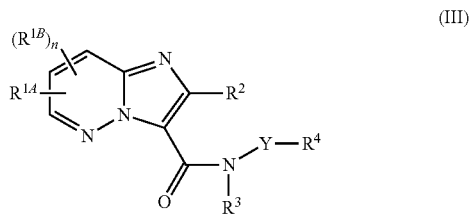

or a pharmaceutically acceptable salt thereof, wherein:

$R^{1A}$ is $C_1$-$C_6$ alkyl, $C_1$-$C_6$ haloalkyl, $C_3$-$C_6$ cycloalkyl, 3-10 membered heterocyclyl, or 6-membered aryl, wherein the cycloalkyl, heterocyclyl, and aryl are optionally substituted with 1, 2, or 3 substituents independently selected from the group consisting of halogen, hydroxyl, $C_1$-$C_6$ alkyl, $C_1$-$C_6$ haloalkyl, $C_3$-$C_6$ cycloalkyl, $C_1$-$C_6$ alkoxy, cyano, —N($R^5$)$_2$, —C(O)—($C_1$-$C_6$ alkyl), —N($R^5$)C(O)—($C_1$-$C_6$ alkyl), and —C(O)N($R^5$)$_2$;

$R^{1B}$ represents independently for each occurrence $C_1$-$C_6$ alkyl, halogen, $C_1$-$C_6$ haloalkyl, $C_3$-$C_6$ cycloalkyl, $C_1$-$C_6$ alkoxy, —($C_1$-$C_4$ alkylene)-O—($C_1$-$C_6$ alkyl), —($C_1$-$C_4$ alkylene)-O—($C_3$-$C_6$ cycloalkyl), 3-6 membered heterocyclyl, 6-membered aryl, cyano, or —N($R^5$)$_2$;

$R^2$ is hydrogen, $C_1$-$C_6$ alkyl, halogen, $C_1$-$C_6$ haloalkyl, $C_3$-$C_6$ cycloalkyl, $C_1$-$C_6$ alkoxy, —($C_1$-$C_4$ alkylene)-O—($C_1$-$C_6$ alkyl), —($C_1$-$C_4$ alkylene)-O—($C_3$-$C_6$ cycloalkyl), 3-6 membered heterocyclyl, 6-membered aryl, cyano, or —N($R^5$)$_2$;

$R^3$ is hydrogen, $C_1$-$C_6$ alkyl, or $C_3$-$C_6$ cycloalkyl;

$R^4$ is one of the following:

$C_3$-$C_8$ cycloalkyl, 3-8 membered heterocycloalkyl, 9-13 membered spiroheterocycloalkyl, —($C_2$-$C_6$ alkylene)-O-phenyl, phenyl, heteroaryl, a partially unsaturated 9-10 membered bicyclic carbocyclyl, or a partially unsaturated 8-10 membered bicyclic heterocyclyl; each of which is optionally substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, —O—($C_3$-$C_6$ cycloalkyl), $C_2$-$C_4$ alkynyl, —($C_2$-$C_4$ alkynyl)-$C_1$-$C_6$ alkoxy, —O—($C_3$-$C_6$ cycloalkyl), aryl, —O-aryl, heteroaryl, saturated 3-8 membered heterocyclyl, amino, and —CO$_2$$R^5$; or $C_{1-6}$ alkyl or $C_{2-6}$ alkynyl;

$R^5$ represents independently for each occurrence hydrogen, $C_1$-$C_6$ alkyl, or $C_3$-$C_6$ cycloalkyl; or two occurrences of $R^5$ attached to the same nitrogen atom are taken together with the nitrogen atom to which they are attached to form a 3-8 membered heterocyclic ring;

Y is a bond, —C(O)—, $C_1$-$C_6$ haloalkylene, $C_3$-$C_6$ cycloalkylene, or $C_1$-$C_6$ alkylene optionally substituted with $C_3$-$C_6$ cycloalkylene; and n is 0, 1, or 2.

Definitions of the variables in Formula III above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii), e.g., such as where $R^{1A}$ is $C_1$-$C_6$ alkyl, $R^2$ is hydrogen, and $R^4$ is $C_3$-$C_8$ cycloalkyl or phenyl; each of which is optionally substituted by 1, 2, or 3 substituents independently selected from the group consisting of $C_1$-$C_8$ alkyl, halogen, $C_1$-$C_6$ haloalkyl, and $C_3$-$C_6$ cycloalkyl.

Accordingly, in certain embodiments, $R^{1A}$ is $C_1$-$C_6$ alkyl. In certain embodiments, $R^{1A}$ is $C_1$-$C_3$ alkyl, 3-6 membered heterocyclyl, or 6-membered aryl, wherein the heterocyclyl and aryl are optionally substituted with 1, 2, or 3 substituents independently selected from the group consisting of halogen, hydroxyl, $C_1$-$C_6$ alkyl, $C_1$-$C_6$ haloalkyl, $C_3$-$C_6$ cycloalkyl, and $C_1$-$C_6$ alkoxy. In certain embodiments, $R^{1A}$ is $C_1$-$C_3$ alkyl. In certain embodiments, $R^{1A}$ is methyl.

In certain embodiments, $R^{1B}$ represents independently for each occurrence $C_1$-$C_6$ alkyl or halogen. In certain embodiments, $R^{1B}$ represents independently for each occurrence $C_1$-$C_3$ alkyl or halogen. In certain embodiments, $R^{1B}$ is $C_1$-$C_6$ alkyl. In certain embodiments, $R^{1B}$ is $C_1$-$C_3$ alkyl. In certain embodiments, $R^{1B}$ is halogen.

In certain embodiments, $R^{1A}$ and $R^{1B}$ are $C_1$-$C_3$ alkyl. In certain embodiments, $R^{1A}$ and $R^{1B}$ are methyl. In certain embodiments, $R^{1A}$ is methyl, and $R^{1B}$ is chloro or fluoro.

In certain embodiments, $R^2$ is hydrogen.

In certain embodiments, $R^3$ is hydrogen.

In certain embodiments, Y is a bond. In certain embodiments, Y is $C_1$-$C_6$ alkylene.

In certain embodiments, $R^4$ is $C_3$-$C_8$ cycloalkyl optionally substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, $C_2$-$C_4$ alkynyl, —($C_2$-$C_4$ alkynyl)-$C_1$-$C_6$ alkoxy, aryl, —O-aryl, heteroaryl, saturated 3-8 membered heterocyclyl, amino, and —CO$_2$$R^5$. In certain embodiments, $R^4$ is $C_3$-$C_8$ cycloalkyl optionally substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, and —($C_2$-$C_4$ alkynyl)-$C_1$-$C_6$ alkoxy. In certain embodiments, $R^4$ is $C_4$-$C_6$ cycloalkyl substituted by 1, 2, or 3 substituents independently selected from the group consisting of $C_1$-$C_6$ alkyl, $C_1$-$C_6$ haloalkyl, $C_3$-$C_6$ cycloalkyl, and $C_1$-$C_6$ alkoxy.

In certain embodiments, $R^4$ is a partially unsaturated 9-10 membered bicyclic carbocyclyl optionally substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, —($C_2$-$C_4$ alkynyl)-$C_1$-$C_6$ alkoxy, aryl, heteroaryl, and saturated 3-8 membered heterocyclyl. In certain embodiments, $R^4$ is a partially unsaturated 9-10 membered bicyclic carbocyclyl optionally substituted by $C_1$-$C_6$ alkyl.

In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, —($C_2$-

$C_4$ alkynyl)-$C_1$-$C_6$ alkoxy, 5-membered heteroaryl, and saturated 3-8 membered heterocyclyl. In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, and —($C_2$-$C_4$ alkynyl)-$C_1$-$C_6$ alkoxy. In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, $C_2$-$C_4$ alkynyl, and —($C_2$-$C_4$ alkynyl)-$C_1$-$C_6$ alkoxy.

In certain embodiments, n is 2. In certain embodiments, n is 1. In certain embodiments, n is 0.

The description above describes multiple embodiments relating to compounds of Formula III. The patent application specifically contemplates all combinations of the embodiments.

Another aspect of the invention provides substituted [1,2,4]triazolo[4,3-b]pyridazine-3-carboxamide compounds. The substituted [1,2,4]triazolo[4,3-b]pyridazine-3-carboxamide compounds are contemplated to be useful in the methods, compositions, and kits described herein. In certain embodiments, the substituted [1,2,4]triazolo[4,3-b]pyridazine-3-carboxamide compound is a compound embraced by Formula IV:

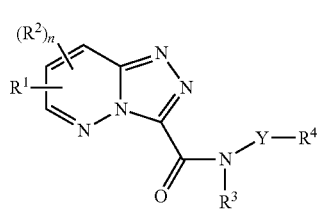

(IV)

or a pharmaceutically acceptable salt thereof, wherein:
$R^1$ is $C_1$-$C_6$ alkyl, $C_1$-$C_6$ haloalkyl, $C_3$-$C_6$ cycloalkyl, 3-10 membered heterocyclyl, or 6-membered aryl, wherein the cycloalkyl, heterocyclyl, and aryl are optionally substituted with 1, 2, or 3 substituents independently selected from the group consisting of halogen, hydroxyl, $C_1$-$C_6$ alkyl, $C_1$-$C_6$ haloalkyl, $C_3$-$C_6$ cycloalkyl, $C_1$-$C_6$ alkoxy, cyano, —N($R^5$)$_2$, —C(O)—($C_1$-$C_6$ alkyl), —N($R^5$)C(O)—($C_1$-$C_6$ alkyl), and —C(O)N($R^5$)$_2$;

$R^2$ represents independently for each occurrence $C_1$-$C_6$ alkyl, halogen, $C_1$-$C_6$ haloalkyl, $C_3$-$C_6$ cycloalkyl, $C_1$-$C_6$ alkoxy, —($C_1$-$C_4$ alkylene)-O—($C_1$-$C_6$ alkyl), —($C_1$-$C_4$ alkylene)-O—($C_3$-$C_6$ cycloalkyl), 3-6 membered heterocyclyl, 6-membered aryl, cyano, or —N($R^5$)$_2$;

$R^3$ is hydrogen, $C_1$-$C_6$ alkyl, or $C_3$-$C_6$ cycloalkyl;

$R^4$ is one of the following:
$C_3$-$C_8$ cycloalkyl, 3-8 membered heterocycloalkyl, 9-13 membered spiroheterocycloalkyl, —($C_2$-$C_6$ alkylene)-O-phenyl, phenyl, heteroaryl, a partially unsaturated 9-10 membered bicyclic carbocyclyl, or a partially unsaturated 8-10 membered bicyclic heterocyclyl; each of which is optionally substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, —O—($C_3$-$C_6$ cycloalkyl), $C_2$-$C_4$ alkynyl, —($C_2$-$C_4$ alkynyl)-$C_1$-$C_6$ alkoxy, —O—($C_3$-$C_6$ cycloalkyl), aryl, —O-aryl, heteroaryl, saturated 3-8 membered heterocyclyl, amino, and —CO$_2R^5$; or
$C_{1-6}$ alkyl or $C_{2-6}$ alkynyl;

$R^5$ represents independently for each occurrence hydrogen, $C_1$-$C_6$ alkyl, or $C_3$-$C_6$ cycloalkyl; or two occurrences of $R^5$ attached to the same nitrogen atom are taken together with the nitrogen atom to which they are attached to form a 3-8 membered heterocyclic ring;

Y is a bond, —C(O)—, $C_1$-$C_6$ haloalkylene, $C_3$-$C_6$ cycloalkylene, or $C_1$-$C_6$ alkylene optionally substituted with $C_3$-$C_6$ cycloalkylene; and n is 0, 1, or 2

Definitions of the variables in Formula IV above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii).

Accordingly, in certain embodiments, $R^1$ is $C_1$-$C_3$ alkyl, 3-6 membered heterocyclyl, or 6-membered aryl, wherein the heterocyclyl and aryl are optionally substituted with 1, 2, or 3 substituents independently selected from the group consisting of halogen, hydroxyl, $C_1$-$C_6$ alkyl, $C_1$-$C_6$ haloalkyl, $C_3$-$C_6$ cycloalkyl, and $C_1$-$C_6$ alkoxy.

In certain embodiments, $R^2$ is hydrogen. In certain embodiments, $R^3$ is hydrogen.

In certain embodiments, Y is $C_1$-$C_6$ alkylene. In certain embodiments, Y is $C_1$-$C_6$ haloalkylene.

In certain embodiments, $R^4$ is $C_3$-$C_8$ cycloalkyl optionally substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, and —($C_2$-$C_4$ alkynyl)-$C_1$-$C_6$ alkoxy. In certain embodiments, $R^4$ is a partially unsaturated 9-10 membered bicyclic carbocyclyl optionally substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, —($C_2$-$C_4$ alkynyl)-$C_1$-$C_6$ alkoxy, aryl, heteroaryl, and saturated 3-8 membered heterocyclyl. In certain embodiments, $R^4$ is a partially unsaturated 9-10 membered bicyclic carbocyclyl optionally substituted by $C_1$-$C_6$ alkyl. In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, —($C_2$-$C_4$ alkynyl)-$C_1$-$C_6$ alkoxy, 5-membered heteroaryl, and saturated 3-8 membered heterocyclyl. In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, and —($C_2$-$C_4$ alkynyl)-$C_1$-$C_6$ alkoxy.

In certain embodiments, n is 1.

The description above describes multiple embodiments relating to compounds of Formula IV. The patent application specifically contemplates all combinations of the embodiments.

Another aspect of the invention provides substituted thieno[3,2-b]pyridine-3-carboxamide and related compounds. The substituted thieno[3,2-b]pyridine-3-carboxamide and related compounds are contemplated to be useful in the methods, compositions, and kits described herein. In certain embodiments, the substituted thieno[3,2-b]pyridine-3-carboxamide or related compound is a compound embraced by Formula V:

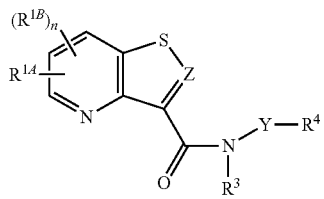

or a pharmaceutically acceptable salt thereof, wherein:
$R^{1A}$ is $C_1$-$C_6$ alkyl, $C_1$-$C_6$ haloalkyl, $C_3$-$C_6$ cycloalkyl, 3-10 membered heterocyclyl, or 6-membered aryl, wherein the cycloalkyl, heterocyclyl, and aryl are optionally substituted with 1, 2, or 3 substituents independently selected from the group consisting of halogen, hydroxyl, $C_1$-$C_6$ alkyl, $C_1$-$C_6$ haloalkyl, $C_3$-$C_6$ cycloalkyl, $C_1$-$C_6$ alkoxy, cyano, —$N(R^5)_2$, —$C(O)$—($C_1$-$C_6$ alkyl), —$N(R^5)C(O)$—($C_1$-$C_6$ alkyl), and —$C(O)N(R^5)_2$;
$R^{1B}$ represents independently for each occurrence $C_1$-$C_6$ alkyl, halogen, $C_1$-$C_6$ haloalkyl, $C_3$-$C_6$ cycloalkyl, $C_1$-$C_6$ alkoxy, —($C_1$-$C_4$ alkylene)-O—($C_1$-$C_6$ alkyl), —($C_1$-$C_4$ alkylene)-O—($C_3$-$C_6$ cycloalkyl), 3-6 membered heterocyclyl, 6-membered aryl, cyano, or —$N(R^5)_2$;
$R^2$ is hydrogen, $C_1$-$C_6$ alkyl, halogen, $C_1$-$C_6$ haloalkyl, $C_3$-$C_6$ cycloalkyl, $C_1$-$C_6$ alkoxy, —($C_1$-$C_4$ alkylene)-O—($C_1$-$C_6$ alkyl), —($C_1$-$C_4$ alkylene)-O—($C_3$-$C_6$ cycloalkyl), 3-6 membered heterocyclyl, 6-membered aryl, cyano, or —$N(R^5)_2$;
$R^3$ is hydrogen, $C_1$-$C_6$ alkyl, or $C_3$-$C_6$ cycloalkyl;
$R^4$ is one of the following:
  $C_3$-$C_8$ cycloalkyl, 3-8 membered heterocycloalkyl, 9-13 membered spiroheterocycloalkyl, —($C_2$-$C_6$ alkylene)-O-phenyl, phenyl, heteroaryl, a partially unsaturated 9-10 membered bicyclic carbocyclyl, or a partially unsaturated 8-10 membered bicyclic heterocyclyl; each of which is optionally substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, —O—($C_3$-$C_6$ cycloalkyl), $C_2$-$C_4$ alkynyl, —($C_2$-$C_4$ alkynyl)-$C_1$-$C_6$ alkoxy, —O—($C_3$-$C_6$ cycloalkyl), aryl, —O-aryl, heteroaryl, saturated 3-8 membered heterocyclyl, amino, and —$CO_2R^5$; or
  $C_{1-6}$ alkyl or $C_{2-6}$ alkynyl;
$R^5$ represents independently for each occurrence hydrogen, $C_1$-$C_6$ alkyl, or $C_3$-$C_6$ cycloalkyl; or two occurrences of $R^5$ attached to the same nitrogen atom are taken together with the nitrogen atom to which they are attached to form a 3-8 membered heterocyclic ring;
Y is a bond, —C(O)—, $C_1$-$C_6$ haloalkylene, $C_3$-$C_6$ cycloalkylene, or $C_1$-$C_6$ alkylene optionally substituted with $C_3$-$C_6$ cycloalkylene;
Z is N or $C(R^2)$; and
n is 0, 1, or 2.

Definitions of the variables in Formula V above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii).

Accordingly, in certain embodiments, $R^{1A}$ is $C_1$-$C_3$ alkyl, 3-6 membered heterocyclyl, or 6-membered aryl, wherein the heterocyclyl and aryl are optionally substituted with 1, 2, or 3 substituents independently selected from the group consisting of halogen, hydroxyl, $C_1$-$C_6$ alkyl, $C_1$-$C_6$ haloalkyl, $C_3$-$C_6$ cycloalkyl, and $C_1$-$C_6$ alkoxy. In certain embodiments, $R^{1B}$ is $C_1$-$C_3$ alkyl or halogen.

In certain embodiments, $R^2$ is hydrogen.
In certain embodiments, $R^3$ is hydrogen.
In certain embodiments, Y is $C_1$-$C_6$ alkylene. In certain embodiments, Y is $C_1$-$C_6$ haloalkylene.

In certain embodiments, $R^4$ is $C_3$-$C_8$ cycloalkyl optionally substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, and —($C_2$-$C_4$ alkynyl)-$C_1$-$C_6$ alkoxy. In certain embodiments, $R^4$ is a partially unsaturated 9-10 membered bicyclic carbocyclyl optionally substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, —($C_2$-$C_4$ alkynyl)-$C_1$-$C_6$ alkoxy, aryl, heteroaryl, and saturated 3-8 membered heterocyclyl. In certain embodiments, $R^4$ is a partially unsaturated 9-10 membered bicyclic carbocyclyl optionally substituted by $C_1$-$C_8$ alkyl. In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, —($C_2$-$C_4$ alkynyl)-$C_1$-$C_6$ alkoxy, 5-membered heteroaryl, and saturated 3-8 membered heterocyclyl. In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, and —($C_2$-$C_4$ alkynyl)-$C_1$-$C_6$ alkoxy.

In certain embodiments, n is 1.

The description above describes multiple embodiments relating to compounds of Formula V. The patent application specifically contemplates all combinations of the embodiments.

Another aspect of the invention provides substituted furo[3,2-b]pyridine-3-carboxamide and related compounds. The substituted furo[3,2-b]pyridine-3-carboxamide and related compounds are contemplated to be useful in the methods, compositions, and kits described herein. In certain embodiments, the substituted furo[3,2-b]pyridine-3-carboxamide or related compound is a compound embraced by Formula VI:

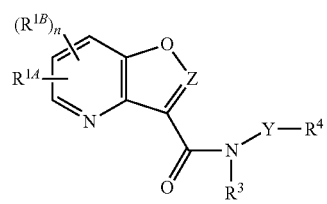

or a pharmaceutically acceptable salt thereof, wherein:
$R^{1A}$ is $C_1$-$C_6$ alkyl, $C_1$-$C_6$ haloalkyl, $C_3$-$C_6$ cycloalkyl, 3-10 membered heterocyclyl, or 6-membered aryl, wherein the cycloalkyl, heterocyclyl, and aryl are optionally substituted with 1, 2, or 3 substituents independently selected from the group consisting of halogen, hydroxyl, $C_1$-$C_6$ alkyl, $C_1$-$C_6$ haloalkyl, $C_3$-$C_6$ cycloalkyl, $C_1$-$C_6$ alkoxy, cyano, —N($R^5$)$_2$, —C(O)—($C_1$-$C_6$ alkyl), —N($R^5$)C(O)—($C_1$-$C_6$ alkyl), and —C(O)N($R^5$)$_2$;

$R^{1B}$ represents independently for each occurrence $C_1$-$C_6$ alkyl, halogen, $C_1$-$C_6$ haloalkyl, $C_3$-$C_6$ cycloalkyl, $C_1$-$C_6$ alkoxy, —($C_1$-$C_4$ alkylene)-O—($C_1$-$C_6$ alkyl), —($C_1$-$C_4$ alkylene)-O—($C_3$-$C_6$ cycloalkyl), 3-6 membered heterocyclyl, 6-membered aryl, cyano, or —N($R^5$)$_2$;

$R^2$ is hydrogen, $C_1$-$C_6$ alkyl, halogen, $C_1$-$C_6$ haloalkyl, $C_3$-$C_6$ cycloalkyl, $C_1$-$C_6$ alkoxy, —($C_1$-$C_4$ alkylene)-O—($C_1$-$C_6$ alkyl), —($C_1$-$C_4$ alkylene)-O—($C_3$-$C_6$ cycloalkyl), 3-6 membered heterocyclyl, 6-membered aryl, cyano, or —N($R^5$)$_2$;

$R^3$ is hydrogen, $C_1$-$C_6$ alkyl, or $C_3$-$C_6$ cycloalkyl;

$R^4$ is one of the following:
  $C_3$-$C_8$ cycloalkyl, 3-8 membered heterocycloalkyl, 9-13 membered spiroheterocycloalkyl, —($C_2$-$C_6$ alkylene)-O-phenyl, phenyl, heteroaryl, a partially unsaturated 9-10 membered bicyclic carbocyclyl, or a partially unsaturated 8-10 membered bicyclic heterocyclyl; each of which is optionally substituted by 1, 2, or 3 substituents independently selected from the group consisting of $C_1$—C alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, —O—($C_3$-$C_6$ cycloalkyl), $C_2$-$C_4$ alkynyl, —($C_2$-$C_4$ alkynyl)-$C_1$-$C_6$ alkoxy, —O—($C_3$-$C_6$ cycloalkyl), aryl, —O-aryl, heteroaryl, saturated 3-8 membered heterocyclyl, amino, and —CO$_2$$R^5$; or
  $C_1$-$C_6$ alkyl or $C_{2-6}$ alkynyl;

$R^5$ represents independently for each occurrence hydrogen, $C_1$-$C_6$ alkyl, or $C_3$-$C_6$ cycloalkyl; or two occurrences of $R^5$ attached to the same nitrogen atom are taken together with the nitrogen atom to which they are attached to form a 3-8 membered heterocyclic ring;

Y is a bond, —C(O)—, $C_1$-$C_6$ haloalkylene, $C_3$-$C_6$ cycloalkylene, or $C_1$-$C_6$ alkylene optionally substituted with $C_3$-$C_6$ cycloalkylene;

Z is N or C($R^2$); and n is 0, 1, or 2.

Definitions of the variables in Formula VI above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii).

Accordingly, in certain embodiments, $R^{1A}$ is $C_1$-$C_3$ alkyl, 3-6 membered heterocyclyl, or 6-membered aryl, wherein the heterocyclyl and aryl are optionally substituted with 1, 2, or 3 substituents independently selected from the group consisting of halogen, hydroxyl, $C_1$-$C_6$ alkyl, $C_1$-$C_6$ haloalkyl, $C_3$-$C_6$ cycloalkyl, and $C_1$-$C_6$ alkoxy. In certain embodiments, $R^{1B}$ is $C_1$-$C_3$ alkyl or halogen. In certain embodiments $R^{1A}$ is $C_1$-$C_3$ alkyl.

In certain embodiments, $R^{1B}$ is $C_1$-$C_3$ alkyl or halogen.

In certain embodiments, $R^2$ is hydrogen. In certain embodiments, $R^3$ is hydrogen. In yet other embodiments, $R^2$ and $R^3$ are hydrogen.

In certain embodiments, Y is a bond. In certain embodiments, Y is $C_1$-$C_6$ alkylene. In certain embodiments, Y is $C_1$-$C_6$ haloalkylene. In yet other embodiments, Y is a bond or $C_1$-$C_6$ alkylene.

In certain embodiments, $R^4$ is $C_3$-$C_8$ cycloalkyl optionally substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, and —($C_2$-$C_4$ alkynyl)-$C_1$-$C_6$ alkoxy. In certain embodiments, $R^4$ is a partially unsaturated 9-10 membered bicyclic carbocyclyl optionally substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, —($C_2$-$C_4$ alkynyl)-$C_1$-$C_6$ alkoxy, aryl, heteroaryl, and saturated 3-8 membered heterocyclyl. In certain embodiments, $R^4$ is a partially unsaturated 9-10 membered bicyclic carbocyclyl optionally substituted by $C_1$-$C_6$ alkyl. In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, —($C_2$-$C_4$ alkynyl)-$C_1$-$C_6$ alkoxy, 5-membered heteroaryl, and saturated 3-8 membered heterocyclyl. In certain embodiments, $R^4$ is phenyl substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, and —($C_2$-$C_4$ alkynyl)-$C_1$-$C_6$ alkoxy. In yet other embodiments, $R^4$ is $C_3$-$C_8$ cycloalkyl, phenyl, or a partially unsaturated 9-10 membered bicyclic carbocyclyl; each of which is optionally substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, and $C_1$-$C_6$ alkoxy.

In certain embodiments, n is 1.

In yet other embodiments, $R^4$ is $C_1$-$C_3$ alkyl, $R^{1B}$ is $C_1$-$C_3$ alkyl or halogen, and n is 1.

The description above describes multiple embodiments relating to compounds of Formula VI. The patent application specifically contemplates all combinations of the embodiments.

Another aspect of the invention provides compounds of Formula VII, which are contemplated to be useful in the methods, compositions, and kits described herein:

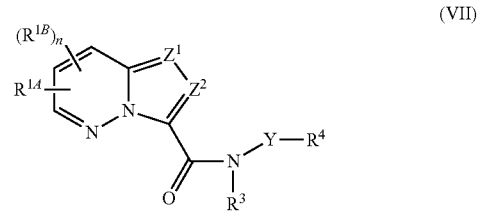

(VII)

or a pharmaceutically acceptable salt thereof, wherein:

$R^{1A}$ is a 3-10 membered oxoheterocyclyl optionally substituted with 1, 2, or 3 substituents independently selected from the group consisting of halogen, hydroxyl, $C_1$-$C_6$ alkyl, $C_1$-$C_6$ haloalkyl, $C_3$-$C_6$ cycloalkyl, $C_1$-$C_6$ alkoxy, cyano, —N($R^5$)$_2$, —C(O)—($C_1$-$C_6$ alkyl), —N($R^5$)C(O)—($C_1$-$C_6$ alkyl), and —C(O)N($R^5$)$_2$;

$R^{1B}$ represents independently for each occurrence $C_1$-$C_6$ alkyl, halogen, $C_1$-$C_6$ haloalkyl, $C_3$-$C_6$ cycloalkyl, $C_1$-$C_6$ alkoxy, —($C_1$-$C_4$ alkylene)-O—($C_1$-$C_6$ alkyl), —(C$_1$-C$_4$ alkylene)-O—(C$_3$-C$_6$ cycloalkyl), 3-6 membered heterocyclyl, 6-membered aryl, cyano, or —N(R$^5$)$_2$; R$^2$ is hydrogen, C$_1$-C$_6$ alkyl, halogen, C$_1$-C$_6$ haloalkyl, C$_3$-C$_6$ cycloalkyl, C$_1$-C$_6$ alkoxy, —(C$_1$-C$_4$ alkylene)-O—(C$_1$-C$_6$ alkyl), —(C$_1$-C$_4$ alkylene)-O—(C$_1$-C$_6$ cycloalkyl), 3-6 membered heterocyclyl, 6-membered aryl, cyano, or —N(R$^5$)$_2$;

R$^3$ is hydrogen, C$_1$-C$_6$ alkyl, or C$_3$-C$_6$ cycloalkyl;

R$^4$ is one of the following:

C$_3$-C$_8$ cycloalkyl, 3-8 membered heterocycloalkyl, 9-13 membered spiroheterocycloalkyl, —(C$_2$-C$_6$ alkylene)-O-phenyl, phenyl, heteroaryl, a partially unsaturated 9-10 membered bicyclic carbocyclyl, or a partially unsaturated 8-10 membered bicyclic heterocyclyl; each of which is optionally substituted by 1, 2, or 3 substituents independently selected from the group consisting of C$_1$-C$_8$ alkyl, halogen, C$_1$-C$_6$ haloalkyl, C$_3$-C$_6$ cycloalkyl, —(C$_1$-C$_6$ alkylene)-(C$_3$-C$_6$ cycloalkyl), hydroxyl, C$_1$-C$_6$ alkoxy, —O—(C$_3$-C$_6$ cycloalkyl), C$_2$-C$_4$ alkynyl, —(C$_2$-C$_4$ alkynyl)-C$_1$-C$_6$ alkoxy, —O—(C$_3$-C$_6$ cycloalkyl), aryl, —O-aryl, heteroaryl, saturated 3-8 membered heterocyclyl, amino, and —CO$_2$R$^5$; or C$_{1-6}$ alkyl or C$_{2-6}$ alkynyl;

R$^5$ represents independently for each occurrence hydrogen, C$_1$-C$_6$ alkyl, or C$_1$-C$_6$ cycloalkyl; or two occurrences of R$^5$ attached to the same nitrogen atom are taken together with the nitrogen atom to which they are attached to form a 3-8 membered heterocyclic ring;

Y is a bond, —C(O)—, C$_1$-C$_6$ haloalkylene, C$_3$-C$_6$ cycloalkylene, or C$_1$-C$_6$ alkylene optionally substituted with C$_3$-C$_6$ cycloalkylene;

Z$^1$ and Z$^2$ are as follows:
(i) Z$^1$ is C(R$^2$), and then Z$^2$ is N; or
(ii) Z$^1$ is N, and then Z$^2$ is C(R$^2$); and
n is 0, 1, or 2.

Definitions of the variables in Formula VII above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii). Accordingly, in certain embodiments, R$^{1B}$ is C$_1$-C$_3$ alkyl.

In certain embodiments, Z$^1$ is C(R$^2$), and then Z$^2$ is N. In certain other embodiments, Z$^1$ is N, and then Z$^2$ is C(R$^2$). In certain embodiments, n is 0, 1, or 2. In certain embodiments, R$^2$ and R$^3$ are hydrogen. In certain embodiments, Y is a bond or C$_1$-C$_6$ alkylene. In certain embodiments, Y is C$_1$-C$_6$ haloalkylene. In certain embodiments, R$^4$ is C$_3$-C$_8$ cycloalkyl, phenyl, or a partially unsaturated 9-10 membered bicyclic carbocyclyl; each of which is optionally substituted by 1, 2, or 3 substituents independently selected from the group consisting of C$_1$-C$_8$ alkyl, halogen, C$_1$-C$_6$ haloalkyl, C$_3$-C$_6$ cycloalkyl, —(C$_1$-C$_6$ alkylene)-(C$_3$-C$_6$ cycloalkyl), hydroxyl, and C$_1$-C$_6$ alkoxy.

In certain other embodiments, the compound is one of the compounds listed in Table 1 or 2 below or a pharmaceutically acceptable salt thereof. In certain embodiments, the compound is one of the compounds listed in Table 3 herein or a pharmaceutically acceptable salt thereof. In certain embodiments, the compound is one of the compounds listed in Table 1, 2, or 3 herein or a pharmaceutically acceptable salt thereof. In certain other embodiments, the compound is 6-(2-cyano-4-fluorophenyl)-8-methyl-N-(1,1,1-trifluoropropan-2-yl)imidazo[1,2-b]pyridazine-3-carboxamide or a pharmaceutically acceptable salt thereof. In certain other embodiments, the compound is 6-(2-cyano-4-fluorophenyl)-N-(1-cyclopropylethyl)-8-methylimidazo[1,2-b]pyridazine-3-carboxamide or a pharmaceutically acceptable salt thereof. In certain embodiments, the compound is one of the compounds listed in Table 4 herein or a pharmaceutically acceptable salt thereof

TABLE 1

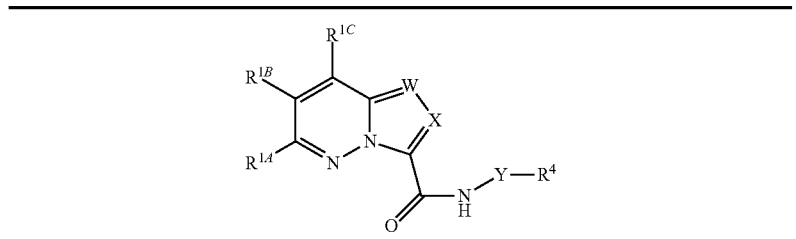

| Compound No. | R$^{1A}$ | R$^{1B}$ | R$^{1C}$ | W | X | Y | R$^4$ |
|---|---|---|---|---|---|---|---|
| I-1 | Cl | H | H | N | CH | a bond | |
| I-2 | —CH$_3$ | H | —CH$_3$ | CH | N | a bond | |

TABLE 1-continued
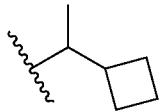 [SMILES: *C(C)C1CCC1]
| Compound No. | R$^{1A}$ | R$^{1B}$ | R$^{1C}$ | W | X | Y | R$^4$ |
|---|---|---|---|---|---|---|---|
| I-3 | Cl | —CH$_3$ | H | N | CH | a bond | 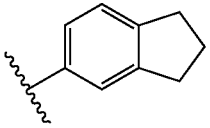 [SMILES: *c1ccc2c(c1)CCC2] |
| I-4 | Cl | H | H | N | CH | a bond | 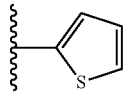 [SMILES: *c1cccs1] |
| I-5 | Cl | H | H | N | CH | a bond | 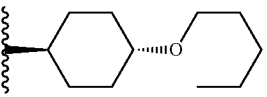 |
| I-6 | Cl | H | H | N | CH | a bond | 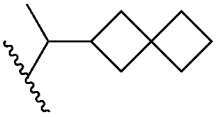 [SMILES: *C(C)C1CC2(CCC2)C1] |
| I-7 | —CH$_3$ | H | —CH$_3$ | N | CH | a bond | 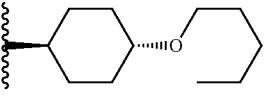 |
| I-8 | —CH$_3$ | H | —CH$_3$ | N | CH | a bond | 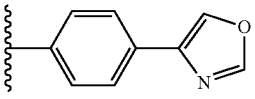 |
| I-9 | —CH$_3$ | H | —CH$_3$ | N | CH | a bond | 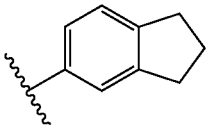 |
| I-10 | —CH$_3$ | H | —CH$_3$ | N | CH | a bond | 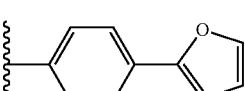 |
| I-11 | —CH$_3$ | H | —CH$_3$ | N | CH | a bond | 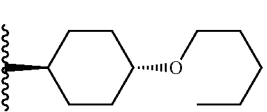 |
| I-12 | Cl | H | —CH$_3$ | N | CH | a bond |  |

TABLE 1-continued

| Compound No. | R^1A | R^1B | R^1C | W | X | Y | R^4 |
|---|---|---|---|---|---|---|---|
| I-13 | Cl | H | —CH$_3$ | N | CH | a bond | 2,3-dihydro-1H-indene |
| I-14 | Cl | —CH$_3$ | H | N | CH | a bond | cyclohexyl-O-isopentyl |
| I-15 | —CH$_3$ | H | —CH$_3$ | CH | N | a bond | phenyl-oxazole |
| I-16 | —CH$_3$ | H | —CH$_3$ | CH | N | a bond | cyclohexyl-O-butyl |
| I-17 | —CH$_3$ | H | —CH$_3$ | CH | N | a bond | pyridinyl-furanyl |
| I-18 | Cl | —CH$_3$ | H | N | CH | C$_1$—C$_4$ alkylene | phenyl |
| I-19 | Cl | H | H | N | CH | C$_1$—C$_4$ alkylene | phenyl |
| I-20 | —CH$_3$ | H | —CH$_3$ | N | CH | C$_1$—C$_4$ alkylene | phenyl |
| I-21 | Cl | H | —CH$_3$ | N | CH | C$_1$—C$_4$ alkylene | cyclobutyl |
| I-22 | Cl | H | —CH$_3$ | CH | N | C$_1$—C$_4$ alkylene | cyclobutyl |
| I-23 | —CH$_3$ | H | —CH$_3$ | N | CH | C$_1$—C$_4$ alkylene | cyclobutyl |

TABLE 1-continued

| Compound No. | $R^{1A}$ | $R^{1B}$ | $R^{1C}$ | W | X | Y | $R^4$ |
|---|---|---|---|---|---|---|---|
| I-24 | Cl | H | —CH$_3$ | N | CH | C$_1$—C$_4$ alkylene | cyclopropyl |
| I-25 | Cl | H | —CH$_3$ | CH | N | C$_1$—C$_4$ alkylene | cyclopropyl |
| I-26 | —CH$_3$ | H | —CH$_3$ | N | CH | C$_1$—C$_4$ alkylene | cyclopropyl |

TABLE 2

| Compound No. | Compound Structure |
|---|---|
| II-1 | 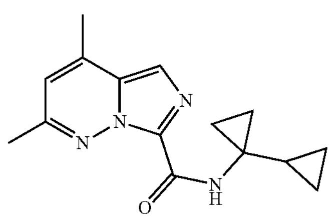 [SMILES: Cc1cc(C)c2cnc(C(=O)NC3(C4CC4)CC3)n2n1] |
| II-2 | 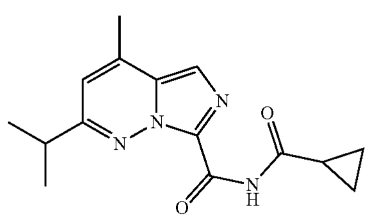 [SMILES: Cc1cc(C(C)C)nn2c(C(=O)NC(=O)C3CC3)ncc12] |
| II-3 | 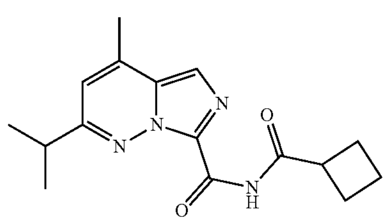 [SMILES: Cc1cc(C(C)C)nn2c(C(=O)NC(=O)C3CCC3)ncc12] |
| II-4 | 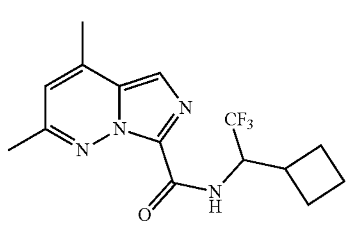 [SMILES: Cc1cc(C)c2cnc(C(=O)NC(C3CCC3)C(F)(F)F)n2n1] |
| II-5 | |
| II-6 | |
| II-7 | |
| II-8 | |

TABLE 2-continued
| Compound No. | Compound Structure |
|---|---|
| II-9 | 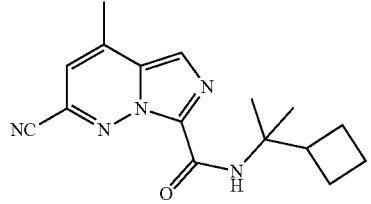 [SMILES: Cc1cc(C#N)nn2c(C(=O)NC(C)(C)C3CCC3)ncc12] |
| II-10 | 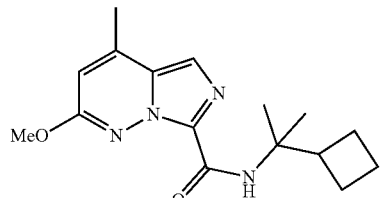 |
| II-11 | 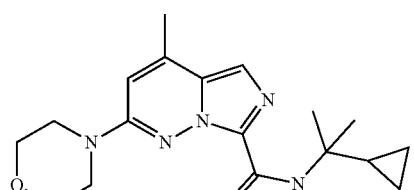 |
| II-12 | 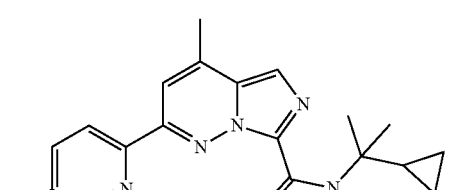 |
| II-13 | 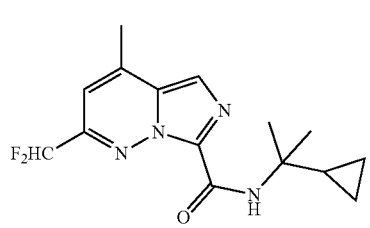 [SMILES: Cc1cc(C(F)F)nn2c(C(=O)NC(C)(C)C3CC3)ncc12] |
| II-14 | 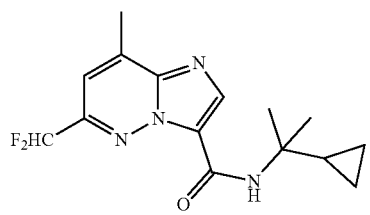 [SMILES: Cc1cc(C(F)F)nn2c(C(=O)NC(C)(C)C3CC3)cnc12] |
| II-15 | 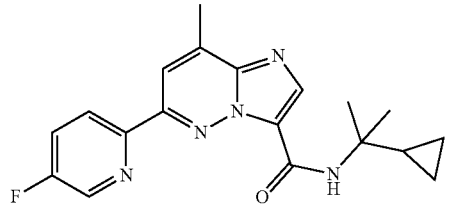 [SMILES: Cc1cc(-c2ccc(F)cn2)nn2c(C(=O)NC(C)(C)C3CC3)cnc12] |
TABLE 2-continued
| Compound No. | Compound Structure |
|---|---|
| II-16 | 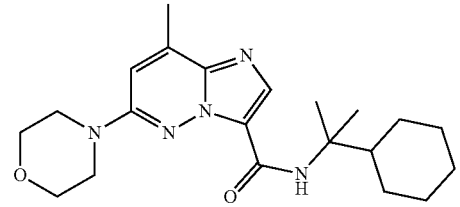 [SMILES: Cc1cc(N2CCOCC2)nn2c(C(=O)NC(C)(C)C3CCCCC3)cnc12] |
| II-17 | 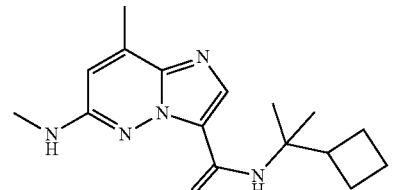 |
| II-18 | 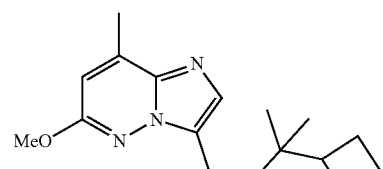 |
| II-19 | 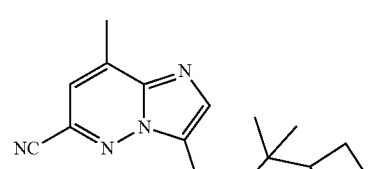 |
| II-20 | 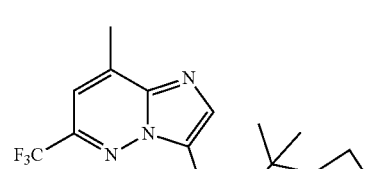 |
| II-21 | 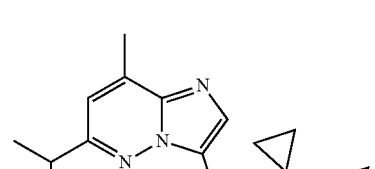 |
| II-22 | 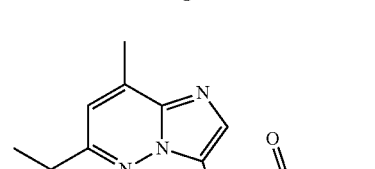 |

TABLE 2-continued

| Compound No. | Compound Structure |
|---|---|
| II-23 | 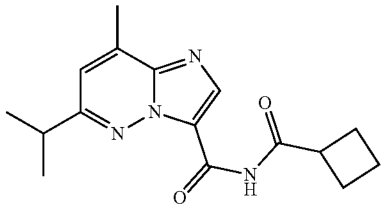 [SMILES: Cc1cc(C(C)C)nn2c(C(=O)NC(=O)C3CCC3)cnc12] |
| II-24 | 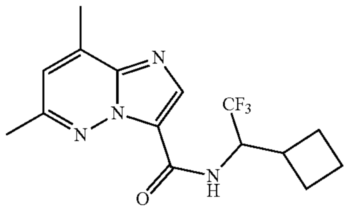 [SMILES: Cc1cc(C)c2ncc(C(=O)NC(C3CCC3)C(F)(F)F)n2n1] |
| II-25 | 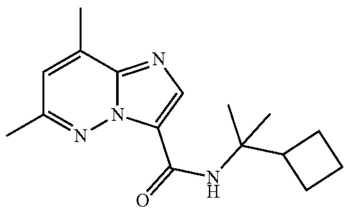 [SMILES: Cc1cc(C)c2ncc(C(=O)NC(C)(C)C3CCC3)n2n1] |
| II-26 | 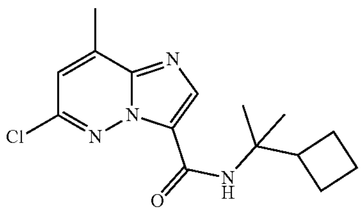 [SMILES: Cc1cc(Cl)nn2c(C(=O)NC(C)(C)C3CCC3)cnc12] |
| II-27 | 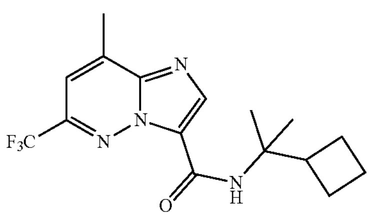 [SMILES: Cc1cc(C(F)(F)F)nn2c(C(=O)NC(C)(C)C3CCC3)cnc12] |
| II-28 | 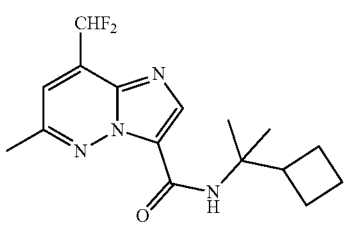 [SMILES: Cc1cc(C(F)F)c2ncc(C(=O)NC(C)(C)C3CCC3)n2n1] |

Methods for preparing exemplary substituted imidazo[1,2-b]pyridazine-3-carboxamide and related compounds described herein are illustrated in the following synthetic scheme. These scheme is provided for the purpose of illustrating the invention, and should not be regarded in any manner as limiting the scope or the spirit of the invention. Starting materials shown in the scheme can be obtained from commercial sources or can be prepared based on procedures described in the literature.

The synthetic route illustrated in Scheme 1 depicts an exemplary procedure for preparing substituted imidazo[1,5-b]pyridazine-7-carboxamide compounds. In the first step, Pd-catalyzed cross-coupling of 3,6-dichloro-4-methylpyridazine ($R^i$=Me, $R^{ii}$=H) A with a variety of aryl or heteroaryl boronic acids, halides or trialkylstannyl reagents may be accomplished using standard cross-coupling procedures (such as $Pd(dppf)_2Cl_2 \cdot CH_2Cl_2$ in DME in the presence of $K_3PO_4$) to afford the substituted pyrimidinyl chloride B. A second Pd-catalyzed cross-coupling reaction of the pyrimidinyl chloride B and $ZnCl_2$ affords the corresponding nitrile, which is reduced to give amine C. Coupling of amine C with ethyl 2-chloro-2-oxoacetate in the presence of $Et_3N$ affords the an amido ester which undergoes an intramolecular condensation in the presence of $POCl_3$ to afford the imidazo[1,5,b]pyrimidine ester. Hydrolysis of the carboxylic ester under basic or neutral conditions affords carboxylic acid D. In the final step, coupling of carboxylic acid D with a variety of substituted aromatic or aliphatic amines may be accomplished using standard peptide coupling procedures (such as HATU and/or HOBT in DMF in the presence of DIPEA) to afford carboxamide E.

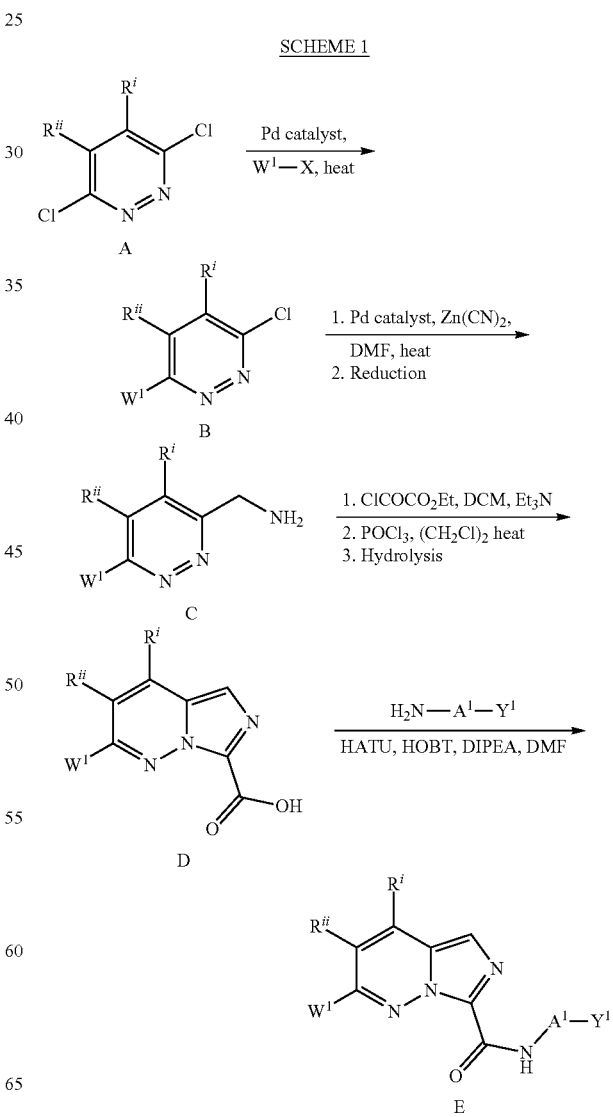

SCHEME 1

The synthetic route illustrated in Scheme 2 depicts an alternative exemplary procedure for preparing substituted imidazo[1,2-b]pyridazine-3-carboxamide compounds. In the first step, substitution of pyrimidinyl chloride B with hydrazine followed by Raney-Ni catalyzed hydrogenation affords amine F. Condensation of amine F with dimethyl acetamide affords an imine which undergoes an imine-enolate condensation with the enolate of ethyl 2-bromo acetate followed by an intramolecular condensation to afford the imidazo[1,2,b]pyrimidine ester. Hydrolysis of the carboxylic ester under basic or neutral conditions affords carboxylic acid G. In the final step, coupling of carboxylic acid G with a variety of substituted aromatic or aliphatic amines may be accomplished using standard peptide coupling procedures (such as HATU and/or HOBT in DMF in the presence of DIPEA) to afford carboxamide H.

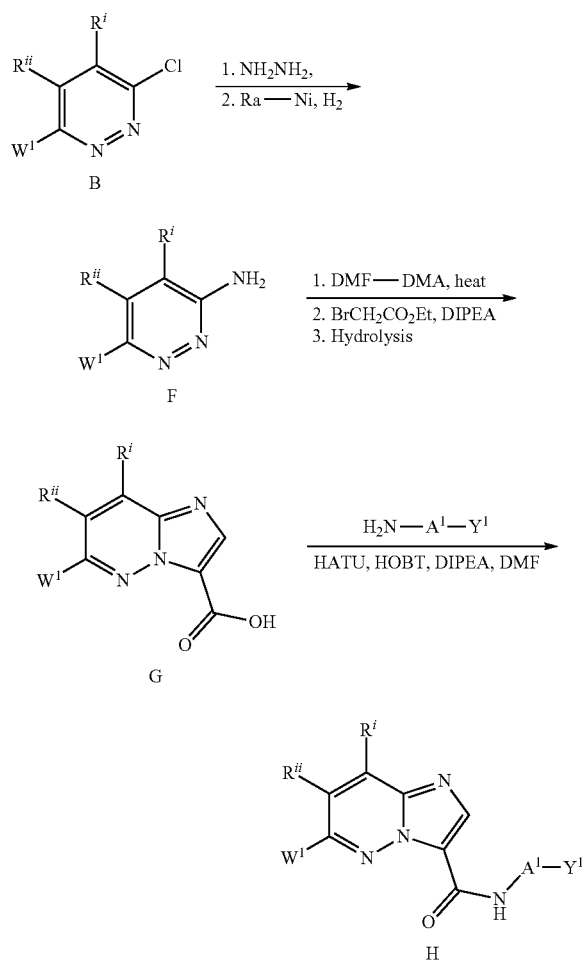

The synthetic route illustrated in Scheme 3 depicts an exemplary procedure for preparing substituted triazolo[4,3-b]pyridazine-3-carboxamide compounds. In the first step, substitution of pyrimidinyl chloride B with hydrazine followed by coupling with ethyl chloro oxalyl and subsequent intramolecular condensation affords triazolo[4,3,b]pyrimidine ester I. In the final step, coupling of carboxylic ester I with a variety of substituted aromatic or aliphatic amines may be accomplished via Weinreb's amide to afford carboxamide J.

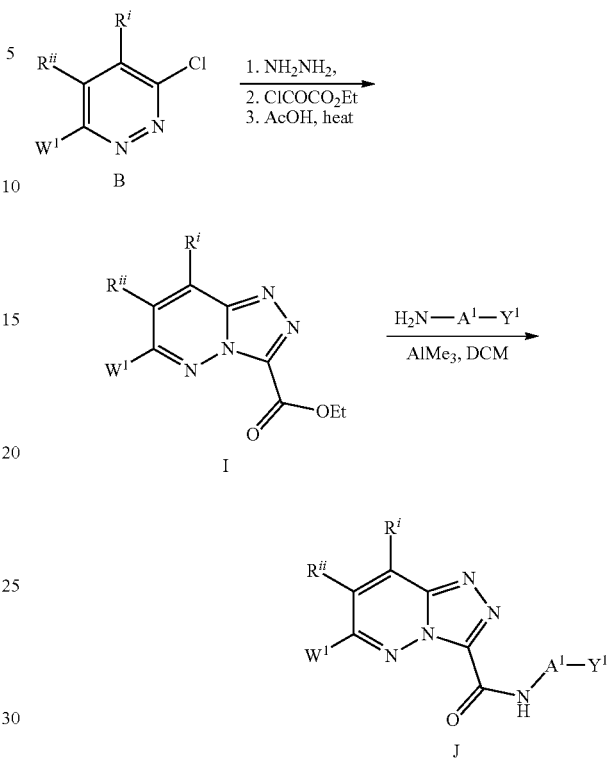

The synthetic route illustrated in Scheme 4 depicts an exemplary procedure for preparing substituted isothiazolo[4,5-b]pyridine-3-carboxamide compounds. In the first step, condensation of methyl 4-aminoisothiazole-3-carboxylate K with 4-methyleneoxetan-2-one affords the corresponding amido carboxylate which undergoes an intramolecular condensation in the presence of PPA to afford the corresponding bicyclic hydroxyl which is transformed to chloro-bicyclo carboxylate L. In the second step, Pd-catalyzed cross-coupling of chloride L with a variety of aryl or heteroaryl boronic acids, halides or trialkylstannyl reagents may be accomplished using standard cross coupling procedures (such as $Pd(dppf)_2Cl_2 \cdot CH_2Cl_2$ in DME in the presence of $K_3PO_4$) to afford substituted isothiazolo[4,5-b]pyridinyl carboxylic ester M. Hydrolysis of the carboxylic ester under basic or neutral conditions affords carboxylic acid N. In the final step, coupling of carboxylic acid N with a variety of substituted aromatic or aliphatic amines may be accomplished using standard peptide coupling procedures (such as HATU and/or HOBT in DMF in the presence of DIPEA) to afford carboxamide O.

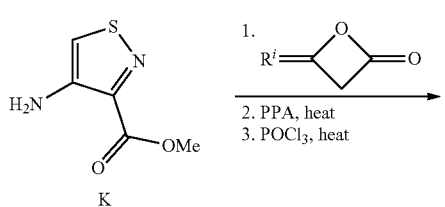

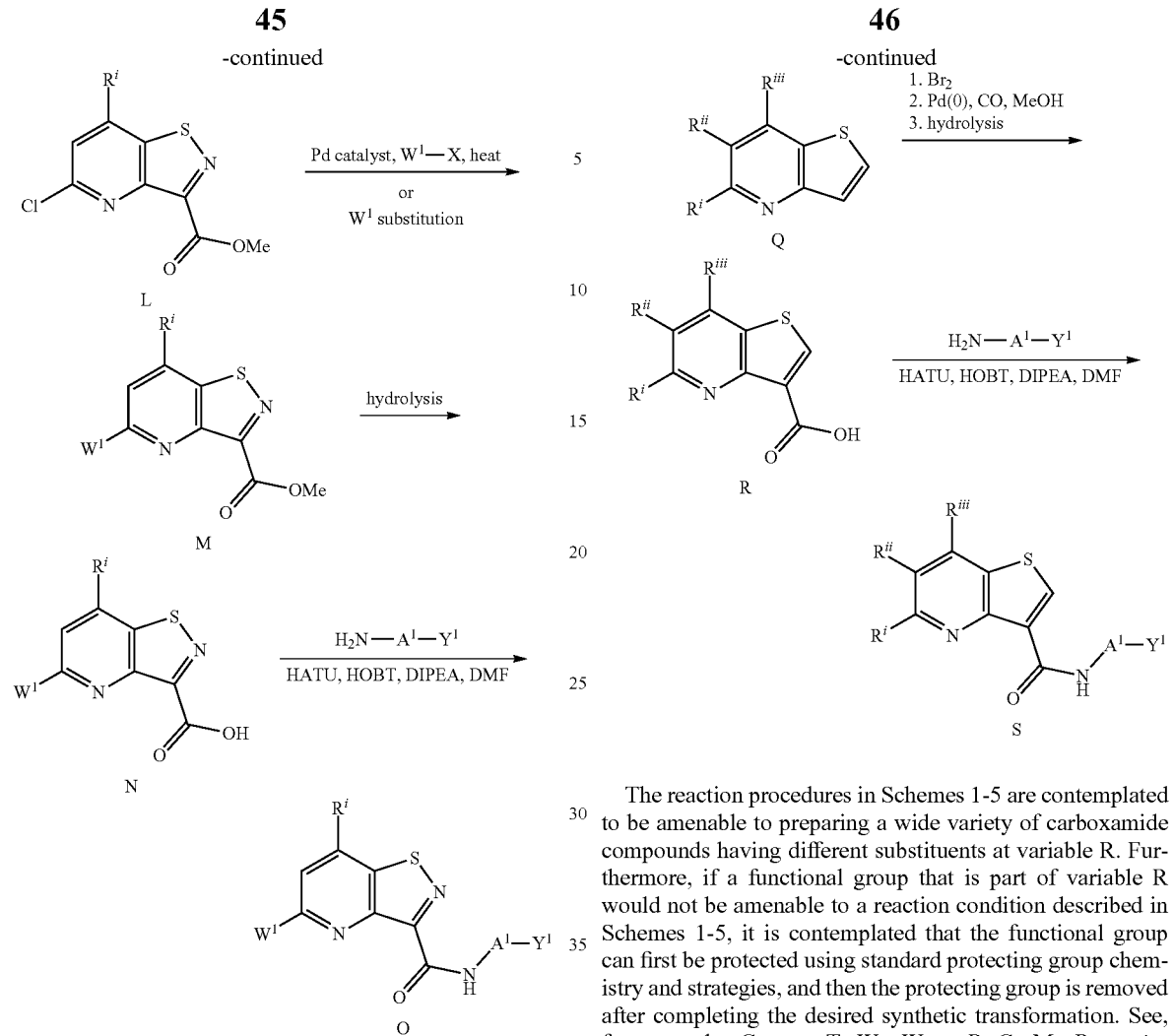

The synthetic scheme illustrated in Scheme 5 illustrates an exemplary procedure for preparing substituted thieno[3,2-b]pyridine-3-carboxamide compounds. In the first step condensation of thiophen-3-amine P with pentane-2,4-dione ($R^i=R^{iii}$=Me, $R^{ii}$=H) in the presence of $H_3PO_4$ affords 5,7-dimethylthieno[3,2-b]pyridine Q. Bromination of bicyclic compound Q followed by Pd(0)-catalysed coupling in methanol to install the methyl carboxylate, followed by hydrolysis affords carboxylic acid R. In the final step, coupling of carboxylic acid R with a variety of substituted aromatic or aliphatic amines may be accomplished using standard peptide coupling procedures (such as HATU and/or HOBT in DMF in the presence of DIPEA) to afford carboxamide S.

SCHEME 5

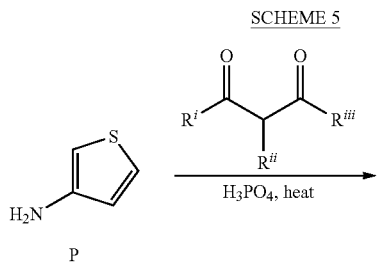

The reaction procedures in Schemes 1-5 are contemplated to be amenable to preparing a wide variety of carboxamide compounds having different substituents at variable R. Furthermore, if a functional group that is part of variable R would not be amenable to a reaction condition described in Schemes 1-5, it is contemplated that the functional group can first be protected using standard protecting group chemistry and strategies, and then the protecting group is removed after completing the desired synthetic transformation. See, for example, Greene, T. W.; Wuts, P. G. M. *Protective Groups in Organic Synthesis*, $2^{nd}$ ed.; Wiley: New York, 1991, for further description of protecting chemistry and strategies. In certain other embodiments, a functional group in substituent R can converted to another functional group using standard functional group manipulation procedures known in the art. See, for example, "Comprehensive Organic Synthesis" (B. M. Trost & I. Fleming, eds., 1991-1992).

Substituted imidazo[1,5-b]pyridazine compounds described herein may be prepared by synthetic methodology analogous to that described above for the substituted imidazo[1,2-b]pyridazine compounds.

III. Therapeutic Applications

The invention provides methods of treating medical disorders, such as Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, endometriosis, and multiple myeloma, using the substituted imidazo[1,2-b]pyridazine compounds, substituted imidazo[1,5-b]pyridazine compounds, related compounds, and pharmaceutical compositions described herein. Treatment methods include the use of a substituted imidazo[1,2-b]pyridazine compound, substituted imidazo[1,5-b]pyridazine compound, or related compound described herein as a stand-alone therapeutic agent and/or as part of a combination therapy with another therapeutic agent. Although not wishing to be bound by a particular theory, it is understood that substituted imidazo[1,2-b]pyridazine compounds, substituted imidazo[1,5-b]pyridazine compounds, and related compounds described herein may activate glucocerebrosidase (Gcase).

Methods of Treating Medical Disorders

One aspect of the invention provides a method of treating a disorder selected from the group consisting of Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, endometriosis, and multiple myeloma. The method comprises administering to a patient in need thereof a therapeutically effective amount of a substituted imidazo[1,2-b]pyridazine compound, substituted imidazo[1,5-b]pyridazine compound, or related compound described herein to treat the disorder. The compound may be a compound of Formula I, which, as described above in Section II, is represented by:

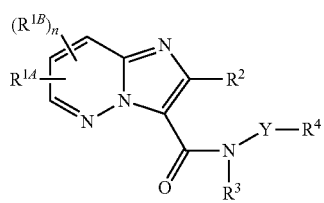

(I)

or a pharmaceutically acceptable salt thereof, wherein:
$R^{1A}$ is $C_1$-$C_6$ alkyl, $C_1$-$C_6$ haloalkyl, $C_3$-$C_6$ cycloalkyl, 3-10 membered heterocyclyl, or 6-membered aryl, wherein the cycloalkyl, heterocyclyl, and aryl are optionally substituted with 1, 2, or 3 substituents independently selected from the group consisting of halogen, hydroxyl, $C_1$-$C_6$ alkyl, $C_1$-$C_6$ haloalkyl, $C_3$-$C_6$ cycloalkyl, $C_1$-$C_6$ alkoxy, cyano, —N($R^5$)$_2$, —C(O)—($C_1$-$C_6$ alkyl), —N($R^5$)C(O)—($C_1$-$C_8$ alkyl), and —C(O)N($R^5$)$_2$;
$R^{1B}$ represents independently for each occurrence $C_1$-$C_6$ alkyl, halogen, $C_1$-$C_6$ haloalkyl, $C_3$-$C_6$ cycloalkyl, $C_1$-$C_6$ alkoxy, —($C_1$-$C_4$ alkylene)-O—($C_1$-$C_6$ alkyl), —($C_1$-$C_4$ alkylene)-O—($C_3$-$C_6$ cycloalkyl), 3-6 membered heterocyclyl, 6-membered aryl, cyano, or —N($R^5$)$_2$;
$R^2$ is hydrogen, $C_1$-$C_6$ alkyl, halogen, $C_1$-$C_6$ haloalkyl, $C_3$-$C_6$ cycloalkyl, $C_1$-$C_6$ alkoxy, —($C_1$-$C_4$ alkylene)-O—($C_1$-$C_6$ alkyl), —($C_1$-$C_4$ alkylene)-O—($C_3$-$C_6$ cycloalkyl), 3-6 membered heterocyclyl, 6-membered aryl, cyano, or —N($R^5$)$_2$;
$R^3$ is hydrogen, $C_1$-$C_6$ alkyl, or $C_3$-$C_6$ cycloalkyl;
$R^4$ is one of the following:
$C_3$-$C_8$ cycloalkyl, 3-8 membered heterocycloalkyl, 9-13 membered spiroheterocycloalkyl, —($C_2$-$C_6$ alkylene)-O-phenyl, phenyl, heteroaryl, a partially unsaturated 9-10 membered bicyclic carbocyclyl, or a partially unsaturated 8-10 membered bicyclic heterocyclyl; each of which is optionally substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, —O—($C_3$-$C_6$ cycloalkyl), $C_2$-$C_4$ alkynyl, —($C_2$-$C_4$ alkynyl)-$C_1$-$C_6$ alkoxy, —O—($C_3$-$C_6$ cycloalkyl), aryl, —O-aryl, heteroaryl, saturated 3-8 membered heterocyclyl, amino, and —CO$_2$$R^5$; or
$C_{1-6}$ alkyl or $C_{2-6}$ alkynyl;
$R^5$ represents independently for each occurrence hydrogen, $C_1$-$C_6$ alkyl, or $C_3$-$C_6$ cycloalkyl; or two occurrences of $R^5$ attached to the same nitrogen atom are taken together with the nitrogen atom to which they are attached to form a 3-8 membered heterocyclic ring;
Y is a bond, —C(O)—, $C_1$-$C_6$ haloalkylene, $C_3$-$C_6$ cycloalkylene, or $C_1$-$C_6$ alkylene optionally substituted with $C_3$-$C_6$ cycloalkylene; and
n is 0, 1, or 2;
provided that when Y—$R^4$ is —CH$_2$-phenyl, then n is 1 or 2.

In yet other embodiments, the compound is a compound of Formula II, as set forth in Section II above. In still other embodiments, the compound is a compound of Formula I-A, as set forth in Section II above. In yet other embodiments, the compound is a compound of Formula III, as set forth in Section II above.

In certain embodiments, the disorder is Gaucher disease, Parkinson's disease, Lewy body disease, dementia, or multiple system atrophy. In certain other embodiments, the disorder is Gaucher disease. In certain embodiments, the disorder is Parkinson's disease. In certain embodiments, the disorder is Lewy body disease. In certain embodiments, the disorder is dementia. In certain embodiments, the disorder is a dementia selected from the group consisting of Alzheimer's disease, frontotemporal dementia, and a Lewy body variant of Alzheimer's disease. In certain embodiments, the disorder is multiple system atrophy.

In certain embodiments, the disorder is an anxiety disorder, such as panic disorder, social anxiety disorder, or generalized anxiety disorder.

Efficacy of the compounds in treating Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, endometriosis, and multiple myeloma may be evaluated by testing the compounds in assays known in the art for evaluating efficacy against these diseases and/or, e.g., for activation of glucocerebrosidase (Gcase), as discussed in the Examples below.

In certain embodiments, the patient is a human.

In certain embodiments, the compound is one of the generic or specific compounds described in Section II, such as a compound of Formula I, a compound embraced by one of the further embodiments describing definitions for certain variables of Formula I, a compound of Formula I-A, a compound embraced by one of the further embodiments describing definitions for certain variables of Formula I-A, a compound of Formula II, a compound embraced by one of the further embodiments describing definitions for certain variables of Formula II, a compound of Formula III, or a compound embraced by one of the further embodiments describing definitions for certain variables of Formula III.

The description above describes multiple embodiments relating to methods of treating various disorders using certain substituted imidazo[1,2-b]pyridazine compounds and substituted imidazo[1,5-b]pyridazine compounds. The patent application specifically contemplates all combinations of the embodiments. For example, the invention contemplates methods for treating Gaucher disease, Parkinson's disease, Lewy body disease, dementia, or multiple system atrophy by administering a therapeutically effective amount of a compound of Formula I-A wherein $R^{1A}$ and $R^{1C}$ are $C_1$-$C_6$ alkyl, $R^2$ is hydrogen, and $R^4$ is $C_3$-$C_8$ cycloalkyl or phenyl; each of which is optionally substituted by 1, 2, or 3 substituents independently selected from the group consisting of $C_1$-$C_8$ alkyl, halogen, $C_1$-$C_6$ haloalkyl, and $C_3$-$C_6$ cycloalkyl.

Medical Use and Preparation of Medicament

Another aspect of the invention relates to compounds and compositions described herein for use in treating a disorder described herein. Another aspect of the invention pertains to use of a compound or composition described herein in the preparation of a medicament for treating a disorder described herein.

Combination Therapy

The invention embraces combination therapy, which includes the administration of a substituted imidazo[1,2-b]pyridazine compound, substituted imidazo[1,5-b]pyridazine compound, or related compound described herein (such as compound of Formula I, I-A, II, III, IV, V, VI, or VII) and a second agent as part of a specific treatment regimen intended to provide the beneficial effect from the co-action of these therapeutic agents. The beneficial effect of the combination may include pharmacokinetic or pharmacodynamic co-action resulting from the combination of therapeutic agents.

Exemplary second agents for use in treating Gaucher disease include, for example, taliglucerase alfa, velaglucerase alfa, eliglustat, and miglustat. Exemplary second agents for use in treating Parkinson's disease include, for example, a glucosylceramide synthase inhibitor (e.g., ibiglustat), an acid ceramidase inhibitor (e.g., carmofur), an acid shingomyelinase activator, or salt thereof. Additional glucosylceramide synthase inhibitors for use in combination therapies include, for example, those described in International Patent Application Publications WO 2015/089067, WO 2014/151291, WO 2014/043068, WO 2008/150486, WO 2010/014554, WO 2012/129084, WO 2011/133915, and WO 2010/091164; U.S. Pat. Nos. U.S. Pat. Nos. 9,126,993, 8,961,959, 8,940,776, 8,729,075, and 8,309,593; and U.S. Patent Application Publications US 2014/0255381 and US 2014/0336174; each of which are hereby incorporated by reference. Additional acid ceramidase inhibitors for use in combination therapies include, for example, those described in International Patent Application Publications WO 2015/173168 and WO 2015/173169, each of which are hereby incorporated by reference.

IV. Pharmaceutical Compositions

The invention provides pharmaceutical compositions comprising a substituted imidazo[1,2-b]pyridazine compound, substituted imidazo[1,5-b]pyridazine compound, or related compound described herein, such as a compound of Formula I, I-A, II, III, IV, V, VI, or VII. In certain embodiments, the pharmaceutical compositions preferably comprise a therapeutically-effective amount of one or more of the substituted imidazo[1,2-b]pyridazine compounds described above, formulated together with one or more pharmaceutically acceptable carriers. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets (e.g., those targeted for buccal, sublingual, and/or systemic absorption), boluses, powders, granules, pastes for application to the tongue; (2) parenteral administration by, for example, subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) jocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration.

The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

V. Kits for Use in Medical Applications

Another aspect of the invention provides a kit for treating a disorder. The kit comprises: i) instructions for treating a medical disorder, such as Gaucher disease, Parkinson's disease, Lewy body disease, dementia, or multiple system atrophy; and ii) a substituted imidazo[1,2-b]pyridazine compound or substituted imidazo[1,5-b]pyridazine compound described herein, such as a compound of Formula I, I-A, II, III, IV, V, VI, or VII. The kit may comprise one or more unit dosage forms containing an amount of a substituted imidazo [1,2-b]pyridazine compound, substituted imidazo[1,5-b] pyridazine compound, or related compound described herein, such as a compound of Formula I, I-A, II, III, IV, V, VI, or VII that is effective for treating said medical disorder, e.g., Gaucher disease, Parkinson's disease, Lewy body disease, dementia, or multiple system atrophy.

The description above describes multiple aspects and embodiments of the invention, including substituted imidazo [1,2-b]pyridazine compounds, substituted imidazo[1,5-b] pyridazine compounds, compositions comprising a substituted imidazo[1,2-b]pyridazine compound or substituted imidazo[1,5-b]pyridazine compound, methods of using the substituted imidazo[1,2-b]pyridazine compounds, substituted imidazo[1,5-b]pyridazine compounds, and related compounds, and kits. The patent application specifically contemplates all combinations and permutations of the aspects and embodiments. For example, the invention contemplates treating Gaucher disease, Parkinson's disease, Lewy body disease, dementia, or multiple system atrophy in a human patient by administering a therapeutically effective amount of a compound of Formula I-A. Further, for example, the invention contemplates a kit for treating Gaucher disease, Parkinson's disease, Lewy body disease, dementia, or multiple system atrophy, the kit comprising (i) instructions for treating Gaucher disease, Parkinson's disease, Lewy body disease, dementia, or multiple system atrophy and (ii) a substituted imidazo[1,2-b]pyridazine compound described herein, such as a compound of Formula I-A.

EXAMPLES

The invention now being generally described, will be more readily understood by reference to the following examples, which are included merely for purposes of illustration of certain aspects and embodiments of the present invention, and are not intended to limit the invention. Standard abbreviations have been used in the Examples in certain instances, such as the abbreviation "RT" for room temperature, and the abbreviation "h" for hours.

Example 1—Preparation of Compounds

Substituted imidazo[1,2-b]pyridazine compounds, substituted imidazo[1,5-b]pyridazine compounds, related compounds were prepared based on general procedures described in Part I below. Exemplary procedures for preparing specific carboxylic acid compounds useful as synthetic intermediates in the preparation of certain substituted imidazo[1,2-b]pyridazine compounds, substituted imidazo [1,5-b]pyridazine compounds, and/or related compounds are provided in Part II below. Specific substituted imidazo[1,2-b]pyridazine compounds, substituted imidazo[1,5-b] pyridazine compounds, and related compounds prepared according to the general procedures are provided in Part III below.

Part I—General Procedures

General Procedure A: Preparation of Amide by Coupling of a Carboxylic Acid Compound with an Amine Compound To a stirred solution of carboxylic acid compound (1.0 equivalent), HATU (1.5 equivalents), and DIPEA (3.75 equivalents) in DCM or DMF (~4 mL/0.2 mmol) is added amine compound (1.25-2.0 equivalents). The reaction mixture is stirred at room temperature for 4-16 hours, and then washed with saturated aqueous $NaHCO_3$ solution (5 mL/0.2 mmol), aqueous citric acid solution (5 mL/0.2 mmol) and brine (5 mL/0.2 mmol). The combined extracts are dried over anhydrous $Na_2SO_4$, filtered and concentrated in vacuo. The resulting crude material is purified by silica gel column chromatography or preparatory HPLC to give the amide compound.

General Procedure B: Conversion of Carboxylic Ester Compound to Carboxylic Acid Compound To a solution of carboxylic ester (1.0 equivalent) in EtOH (5.0 mL/1.0 mmol) and water (0-3.0 mL/1.0 mmol) is added NaOH (2.0-5.0 equivalents) and the mixture is heated at 80° C. for 2 hours and then concentrated. To the concentrate, 6N HCl solution is added to adjust the pH to 5~6 and then the mixture is stirred for 10 minutes and subsequently filtered. The resulting solid is collected and dried to give the carboxylic acid compound.

General Procedure C: Preparation of Coupled Aryl and Heteroaryl Groups Using Suzuki Catalyzed Coupling Conditions Between an Organoboronic Acid or Ester and an Aryl Halide or Heteroaryl Halide A suspension of heteroaryl chloride (1 equivalent), organoboronic acid or organoboronic ester (1.2 equivalents), $K_3PO_4$ (3.0 equivalents) and $Pd(dppf)Cl_2 \cdot DCM$ (5 mol %) or $Pd_2(dba)_3$ (10 mol %) in DME or 1,4-dioxane (40 mL/mmol) is stirred at 70-100° C. for 2-6 hours under $N_2$. Then, the reaction mixture is quenched with water (30 mL/mmol) and resulting mixture extracted with EtOAc (30 mL/mmol×3). The organic phases are washed with water (30 mL/mmol) and brine (30 mL/mmol), dried over anhydrous $Na_2SO_4$ and filtered. The filtrate is concentrated in vacuo, and the resulting residue is purified by silica gel column chromatography to afford the coupled ring system.

General Procedure D: Preparation of Coupled Aryl and Heteroaryl Groups Using Buchwald Catalyzed Coupling Conditions Between an Organohalide and Organotin Reagent A solution of organochloride (1.0 equivalent) and organotin reagent (1.0 equivalent) in 1,4-dioxane (20 mL/mmol) is stirred and purged with N$_2$ three times at RT. Then Pd(dppf)Cl$_2$·DCM (10 mol %) is quickly added under a N$_2$ atmosphere to the reaction mixture, followed by additional purging with N$_2$ (×3) and the resulting mixture is stirred at 120° C. for overnight. Next, the reaction mixture is cooled to RT and then quenched with water (20 mL/mmol). The resulting mixture is extracted with EA (20 mL/mmol×3), and the organic phases are dried over anhydrous Na$_2$SO$_4$ and filtered and concentrated in vacuo. The resulting residue is purified by silica gel column chromatography or preparative-TLC to afford the coupled ring system.

General Procedure E: Preparation of Heteroaryl Nitriles Using Pd Catalyzed Cross Coupling Between an Organohalide and Dicyanozinc.

A solution of organohalide (1.0 equivalent), Pd$_2$(dba)$_3$ (5 mol %), dppf (10 mol %), and Zn(CN)$_2$ (2.0 equivalents) in DMF (5 mL/mmol) is stirred at 120° C. under N$_2$ overnight, then cooled to RT and filtered. The filtrate is concentrated in vacuo and the residue is purified by column chromatography on silica gel to afford the heteroaryl nitrile.

General Procedure F: Preparation of Heteroaryl Amines Using Hydrogenation of Nitriles A suspension of heteroaryl nitrile (1.0 equivalent) and 10% Pd/C (25 mg/mmol) in MeOH (5 mL/mmol) in the presence of 6N HCl (1.25 mL/mmol) is stirred at RT for 12 h under a H$_2$ atmosphere. The reaction mixture is filtered through celite and washed with MeOH (5 mL/mmol). The filtrate is concentrated in vacuo to afford the heteroaryl amine as the HCl salt. This is used in the next step without purification.

General Procedure G: Preparation of Pyrimidino Amido Ester Using Amino Coupling of Ethyl Oxalyl Chloride To a solution of amine hydrochloride (1.0 equivalent) in DCM (4 mL/mmol) is added Et$_3$N (4.0 equivalents), followed by the addition of ethyl 2-chloro-2-oxoacetate (1.5 equivalents). The reaction mixture is stirred for 2 hours, diluted with DCM (8 mL/mmol), washed with brine (4 mL/mmol), separated and dried over anhydrous Na$_2$SO$_4$ and filtered. The filtrate is concentrated in vacuo and the residue is purified by silica gel chromatography to afford the amido ester.

General Procedure H: Preparation of Imidazo[1,5-b]Pyridazines Using Intramolecular Condensation of Pyrimidino Amido Ester To a suspension of pyrimidino amido ester (1.0 equivalent) in 1,2-dichloroethane (10 mL/mmol) was added POCl$_3$ (3.0 equivalents). The reaction mixture is stirred at 70° C. for 24 h, then cooled to RT, and poured into ice water (5 mL/mmol). The resulting mixture is separated, and the aqueous phase is extracted with DCM (5 mL/mmol×3). The combined organic phases are washed with saturated NaHCO$_3$ (10 mL/mmol) and brine (10 mL/mmol), dried over anhydrous Na$_2$SO$_4$ and filtered. The filtrate is concentrated in vacuo, and the resulting residue is purified by silica gel chromatography to afford the imidazo[1,5-b]pyridazine.

Part II—Preparation of Specific Carboxylic Acid Compounds

Exemplary procedures for preparing specific carboxylic acid compounds useful in the preparation of certain substituted carboxamide compounds are provided below.

6,8-Dimethylimidazo[1,2-b]pyridazine-3-carboxylic acid

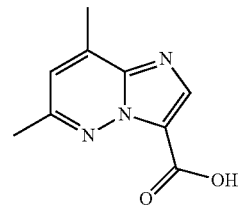

To a solution of 4H-1,2,4-triazol-4-amine (5 g, 60 mmol) in anhydrous toluene (25 mL) was added 2,4-pentanedione (7.1 g, 60 mmol) and p-TsOH (1.0 g, 6.0 mmol) and the mixture was heated at reflux for 16 h in a Dean Stark trap. Once the reaction was complete, the resulting yellow, transparent solution was cooled to RT and concentrated in vacuo. The resulting crude oil was dissolved in DCM and washed with saturated NaHCO$_3$ solution. The organic layer was isolated, dried over anhydrous Na$_2$SO$_4$ and filtered. The filtrate was concentrated in vacuo and the crude was purified by silica gel column chromatography (DCM/MeOH, 20:1 v/v) to give 6,8-dimethyl-[1,2,4]triazolo[4,3-b]pyridazine (7.0 g, 80%) as a yellow solid; LC-MS m/z: 149.1 [M+H]$^+$.

To a solution of 6,8-dimethyl-[1,2,4]triazolo[4,3-b]pyridazine (6.0 g, 40.5 mmol) in nitromethane (35 mL) was added bromoacetophenone (8.1 g, 40.5 mmol). The reaction mixture was heated at reflux under an inert atmosphere for 2.5 h. Then, the reaction mixture was allowed to cool and next concentrated in vacuo to afford a red sticky oil, which was purified by silica gel column chromatography (DCM/MeOH, 7:1 (v/v)) to afford 6,8-dimethyl-2-(2-oxo-2-phenylethyl)-[1,2,4]triazolo[4,3-b]pyridazin-2-ium bromide (6.0 g, 75%) as orange crystals; LC-MS m/z: 268.1 [M+H]$^+$.

A solution of 6,8-dimethyl-2-(2-oxo-2-phenylethyl)-[1,2,4]triazolo[4,3-b]pyridazin-2-ium bromide (5.0 g, 14.4 mmol) in 20% aqueous NaOH solution (72.0 mmol) was heated at reflux for 16 h. Then, the reaction mixture was concentrated in vacuo and the residue was purified by silica gel column chromatography (DCM/MeOH, 10:1 (v/v)) to afford 4,6-dimethylpyridazin-3-amine (1.7 g, 96%) as a pale brown powder; LC-MS m/z: 124.1 [M+H]$^+$.

To a suspension of 4,6-dimethylpyridazin-3-amine (1.23 g, 10.0 mmol) in 10 mL of EtOH was added DIPEA (12.9 g, 100 mmol) and ethyl 2-chloro-3-oxopropanoate (3.00 g, 20.0 mmol). The reaction mixture was stirred at 75° C. for 16 h, cooled to RT, and concentrated in vacuo. The resulting residue was partitioned between EtOAc and water, and the organic layer was separated, washed with brine (20 mL), dried over MgSO$_4$, filtered, and concentrated in vacuo. The resulting residual brown solid was purified on a silica gel flash chromatography column (EA/PE; 1:1) to give ethyl 6,8-dimethylimidazo[1,2-b]pyridazine-3-carboxylate (300 mg, 14%) as a yellow solid. $^1$H NMR (500 MHz, CDCl$_3$): δ 8.27 (s, 1H), 9.40 (s, 1H), 4.47 (q, J=9.0 Hz, 2H), 2.66 (s, 6H), 1.45 (t, J=9.0 Hz, 3H). LC-MS m/z: 220.1 [M+H]$^+$ Following general procedure B, ethyl 6,8-dimethylimidazo[1,2-b]pyridazine-3-carboxylate (180 mg, 0.82 mmol) afforded the tile compound (154 mg, 98%) as a yellow solid. LC-MS m/z: 220.1 [M+H]$^+$.

6-Chloro-8-methylimidazo[1,2-b]pyridazine-3-carboxylic acid

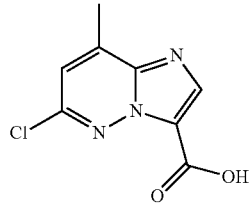

To a solution of 3,6-dichloro-4-methylpyridazine (3.0 g, 18.4 mmol) in MeOH (20 mL) was added NH$_3$/MeOH (20 mL). The reaction mixture was heated at 120° C. in a sealed tube for 12 h. Then, the reaction mixture was cooled to RT and concentrated in vacuo. The resulting residue was recrystallized in EtOH to give a mixture of 6-chloro-4-methylpyridazin-3-amine and 6-chloro-5-methylpyridazin-3-amine (2.4 g, 89%) as a yellow solid. LC-MS m/z: 144.1 [M+H]$^+$.

A suspension of a mixture of 6-chloro-4-methylpyridazin-3-amine and 6-chloro-5-methylpyridazin-3-amine (1.5 g, 10.5 mmol) in DMF-DMA (20 mL) was stirred at reflux for 5 h. The reaction mixture was concentrated in vacuo to give a mixture of (E)-N-(6-chloro-5-methylpyridazin-3-yl)-N,N-dimethylformimidamide and (E)-N-(6-chloro-4-methylpyridazin-3-yl)-N,N-dimethylformimidamide, which was used directly in the next step. LC-MS m/z: 179.1 [M+H]$^+$.

To a mixture of (E)-N-(6-chloro-5-methylpyridazin-3-yl)-N,N-dimethylformimidamide and (E)-N-(6-chloro-4-methylpyridazin-3-yl)-N,N-dimethylformimidamide in CH$_3$CN (20 mL) was added ethylbromoacetate (3.5 g, 21.0 mmol) and the mixture was refluxed for 18 h. The reaction mixture was concentrated in vacuo and the residue was dissolved in MeCN (20 mL) followed by the addition of DIPEA (2.7 g, 21.0 mmol) at 0° C. Then, the reaction mixture was stirred at RT for 3 h, concentrated in vacuo, and the residue filtered through a silica gel pad using DCM. The filtrate was concentrated in vacuo, and the resulting residue was purified by flash column chromatography on silica gel (pet ether/EtOAc, 2:1) to give ethyl 6-chloro-8-methylimidazo[1,2-b]pyridazine-3-carboxylate as a pale yellow solid (80 mg) and ethyl 6-chloro-7-methylimidazo[1,2-b]pyridazine-3-carboxylate as a yellow solid (600 mg).

Ethyl 6-chloro-8-methylimidazo[1,2-b]pyridazine-3-carboxylate: $^1$H NMR (500 MHz, CDCl$_3$): δ 8.31 (s, 1H), 7.10 (s, 1H), 4.48 (q, J=7.0 Hz, 2H), 2.71 (s, 3H), 1.45 (t, J=7.0 Hz, 3H). LC-MS m/z: 240.1 [M+H]$^+$.

Ethyl 6-chloro-7-methylimidazo[1,2-b]pyridazine-3-carboxylate: $^1$H NMR (500 MHz, CDCl$_3$): δ 8.31 (s, 1H), 7.87 (s, 1H), 4.47 (q, J=7.0 Hz, 2H), 2.51 (s, 3H), 1.44 (t, J=7.0 Hz, 3H). LC-MS m/z: 240.1 [M+H]$^+$.

Following general procedure B, ethyl 6-chloro-8-methylimidazo[1,2-b]pyridazine-3-carboxylate (80 mg, 0.33 mmol) afforded the title compound (60 mg, 80%) as a yellow solid. LC-MS m/z: 212.1 [M+H]$^+$.

6-Chloro-7-methylimidazo[1,2-b]pyridazine-3-carboxylic acid

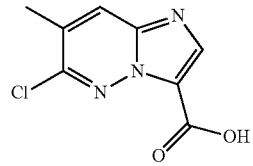

Following general procedure B, ethyl 6-chloro-7-methylimidazo[1,2-b]pyridazine-3-carboxylate (160 mg, 0.67 mmol) afforded the title compound (130 mg, 93%) as a yellow solid. LC-MS m/z: 212.1 [M+H]$^+$.

2,4-Dimethylimidazo[1,5-b]pyridazine-7-carboxylic acid

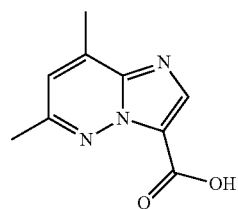

Following general procedure E, 3-chloro-4,6-dimethylpyridazine (400 mg, 2.81 mmol) afforded 4,6-dimethylpyridazine-3-carbonitrile (342 mg, 91%) as a pale yellow solid. LC-MS m/z: 134.3 [M+H]$^+$. LCMS: $t_R$=1.40 min. Purity (254 nm): >99%.

Following general procedure F, 4,6-dimethylpyridazine-3-carbonitrile (342 mg, 2.57 mmol) afforded (4,6-dimethylpyridazin-3-yl)methanamine hydrochloride (400 mg) as a dark brown solid which was used directly in the next step. LC-MS m/z: 138.3 [M+H]$^+$. LCMS: $t_R$=0.31 min.

Following general procedure G, (4,6-dimethylpyridazin-3-yl)methanamine hydrochloride (400 mg) afforded ethyl 2-(((4,6-dimethylpyridazin-3-yl)methyl)amino)-2-oxoacetate (580 mg, 95% over two steps) as a pale yellow solid. LC-MS m/z: 238.2 [M+H]$^+$. LCMS: $t_R$=1.44 min. Purity (254 nm): >99%.

Following general procedure H, ethyl 2-(((4,6-dimethylpyridazin-3-yl)methyl)amino)-2-oxoacetate (580 mg, 2.44 mmol) afforded ethyl 2,4-dimethylimidazo[1,5-b]pyridazine-7-carboxylate (530 mg, 96%) as a pale white solid. $^1$H NMR (500 MHz, DMSO-d$_6$) δ 7.60 (s, 1H), 6.57 (d, J=1.5 Hz, 1H), 4.52 (q, J=7.0 Hz, 2H), 2.60 (s, 3H), 2.53 (s, 3H), 1.48 (t, J=7.0 Hz, 3H). LC-MS m/z: 220.2 [M+H]$^+$. LCMS: Purity (214 nm): >99%; $t_R$=1.63 min.

Following general procedure B, ethyl 2,4-dimethylimidazo[1,5-b]pyridazine-7-carboxylate (410 mg, 1.87 mmol) afforded the title compound (215 mg, 70%) as a pale white solid. $^1$H NMR (500 MHz, DMSO-d$_6$) δ 8.98 (s, 1H), 7.75 (s, 1H), 6.68 (s, 1H), 2.45 (s, 3H), 2.43 (s, 3H). LC-MS m/z: 192.0 [M+H]$^+$. LCMS: Purity (254 nm): 92%; $t_R$=1.03 min.

5,7-Dimethylthieno[3,2-b]pyridine-3-carboxylic acid

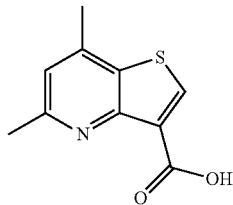

A mixture of dihydrothiophen-3(2H)-one (40 g, 392.1 mmol) and NH₂OH·HCl (40 g, 580 mmol) in MeOH (300 mL) was stirred at RT overnight, poured into water (200 mL) and basified with solid NaHCO₃ to pH ~8. The mixture was extracted with EA (300 mL×4), dried over anhydrous Na₂SO₄ and filtered. The filtrate was concentrated in vacuo, and the resulting residue was purified by silica gel column chromatography (PE/EA=4/1) to afford thiophen-3-amine (15.0 g, 39%) as a black oil. ¹H NMR (500 MHz, CDCl₃): δ 7.15 (dd, J=5.0 Hz, 3.0 Hz, 1H), 6.67 (dd, J=5.0 Hz, 3.0 Hz, 1H), 6.19 (dd, J=5.0 Hz, 3.0 Hz, 1H), 3.63 (brs, 2H).

A mixture of thiophen-3-amine (15 g, 150 mmol), pentane-2,4-dione (15 g, 151 mmol) and ZnCl₂/Et₂O (1 mol/L, 15 mL, 15.0 mmol) in EtOH (150 mL) was stirred under reflux overnight. Then, the mixture was concentrated and the resulting residue was purified by silica gel column chromatography (EA/PE=10 to 100%) to afford a mixture of 4-(thiophen-3-ylimino)pentan-2-one and 5,7-dimethylthieno[3,2-b]pyridine (16 g) as a black oil. LC-MS m/z: 182.0 [M+H]⁺. $t_R$=1.70 min.

A mixture of 4-(thiophen-3-ylimino)pentan-2-one and 5,7-dimethylthieno[3,2-b]pyridine (10 g, crude) in H₃PO₄ (20 mL) was stirred overnight at 90° C. The reaction was quenched by the addition of H₂O (200 mL) and the reaction mixture was neutralized with solid NaOH until pH>8. The mixture was then extracted with EA (300 mL×3), dried over anhydrous Na₂SO₄ and filtered. The filtrate was concentrated in vacuo, and the resulting residue was purified by silica gel column chromatography (PE/EA=9/1) to afford 5,7-dimethylthieno[3,2-b]pyridine (5.2 g, 53%) as a red-brown oil. ¹H NMR (500 MHz, CDCl₃): δ 7.69 (d, J=5.5 Hz, 1H), 7.52 (d, J=5.5 Hz, 1H), 6.98 (s, 1H), 2.66 (s, 3H), 2.58 (s, 3H). LC-MS m/z: 164.1 [M+H]⁺. $t_R$=1.10 min.

To a mixture of 5,7-dimethylthieno[3,2-b]pyridine (4.2 g, 25.7 mmol), NaHCO₃ (2.16 g, 25.7 mmol), K₂HPO₄ (6.72 g, 38.6 mmol), and MgSO₄ (4.0 g, 33.4 mmol) in CHCl₃ (100 mL) under N₂ was added a solution of Br₂ (4.93 g, 30.8 mmol) in CHCl₃ (10 ml) dropwise under reflux. After the addition was complete the mixture was quenched with saturated NaHCO₃, extracted with DCM (150 mL×3) and dried over anhydrous Na₂SO₄ and filtered. The filtrate was concentrated in vacuo, and the resulting residue was purified by silica gel column chromatography (PE/EA=25/1 to 4/1) to afford 3-bromo-5,7-dimethylthieno[3,2-b]pyridine (3.2 g, 52%) as a light yellow solid. LC-MS m/z: 241.9 [M+H]⁺. $t_R$=1.76 min.

A mixture of 3-bromo-5,7-dimethylthieno[3,2-b]pyridine (2.06 g, 8.54 mmol), Pd(dppf)Cl₂·DCM (697 mg, 0.85 mmol) and Et₃N (2.59 g, 25.62 mmol) in CH₃OH (150 mL) was stirred at 80° C. under CO (10 atm) for 20 h. The mixture was concentrated and the resulting residue was purified by silica gel column chromatography (PE/EA=9/1 to 4/1) to afford methyl 5,7-dimethylthieno[3,2-b]pyridine-3-carboxylate (1.1 g, 58%) as a yellow oil. ¹H NMR (500 MHz, CDCl₃): δ 8.56 (s, 1H), 7.06 (s, 1H), 4.00 (s, 3H), 2.76 (s, 3H), 2.58 (s, 3H). LC-MS m/z: 222.1 [M+H]⁺. $t_R$=1.61 min.

Following general procedure B, methyl 5,7-dimethylthieno[3,2-b]pyridine-3-carboxylate (1.0 g, 4.52 mmol) afforded 5,7-dimethylthieno[3,2-b]pyridine-3-carboxylic acid (500 mg, 53%) as a yellow solid. ¹H NMR (500 MHz, DMSO-d₆): δ 9.14 (s, 1H), 7.61 (s, 1H), 2.79 (s, 3H), 2.71 (s, 3H). LC-MS m/z: 207.9 [M+H]⁺. $t_R$=1.17 min.

Part III—Compounds Prepared Following General Procedures

The following compounds were prepared based on the general procedures described in Part I above.

6,8-Dimethyl-N-((1S,4S)-4-(pentyloxy) cyclohexyl) imidazo[1,2-b]pyridazine-3-carboxamide

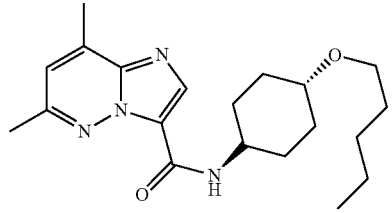

Following general procedure A, 6,8-dimethylimidazo[1,2-b]pyridazine-3-carboxylic acid (30 mg, 0.16 mmol) and (1R,4R)-4-(pentyloxy)cyclohexan-1-amine afforded the title compound (40 mg, 71%) as a white solid. ¹H NMR (500 MHz, CDCl₃): δ 8.70 (d, J=7.5 Hz, 1H), 8.38 (s, 1H), 6.90 (d, J=0.5 Hz, 1H), 4.09-4.06 (m, 1H), 3.46 (t, J=6.5 Hz, 2H), 3.33-3.31 (m, 1H), 2.67 (s, 3H), 2.61 (s, 3H), 2.21-2.18 (m, 2H), 2.08-2.05 (m, 2H), 1.62-1.32 (m, 10H), 0.92 (1, J=6.5 Hz, 3H). LC-MS m/z: 359.2 [M+H]⁺. HPLC Purity (214 nm): >99%; $t_R$=9.11 min.

6,8-Dimethyl-N-(4-(oxazol-4-yl)phenyl)imidazo[1,2-b]pyridazine-3-carboxamide

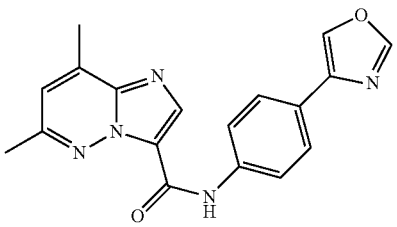 [SMILES: Cc1cc(C)c2ncc(C(=O)Nc3ccc(-c4cocn4)cc3)n2n1]

Following general procedure A, 6,8-dimethylimidazo[1,2-b]pyridazine-3-carboxylic acid (30 mg, 0.16 mmol) and 4-(oxazol-4-yl)aniline afforded the title compound (52 mg, 95%) as a yellow solid. ¹H NMR (500 MHz, DMSO-d₆): δ 10.79 (s, 1H), 8.61 (s, 1H), 8.47 (s, 1H), 8.32 (s, 1H), 7.86 (d, J=8.5 Hz, 1H), 7.82 (d, J=9.0 Hz, 1H), 7.30 (s, 1H), 2.69 (s, 3H), 2.60 (s, 3H). LC-MS m/z: 334.1 [M+H]⁺. HPLC Purity (214 nm): >92%; $t_R$=7.12 min.

N-(2,3-Dihydro-1H-inden-5-yl)-6,8-dimethylimidazo[1,2-b]pyridazine-3-carboxamide

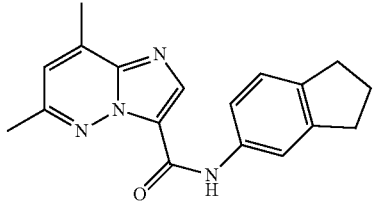 [SMILES: Cc1cc(C)c2ncc(C(=O)Nc3ccc4c(c3)CCC4)n2n1]

Following general procedure A, 6,8-dimethylimidazo[1,2-b]pyridazine-3-carboxylic acid (30 mg, 0.16 mmol) and 2,3-dihydro-1H-inden-5-amine afforded the title compound (44 mg, 91%) as a white solid. $^1$H NMR (500 MHz, DMSO-$d_6$): δ 10.65 (s, 1H), 8.28 (s, 1H), 7.67 (s, 1H), 7.49 (d, J=10.0 Hz, 1H), 7.29 (s, 1H), 7.23 (d, J=10.0 Hz, 1H), 2.89 (t, J=9.0 Hz, 2H), 2.84 (t, J=9.0 Hz, 2H), 2.67 (s, 3H), 2.60 (s, 3H), 2.07-2.00 (m, 2H). LC-MS m/z: 307.3 [M+H]$^+$. HPLC Purity (214 nm): >99%; $t_R$=8.77 min.

6,8-Dimethyl-N-(1,2,3,4-tetrahydronaphthalen-1-yl)imidazo[1,2-b]pyridazine-3-carboxamide

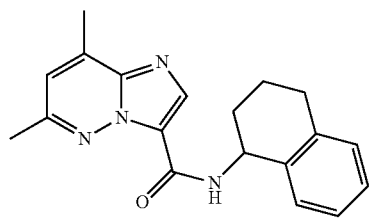 [SMILES: Cc1cc(C)c2ncc(C(=O)NC3CCCc4ccccc43)n2n1]

Following general procedure A, 6,8-dimethylimidazo[1,2-b]pyridazine-3-carboxylic acid (30 mg, 0.16 mmol) and 1,2,3,4-tetrahydronaphthalen-1-amine afforded the title compound (41 mg, 82%) as a white solid. $^1$H NMR (500 MHz, CDCl$_3$): δ 9.09 (d, J=8.5 Hz, 1H), 8.44 (s, 1H), 7.47 (d, J=7.0 Hz, 1H), 7.21-7.14 (m, 3H), 6.87 (d, J=0.5 Hz, 1H), 5.53-5.49 (m, 1H), 2.93-2.83 (m, 2H), 2.67 (s, 3H), 2.45 (s, 3H), 2.28-2.23 (m, 1H), 1.98-1.94 (m, 3H). LC-MS m/z: 321.2 [M+H]$^+$. HPLC Purity (214 nm): >99%; $t_R$=8.15 min.

6,8-Dimethyl-N-(1-phenylpropyl)imidazo[1,2-b]pyridazine-3-carboxamide

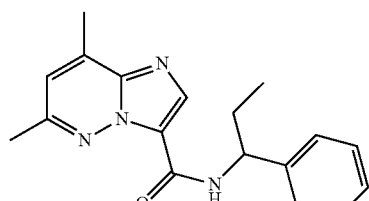

Following general procedure A, 6,8-dimethylimidazo[1,2-b]pyridazine-3-carboxylic acid (30 mg, 0.16 mmol) and 1-phenylpropan-1-amine afforded the title compound (34 mg, 68%) as a white solid. $^1$H NMR (500 MHz, CDCl$_3$): δ 9.24 (d, J=8.0 Hz, 1H), 8.37 (s, 1H), 7.41-7.34 (m, 4H), 7.26-7.25 (m, 1H), 6.91 (d, J=1.0 Hz, 1H), 5.20 (q, J=7.5 Hz, 1H), 2.67 (s, 3H), 2.63 (s, 3H), 2.06-1.94 (m, 2H), 1.00 (t, J=7.5 Hz, 3H). LC-MS m/z: 309.2 [M+H]$^+$. HPLC Purity (214 nm): >98%; $t_R$=7.97 min.

6,8-Dimethyl-N-(1-methyl-1,2,3,4-tetrahydronaphthalen-1-yl)imidazo[1,2-b]pyridazine-3-carboxamide

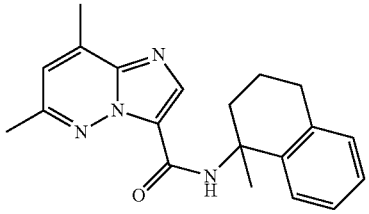 [SMILES: Cc1cc(C)c2ncc(C(=O)NC3(C)CCCc4ccccc43)n2n1]

Following general procedure A, 6,8-dimethylimidazo[1,2-b]pyridazine-3-carboxylic acid (40 mg, 0.21 mmol) and 1-methyl-1,2,3,4-tetrahydronaphthalen-1-amine afforded the title compound (5.4 mg, 8%) as a yellow solid. $^1$H NMR (500 MHz, CDCl$_3$): δ 9.19 (s, 1H), 8.32 (d, J=4.0 Hz, 1H), 7.59 (d, J=7.5 Hz, 1H), 7.24-7.17 (m, 2H), 7.13 (d, J=8.0 Hz, 1H), 6.85 (d, J=1.0 Hz, 1H), 2.93-2.74 (m, 3H), 2.66 (s, 3H), 2.47 (s, 3H), 2.17-2.13 (m, 1H), 1.97-1.92 (m, 2H), 1.90 (s, 3H). LC-MS m/z: 335.2 [M+H]$^+$. HPLC Purity (214 nm): >97%; $t_R$=9.26 min.

N-(4-Ethynylphenyl)-6,8-dimethylimidazo[1,2-b]pyridazine-3-carboxamide

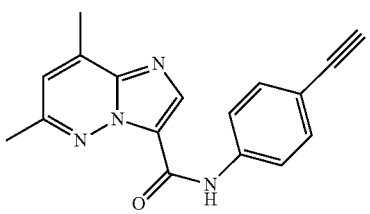 [SMILES: C#Cc1ccc(NC(=O)c2cnc3c(C)cc(C)nn23)cc1]

Following general procedure A, 6,8-dimethylimidazo[1,2-b]pyridazine-3-carboxylic acid (40 mg, 0.21 mmol) and 4-ethynylaniline afforded the title compound (6.0 mg, 10%) as a yellow solid. $^1$H NMR (500 MHz, CDCl$_3$): δ 10.87 (s, 1H), 8.50 (s, 1H), 7.74 (d, J=8.5 Hz, 2H), 7.53 (d, J=9.0 Hz, 2H), 6.98 (s, 1H), 3.07 (s, 1H), 2.72 (s, 3H), 2.71 (s, 3H). LC-MS m/z: 291.1 [M+H]$^+$. HPLC Purity (214 nm): >98%; $t_R$=8.45 min.

6-Chloro-N-((1S,4S)-4-(hexyloxy)cyclohexyl)-8-methylimidazo[1,2-b]pyridazine-3-carboxamide

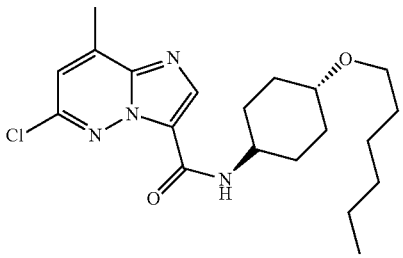

Following general procedure A, 6-chloro-8-methylimidazo[1,2-b]pyridazine-3-carboxylic acid (30 mg, 0.14 mmol) and (1R,4R)-4-(hexyloxy)cyclohexan-1-amine afforded the title compound (13.5 mg, 24%) as a yellow solid. $^1$H NMR (500 MHz, CDCl$_3$): δ 8.43 (s, 1H), 8.21 (d, J=8.0 Hz, 1H), 7.07 (d, J=1.0 Hz, 1H), 4.08-4.06 (m, 1H), 3.46 (t, J=13.5 Hz, 2H), 3.34-3.31 (m, 1H), 2.73 (s, 3H), 2.20-2.17 (m, 2H), 2.08-2.05 (m, 2H), 1.33-1.28 (m, 12H), 0.91 (t, J=13.0 Hz, 3H). LC-MS m/z: 393.3 [M+H]$^+$. HPLC Purity (214 nm): >99%; t$_R$=11.75 min.

6-Chloro-N-(2,3-dihydro-1H-inden-5-yl)-8-methylimidazo[1,2-b]pyridazine-3-carboxamide

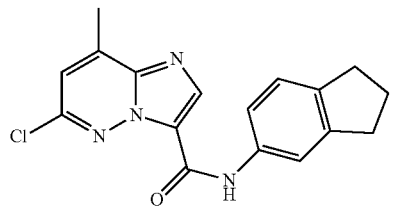 [SMILES: Cc1cc(Cl)nn2c(C(=O)Nc3ccc4c(c3)CCC4)cnc12]

Following general procedure A, 6-chloro-8-methylimidazo[1,2-b]pyridazine-3-carboxylic acid (21 mg, 0.10 mmol) and 2,3-dihydro-1H-inden-5-amine afforded the title compound (20 mg, 63%) as a white solid. $^1$H NMR (500 MHz, CDCl$_3$): δ 10.14 (s, 1H), 8.53 (s, 1H), 7.68 (s, 1H), 7.43 (d, J=8.0 Hz, 1H), 7.23 (d, J=8.0 Hz, 1H), 7.12 (s, 1H), 2.97 (t, J=7.5 Hz, 2H), 2.92 (t, J=7.5 Hz, 2H), 2.76 (s, 1H), 2.12-2.09 (m, 2H). LC-MS m/z: 323.2 [M+H]$^+$. HPLC Purity (214 nm): >95%; t$_R$=10.90 min.

6-Chloro-7-methyl-N-((1S,4S)-4-(pentyloxy)cyclohexyl)imidazo[1,2-b]pyridazine-3-carboxamide

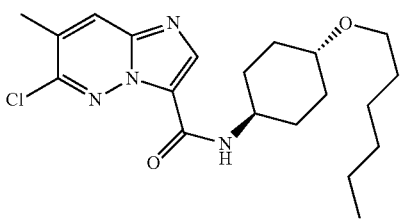 [SMILES: CCCCCCO[C@H]1CC[C@H](NC(=O)c2cnc3cc(C)c(Cl)nn23)CC1]

Following general procedure A, 6-chloro-7-methylimidazo[1,2-b]pyridazine-3-carboxylic acid (40 mg, 0.18 mmol) and (1R,4R)-4-(pentyloxy)cyclohexan-1-amine afforded the title compound (51 mg, 710%) as a white solid. $^1$H NMR (500 MHz, CDCl$_3$): δ 8.42 (s, 1H), 8.12 (d, J=7.5 Hz, 1H), 7.92 (d, J=1.0 Hz, 1H), 4.08-4.07 (m, 1H), 3.46 (t, J=13.5 Hz, 2H), 3.33-3.32 (m, 1H), 2.52 (s, 3H), 2.19-2.17 (m, 2H), 2.07-2.05 (m, 2H), 1.59-1.33 (m, 10H), 0.91 (t, J=7.0 Hz, 3H). LC-MS m/z: 379.3 [M+H]$^+$. HPLC Purity (214 nm): >98%; t$_R$=11.4 min.

6-Chloro-N-(2,3-dihydro-1H-inden-5-yl)-7-methylimidazo[1,2-b]pyridazine-3-carboxamide

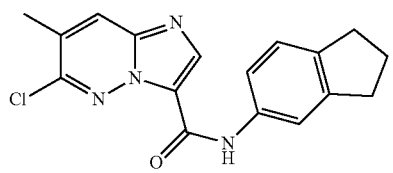 [SMILES: Cc1cc2ncc(C(=O)Nc3ccc4c(c3)CCC4)n2nc1Cl]

Following general procedure A, 6-chloro-7-methylimidazo[1,2-b]pyridazine-3-carboxylic acid (50 mg, 0.24 mmol) and 2,3-dihydro-1H-inden-5-amine afforded the title compound (30 mg, 39%) as a white solid. $^1$H NMR (500 MHz, MeOD-d$_4$): δ 10.05 (s, 1H), 8.53 (s, 1H), 7.97 (d, J=0.5 Hz, 1H), 7.69 (s, 1H), 7.44 (d, J=8.0 Hz, 1H), 7.24 (d, J=8.0 Hz, 1H), 2.96 (t, J=15.0 Hz, 2H), 2.91 (t, J=15.0 Hz, 2H), 2.56 (s, 3H), 2.12-2.09 (m, 2H). LC-MS m/z: 327.1 [M+H]$^+$. HPLC Purity (254 nm): >99%; t$_R$=10.8 min.

6-Chloro-7-methyl-N-(1,2,3,4-tetrahydronaphthalen-1-yl)imidazo[1,2-b]pyridazine-3-carboxamide

Following general procedure A, 6-chloro-7-methylimidazo[1,2-b]pyridazine-3-carboxylic acid (30 mg, 0.14 mmol) and 1,2,3,4-tetrahydronaphthalen-1-amine afforded the title compound (32 mg, 67%) as a white solid. $^1$H NMR (500 MHz, CDCl$_3$): δ 8.50 (d, J=9.5 Hz, 2H), 7.91 (d, J=1.0 Hz, 1H), 7.46 (d, J=7.0 Hz, 1H), 7.19-7.14 (m, 3H), 5.53-7.51 (m, 1H), 2.92-2.85 (m, 2H), 2.49 (s, 3H), 2.25-2.24 (m, 1H), 2.00-1.94 (m, 3H). LC-MS m/z: 341.2 [M+H]$^+$. HPLC Purity (214 nm): >99%; t$_R$=10.25 min.

6-Chloro-7-methyl-N-(1-phenylpropyl)imidazo[1,2-b]pyridazine-3-carboxamide

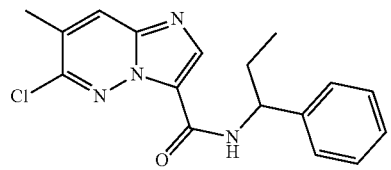 [SMILES: CCC(NC(=O)c1cnc2cc(C)c(Cl)nn12)c1ccccc1]

Following general procedure A, 6-chloro-7-methylimidazo[1,2-b]pyridazine-3-carboxylic acid (40 mg, 0.18 mmol) and -phenylpropan-1-amine afforded the title compound (30 mg, 64%) as a white solid. $^1$H NMR (500 MHz, CDCl$_3$): δ 8.67 (d, J=8.0 Hz, 1H), 8.41 (s, 1H), 7.93 (g, J=1.0 Hz, 1H), 7.41-7.25 (m, 5H), 5.20 (q, J=7.5 Hz, 1H), 2.52 (s, 3H), 2.04-1.96 (m, 2H), 0.99 (t, J=14.5 Hz, 3H). LC-MS m/z: 329.2 [M+H]$^+$. HPLC Purity (214 nm): >99%; t$_R$=10.22 min.

6-Chloro-N-(2,3-dihydro-1H-inden-5-yl)imidazo[1,2-b]pyridazine-3-carboxamide

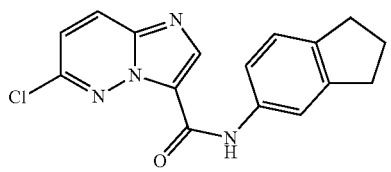 [SMILES: O=C(Nc1ccc2c(c1)CCC2)c1cnc2ccc(Cl)nn12]

Following general procedure A, 6-chloroimidazo[1,2-b]pyridazine-3-carboxylic acid (38 mg, 0.19 mmol), and 2,3-dihydro-1H-inden-5-amine afforded the title compound (29 mg, 49%) as an off-white solid. $^1$H NMR (500 MHz, DMSO-d$_6$): δ 10.21 (s, 1H), 8.44-8.42 (m, 2H), 7.65-7.63 (m, 2H), 7.44 (dd, J=8.0, 1.5 Hz, 1H), 7.24 (d, J=8.0 Hz, 1H), 2.89 (t, J=7.5 Hz, 2H), 2.85 (t, J=7.5 Hz, 2H), 2.07-2.03 (m, 2H). LC-MS m/z: 313.1 [M+H]$^+$. HPLC Purity (214 nm): >95%; t$_R$=8.77 min.

6-Chloro-N-(1,2,3,4-tetrahydronaphthalen-1-yl)imidazo[1,2-b]pyridazine-3-carboxamide

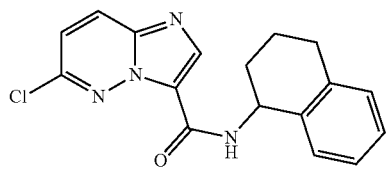 [SMILES: O=C(NC1CCCc2ccccc21)c1cnc2ccc(Cl)nn12]

Following general procedure A, 6-chloroimidazo[1,2-b]pyridazine-3-carboxylic acid (38 mg, 0.19 mmol) and 1,2,3,4-tetrahydronaphthalen-1-amine afforded the title compound (42 mg, 66%) as a light yellow solid. $^1$H NMR (500 MHz, DMSO-d$_6$): δ 8.64 (d, J=8.5 Hz, 1H), 8.39 (d, J=10.0 Hz, 1H), 8.36 (s, 1H), 7.57 (d, J=9.0 Hz, 1H), 7.36 (d, J=7.0 Hz, 1H), 7.21-7.14 (m, 3H), 5.30-5.26 (m, 1H), 2.87-2.76 (m, 2H), 2.12-2.08 (m, 1H), 1.92-1.84 (m, 3H). LC-MS m/z: 327.1 [M+H]$^+$. HPLC Purity (214 min): >99%; t$_R$=8.16 min.

6-Chloro-N-(4-ethynylphenyl)imidazo[1,2-b]pyridazine-3-carboxamide

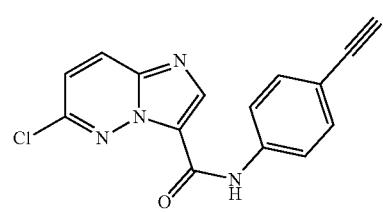 [SMILES: C#Cc1ccc(NC(=O)c2cnc3ccc(Cl)nn23)cc1]

Following general procedure A, 6-chloroimidazo[1,2-b]pyridazine-3-carboxylic acid (40 mg, 0.20 mmol) and 4-ethynylaniline afforded the compound (13 mg, 22%) as a yellow solid. $^1$H NMR (500 MHz, DMSO-d$_6$): δ 10.45 (s, 1H), 8.47 (s, 1H), 8.43 (d, J=9.5 Hz, 1H), 7.77 (d, J=9.0 Hz, 2H), 7.64 (d, J=9.5 Hz, 1H), 7.52 (d, J=9.0 Hz, 2H), 4.15 (s, 1H). LC-MS m/z: 297.1 [M+H]$^+$. HPLC Purity (214 nm): 95%; t$_R$=7.82 min.

(S)—N-(1-Cyclopropylethyl)-6,8-dimethylimidazo[1,2-b]pyridazine-3-carboxamide

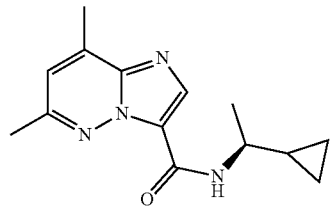 [SMILES: Cc1cc(C)c2ncc(C(=O)N[C@@H](C)C3CC3)n2n1]

Following general procedure A, 6,8-dimethylimidazo[1,2-b]pyridazine-3-carboxylic acid (30 mg, 0.14 mmol) and (S)-1-cyclopropylethanamine afforded the title compound (3.3 mg, 8%) as a yellow solid. $^1$H NMR (500 MHz, CDCl$_3$): δ 8.75 (brs, 1H), 8.38 (s, 1H), 6.90 (s, 1H), 3.81-3.76 (m, 1H), 2.68 (s, 3H), 2.63 (s, 3H), 1.36 (d, J=6.5 Hz, 1H), 1.03-0.99 (m, 1H), 0.58-0.45 (m, 3H), 0.35-0.31 (m, 1H). LC-MS m/z: 259.2 [M+H]$^+$. HPLC Purity (214 nm): >99%; t$_R$=8.93 min.

N-(2-Cyclopropylpropan-2-yl)-6,8-dimethylimidazo[1,2-b]pyridazine-3-carboxamide

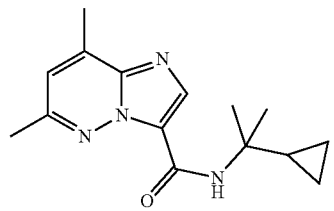 [SMILES: Cc1cc(C)c2ncc(C(=O)NC(C)(C)C3CC3)n2n1]

Following general procedure A, 6,8-dimethylimidazo[1,2-b]pyridazine-3-carboxylic acid (30 mg, 0.14 mmol) and 2-cyclopropylpropan-2-amine afforded the title compound (2.9 mg, 7%) as a light yellow solid. $^1$H NMR (500 MHz, CDCl$_3$): δ 8.80 (s, 1H), 8.35 (d, J=1.0 Hz, 1H), 6.89 (s, 1H), 2.68 (s, 3H), 2.61 (s, 3H), 1.46 (s, 6H), 1.40-1.34 (m, 1H), 0.55-0.50 (m, 4H). LC-MS m/z: 273.2 [M+H]$^+$. HPLC Purity (214 nm): >99%; t$_R$=7.83 min.

N-(1-Cyclopropyl-2,2,2-trifluoroethyl)-6,8-dimethylimidazo[1,2-b]pyridazine-3-carboxamide

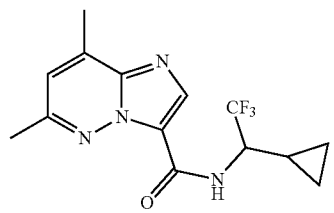 [SMILES: Cc1cc(C)c2ncc(C(=O)NC(C3CC3)C(F)(F)F)n2n1]

Following general procedure A, 6,8-dimethylimidazo[1,2-b]pyridazine-3-carboxylic acid (100 mg, 0.46 mmol) and 1-cyclopropyl-2,2,2-trifluoroethanamine hydrochloride afforded the title compound (65 mg, 45%) as a white solid. $^1$H NMR (500 MHz, DMSO-$d_6$): δ 9.08 (d, J=9.0 Hz, 1H), 8.26 (s, 1H), 7.28 (s, 1H), 4.52-4.43 (m, 1H), 2.60 (s, 3H), 2.59 (s, 3H), 1.35-1.27 (m, 1H), 0.71-0.66 (m, 1H), 0.62-0.58 (m, 2H), 0.40-0.38 (m, 1H). LC-MS m/z: 313.1 [M+H]$^+$. HPLC Purity (214 nm): >99%; $t_R$=7.79 min.

N-(2-Cyclopropylpropan-2-yl)-6-(4-fluorophenyl)-8-methylimidazo[1,2-b]pyridazine-3-carboxamide

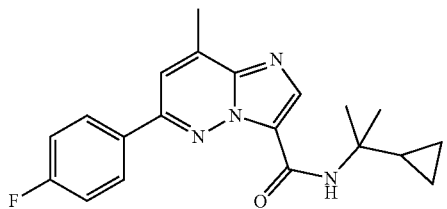 [SMILES: Cc1cc(-c2ccc(F)cc2)nn2c(C(=O)NC(C)(C)C3CC3)cnc12]

Following general procedure C, 3,6-dichloro-4-methylpyridazine (10 g, 61 mmol) and 4-fluorophenylboronic acid afforded 3-chloro-6-(4-fluorophenyl)-4-methylpyridazine (7 g, 51%) as a white solid. LC-MS m/z: 223.2 [M+H]$^+$.

A mixture of 3-chloro-6-(4-fluorophenyl)-4-methylpyridazine (4.9 g, 22 mmol), hydrazine hydrate (5 mL) in i-PrOH (10 mL) was stirred at 120° C. for 2 days in a sealed tube. The mixture was cooled, and concentrated in vacuo. The residue was purified by silica gel column chromatography (DCM/MeOH=10:1) to afford 6-(4-fluorophenyl)-3-hydrazinyl-4-methylpyridazine (3 g, 62%) as a white solid. LC-MS m/z: 219.1 [M+H]$^+$.

A mixture of 6-(4-fluorophenyl)-3-hydrazinyl-4-methylpyridazine (3 g, 13.7 mmol) and Raney nickel (1.3 g) in MeOH (50 mL) was stirred at RT for 2 h under $H_2$, and filtered. The filtrate was concentrated in vacuo to afford crude 6-(4-fluorophenyl)-4-methylpyridazin-3-amine (1.3 g, 48%) as a white solid, which was used directly. LC-MS m/z: 204.2 [M+H]$^+$.

A solution of 6-(4-fluorophenyl)-4-methylpyridazin-3-amine (300 mg, 1.5 mmol) in DMF-DMA (5 mL) was stirred at 100° C. for 4 h, cooled and concentrated in vacuo to afford crude N'-(6-(4-fluorophenyl)-4-methylpyridazin-3-yl)-N,N-dimethylformimidamide (380 mg, 100%) as a white solid, which was used. LC-MS m/z: 259.2 [M+H]$^+$.

A mixture of N'-(6-(4-fluorophenyl)-4-methylpyridazin-3-yl)-N,N-dimethylformimidamide (380 mg, 1.5 mmol), ethyl bromoacetate (500 mg, 3 mmol) and DIPEA (580 mg, 4.5 mmol) in DMF (5 mL) was stirred at 130° C. for 4 h, cooled and diluted with water (50 mL). The mixture was extracted with EA (50 mL×3). The organic layers were dried over anhydrous $Na_2SO_4$ and filtered. The filtrate was concentrated in vacuo, and the residue was purified by prep-TLC plate to afford ethyl 6-(4-fluorophenyl)-8-methylimidazo[1,2-b]pyridazine-3-carboxylate (240 mg, 55%) as a yellow solid. LC-MS m/z: 300.2 [M+H]$^+$.

Following general procedure B, ethyl 6-(4-fluorophenyl)-8-methylimidazo[1,2-b]pyridazine-3-carboxylate (240 mg, 0.8 mmol) afforded 6-(4-fluorophenyl)-8-methylimidazo[1,2-b]pyridazine-3-carboxylic acid (240 mg, 77%) as a yellow solid. LC-MS m/z: 272.1 [M+H]$^+$.

Following general procedure A, 6-(4-fluorophenyl)-8-methylimidazo[1,2-b]pyridazine-3-carboxylic acid (120 mg, 0.44 mmol) and 2-cyclopropylpropan-2-amine afforded the title compound (20 mg, 13%) as a white solid. $^1$H NMR (500 MHz, MeOD-$d_4$) δ 8.30 (s, 1H), 8.11 (dd, J=8.5 Hz, 5.5 Hz, 2H), 7.79 (d, J=1.0 Hz, 1H), 7.34 (t, J=9.0 Hz, 2H), 2.76 (d, J=1.0 Hz, 3H), 1.47 (s, 6H), 1.47-1.41 (m, 1H), 0.54-0.52 (m, 4H). LC-MS m/z: 353.2 [M+H]$^+$. HPLC: Purity (254 nm): 99.75%; $t_R$=10.81 min.

(S)—N-(1-Cyclopropylethyl)-6-(4-fluorophenyl)-8-methylimidazo[1,2-b]pyridazine-3-carboxamide

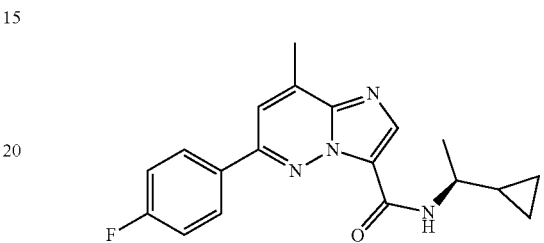

Following general procedure A, 6-(4-fluorophenyl)-8-methylimidazo[1,2-b]pyridazine-3-carboxylic acid (120 mg, 0.44 mmol) and (S)-1-cyclopropylethanamine afforded the title compound (16 mg, 11%) as a white solid. $^1$H NMR (500 MHz, MeOD-$d_4$) δ 8.32 (s, 1H), 8.11 (dd, J=8.5 Hz, 5.5 Hz, 2H), 7.84 (s, 1H), 7.38 (t, J=9.0 Hz, 2H), 3.71-3.64 (m, 1H), 2.77 (s, 3H), 1.42 (d, J=6.5 Hz, 3H), 1.17-1.08 (m, 1H), 0.68-0.60 (m, 1H), 0.60-0.57 (m, 1H), 0.49-0.41 (m, 1H), 0.41-0.38 (m, 1H). LC-MS m/z: 339.1 [M+H]$^+$. HPLC: Purity (254 nm): 99.59%; $t_R$=10.31 min.

N-(1-Cyclopropyl-2,2,2-trifluoroethyl)-8-methyl-6-(pyridin-3-yl)imidazo[1,2-b]pyridazine-3-carboxamide

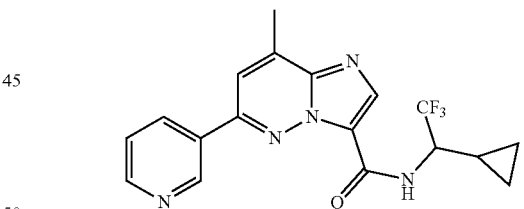

Following general procedure C, 3,6-dichloro-4-methylpyridazine (5.0 g, 30.86 mmol) and pyridin-3-ylboronic acid afforded 3-chloro-4-methyl-6-(pyridin-3-yl)pyridazine (1.6 g, 25%), as a white solid. LC-MS m/z: 206.0 [M+H]$^+$. $t_R$=1.55 min.

A mixture of 3-chloro-4-methyl-6-(pyridin-3-yl)pyridazine (750 mg, 3.65 mmol) and $N_2H_4 \cdot H_2O$ (85%, 1 mL) in propan-2-ol (15 mL) was stirred at 120° C. overnight in a sealed tube, cooled and concentrated in vacuo to afford the crude 3-hydrazinyl-4-methyl-6-(pyridin-3-yl)pyridazine. LC-MS m/z: 202.1 [M+H]$^+$. $t_R$=1.26 min.

A mixture of crude 3-hydrazinyl-4-methyl-6-(pyridin-3-yl)pyridazine (previous step) and Raney Ni (100 mg, 1 mL) in MeOH (20 mL) was stirred at RT overnight under $H_2$, and filtrated. The filtrate was concentrated in vacuo, and the residue was purified by prep-TLC (DCM:MeOH=10:1) to afford 4-methyl-6-(pyridin-3-yl)pyridazin-3-amine (pure: 140 mg; impure: 200 mg). LC-MS m/z: 187.1 [M+H]$^+$. $t_R$=1.29 min.

A mixture of 4-methyl-6-(pyridin-3-yl)pyridazin-3-amine (140 mg) in DMF-DMA (2 mL) was stirred at 120° C. for 2 hours, cooled and concentrated in vacuo to afford crude N,N-dimethyl-N'-(4-methyl-6-(pyridin-3-yl)pyridazin-3-yl)formimidamide. LC-MS m/z: 242.1 [M+H]$^+$. $t_R$=1.50 min.

A mixture of N,N-dimethyl-N'-(4-methyl-6-(pyridin-3-yl)pyridazin-3-yl)formimidamide (crude, previous step), ethyl 2-bromoacetate (125 mg, 1.50 mmol) and DIPEA (290 mg, 2.25 mmol) in DMF (5 mL) was stirred at 120° C. for 2 hours, cooled and diluted with water. The mixture was extracted with EA (30 mL×3) and the organic phases were dried over anhydrous Na$_2$SO$_4$ and filtered. The filtrate was concentrated in vacuo, and the residue was purified by prep-TLC (EA) to afford ethyl 8-methyl-6-(pyridin-3-yl)imidazo[1,2-b]pyridazine-3-carboxylate (20 mg) as a white solid. LC-MS m/z: 283.1 [M+H]$^+$. $t_R$=1.55 min.

Following general procedure B, ethyl 8-methyl-6-(pyridin-3-yl)imidazo[1,2-b]pyridazine-3-carboxylate (20 mg, 0.07 mmol) afforded 8-methyl-6-(pyridin-3-yl)imidazo[1,2-b]pyridazine-3-carboxylic acid. LC-MS m/z: 255.1 [M+H]$^+$. $t_R$=1.05 min.

Following general procedure A, 8-methyl-6-(pyridin-3-yl)imidazo[1,2-b]pyridazine-3-carboxylic acid and 1-cyclopropyl-2,2,2-trifluoroethanamine afforded the title compound as a white solid (4.4 mg, 17% two steps). $^1$H NMR (500 MHz, MeOD-d$_4$) δ 9.26 (d, J=2.0 Hz, 1H), 8.78 (dd, J=4.5 Hz, 1.0 Hz, 1H), 8.52 (dt, J=7.5 Hz, 2.0 Hz, 1H), 8.44 (s, 1H), 7.97 (s, 1H), 7.71 (dd, J=8.5 Hz, 5.5 Hz, 1H), 4.47-4.40 (m, 1H), 2.83 (s, 3H), 1.35-1.28 (m, 1H), 0.84-0.78 (m, 1H), 0.71-0.62 (m, 2H), 0.53-0.47 (m, 1H). LC-MS m/z: 376.0 [M+H]$^+$. HPLC: Purity (214 nm): >99%; $t_R$=7.16 min.

N-(2-Cyclopropylpropan-2-yl)-6-(3-fluorophenyl)-8-methylimidazo[1,2-b]pyridazine-3-carboxamide

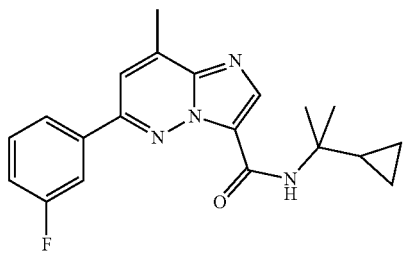 [SMILES: Cc1cc(-c2cccc(F)c2)nn2c(C(=O)NC(C)(C)C3CC3)cnc12]

Following general procedure C, 3,6-dichloro-4-methylpyridazine (8.1 g, 50.0 mmol), and 3-fluorophenylboronic acid afforded 3-chloro-6-(3-fluorophenyl)-4-methylpyridazine (2.0 g, 14%) as a pink solid. LC-MS m/z: 223.1 [M+H]$^+$; $t_R$=1.46 min.

A mixture of 3-chloro-6-(3-fluorophenyl)-4-methylpyridazine (1.0 g, 4.5 mmol), and hydrazine hydrate (4 mL) in i-PrOH (40 mL) was stirred at 100° C. overnight to afforded 6-(3-fluorophenyl)-3-hydrazinyl-4-methylpyridazine which was used directly in the next step. LC-MS m/z: 219.2 [M+H]$^+$; $t_R$=1.14 min.

To the mixture above was added MeOH (20 mL) and Raney Ni (1.0 g). The resulting mixture was stirred at RT under H$_2$ overnight, and filtered. The filtrate was concentrated in vacuo and the residue was purified by silica gel column chromatography (1% MeOH in EA) to afford 6-(3-fluorophenyl)-4-methylpyridazin-3-amine (140 mg, 15%) as a grey solid. LC-MS m/z: 204.2 [M+H]$^+$; $t_R$=1.18 min.

A mixture of 6-(3-fluorophenyl)-4-methylpyridazin-3-amine (140 mg, crude) in DMF-DMA (3 mL) was stirred at 110° C. for 2 h, diluted with H$_2$O (40 mL), and extracted with EA (50 mL×3). The combined organic phases were dried over anhydrous Na$_2$SO$_4$, filtered and concentrated in vacuo to afford N'-(6-(3-fluorophenyl)-4-methylpyridazin-3-yl)-N,N-dimethylformimidamide (3.1 g, crude) as a black oil, which was used in the next step without further purification. LC-MS m/z: 259.2 [M+H]$^+$; $t_R$=1.40 min.

A mixture of N'-(6-(3-fluorophenyl)-4-methylpyridazin-3-yl)-N,N-dimethylformimidamide (3.1 g, crude), ethyl 2-bromoacetate (228 mg, 1.36 mmol), and DIPEA (263 mg, 2.04 mmol) in DMF (8 mL) was stirred at 120° C. for 2 h, cooled, poured into H$_2$O (20 mL), and extracted with EA (40 mL×3). The combined organic phases were dried over anhydrous Na$_2$SO$_4$ and filtered. The filtrate was concentrated in vacuo and purified by silica gel column chromatography (PE/EA=4:1) to afford ethyl 6-(3-fluorophenyl)-8-methylimidazo[1,2-b]pyridazine-3-carboxylate (100 mg, 49%) as a grey solid. LC-MS m/z: 300.1 [M+H]$^+$; $t_R$=1.53 min.

Following general procedure B, ethyl 6-(3-fluorophenyl)-8-methylimidazo[1,2-b]pyridazine-3-carboxylate (100 mg, 0.33 mmol) afforded 6-(3-fluorophenyl)-8-methylimidazo[1,2-b]pyridazine-3-carboxylic acid (40 mg, 44%) as a grey solid. LC-MS m/z: 272.0 [M+H]$^+$; $t_R$=1.25 min.

Following general procedure A, 6-(3-fluorophenyl)-8-methylimidazo[1,2-b]pyridazine-3-carboxylic acid (40 mg, 0.15 mmol) and 2-cyclopropylpropan-2-amine afforded the title compound (19 mg, 36%) as a light yellow solid. $^1$H NMR (500 MHz, DMSO-d$_6$): δ 8.69 (s, 1H), 8.26 (s, 1H), 7.98 (s, 1H), 7.95-7.91 (m, 2H), 7.69-7.64 (m, 1H), 7.44 (td, J=9.0 Hz, 2.5 Hz, 1H), 2.70 (s, 3H), 1.44-1.40 (m, 1H), 1.38 (s, 6H), 0.48-0.43 (m, 4H). LC-MS m/z: 353.2 [M+H]$^+$. HPLC: Purity (214 nm): >96%; $t_R$=8.90 min.

N-(1-Cyclopropyl-2,2,2-trifluoroethyl)-6-(3-fluorophenyl)-8-methylimidazo[1,2-b]pyridazine-3-carboxamide

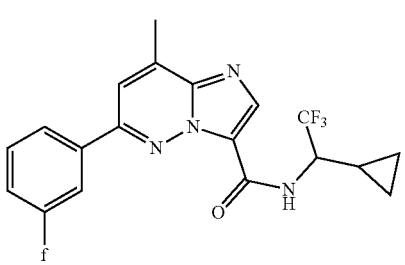

Following general procedure A, 6-(3-fluorophenyl)-8-methylimidazo[1,2-b]pyridazine-3-carboxylic acid (30 mg, 0.11 mmol) and 1-cyclopropyl-2,2,2-trifluoroethanamine hydrochloride afforded the title compound (18 mg, 41%) as a yellow solid. $^1$H NMR (500 MHz, DMSO-d$_6$): δ 9.10 (d, J=9.5 Hz, 1H), 8.37 (s, 1H), 8.05 (s, 1H), 7.94 (d, J=8.0 Hz, 1H), 7.91 (dt, J=8.0 Hz, 2.0 Hz, 1H), 7.68 (dd, J=14.0 Hz, 8.0 Hz, 1H), 7.46 (td, J=8.0 Hz, 2.0 Hz, 1H), 4.52-4.43 (m, 1H), 2.73 (s, 3H), 1.30-1.23 (m, 1H), 0.74-0.68 (m, 1H), 0.66-0.55 (m, 2H), 0.43-0.37 (m, 1H). LC-MS m/z: 393.1 [M+H]⁺. HPLC: Purity (214 nm): 99.81%; $t_R$=8.73 min.

N-(1-Cyclopropyl-2,2,2-trifluoroethyl)-6-(3-methoxyphenyl)-8-methylimidazo[1,2-b]pyridazine-3-carboxamide

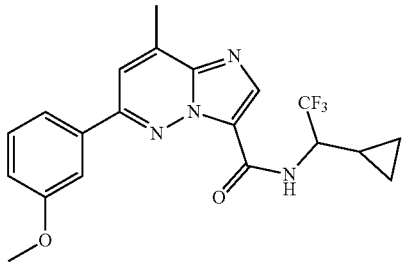 [SMILES: COc1cccc(-c2cc(C)c3ncc(C(=O)NC(C4CC4)C(F)(F)F)n3n2)c1]

Following general procedure C, 3,6-dichloro-4-methylpyridazine (5 g, 30.7 mmol), and 3-methoxyphenylboronic afforded 3-chloro-6-(3-methoxyphenyl)-4-methylpyridazine (1.8 g, 26%) as a white solid. LC-MS m/z: 235.1 [M+H]⁺; Purity (254 nm): >90%; $t_R$=1.43 min.

A mixture of 3-chloro-6-(3-methoxyphenyl)-4-methylpyridazine (2.6 g, 11.11 mmol), and hydrazine hydrate (7 mL) in i-PrOH (70 mL) was stirred at 100° C. overnight. LCMS showed 6-(3-methoxyphenyl)-3-hydrazinyl-4-methylpyridazine was successfully generated, which was used directly in the next step. LC-MS m/z: 231.2 [M+H]⁺; $t_R$=1.12 min.

To the mixture above was added EA (100 mL) and Raney Ni (2.4 g). The resulting mixture was stirred at RT under H₂ for 3 h, and filtered. The filtrate was concentrated in vacuo and purified by silica gel column chromatography (1% MeOH in EA) to afford 6-(3-methoxyphenyl)-4-methylpyridazin-3-amine (500 mg, 20%) as a brown solid. LC-MS m/z: 216.1 [M+H]⁺; $t_R$=1.16 min.

A mixture of 6-(3-methoxyphenyl)-4-methylpyridazin-3-amine (400 mg, 1.86 mmol) in DMF-DMA (3 mL) was stirred at 110° C. for 2 h until that was completely converted to N'-(6-(3-methoxyphenyl)-4-methylpyridazin-3-yl)-N,N-dimethylformimidamide. To the reaction mixture was added ethyl 2-bromoacetate (372 mg, 2.23 mmol) and DIPEA (480 mg, 3.72 mmol). The mixture was stirred for 2 h at RT and then poured into H₂O (300 mL) and extracted with EA (100 mL×3). The combined organic layers were dried over anhydrous Na₂SO₄, and filtered. The filtrate was concentrated in vacuo, and the residue was purified by silica gel column chromatography (pet ether/EA=4:1) to afford ethyl 6-(3-methoxyphenyl)-8-methylimidazo[1,2-b]pyridazine-3-carboxylate (200 mg, 49%) as a brown solid. LC-MS m/z: 312.1 [M+H]⁺; $t_R$=1.51 min.

Following general procedure B, ethyl 6-(3-methoxyphenyl)-8-methylimidazo[1,2-b]pyridazine-3-carboxylate (240 mg, 0.77 mmol) afforded 6-(3-methoxyphenyl)-8-methylimidazo[1,2-b]pyridazine-3-carboxylic acid (80 mg, 30%) as a yellow solid. LC-MS m/z: 284.1 [M+H]⁺; Purity (254 nm): >80%; $t_R$=0.93 min.

Following general procedure A, 6-(3-methoxyphenyl)-8-methylimidazo[1,2-b]pyridazine-3-carboxylic acid (20 mg, 0.07 mmol) and 1-cyclopropyl-2,2,2-trifluoroethanamine hydrochloride afforded the title compound (4.5 mg, 20%) as a white solid. ¹H NMR (500 MHz, DMSO-d₆): δ 9.14 (d, J=10.0 Hz, 1H), 8.36 (s, 1H), 8.02 (s, 1H), 7.63 (d, J=7.5 Hz, 1H), 7.60 (t, J=2.5 Hz, 1H), 7.54 (t, J=8.0 Hz, 1H), 7.18 (dd, J=8.5 Hz, 2.5 Hz, 1H), 4.52-4.46 (m, 1H), 3.87 (s, 3H), 2.72 (s, 3H), 1.26-1.20 (m, 1H), 0.73-0.67 (m, 1H), 0.67-0.55 (m, 2H), 0.42-0.36 (m, 1H). LC-MS m/z: 405.2 [M+H]⁺. HPLC: Purity (214 nm): >99%; $t_R$=8.70 min.

N-(Dicyclopropylmethyl)-6-(3-methoxyphenyl)-8-methylimidazo[1,2-b]pyridazine-3-carboxamide

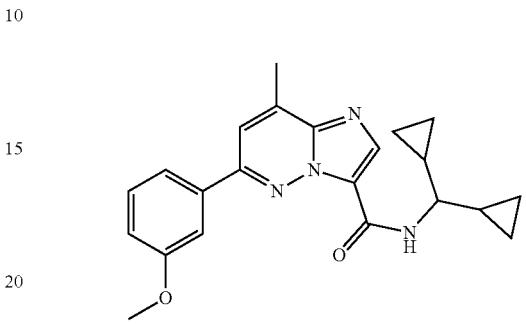

Following general procedure A, 6-(3-methoxyphenyl)-8-methylimidazo[1,2-b]pyridazine-3-carboxylic acid (20 mg, 0.07 mmol) and dicyclopropylmethanamine afforded the title compound (4.7 mg, 20%) as a white solid. ¹H NMR (500 MHz, DMSO-d₆): δ 8.79 (d, J=9.0 Hz, 1H), 8.26 (s, 1H), 7.99 (s, 1H), 7.68 (d, J=7.5 Hz, 1H), 7.63 (t, J=2.5 Hz, 1H), 7.55 (t, J=8.0 Hz, 1H), 7.18 (dd, J=7.5 Hz, 2.5 Hz, 1H), 3.88 (s, 3H), 3.40-3.34 (m, 1H), 2.71 (s, 3H), 1.12-1.05 (m, 2H), 0.55-0.50 (m, 2H), 0.45-0.39 (m, 6H). LC-MS m/z: 377.2 [M+H]⁺. HPLC: Purity (214 nm): >99%; $t_R$=8.70 min.

N-(2-Cyclopropylpropan-2-yl)-6-(isothiazol-5-yl)-8-methylimidazo[1,2-b]pyridazine-3-carboxamide

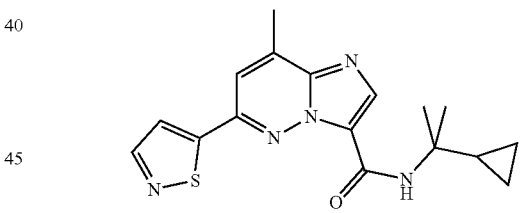

A mixture of 3,6-dichloro-4-methylpyridazine (10 g, 61.7 mmol) and concentrated NH₄OH solution (100 ml) was heated at 135° C. in a sealed autoclave for 20 h at 20 bar, cooled to RT, diluted with water (200 mL) and stirred in an ice bath for 2 h. The solid was collected by filtration, washed with water and dried in vacuo to afford a mixture of 6-chloro-5-methylpyridazin-3-amine and 6-chloro-4-methylpyridazin-3-amine (7.9 g, 90%) as a yellow solid. LC-MS m/z: 114.1 [M+H]⁺.

The suspension of a mixture of 6-chloro-5-methylpyridazin-3-amine and 6-chloro-4-methylpyridazin-3-amine (7.5 g, 55.2 mmol) in DMF-DMA (30 mL) was stirred under reflux for 4 h, and concentrated in vacuo to afford a mixture of N'-(6-chloro-5-methylpyridazin-3-yl)-N,N-dimethylformimidamide and N'-(6-chloro-4-methylpyridazin-3-yl)-N,N-dimethylformimidamide, which was used for the next step directly. LC-MS m/z: 199.1 [M+H]⁺.

The mixture of N'-(6-chloro-5-methylpyridazin-3-yl)-N,N-dimethylformimidamide and N'-(6-chloro-4-methylpyridazin-3-yl)-N,N-dimethylformimidamide (previous step) and ethylbromoacetate (27.6 g, 165.6 mmol) in MeCN (150 mL) was refluxed for 48 h, and concentrated in vacuo. The residue was dissolved in MeCN (80 mL), and DIPEA (22 g, 165.6 mmol) was added at 0° C. The reaction mixture was stirred at RT for 3 h, and concentrated in vacuo. The residue was purified by flash column chromatography on silica gel (PE/EA: 1/1) to afford ethyl 6-chloro-8-methylimidazo[1,2-b]pyridazine-3-carboxylate (1.9 g, 14% over 2 steps) and ethyl 6-chloro-7-methylimidazo[1,2-b]pyridazine-3-carboxylate (3.8 g, 28% over 2 steps) as yellow solids.

Ethyl 6-chloro-8-methylimidazo[1,2-b]pyridazine-3-carboxylate: $^1$H NMR (500 MHz, CDCl$_3$): δ 8.31 (s, 1H), 7.10 (s, 1H), 4.48 (q, J=7.0 Hz, 2H), 2.71 (s, 3H), 1.45 (t, J=7.0 Hz, 3H). LC-MS m/z: 240.0 [M+H]$^+$. Purity (214 nm): 85%; $t_R$=2.21 min.

Ethyl 6-chloro-7-methylimidazo[1,2-b]pyridazine-3-carboxylate: $^1$H NMR (500 MHz, CDCl$_3$): δ 8.31 (s, 1H), 7.87 (s, 1H), 4.47 (q, J=7.0 Hz, 2H), 2.51 (s, 3H), 1.44 (t, J=7.0 Hz, 3H). LC-MS m/z: 240.0 [M+H]$^+$. Purity (214 nm): 91%; $t_R$=2.17 min.

To a solution of ethyl 6-chloro-8-methylimidazo[1,2-b]pyridazine-3-carboxylate (239 mg, 1 mmol) in dioxane (30 ml) was added Bu$_6$Sn$_2$ (1160 mg, 2 mmol), 5-bromoisothiazole (326 mg, 2 mmol) and Pd(dppf)Cl$_2$-DCM (73.1 mg, 0.1 mmol). The mixture was purged three times with N$_2$, then stirred under reflux for 20 h, and concentrated in vacuo. The residue was purified by flash column chromatography on silica gel (EA) to afford ethyl 6-(isothiazol-5-yl)-8-methylimidazo[1,2-b]pyridazine-3-carboxylate (90 mg, 31%) as a yellow solid. LC-MS m/z: 289.0 [M+H]$^+$. Purity (214 nm): 81%; $t_R$=2.29 min.

Following general procedure B, ethyl 6-(isothiazol-5-yl)-8-methylimidazo[1,2-b]pyridazine-3-carboxylate (98 mg, 0.34 mmol) afforded 6-(isothiazol-5-yl)-8-methylimidazo[1,2-b]pyridazine-3-carboxylic acid lithium salt (80 mg, 90%). LC-MS m/z: 261.1 [M+H]$^+$. Purity (254 nm): 96%; $t_R$=1.75 min.

Following general procedure A, 6-(isothiazol-5-yl)-8-methylimidazo[1,2-b]pyridazine-3-carboxylic acid (40 mg, 0.15 mmol) and 2-cyclopropylpropan-2-amine afforded the title compound (28 mg, 54%) as a white solid. $^1$H NMR (500 MHz, MeOD-d$_4$): δ 8.68 (s, 1H), 8.34 (s, 1H), 8.09 (d, J=1.5 Hz, 1H), 7.92 (s, 1H), 2.80 (s, 3H), 1.55-1.51 (m, 1H), 1.55 (s, 6H), 0.61-0.56 (m, 4H). LC-MS m/z: 342.2 [M+H]$^+$. HPLC Purity (214 nm): >99%; $t_R$=7.86 min.

6-(Isothiazol-5-yl)-8-methyl-N-(2-methylbut-3-yn-2-yl)imidazo[1,2-b]pyridazine-3-carboxamide

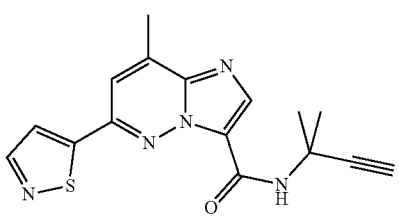 [SMILES: C#CC(C)(C)NC(=O)c1cnc2c(C)cc(-c3ccns3)nn12]

Following general procedure A, 6-(isothiazol-5-yl)-8-methylimidazo[1,2-b]pyridazine-3-carboxylic acid (40 mg, 0.15 mmol) and 2-methylbut-3-yn-2-amine afforded the title compound (20.7 mg, 41%) as a white solid. $^1$H NMR (500 MHz, MeOD-d$_4$): δ 8.67 (s, 1H), 8.37 (s, 1H), 8.09 (s, 1H), 7.93 (s, 1H), 2.90 (s, 1H), 2.80 (s, 3H), 1.89 (s, 6H). LC-MS m/z: 326.1 [M+H]$^+$. HPLC Purity (214 nm): >99%; $t_R$=7.04 min.

N-(1-Cyclopropyl-2,2,2-trifluoroethyl)-6-(isothiazol-5-yl)-8-methylimidazo[1,2-b]pyridazine-3-carboxamide

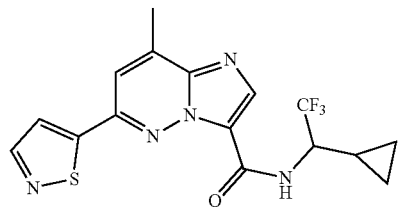 [SMILES: Cc1cc(-c2ccns2)nn2c(C(=O)NC(C3CC3)C(F)(F)F)cnc12]

Following general procedure A, 6-(isothiazol-5-yl)-8-methylimidazo[1,2-b]pyridazine-3-carboxylic acid (40 mg, 0.15 mmol) and 1-cyclopropyl-2,2,2-trifluoroethanamine hydrochloride afforded the title compound (19 mg, 33%) as a white solid. $^1$H NMR (500 MHz, MeOD-d$_4$): δ 8.69 (d, J=1.5 Hz, 1H), 8.44 (s, 1H), 8.11 (d, J=1.5 Hz, 1H), 7.98 (s, 1H), 4.44-4.39 (m, 1H), 2.82 (s, 3H), 1.40-1.36 (m, 1H), 0.88-0.82 (m, 1H), 0.74-0.64 (m, 2H), 0.56-0.51 (m, 1H). LC-MS m/z: 382.1 [M+H]$^+$. HPLC Purity (214 nm): >99%; $t_R$=8.01 min.

(S)-6-(Benzo[d]oxazol-5-yl)-N-(1-cyclopropylethyl)-8-methylimidazo[1,2-b]pyridazine-3-carboxamide

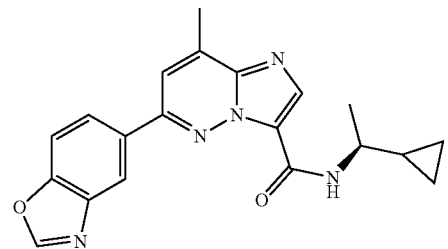 [SMILES: Cc1cc(-c2ccc3ocnc3c2)nn2c(C(=O)N[C@@H](C)C3CC3)cnc12]

Following general procedure B, ethyl 6-chloro-8-methylimidazo[1,2-b]pyridazine-3-carboxylate (1.0 g, 4.18 mmol) afforded 6-chloro-8-methylimidazo[1,2-b]pyridazine-3-carboxylic acid (560 mg, 63%) as a white solid. LC-MS m/z: 212.1 [M+H]$^+$. $t_R$=1.41 min.

Following general procedure A, 6-chloro-8-methylimidazo[1,2-b]pyridazine-3-carboxylic acid (200 mg, 0.95 mmol) and (S)-1-cyclopropylethanamine afforded (S)-6-chloro-N-(1-cyclopropylethyl)-8-methylimidazo[1,2-b]pyridazine-3-carboxamide (180 mg, 57%) as a yellow solid. LC-MS m/z: 279.0 [M+H]$^+$. Purity (214 nm): 92%; $t_R$=1.73 min.

Following general procedure C, (S)-6-chloro-N-(1-cyclopropylethyl)-8-methylimidazo[1,2-b]pyridazine-3-carboxamide (100 mg, 0.36 mmol) and 5-(4,4,5,5-tetramethyl-1,3,2-dioxaborolan-2-yl)benzo[d]oxazole afforded the title compound (29 mg, 11%) as a white solid. $^1$H NMR (500 MHz, DMSO-d$_6$) δ 8.90 (s, 1H), 8.84 (d, J=7.0 Hz, 1H), 8.57 (d, J=1.0 Hz, 1H), 8.26 (s, 1H), 8.20 (dd, J=8.5 Hz, 1.5 Hz, 1H), 8.10 (s, 1H), 8.05 (d, J=8.5 Hz, 1H), 3.66-3.59 (m, 1H), 2.72 (s, 3H), 1.31 (d, J=6.5 Hz, 3H), 1.15-1.05 (m, 1H), 0.59-0.51 (m, 2H), 0.43-0.32 (m, 2H). LC-MS m/z: 362.1 [M+H]⁺. HPLC: Purity (214 nm): >99%; $t_R$=7.43 min.

6-(Benzo[d]oxazol-5-yl)-N-(1-cyclopropyl-2,2,2-trifluoroethyl)-8-methylimidazo[1,2-b]pyridazine-3-carboxamide

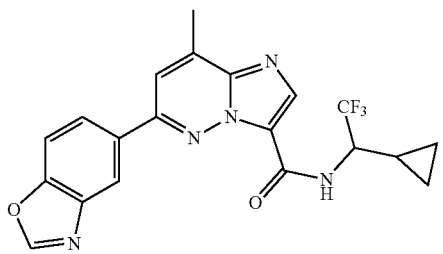

Following general procedure A, 6-chloro-8-methylimidazo[1,2-b]pyridazine-3-carboxylic acid (400 mg, 1.89 mmol) and 1-cyclopropyl-2,2,2-trifluoroethanamine hydrochloride afforded 6-chloro-N-(1-cyclopropyl-2,2,2-trifluoroethyl)-8-methylimidazo[1,2-b]pyridazine-3-carboxamide (240 mg, 38%) as a white solid. LC-MS m/z: 333.0 [M+H]⁺. $t_R$=1.82 min.

Following general procedure C, 6-chloro-N-(1-cyclopropyl-2,2,2-trifluoroethyl)-8-methylimidazo[1,2-b] pyridazine-3-carboxamide (40 mg, 0.12 mmol) and 5-(4,4,5,5-tetramethyl-1,3,2-dioxaborolan-2-yl)benzo[d]oxazole afforded the title compound (20 mg, 40%) as a yellow solid. ¹H NMR (500 MHz, DMSO-d₆): δ 9.19 (d, J=9.0 Hz, 1H), 8.90 (s, 1H), 8.53 (s, 1H), 8.36 (s, 1H), 8.16 (d, J=8.5 Hz, 1H), 8.13 (s, 1H), 8.04 (d, J=8.5 Hz, 1H), 4.52-4.46 (m, 1H), 2.73 (s, 3H), 1.28-1.26 (m, 1H), 0.73-0.60 (m, 3H), 0.42-0.37 (m, 1H). LC-MS m/z: 416.0 [M+H]⁺. HPLC: Purity (214 nm): 99%; $t_R$=7.99 min.

6-(Benzo[d]oxazol-4-yl)-N-(1-cyclopropyl-2,2,2-trifluoroethyl)-8-methylimidazo[1,2-b]pyridazine-3-carboxamide

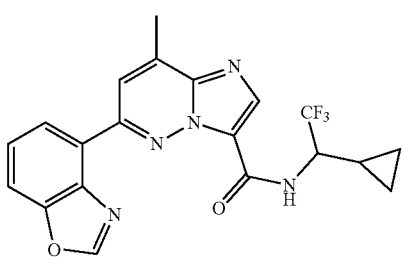 [SMILES: Cc1cc(-c2cccc3ocnc23)nn2c(C(=O)NC(C3CC3)C(F)(F)F)cnc12]

Following general procedure C, 6-chloro-N-(1-cyclopropyl-2,2,2-trifluoroethyl)-8-methylimidazo[1,2-b]pyridazine-3-carboxamide (75 mg, 0.23 mmol) and 5-(4,4,5,5-tetramethyl-1,3,2-dioxaborolan-2-yl)benzo[d]oxazole afforded the title compound (1.5 mg, 2%) as a white solid. ¹H NMR (500 MHz, DMSO-d₆): δ 9.70 (d, J=9.5 Hz, 1H), 9.03 (s, 1H), 8.40 (s, 1H), 8.30 (s, 1H), 8.19 (d, J=8.0 Hz, 1H), 8.05 (d, J=8.0 Hz, 1H), 7.70 (t, J=8.0 Hz, 1H), 4.43-4.39 (m, 1H), 2.76 (s, 3H), 1.46-1.41 (m, 1H), 0.79-0.62 (m, 2H), 0.59-0.56 (m, 1H), 0.36-0.30 (m, 1H). LC-MS m/z: 416.1 [M+H]⁺. HPLC: Purity (214 nm): 99%; $t_R$=8.44 min.

N-(1-Cyclopropyl-2,2,2-trifluoroethyl)-6-(6-methoxypyridin-2-yl)-8-methylimidazo[1,2-b]pyridazine-3-carboxamide

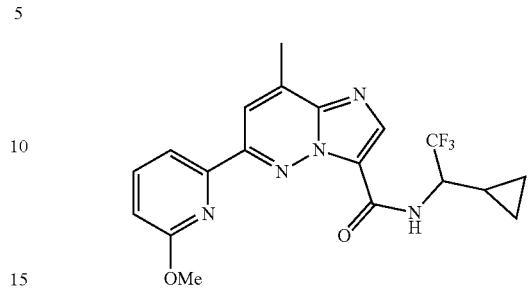

Following general procedure D, 6-chloro-N-(1-cyclopropyl-2,2,2-trifluoroethyl)-8-methylimidazo[1,2-b]pyridazine-3-carboxamide (80 mg, 0.24 mmol) and 2-methoxy-6-(tributylstannyl)pyridine afforded the title compound (11 mg, 11%) as a yellow solid. ¹H NMR (500 MHz, DMSO-d₆): δ 9.09 (d, J=9.2 Hz, 1H), 8.38 (s, 1H), 8.22 (s, 1H), 7.98 (t, J=8.0 Hz, 1H), 7.81 (d, J=8.0 Hz, 1H), 7.03 (d, J=8.0 Hz, 1H), 4.47-4.39 (m, 1H), 4.03 (m, 3H), 2.74 (s, 3H), 1.33-1.28 (m, 1H), 0.72-0.56 (m, 3H), 0.42-0.37 (m, 1H). LC-MS m/z: 406.0 [M+H]⁺. HPLC: Purity (214 nm): >99%; $t_R$=9.19 min.

6-(3-Fluorophenyl)-8-methyl-N-(1,1,1-trifluoropropan-2-yl)imidazo[1,2-b]pyridazine-3-carboxamide

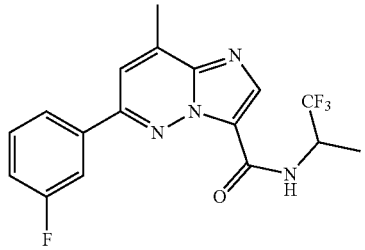 [SMILES: Cc1cc(-c2cccc(F)c2)nn2c(C(=O)NC(C)C(F)(F)F)cnc12]

Following general procedure A, 6-(3-fluorophenyl)-8-methylimidazo[1,2-b]pyridazine-3-carboxylic acid (150 mg, 0.20 mmol) and 1,1,1-trifluoropropan-2-amine hydrochloride afforded the title compound (3.5 mg, 7% yield). ¹H NMR (400 MHz, MeOD-d₄) δ 8.40 (s, 1H), 7.90 (s, 1H), 7.88 (d, J=7.2 Hz, 1H), 7.80 (d, J=10.0 Hz, 1H), 7.63 (dd, J=14.0 Hz, 8.0 Hz, 1H), 7.35 (t, J=8.0 Hz, 1H), 5.09-5.00 (m, 1H), 2.79 (s, 3H), 1.52 (d, J=7.2 Hz, 3H). LC-MS m/z: 367.1 [M+H]⁺. HPLC: Purity (214 nm): >99%; $t_R$=9.80 min.

6-(Benzo[d]oxazol-7-yl)-N-(1-cyclopropyl-2,2,2-trifluoroethyl)-8-methylimidazo[1,2-b]pyridazine-3-carboxamide

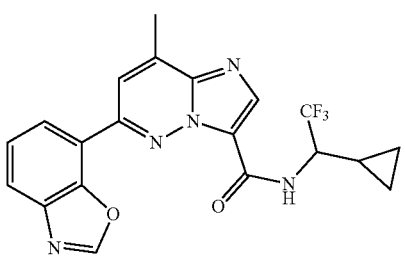 [SMILES: Cc1cc(-c2cccc3ncoc23)nn2c(C(=O)NC(C3CC3)C(F)(F)F)cnc12]

Following general procedure C, 6-chloro-N-(1-cyclopropyl-2,2,2-trifluoroethyl)-8-methylimidazo[1,2-b]pyridazine-3-carboxamide (70 mg, 0.21 mmol) and 7-(4,4,5,5-tetramethyl-1,3,2-dioxaborolan-2-yl)benzo[d]oxazole afforded the title compound (4.9 mg, 6%) as a white solid. $^1$H NMR (500 MHz, DMSO-$d_6$) δ 9.22 (d, J=8.0 Hz, 1H), 8.92 (s, 1H), 8.43 (s, 1H), 8.15 (s, 2H), 8.06 (d, J=8.0 Hz, 1H), 7.67 (t, J=8.0 Hz, 1H), 4.50-4.42 (m, 1H), 2.76 (s, 3H), 1.32-1.26 (m, 1H), 0.73-0.35 (m, 4H). LC-MS m/z: 416.1 [M+H]$^+$. HPLC Purity (214 nm): >99%; $t_R$=8.09 min.

6-(Benzo[d]oxazol-7-yl)-8-methyl-N-(1,1,1-trifluoropropan-2-yl)imidazo[1,2-b]pyridazine-3-carboxamide

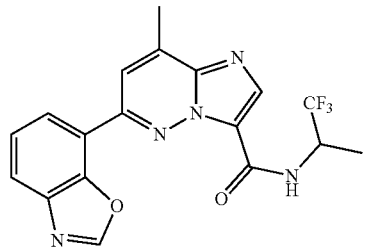 [SMILES: Cc1cc(-c2cccc3ncoc23)nn2c(C(=O)NC(C)C(F)(F)F)cnc12]

Following general procedure A, 6-chloro-8-methylimidazo[1,2-b]pyridazine-3-carboxylic acid (300 mg, 1.42 mmol) and 1,1,1-trifluoropropan-2-amine hydrochloride afforded 6-chloro-8-methyl-N-(1,1,1-trifluoropropan-2-yl)imidazo[1,2-b]pyridazine-3-carboxamide (410 mg, 94%) as a white solid. LC-MS m/z: 307.0 [M+H]$^+$. Purity (214 nm): 97.8%; $t_R$=1.74 min.

Following general procedure C, 6-chloro-8-methyl-N-(1,1,1-trifluoropropan-2-yl)imidazo[1,2-b]pyridazine-3-carboxamide (70 mg, 0.23 mmol) and 7-(4,4,5,5-tetramethyl-1,3,2-dioxaborolan-2-yl)benzo[d]oxazole afforded the title compound (19 mg, 22%) as a white solid. $^1$H NMR (400 MHz, DMSO-$d_6$): δ 9.09 (d, J=9.6 Hz, 1H), 8.93 (s, 1H), 8.41 (s, 1H), 8.15 (d, J=8.0 Hz, 1H), 8.14 (s, 1H), 8.05 (d, J=8.0 Hz, 1H), 7.66 (t, J=8.0 Hz, 1H), 5.11-5.05 (m, 1H), 2.75 (s, 3H), 1.46 (d, J=7.2 Hz, 3H). LC-MS m/z: 390.1 [M+H]$^+$. HPLC: Purity (214 nm): >99%; $t_R$=8.28 min.

6-(Benzo[d]oxazol-5-yl)-8-methyl-N-(1,1,1-trifluoropropan-2-yl)imidazo[1,2-b]pyridazine-3-carboxamide

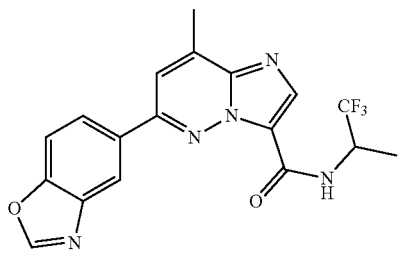 [SMILES: Cc1cc(-c2ccc3ocnc3c2)nn2c(C(=O)NC(C)C(F)(F)F)cnc12]

Following general procedure C, 6-chloro-8-methyl-N-(1,1,1-trifluoropropan-2-yl)imidazo[1,2-b]pyridazine-3-carboxamide (100 mg, 0.33 mmol) and 5-(4,4,5,5-tetramethyl-1,3,2-dioxaborolan-2-yl)benzo[d]oxazole afforded the title compound (61 mg, 48%) as a yellow solid. $^1$H NMR (500 MHz, DMSO-$d_6$): δ 9.08 (d, J=9.0 Hz, 1H), 8.90 (s, 1H), 8.53 (d, J=1.0 Hz, 1H), 8.35 (s, 1H), 8.16 (dd, J=8.5 Hz, 1.5 Hz, 1H), 8.12 (s, 1H), 8.03 (d, J=8.5 Hz, 1H), 5.05-5.01 (m, 1H), 2.72 (s, 3H), 1.46 (d, J=7.0 Hz, 3H). LC-MS m/z: 390.0 [M+H]$^+$. HPLC: Purity (214 nm): 91%; $t_R$=7.91 min.

6-(2-Cyano-4-fluorophenyl)-N-(1-cyclopropyl-2,2,2-trifluoroethyl)-8-methylimidazo[1,2-b]pyridazine-3-carboxamide

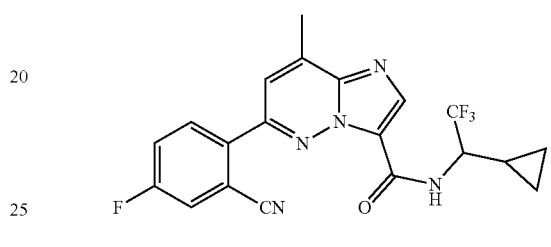

Following general procedure C, 6-chloro-N-(1-cyclopropyl-2,2,2-trifluoroethyl)-8-methylimidazo[1,2-b]pyridazine-3-carboxamide (100 mg, 0.30 mmol) and 2-cyano-4-fluorophenylboronic acid afforded the title compound (40 mg, 32%) as a white solid. $^1$H NMR (500 MHz, DMSO-$d_6$): δ 8.82 (d, J=9.0 Hz, 1H), 8.44 (s, 1H), 8.20 (d, J=7.5 Hz, 1H), 8.08 (t, J=7.5 Hz, 1H), 7.89 (t, J=7.5 Hz, 1H), 7.83 (s, 1H), 4.40-4.30 (m, 1H), 2.74 (s, 3H), 1.35-1.25 (m, 1H), 0.70-0.62 (m, 2H), 0.53-0.49 (m, 1H), 0.37-0.33 (m, 1H). LC-MS m/z: 418.1 [M+H]$^+$. HPLC: Purity (214 nm): >99%; $t_R$=8.95 min.

6-(2-Cyano-4-fluorophenyl)-8-methyl-N-(1,1,1-trifluoropropan-2-yl)imidazo[1,2-b]pyridazine-3-carboxamide

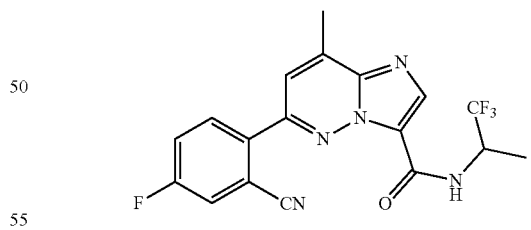

Following general procedure C, 6-chloro-8-methyl-N-(1,1,1-trifluoropropan-2-yl)imidazo[1,2-b]pyridazine-3-carboxamide (100 mg, 0.33 mmol) and 2-cyano-4-fluorophenylboronic acid afforded the title compound (7.2 mg, 9%) as a yellow solid. $^1$H NMR (500 MHz, DMSO-$d_6$): δ 8.69 (d, J=9.5 Hz, 1H), 8.44 (s, 1H), 8.21 (dd, J=9.0 Hz, 2.5 Hz, 1H), 8.09 (dd, J=9.0 Hz, 5.5 Hz, 1H), 7.89 (td, J=9.0 Hz, 2.5 Hz, 1H), 7.83 (s, 1H), 5.06-4.97 (m, 1H), 2.73 (s, 3H), 1.43 (d, J=7.0 Hz, 3H). LC-MS m/z: 392.0 [M+H]$^+$. HPLC: Purity (214 nm): >99%; $t_R$=8.58 min.

(S)-6-(2-Cyano-4-fluorophenyl)-N-(1-cyclopropylethyl)-8-methylimidazo[1,2-b]pyridazine-3-carboxamide

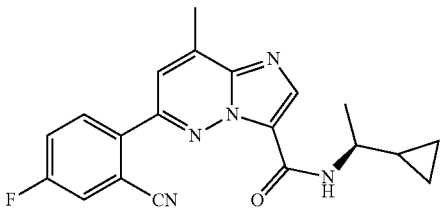 [SMILES: Cc1cc(-c2ccc(F)cc2C#N)nn2c(C(=O)N[C@@H](C)C3CC3)cnc12]

Following general procedure C, (S)-6-chloro-N-(1-cyclopropylethyl)-8-methylimidazo[1,2-b]pyridazine-3-carboxamide (80 mg, 0.29 mmol) and 2-cyano-4-fluorophenylboronic acid afforded the title compound (16 mg, 15%) as a white solid. $^1$H NMR (500 MHz, DMSO-$d_6$) δ 8.52 (d, J=8.0 Hz, 1H), 8.34 (s, 1H), 8.22 (dd, J=8.5 Hz, 2.5 Hz, 1H), 8.11 (dd, J=8.5 Hz, 5.0 Hz, 1H), 7.89 (td, J=9.0 Hz, 3.0 Hz, 1H), 7.80 (s, 1H), 3.60-3.52 (m, 1H), 2.73 (s, 3H), 1.28 (d, J=6.0 Hz, 3H), 1.11-1.03 (m, 1H), 0.49-0.19 (m, 4H). LC-MS m/z: 364.1 [M+H]$^+$. HPLC: Purity (214 nm): >99%; $t_R$=8.53 min.

6-(3-Cyanophenyl)-N-(1-cyclopropyl-2,2,2-trifluoroethyl)-8-methylimidazo[1,2-b]pyridazine-3-carboxamide

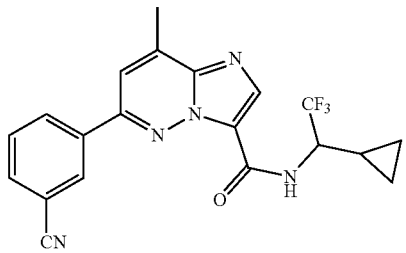 [SMILES: Cc1cc(-c2cccc(C#N)c2)nn2c(C(=O)NC(C3CC3)C(F)(F)F)cnc12]

Following general procedure C, 6-chloro-N-(1-cyclopropyl-2,2,2-trifluoroethyl)-8-methylimidazo[1,2-b]pyridazine-3-carboxamide (100 mg, 0.30 mmol) and 3-cyanophenylboronic acid afforded the title compound (52 mg, 43%) as a white solid. $^1$H NMR (500 MHz, MeOD-$d_4$): δ 8.47 (s, 1H), 8.43 (s, 1H), 8.38 (d, J=7.5 Hz, 1H), 7.98 (d, J=7.5 Hz, 1H), 7.82 (t, J=7.5 Hz, 1H), 4.48-4.42 (m, 1H), 2.82 (s, 3H), 1.34-1.30 (m, 1H), 0.84-0.80 (m, 1H), 0.72-0.62 (m, 2H), 0.55-0.50 (m, 1H). LC-MS m/z: 399.8 [M+H]$^+$. HPLC: Purity (214 nm): >99%; $t_R$=8.33 min.

N-(1-Cyclopropyl-2,2,2-trifluoroethyl)-6-(3,3-difluoropyrrolidin-1-yl)-8-methylimidazo[1,2-b]pyridazine-3-carboxamide

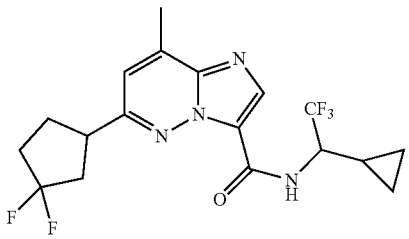 [SMILES: Cc1cc(C2CCC(F)(F)C2)nn2c(C(=O)NC(C3CC3)C(F)(F)F)cnc12]

A suspension of 6-chloro-N-(1-cyclopropyl-2,2,2-trifluoroethyl)-8-methylimidazo[1,2-b]pyridazine-3-carboxamide (100 mg, 0.30 mmol), 3,3-difluoropyrrolidine hydrochloride (86 mg, 0.60 mmol) and DIEA (116 mg, 0.90 mmol) in NMP (3 mL) was stirred at 150° C. for 2 h. The mixture was purified by pre-HPLC (MeCN/NH$_4$HCO$_3$) to afford the title compound (19 mg, 16%) as a pink powder. $^1$H NMR (500 MHz, DMSO-$d_6$): δ 9.22 (d, J=9.0 Hz, 1H), 8.06 (s, 1H), 7.06 (d, J=1.0 Hz, 1H), 4.41-4.37 (m, 1H), 4.00-3.90 (m, 2H), 3.80-3.71 (m, 2H), 2.67-2.61 (m, 2H), 2.56 (s, 3H), 1.28-1.24 (m, 1H), 0.70-0.62 (m, 1H), 0.62-0.57 (m, 2H), 0.38-0.34 (m, 1H). LC-MS m/z: 404.1 [M+H]$^+$. HPLC: Purity (214 nm): >99%; $t_R$=8.32 min.

6-(3-Cyanofuran-2-yl)-N-(1-cyclopropyl-2,2,2-trifluoroethyl)-8-methylimidazo[1,2-b]pyridazine-3-carboxamide

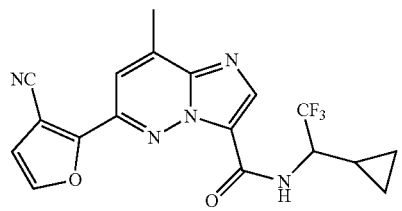 [SMILES: Cc1cc(-c2occc2C#N)nn2c(C(=O)NC(C3CC3)C(F)(F)F)cnc12]

Following general procedure D, 6-chloro-N-(1-cyclopropyl-2,2,2-trifluoroethyl)-8-methylimidazo[1,2-b]pyridazine-3-carboxamide (149 mg, 0.45 mmol) and 2-(tributylstannyl)furan-3-carbonitrile afforded the title compound (59.6 mg, 34%) as a light yellow solid. $^1$H NMR (400 MHz, DMSO-$d_6$) δ 8.59 (d, J=9.2 Hz, 1H), 8.45 (s, 1H), 8.30 (d, J=1.6 Hz, 1H), 7.85 (s, 1H), 7.33 (d, J=2.0 Hz, 1H), 4.32-4.21 (m, 1H), 2.73 (s, 3H), 1.59-1.51 (m, 1H), 0.75-0.63 (m, 2H), 0.57-0.50 (m, 1H), 0.36-0.30 (m, 1H). LC-MS m/z: 389.8 [M+H]$^+$. HPLC: Purity (214 nm): 97%; $t_R$=8.31 min.

2,4-Dimethyl-N-(4-(oxazol-4-yl)phenyl)imidazo[1,5-b]pyridazine-7-carboxamide

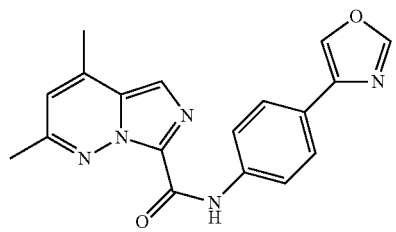 [SMILES: Cc1cc(C)c2cnc(C(=O)Nc3ccc(-c4cocn4)cc3)n2n1]

Following general procedure A, 2,4-dimethylimidazo[1,5-b]pyridazine-7-carboxylic acid (30 mg, 0.16 mmol) and 4-(oxazol-4-yl)aniline afforded the tile compound (15 mg, 29%) as a yellow solid. $^1$H NMR (500 MHz, CDCl$_3$): δ 10.43 (s, 1H), 7.95 (s, 2H), 7.87 (d, J=8.5 Hz, 2H), 7.78 (d, J=8.5 Hz, 2H), 7.66 (s, 1H), 6.58 (s, 1H), 2.65 (s, 3H), 2.56 (s, 3H). LC-MS m/z: 334.2 [M+H]$^+$. HPLC Purity (214 nm): >99%; $t_R$=8.96 min.

N-(4-Ethynylphenyl)-2,4-dimethylimidazo[1,5-b]pyridazine-7-carboxamide

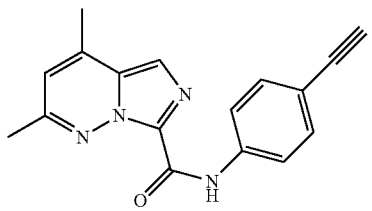 [SMILES: C#Cc1ccc(NC(=O)c2ncc3c(C)cc(C)nn23)cc1]

Following general procedure A, 2,4-dimethylimidazo[1,5-b]pyridazine-7-carboxylic acid (30 mg, 0.16 mmol) and 4-ethynylaniline afforded the title compound (30 mg, 66%) as a yellow solid. $^1$H NMR (500 MHz, CDCl$_3$): δ 7.83 (d, J=8.5 Hz, 2H), 7.80 (s, 1H), 7.52 (d, J=8.5 Hz, 2H), 6.87 (s, 1H), 3.49 (s, 1H), 2.68 (s, 3H), 2.62 (s, 3H). LC-MS m/z: 291.1 [M+H]$^+$. HPLC Purity (214 nm): >99%; $t_R$=9.62 min.

N-((1S,4S)-4-Pentyloxycyclohexyl)-2,4-dimethylimidazo[1,5-b]pyridazine-7-carboxamide

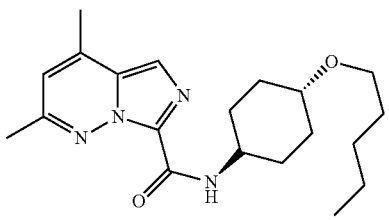

Following general procedure A, 2,4-dimethylimidazo[1,5-b]pyridazine-7-carboxylic acid (30 mg, 0.16 mmol) and (1R,4R)-4-(pentyloxy)cyclohexan-1-amine afforded the title compound (17 mg, 30%) as a yellow solid. $^1$H NMR (400 MHz, CDCl$_3$): δ 8.43 (d, J=7.6 Hz, 1H), 7.59 (s, 1H), 6.50 (d, J=0.8 Hz, 1H), 4.12-4.06 (m, 1H), 3.45 (t, J=13.6 Hz, 2H), 3.31-3.27 (m, 1H), 2.56 (s, 3H), 2.52 (s, 3H), 2.22-2.18 (m, 2H), 2.08-2.04 (m, 2H), 1.61-1.31 (m, 10H), 0.92 (t, J=13.6 Hz, 3H). LC-MS m/z: 359.3 [M+H]$^+$. HPLC Purity (214 nm): >98%; $t_R$=10.65 min.

2,4-Dimethyl-N-(1,2,3,4-tetrahydronaphthalen-1-yl)imidazo[1,5-b]pyridazine-7-carboxamide

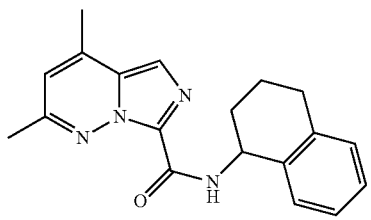 [SMILES: Cc1cc(C)c2cnc(C(=O)NC3CCCc4ccccc43)n2n1]

Following general procedure A, 2,4-dimethylimidazo[1,5-b]pyridazine-7-carboxylic acid (40 mg, 0.21 mmol) and 1,2,3,4-tetrahydronaphthalen-1-amine afforded the title compound (17 mg, 27%) as a white solid. $^1$H NMR (500 MHz, DMSO-d$_6$): δ 10.65 (s, 1H), 7.78 (s, 1H), 7.74 (s, 1H), 7.53 (d, J=8.5 Hz, 1H), 7.21 (d, J=8.5 Hz, 1H), 6.84 (s, 1H), 2.88 (t, J=7.5 Hz, 2H), 2.84 (t, J=7.5 Hz, 2H), 2.54 (s, 3H), 2.53 (s, 3H), 2.03 (m, J=7.5 Hz, 2H). LC-MS m/z: 307.2 [M+H]$^+$. HPLC Purity (214 nm): >99%; $t_R$=10.28 min.

2,4-Dimethyl-N-(1-phenylpropyl)imidazo[1,5-b]pyridazine-7-carboxamide

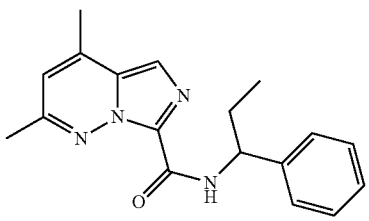 [SMILES: CCC(NC(=O)c1ncc2c(C)cc(C)nn12)c1ccccc1]

Following general procedure A, 2,4-dimethylimidazo[1,5-b]pyridazine-7-carboxylic acid (40 mg, 0.21 mmol), and 1-phenylpropan-1-amine afforded the title compound (6 mg, 10%) as a yellow oil. $^1$H NMR (500 MHz, CDCl$_3$): δ 8.95 (d, J=7.5 Hz, 1H), 7.62 (s, 1H), 7.43 (d, J=7.5 Hz, 2H), 7.36 (t, J=7.5 Hz, 2H), 7.28 (d, J=7.5 Hz, 1H), 6.52 (d, J=1.0 Hz, 1H), 5.28 (q, J=7.5 Hz, 1H), 2.58 (s, 3H), 2.54 (s, 3H), 2.09-1.95 (m, 2H), 0.99 (t, J=7.5 Hz, 3H). LC-MS m/z: 309.3 [M+H]$^+$. HPLC Purity (214 nm): 99%; $t_R$=9.66 min.

N-(2,3-Dihydro-1H-inden-5-yl)-2,4-dimethylimidazo[1,5-b]pyridazine-7-carboxamide

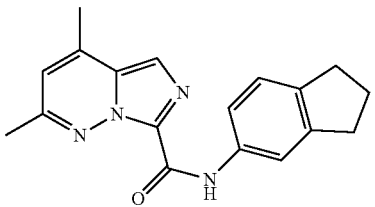 [SMILES: Cc1cc(C)c2cnc(C(=O)Nc3ccc4c(c3)CCC4)n2n1]

Following general procedure A, 2,4-dimethylimidazo[1,5-b]pyridazine-7-carboxylic acid (40 mg, 0.21 mmol) and 2,3-dihydro-1H-inden-5-amine afforded the title compound (17 mg, 27%) as a white solid. $^1$H NMR (500 MHz, DMSO-d$_6$): δ 10.65 (s, 1H), 7.78 (s, 1H), 7.74 (s, 1H), 7.53 (d, J=8.5 Hz, 1H), 7.21 (d, J=8.5 Hz, 1H), 6.84 (s, 1H), 2.88 (t, J=7.5 Hz, 2H), 2.84 (t, J=7.5 Hz, 2H), 2.54 (s, 3H), 2.53 (s, 3H), 2.03 (m, J=7.5 Hz, 2H). LC-MS m/z: 307.2 [M+H]$^+$. HPLC Purity (214 nm): >99%; $t_R$=10.28 min.

(S)—N-(1-Cyclopropylethyl)-2,4-dimethylimidazo[1,5-b]pyridazine-7-carboxamide

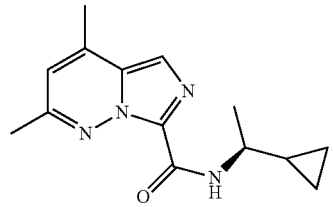 [SMILES: Cc1cc(C)c2cnc(C(=O)N[C@@H](C)C3CC3)n2n1]

Following general procedure A, 2,4-dimethylimidazo[1,5-b]pyridazine-7-carboxylic acid (30 mg, 0.16 mmol) and (S)-1-cyclopropylethanamine afforded the title compound (11.4 mg, 28%) as a white solid. ¹H NMR (500 MHz, CDCl₃): δ 8.44 (d, J=6.0 Hz, 1H), 7.58 (s, 1H), 6.49 (d, J=0.5 Hz, 1H), 3.81-3.75 (m, 1H), 2.56 (s, 3H), 2.52 (s, 3H), 1.35 (d, J=6.5 Hz, 3H), 1.02-0.97 (m, 1H), 0.60-0.41 (m, 3H), 0.33-0.29 (m, 1H). LC-MS m/z: 259.0 [M+H]⁺. HPLC Purity (214 nm): 96%; t_R=8.88 min.

N-(2-Cyclopropylpropan-2-yl)-2,4-dimethylimidazo[1,5-b]pyridazine-7-carboxamide

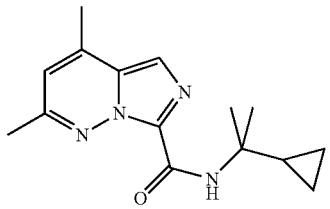 [SMILES: Cc1cc(C)c2cnc(C(=O)NC(C)(C)C3CC3)n2n1]

Following general procedure A, 2,4-dimethylimidazo[1,5-b]pyridazine-7-carboxylic acid (30 mg, 0.16 mmol) and 2-cyclopropylpropan-2-amine afforded the title compound (3 mg, 7%) as a white solid. ¹H NMR (500 MHz, CDCl₃): δ 8.38 (brs, 1H), 7.55 (s, 1H), 6.47 (s, 1H), 2.55 (s, 3H), 2.51 (s, 3H), 1.45 (s, 6H), 1.43-1.38 (m, 1H), 0.50-0.47 (m, 4H). LC-MS m/z: 273.2 [M+H]⁺. HPLC Purity (214 nm): >99%; t_R=9.34 min.

N-(1-Cyclopropyl-2,2,2-trifluoroethyl)-2,4-dimethylimidazo[1,5-b]pyridazine-7-carboxamide

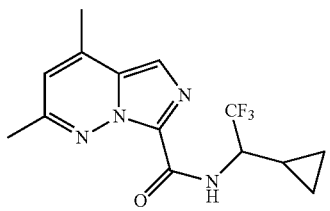 [SMILES: Cc1cc(C)c2cnc(C(=O)NC(C3CC3)C(F)(F)F)n2n1]

Following general procedure A, 2,4-dimethylimidazo[1,5-b]pyridazine-7-carboxylic acid (20 mg, 0.064 mmol) and 1-cyclopropyl-2,2,2-trifluoroethanamine hydrochloride afforded the title compound (13 mg, 65%) as a white solid. ¹H NMR (500 MHz, DMSO-d₆): δ 9.26 (d, J=9.5 Hz, 1H), 7.78 (s, 1H), 6.85 (s, 1H), 4.31-4.26 (m, 1H), 2.53 (s, 3H), 2.51 (s, 3H), 1.37-1.33 (m, 1H), 0.70-0.67 (m, 1H), 0.61-0.56 (m, 2H), 0.36-0.33 (m, 1H). LC-MS m/z: 313.1 [M+H]⁺. HPLC Purity (214 nm): 96%; t_R=7.47 min.

N-(2-Cyclopropylpropan-2-yl)-2-(4-fluorophenyl)-4-methylimidazo[1,5-b]pyridazine-7-carboxamide

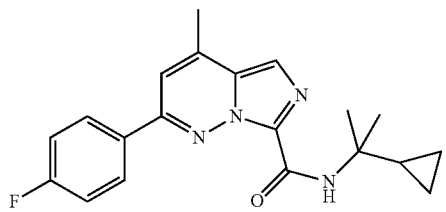 [SMILES: Cc1cc(-c2ccc(F)cc2)nn2c(C(=O)NC(C)(C)C3CC3)ncc12]

Following general procedure C, 3,6-dichloro-4-methylpyridazine (3.0 g, 18.4 mmol) and 4-fluorophenylboronic acid afforded 3-chloro-6-(4-fluorophenyl)-4-methylpyridazine (1.88 g, 46%) as a pale yellow solid. LC-MS m/z: 223.0 [M+H]⁺. LCMS: Purity (214 nm): 93.1%; t_R=1.77 min.

Following general procedure E, 3-chloro-6-(4-fluorophenyl)-4-methylpyridazine (1.88 g, 8.44 mmol) afforded 6-(4-fluorophenyl)-4-methylpyridazine-3-carbonitrile (1.7 g, 94%) as a pale green solid. LC-MS m/z: 214.1 [M+H]⁺. LCMS: Purity (214 nm): 83.8%; t_R=1.76 min.

Following general procedure F, 6-(4-fluorophenyl)-4-methylpyridazine-3-carbonitrile (1.7 g, 7.98 mmol) afforded (6-(4-fluorophenyl)-4-methylpyridazin-3-yl)methanamine hydrochloride (2.14 g, 93%) as a dark brown solid, which was used directly in the next step. LC-MS m/z: 218.1 [M+H]⁺. LCMS: Purity (254 nm): 97%; t_R=1.76 min.

Following general procedure G, (6-(4-fluorophenyl)-4-methylpyridazin-3-yl)methanamine hydrochloride (2.14 g, 7.3 mmol) afforded ethyl 2-((6-(4-fluorophenyl)-4-methylpyridazin-3-yl)methylamino)-2-oxoacetate (1.7 g, 73%) as a pale green solid. LC-MS m/z: 318.1 [M+H]⁺. LCMS: Purity (254 nm): 69.9%; t_R=1.29 min.

Following general procedure H, ethyl 2-((6-(4-fluorophenyl)-4-methylpyridazin-3-yl)methylamino)-2-oxoacetate (1.65 g, 5.2 mmol) afforded ethyl 2-(4-fluorophenyl)-4-methylimidazo[1,5-b]pyridazine-7-carboxylate (1.35 g, 84.3%) as a pale solid. LC-MS m/z: 300.0 [M+H]⁺. LCMS: Purity (214 nm): 85.7%; t_R=1.94 min.

Following general procedure B, ethyl 2-(4-fluorophenyl)-4-methylimidazo[1,5-b]pyridazine-7-carboxylate (1.35 g, 4.51 mmol) afforded 2-(4-fluorophenyl)-4-methylimidazo[1,5-b]pyridazine-7-carboxylic acid (1.1 g, 90%) as a pale yellow solid. LC-MS m/z: 272.1 [M+H]⁺. LCMS: Purity (214 nm): 95.6%; t_R=1.48 min.

Following general procedure A, 2-(4-fluorophenyl)-4-methylimidazo[1,5-b]pyridazine-7-carboxylic acid (40 mg, 0.14 mmol) and 2-cyclopropylpropan-2-amine afforded the title compound (17.4 mg, 34%) as a yellow solid. ¹H NMR (400 MHz, MeOD-d₄): δ 8.11 (dd, J=8.8 Hz, 3.2 Hz, 2H), 7.80 (s, 1H), 7.37 (s, 1H), 7.33 (t, J=8.8 Hz, 2H), 2.69 (s, 3H), 1.47 (s, 6H), 1.47-1.45 (m, 1H), 0.53-0.50 (m, 4H). LC-MS m/z: 353.1 [M+H]⁺. HPLC Purity (214 nm): >99%; t_R=10.53 min.

(S)—N-(1-Cyclopropylethyl)-2-(4-fluorophenyl)-4-methylimidazo[1,5-b]pyridazine-7-carboxamide

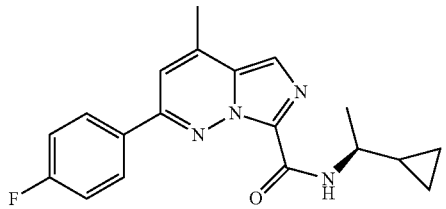 [SMILES: Cc1cc(-c2ccc(F)cc2)nn2c(C(=O)N[C@@H](C)C3CC3)ncc12]

Following general procedure A, 2-(4-fluorophenyl)-4-methylimidazo[1,5-b]pyridazine-7-carboxylic acid (40 mg, 0.14 mmol) and (S)-1-cyclopropylethanamine afforded the title compound (23.3 mg, 47%) as a yellow solid. ¹H NMR (500 MHz, MeOD-d₄) δ 8.13 (dd, J=8.8 Hz, 3.2 Hz, 2H), 7.80 (s, 1H), 7.40 (s, 11H), 7.34 (t, J=8.8 Hz, 2H), 3.72-3.62 (m, 1H), 2.70 (s, 3H), 1.41 (d, J=6.8 Hz, 3H), 1.17-1.08 (m, 1H), 0.68-0.51 (m, 2H), 0.50-0.42 (m, 1H), 0.40-0.36 (m, 1H). LC-MS m/z: 339.1 [M+H]⁺. HPLC: Purity (254 nm): 99%; $t_R$=10.16 min.

N-(1-Cyclopropyl-2,2,2-trifluoroethyl)-2-(4-fluorophenyl)-4-methylimidazo[1,5-b]pyridazine-7-carboxamide

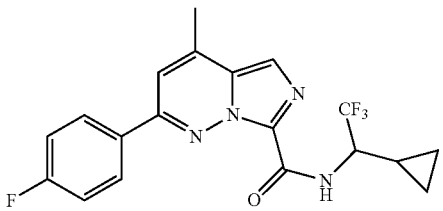 [SMILES: Cc1cc(-c2ccc(F)cc2)nn2c(C(=O)NC(C3CC3)C(F)(F)F)ncc12]

Following general procedure A, 2-(4-fluorophenyl)-4-methylimidazo[1,5-b]pyridazine-7-carboxylic acid (50 mg, 0.18 mmol) and 1-cyclopropyl-2,2,2-trifluoroethanamine hydrochloride afforded the title compound as a yellow solid (70 mg, 99%). ¹H NMR (500 MHz, DMSO-d₆): δ 8.30 (d, J=9.5 Hz, 1H), 8.18 (td, J=5.5 Hz, 4.0 Hz, 2H), 7.87 (s, 1H), 7.56 (d, J=1.0 Hz, 1H), 7.46 (td, J=9.0 Hz, 2.0 Hz, 2H), 4.30-4.22 (m, 1H), 2.64 (d, J=1.0 Hz, 3H), 1.40-1.34 (m, 1H), 0.72-0.70 (m, 1H), 0.64-0.61 (m, 1H), 0.58-0.55 (m, 1H), 0.38-0.34 (m, 1H). LC-MS m/z: 393.1 [M+H]⁺. HPLC Purity (254 nm): 96%; $t_R$=8.77 min.

N-(2-Cyclopropylpropan-2-yl)-2-(3-fluorophenyl)-4-methylimidazo[1,5-b]pyridazine-7-carboxamide

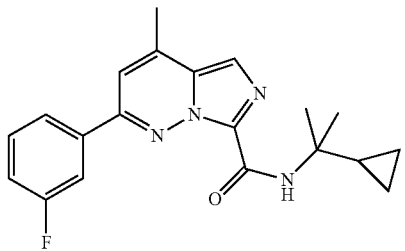 [SMILES: Cc1cc(-c2cccc(F)c2)nn2c(C(=O)NC(C)(C)C3CC3)ncc12]

Following general procedure E, chloro-6-(3-fluorophenyl)-4-methylpyridazine (510 mg, 2.29 mmol) afforded 6-(3-fluorophenyl)-4-methylpyridazine-3-carbonitrile (435 mg, 89%) as an off-white solid. LC-MS m/z: 214.1 [M+H]⁺. LCMS: Purity (254 nm): 96.3%; $t_R$=1.79 min.

Following general procedure F, 6-(3-fluorophenyl)-4-methylpyridazine-3-carbonitrile (435 mg, 2.04 mmol) afforded (6-(3-fluorophenyl)-4-methylpyridazin-3-yl)methanamine hydrochloride (500 mg) as a light brown solid, which was used directly in the next step. LC-MS m/z: 218.1 [M+H]⁺. LCMS: Purity (254 nm): 93.7%; $t_R$=1.40 min.

Following general procedure G, (6-(3-fluorophenyl)-4-methylpyridazin-3-yl)methanamine hydrochloride (500 mg) afforded ethyl 2-((6-(3-fluorophenyl)-4-methylpyridazin-3-yl)methylamino)-2-oxoacetate (423 mg, 65% over 2 steps) as a white solid. LC-MS m/z: 318.1 [M+H]⁺. LCMS: Purity (254 nm): 93.6%; $t_R$=1.29 min.

Following general procedure H, ethyl 2-((6-(3-fluorophenyl)-4-methylpyridazin-3-yl)methylamino)-2-oxoacetate (420 mg, 1.320 mmol) afforded ethyl 2-(3-fluorophenyl)-4-methylimidazo[1,5-b]pyridazine-7-carboxylate (300 mg, 76%) as a light yellow solid. LC-MS m/z: 300.0 [M+H]⁺. LCMS: Purity (214 nm): 94.1%; $t_R$=1.47 min.

Following general procedure B, ethyl 2-(3-fluorophenyl)-4-methylimidazo[1,5-b]pyridazine-7-carboxylate (280 mg, 0.94 mmol) afforded 2-(3-fluorophenyl)-4-methylimidazo[1,5-b]pyridazine-7-carboxylic acid sodium salt (450 mg, >95% crude yield) as an off-white solid. LC-MS m/z: 272.1 [M+H]⁺. LCMS: Purity (214 nm): 94.1%; $t_R$=1.62 min.

Following general procedure A, 2-(3-fluorophenyl)-4-methylimidazo[1,5-b]pyridazine-7-carboxylic acid sodium salt (220 mg, 0.736 mmol) and 2-cyclopropylpropan-2-amine afforded the title compound as a yellow solid (15 mg, 12%). ¹H NMR (500 MHz, MeOD-d₄): δ 7.92 (d, J=8.0 Hz, 1H), 7.87 (dt, J=8.4 Hz, 2.0 Hz, 1H), 7.82 (s, 1H), 7.62 (ddd, J=15.0 Hz, 7.5 Hz, 2.0 Hz, 1H), 7.41 (s, 1H), 7.36 (td, J=8.0 Hz, 2.0 Hz, 1H), 2.75 (s, 3H), 1.49 (s, 6H), 1.49-1.43 (m, 1H), 0.55 (d, J=7.0 Hz, 4H). LC-MS m/z: 353.2 [M+H]⁺. HPLC Purity (254 nm): 98%; $t_R$=8.70 min.

N-(1-Cyclopropyl-2,2,2-trifluoroethyl)-2-(3-fluorophenyl)-4-methylimidazo[1,5-b]pyridazine-7-carboxamide

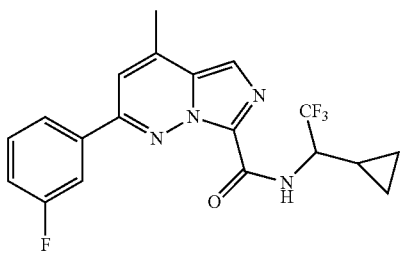 [SMILES: Cc1cc(-c2cccc(F)c2)nn2c(C(=O)NC(C3CC3)C(F)(F)F)ncc12]

Following general procedure A, 2-(3-fluorophenyl)-4-methylimidazo[1,5-b]pyridazine-7-carboxylic acid sodium salt (150 mg, 0.171 mmol) and 1-cyclopropyl-2,2,2-trifluoroethanamine hydrochloride afforded the title compound as a yellow solid (14 mg, 27%). ¹H NMR (500 MHz, MeOD-d₄): δ 7.92 (d, J=7.5 Hz, 1H), 7.89 (s, 1H), 7.87 (d, J=8.5 Hz, 1H), 7.63 (ddd, J=15.0 Hz, 7.0 Hz, 2.0 Hz, 1H), 7.49 (s, 1H), 7.37 (td, J=8.5 Hz, 2.5 Hz, 2H), 4.48-4.40 (m, 1H), 2.73 (s, 3H), 1.34-1.26 (m, 1H), 0.84-0.78 (m, 1H), 0.70-0.61 (m, 2H), 0.56-0.48 (m, 1H). LC-MS m/z: 393.1 [M+H]⁺. HPLC Purity (254 nm): 92%; $t_R$=8.63 min.

N-(1-Cyclopropyl-2,2,2-trifluoroethyl)-2-(3-methoxyphenyl)-4-methylimidazo[1,5-b]pyridazine-7-carboxamide

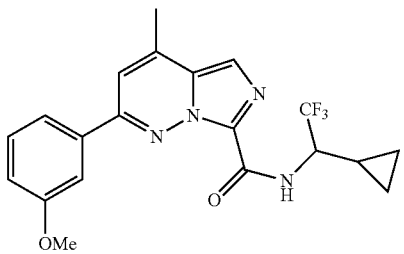 [SMILES: COc1cccc(-c2cc(C)c3cnc(C(=O)NC(C4CC4)C(F)(F)F)n3n2)c1]

Following general procedure C, 3,6-dichloro-4-methylpyridazine (5 g, 30.6 mmol), and 3-methoxyphenylboronic acid afforded 3-chloro-6-(3-methoxyphenyl)-4-methylpyridazine (1.88 g, 26%) as a white solid. LC-MS m/z: 235.1 [M+H]⁺. LCMS: Purity (214 nm): 93.1%; $t_R$=1.93 min.

Following general procedure E, 3-chloro-6-(3-methoxyphenyl)-4-methylpyridazine (1 g, 4.26 mmol) afforded 6-(3-methoxyphenyl)-4-methylpyridazine-3-carbonitrile (900 mg, 94%) as a pale yellow solid. LC-MS m/z: 226.1 [M+H]⁺. LCMS: Purity (214 nm): 93.5%; $t_R$=1.88 min.

Following general procedure F, 6-(3-methoxyphenyl)-4-methylpyridazine-3-carbonitrile (900 mg, 4 mmol) afforded (6-(3-methoxyphenyl)-4-methylpyridazin-3-yl)methanamine hydrochloride (1.0 g) as a dark brown solid, which was used directly in the next step. LC-MS m/z: 230.0 [M+H]⁺. LCMS: Purity (214 nm): 93.5%; $t_R$=1.40 min.

Following general procedure G, (6-(3-methoxyphenyl)-4-methylpyridazin-3-yl)methanamine hydrochloride (1 g) afforded ethyl 2-((6-(3-methoxyphenyl)-4-methylpyridazin-3-yl)methylamino)-2-oxoacetate (1.14 g, 86% over 2 steps) as a pale green solid. LC-MS m/z: 330.1 [M+H]⁺. LCMS: Purity (214 nm): 94.6%; $t_R$=1.60 min.

Following general procedure H, ethyl 2-((6-(3-methoxyphenyl)-4-methylpyridazin-3-yl)methylamino)-2-oxoacetate (1.14 g, 3.46 mmol afforded ethyl 2-(3-methoxyphenyl)-4-methylimidazo[1,5-b]pyridazine-7-carboxylate (900 mg, 84%) as a white solid. LC-MS m/z: 312.1 [M+H]⁺. LCMS: Purity (214 nm): 97.5%; $t_R$=1.45 min.

Following general procedure B, ethyl 2-(3-methoxyphenyl)-4-methylimidazo[1,5-b]pyridazine-7-carboxylate (900 mg, 2.89 mmol) afforded 2-(3-methoxyphenyl)-4-methylimidazo[1,5-b]pyridazine-7-carboxylic acid (741 mg, 90%) as a pale solid. LC-MS m/z: 284.2 [M+H]⁺. LCMS: Purity (254 nm): 83.3%; $t_R$=1.63 min.

Following general procedure A, 2-(3-methoxyphenyl)-4-methylimidazo[1,5-b]pyridazine-7-carboxylic acid (45 mg, 0.16 mmol) and 1-cyclopropyl-2,2,2-trifluoroethanamine hydrochloride afforded the title compound (40 mg, 62%) as a pale yellow solid. ¹H NMR (500 MHz, DMSO-d₆): δ 9.33 (d, J=9.0 Hz, 1H), 7.87 (s, 1H), 7.68 (d, J=8.0 Hz, 1H), 7.64 (s, 1H), 7.57 (s, 1H), 7.51 (t, J=8.0 Hz, 1H), 7.17 (d, J=6.5 Hz, 1H), 4.34-4.29 (m, 1H), 3.86 (s, 3H), 2.64 (s, 3H), 1.36-1.29 (m, 1H), 0.72-0.66 (m, 1H), 0.65-0.51 (m, 2H), 0.40-0.30 (m, 1H). LC-MS m/z: 405.1 [M+H]⁺. HPLC Purity (254 nm): >99%; $t_R$=8.57 min.

2-(3-Fluorophenyl)-4-methyl-N-(1,1,1-trifluoropropan-2-yl)imidazo[1,5-b]pyridazine-7-carboxamide

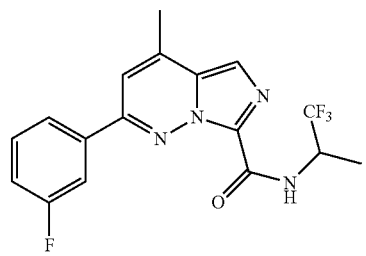 [SMILES: Cc1cc(-c2cccc(F)c2)nn2c(C(=O)NC(C)C(F)(F)F)ncc12]

Following general procedure A, 2-(3-fluorophenyl)-4-methylimidazo[1,5-b]pyridazine-7-carboxylate sodium salt (150 mg, 0.20 mmol) and 1,1,1-trifluoropropan-2-amine hydrochloride afforded the title compound (3.5 mg, 7%) as an off white solid. ¹H NMR (500 MHz, MeOD-d₄) δ 7.92 (d, J=7.5 Hz, 1H), 7.88 (d, J=9.5 Hz, 1H), 7.87 (s, 1H), 7.63 (dd, J=14.0 Hz, 8.0 Hz, 1H), 7.48 (s, 1H), 7.37 (dd, J=8.5 Hz, 2.5 Hz, 1H), 5.09-5.02 (m, 1H), 2.73 (s, 3H), 1.54 (d, J=7.0 Hz, 3H). LC-MS m/z: 367.1 [M+H]⁺. HPLC: Purity (214 nm): 98%; $t_R$=8.44 min.

2-(4-Fluorophenyl)-4-methyl-N-(1,1,1-trifluoropropan-2-yl)imidazo[1,5-b]pyridazine-7-carboxamide

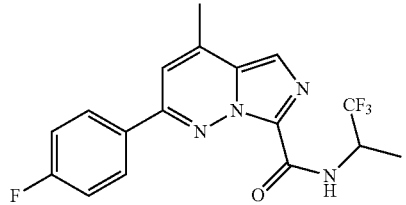 [SMILES: Cc1cc(-c2ccc(F)cc2)nn2c(C(=O)NC(C)C(F)(F)F)ncc12]

Following general procedure A, 2-(4-fluorophenyl)-4-methylimidazo[1,5-b]pyridazine-7-carboxylic acid (30 mg, 0.11 mmol) and 1,1,1-trifluoropropan-2-amine hydrochloride afforded the title compound (15 mg, 38%) as a pale solid. ¹H NMR (500 MHz, DMSO-d₆) δ 9.18 (d, J=8.5 Hz, 1H), 8.18 (dd, J=8.5 Hz, 5.5 Hz, 2H), 7.85 (s, 1H), 7.56 (s, 1H), 7.46 (t, J=8.5 Hz, 2H), 4.96-4.91 (m, 1H), 2.64 (s, 3H), 1.42 (d, J=6.5 Hz, 3H). LC-MS m/z: 367.1 [M+H]⁺. HPLC: Purity (214 nm): >99%; $t_R$=8.46 min.

(S)—N-(1-Cyclopropylethyl)-6-(4-fluorophenyl)-8-methyl-[1,2,4]triazolo[4,3-b]pyridazine-3-carboxamide

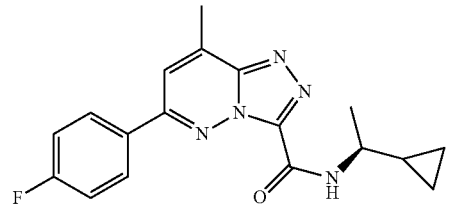 [SMILES: Cc1cc(-c2ccc(F)cc2)nn2c(C(=O)N[C@@H](C)C3CC3)nnc12]

To a solution of 6-(4-fluorophenyl)-3-hydrazinyl-4-methylpyridazine (100 mg, 0.458 mmol) in anhydrous dioxane (5 mL) was added Et₃N (70 mg, 0.688 mmol). The mixture was stirred for 5 minutes at RT, followed by the addition of ethyl oxalyl monochloride (680 mg, 0.545 mmol) dropwise, then stirred at 60° C. for 4 h, and concentrated in vacuo to afford ethyl 2-(2-(6-(4-fluorophenyl)-4-methylpyridazin-3-yl)hydrazinyl)-2-oxoacetate, which was used directly in the next step.

A solution of ethyl 2-(2-(6-(4-fluorophenyl)-4-methylpyridazin-3-yl)hydrazinyl)-2-oxoacetate (not weight) in AcOH (5 mL) was heated at 120° C. for 2 h, and concentrated in vacuo. The residue was dissolved in 10% NaHCO₃ solution (30 mL) and extracted with EA (20 mL×3). The organic layers were dried over anhydrous Na₂SO₄, filtered and concentrated in vacuo. The residue was triturated in a mixed solvent of PE/EA (30/1, 3 mL) and filtered to collect ethyl 6-(4-fluorophenyl)-8-methyl-[1,2,4]triazolo[4,3-b]pyridazine-3-carboxylate as a white solid (89 mg, 64% two steps). LC-MS m/z: 301.1 [M+H]⁺. $t_R$=1.84 min.

To a solution of (S)-1-cyclopropylethanamine (145 mg, 1.7 mmol) in 10 mL of DCM was added Al(Me)₃ (0.85 mL, 1.7 mmol) dropwise at RT under N₂. The reaction mixture was stirred for 30 min, followed by the addition of a solution of ethyl 6-(4-fluorophenyl)-8-methyl-[1,2,4]triazolo[4,3-b]pyridazine-3-carboxylate (100 mg, 0.34 mmol) in DCM (5 mL), and stirred at RT overnight. The mixture was poured into 50 mL of ice-water, basified to pH value to 8, and extracted with EA (50 mL×3). The organic phases were dried over anhydrous $Na_2SO_4$, filtered, concentrated in vacuo, and purified by pre-TLC to afford the title compound (30 mg, 28%) as a white solid. $^1$H NMR (400 MHz, DMSO-$d_6$) δ 8.94 (d, J=8.4 Hz, 1H), 8.19 (dd, J=8.8 Hz, 5.6 Hz, 2H), 8.00 (s, 1H), 7.48 (t, J=8.8 Hz, 2H), 3.61-3.52 (m, 1H), 2.74 (s, 3H), 1.30 (d, J=6.4 Hz, 3H), 1.15-1.06 (m, 1H), 0.55-0.41 (m, 2H), 0.40-0.32 (m, 1H), 0.31-0.25 (m, 1H). LC-MS m/z: 340.1 [M+H]$^+$. HPLC: Purity (214 nm): 97%; $t_R$=7.75 min.

N-(1-Cyclopropyl-2,2,2-trifluoroethyl)-7-methyl-5-(pyridin-3-yl)isothiazolo[4,5-b]pyridine-3-carboxamide

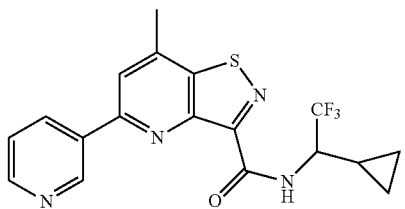 [SMILES: Cc1cc(-c2cccnc2)nc2c(C(=O)NC(C3CC3)C(F)(F)F)nsc12]

Following general procedure A, 7-methyl-5-(pyridin-3-yl)isothiazolo[4,5-b]pyridine-3-carboxylic acid (40 mg, 0.185 mmol) and 1-cyclopropyl-2,2,2-trifluoroethanamine afforded the title compound (6 mg, 9%) as a pale yellow solid. $^1$H NMR (500 MHz, CDCl$_3$) δ 10.25 (d, J=9.0 Hz, 1H), 9.11 (d, J=2.5 Hz, 1H), 8.82 (dd, J=5.0 Hz, 1.5 Hz, 1H), 8.33 (dt, J=7.5 Hz, 2.0 Hz, 1H), 8.01 (s, 1H), 7.71 (dd, J=8.0 Hz, 5.0 Hz, 1H), 4.54-4.52 (m, 1H), 2.82 (s, 3H), 1.34-1.30 (m, 1H), 0.72-0.68 (m, 1H), 0.68-0.60 (m, 2H), 0.50-0.45 (m, 1H). LC-MS m/z: 393.1 [M+H]$^+$. HPLC: Purity (214 nm): 95%; $t_R$=8.14 min.

(S)—N-(1-Cyclopropylethyl)-5-(6-methoxypyridin-2-yl)-7-methylisothiazolo[4,5-b]pyridine-3-carboxamide

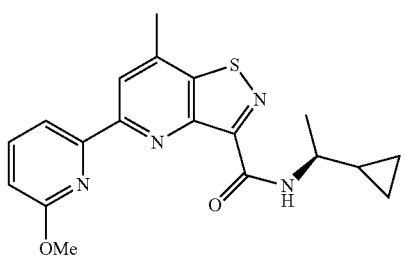 [SMILES: COc1cccc(-c2cc(C)c3snc(C(=O)N[C@@H](C)C4CC4)c3n2)n1]

Following general procedure D, methyl 5-chloro-7-methylisothiazolo[4,5-b]pyridine-3-carboxylate (100 mg, 0.413 mmol) and 2-methoxy-6-(tributylstannyl)pyridine afforded 5-(6-methoxypyridin-2-yl)-7-methylisothiazolo[4,5-b]pyridine-3-carboxylic acid (60 mg, 48%) as a yellow solid. LC-MS m/z: 302.1 [M+H]$^+$. Purity (214 nm): 68%; $t_R$=0.98 min.

Following general procedure A, 5-(6-methoxypyridin-2-yl)-7-methylisothiazolo[4,5-b]pyridine-3-carboxylic acid (40 mg, 0.13 mmol) and (S)-1-cyclopropylethanamine afforded the title compound (26 mg, 35%) as a yellow solid. $^1$H NMR (500 MHz, DMSO-$d_6$) δ 9.79 (d, J=8.0 Hz, 1H), 8.43 (s, 1H), 8.21 (d, J=7.0 Hz, 1H), 8.03 (t, J=8.0 Hz, 1H), 7.09 (d, J=8.0 Hz, 1H), 4.22 (s, 3H), 3.94-3.88 (m, 1H), 2.84 (s, 3H), 1.32 (d, J=6.5 Hz, 3H), 1.14-1.07 (m, 1H), 0.58-0.42 (m, 2H), 0.42-0.39 (m, 1H), 0.39-0.31 (m, 1H). LC-MS m/z: 369.1 [M+H]$^+$. HPLC Purity (214 nm): >99%; $t_R$=9.07 min.

N-(2-Cyclopropylpropan-2-yl)-7-methyl-5-(pyridin-3-yl)isothiazolo[4,5-b]pyridine-3-carboxamide

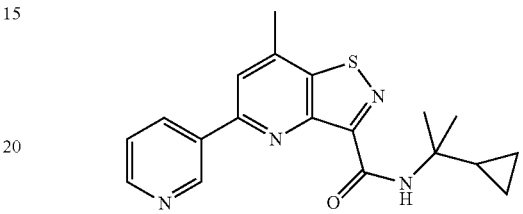

To a solution of 2-cyanoacetamide (10.0 g, 0.119 mol) and sodium nitrite (10.0 g, 0.145 mol) in water (100 g, 5 mol) was added AcOH (13.3 mL, 0.234 mol) dropwise over 30 mins maintaining the temperature below 20° C. with the ice bath. The reaction mixture was then stirred overnight, gradually warming to RT. After 12 h the aqueous layer was extracted with EA (100 mL×2). The combined organic layers were dried over $Mg_2SO_4$, and filtered. The filtrate was concentrated in vacuo to afford 2-amino-N-hydroxy-2-oxoacetimidoyl cyanide (12 g, 89%) as a white solid. $^1$H NMR (500 MHz, DMSO-$d_6$) δ 14.45 (s, 1H), 7.90 (s, 1H), 7.83 (s, 1H). LC-MS m/z: 135.9 [M+Na]$^+$. $t_R$=0.33 min.

To a suspension of 2-amino-N-hydroxy-2-oxoacetimidoyl cyanide (10 g, 88 mmol) in anhydrous $CH_2Cl_2$ (100 mL) was added pyridine (8.39 g, 0.10 mol). The resulting clear yellow solution was cooled in an ice bath under an atmosphere of $N_2$ and TsCl (18.5 g, 97 mmol) was added thereto. The reaction mixture was stirred at 0° C. for 30 minutes and then at RT for 2 h followed by the addition of DCM (200 mL) was added to this reaction mixture, which was washed with water (50 mL×3) and brine (100 mL). The organic phase was dried over anhydrous $Na_2SO_4$, and filtered. The filtrate was concentrated in vacuo, and the residue was recrystallized from DCM/hexane to afford 2-amino-2-oxo-N-(tosyloxy)acetimidoyl cyanide (23 g, 91%) as a white solid. LC-MS m/z: 267.9 [M+H]$^+$. LC-MS: Purity (214 nm): 75%; $t_R$=1.72 min.

To a stirred suspension of 2-amino-2-oxo-N-(tosyloxy) acetimidoyl cyanide (10 g, 37.4 mmol) in ethanol (50 mL) was added ethyl 2-mercaptoacetate (5.38 g, 44.9 mmol) at 0° C., followed by the addition of morpholine (4.89 g, 56.1 mmol) over fifteen minutes. The reaction mixture was stirred for twenty minutes, and diluted with ice water (150 mL). The precipitate was collected by filtration and dried in vacuo to afford ethyl 4-amino-3-carbamoylisothiazole-5-carboxylate (5 g, 62%) as a white solid. $^1$H NMR (500 MHz, DMSO-$d_6$) δ 8.13 (s, 1H), 7.77 (s, 1H), 6.84 (s, 2H), 4.30 (q, J=7.0 Hz, 2H), 1.30 (t, J=7.5 Hz, 3H). LC-MS m/z: 215.9 [M+Na]$^+$. LCMS: Purity (214 nm): 96.9%; $t_R$=1.60 min.

A solution of ethyl 4-amino-3-carbamoylisothiazole-5-carboxylate (2 g, 9.30 mmol) in concentrated HCl (12 N, 20 mL) was stirred under reflux for 12 h, and concentrated in vacuo to afford crude 4-aminoisothiazole-3-carboxylic acid as a light green solid. LC-MS m/z: 145.0 [M+H]$^+$. $t_R$=0.60 min.

To a solution of 4-aminoisothiazole-3-carboxylic acid (crude, prepared in the last step) in methanol (10 mL) was added thionyl chloride (3.3 g, 27.9 mmol) dropwise at 0° C. The mixture was stirred 70° C. for 2 h, and concentrated in vacuo. The residue was diluted with EA (100 mL), washed with saturated NaHCO$_3$ (100 mL) and brine (50 mL), dried over anhydrous Na$_2$SO$_4$, and filtered. The filtrate was concentrated in vacuo to afford methyl 4-aminoisothiazole-3-carboxylate (1.03 g, 68% two steps) as brown oil. LC-MS m/z: 159.0 [M+H]$^+$. LCMS: Purity (214 nm): 97.8%; t$_R$=1.24 min.

The solution of methyl 4-aminoisothiazole-3-carboxylate (910 mg, 5.76 mmol) and 4-methyleneoxetan-2-one (580 mg, 6.91 mmol) in AcOH (10 mL) was stirred at 100° C. for 1 h until the reaction was complete and concentrated in vacuo. The residue was purified by silica gel column (PE/EA: 1/1) to afford methyl 4-(3-oxobutanamido)isothiazole-3-carboxylate (1.28 g, 92%) as a white solid. LC-MS m/z: 242.9 [M+H]$^+$. LC-MS Purity (214 nm): >99%; t$_R$=1.44 min.

A suspension of methyl 4-(3-oxobutanamido)isothiazole-3-carboxylate (835 mg, 3.45 mmol) in PPA (4.8 g, 44.5 mmol) was stirred at 90° C. for 6 h, cooled to RT and diluted with water (50 mL). After stirring at RT for 1 h, the reaction mixture was extracted with EA (50 mL×3). The combined organic layers were washed with brine (30 mL), dried over anhydrous Na$_2$SO$_4$ and filtered. The filtrate was concentrated in vacuo, and the residue was purified by silica gel column (MeOH/EA: 1/20) to afford methyl 5-hydroxy-7-methylisothiazolo[4,5-b]pyridine-3-carboxylate (380 mg, 49%) as a pale solid. $^1$H NMR (500 MHz, DMSO-d$_6$) δ 11.50 (s, 1H), 6.08 (s, 1H), 3.99 (s, 3H), 2.48 (s, 3H). LC-MS m/z: 225.1 [M+H]$^+$. LCMS: Purity (214 nm): 97.5%; t$_R$=0.88 min.

A solution of methyl 5-hydroxy-7-methylisothiazolo[4,5-b]pyridine-3-carboxylate (380 mg, 1.69 mmol) in POCl$_3$ (1.25 g, 8.18 mmol) was stirred at 70° C. for 2 h under N$_2$, cooled, diluted with DCM (60 mL), and poured into ice. The organic phase was separated, washed with saturated NaHCO$_3$ (30 mL) and brine (20 mL), dried over anhydrous Na$_2$SO$_4$, and filtered. The filtrate was concentrated in vacuo, and the residue was purified by silica gel column (PE/EA 4:1) to afford methyl 5-chloro-7-methylisothiazolo[4,5-b]pyridine-3-carboxylate (224 mg, 54%) as a white solid. LC-MS m/z: 243.1 [M+H]$^+$. LCMS: Purity (214 nm): 97%; t$_R$=1.81 min.

Following general procedure C, methyl 5-chloro-7-methylisothiazolo[4,5-b]pyridine-3-carboxylate (60 mg, 0.248 mmol) and 3-pyridylboronic acid afforded a mixture of methyl 7-methyl-5-(pyridin-3-yl)isothiazolo[4,5-b]pyridine-3-carboxylate (LC-MS m/z: 286.0 [M+H]$^+$. LCMS: Purity (214 nm): 6.51%; t$_R$=1.51 min) and 7-methyl-5-(pyridin-3-yl)isothiazolo[4,5-b]pyridine-3-carboxylic acid (LC-MS m/z: 272.0 [M+H]$^+$. LCMS: Purity (214 nm): 43%; t$_R$=1.10 min).

Following general procedure B, a crude mixture of methyl 7-methyl-5-(pyridin-3-yl)isothiazolo[4,5-b]pyridine-3-carboxylate and 7-methyl-5-(pyridin-3-yl)isothiazolo[4,5-b]pyridine-3-carboxylic acid (prepared in the last step) afforded 7-methyl-5-(pyridin-3-yl)isothiazolo[4,5-b]pyridine-3-carboxylic acid (35 mg, 49%, two steps) as a pale solid. LC-MS m/z: 272.1 [M+H]$^+$. LCMS: Purity (214 nm): 95.8%; t$_R$=0.79 min.

Following general procedure A, 7-methyl-5-(pyridin-3-yl)isothiazolo[4,5-b]pyridine-3-carboxylic acid (35 mg, 0.13 mmol) and 2-cyclopropylpropan-2-amine afforded the title compound (7 mg, 15%) as a pale yellow solid. $^1$H NMR (500 MHz, CDCl$_3$) δ 9.93 (s, 1H), 9.09 (d, J=2.0 Hz, 1H), 8.81 (dd, J=8.0 Hz, 2.0 Hz, 1H), 8.31 (dt, J=4.5 Hz, 1.0 Hz, 1H), 7.99 (s, 1H), 7.71 (dd, J=8.0 Hz, 4.5 Hz, 1H), 2.82 (s, 3H), 1.42 (s, 6H), 1.42-1.38 (m, 1H), 0.54-0.50 (m, 4H). LC-MS m/z: 353.0 [M+H]$^+$. HPLC: Purity (214 nm): >99%; t$_R$=8.15 min.

N-(1-Cyclopropyl-2,2,2-trifluoroethyl)-7-methyl-5-(pyridin-2-yl)isothiazolo[4,5-b]pyridine-3-carboxamide

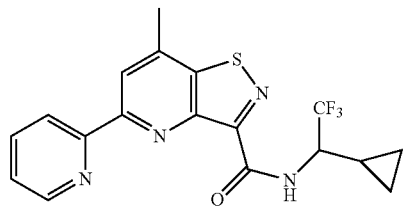 [SMILES: Cc1cc(-c2ccccn2)nc2c(C(=O)NC(C3CC3)C(F)(F)F)nsc12]

Following general procedure D, methyl 5-chloro-7-methylisothiazolo[4,5-b]pyridine-3-carboxylate (80 mg, 0.33 mmol) and 2-(tributylstannyl)pyridine afforded a mixture of methyl 7-methyl-5-(pyridin-3-yl)isothiazolo[4,5-b]pyridine-3-carboxylate (LC-MS m/z: 286.0 [M+H]$^+$. LCMS: Purity (214 nm): 55%; t$_R$=1.35 min) and 7-methyl-5-(pyridin-2-yl)isothiazolo[4,5-b]pyridine-3-carboxylic acid (LC-MS m/z: 272.0 [M+H]$^+$. LCMS: Purity (214 nm): 23%; t$_R$=0.89 mi).

Following general procedure B, a crude mixture of methyl 7-methyl-5-(pyridin-2-yl)isothiazolo[4,5-b]pyridine-3-carboxylate and 7-methyl-5-(pyridin-2-yl)isothiazolo[4,5-b]pyridine-3-carboxylic acid (prepared in the last step) afforded 7-methyl-5-(pyridin-2-yl)isothiazolo[4,5-b]pyridine-3-carboxylic acid (50 mg, 56%, over two steps) as a pale solid. LC-MS m/z: 272.1 [M+H]$^+$. LCMS: Purity (214 nm): 73%; t$_R$=0.89 min.

Following general procedure A, 7-methyl-5-(pyridin-2-yl)isothiazolo[4,5-b]pyridine-3-carboxylic acid (50 mg, 0.185 mmol) and 1-cyclopropyl-2,2,2-trifluoroethanamine afforded the title compound (4.4 mg, 6.1%) as a pale yellow solid. $^1$H NMR (500 MHz, CDCl$_3$) δ 10.31 (d, J=9.5 Hz, 1H), 8.97 (d, J=4.5 Hz, 1H), 8.63 (d, J=8.0 Hz, 1H), 8.52 (s, 1H), 8.16 (td, J=7.5 Hz, 1.5 Hz, 1H), 7.66 (dd, J=12.5 Hz, 5.0 Hz, 1H), 4.56-4.51 (m, 1H), 2.85 (s, 3H), 1.36-1.31 (m, 1H), 0.72-0.60 (m, 3H), 0.50-0.46 (m, 1H). LC-MS m/z: 393.1 [M+H]$^+$. HPLC: Purity (214 nm): >99%; t$_R$=9.02 min.

5-(3-Carbamoylphenyl)-N-(1-cyclopropyl-2,2,2-trifluoroethyl)-7-methylisothiazolo[4,5-b]pyridine-3-carboxamide

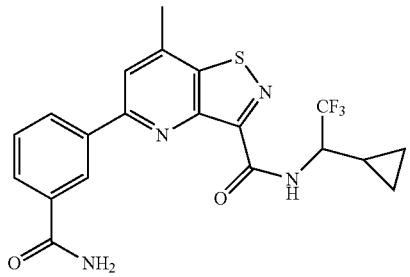 [SMILES: Cc1cc(-c2cccc(C(N)=O)c2)nc2c(C(=O)NC(C3CC3)C(F)(F)F)nsc12]

A mixture of methyl 5-chloro-7-methylisothiazolo[4,5-b]pyridine-3-carboxylate (50 mg, 0.21 mmol), (Bu₃Sn)₂O (246 mg, 0.41 mmol) in toluene (2 mL) was stirred at 110° C. for 15 h, cooled and concentrated in vacuo. The residue was purified by column chromatography on silica gel (DCM/MeOH: 10/1) to afford 5-chloro-7-methylisothiazolo[4,5-b]pyridine-3-carboxylic acid as a yellow solid (70 mg, 90%). LC-MS m/z: 229.1 [M+H]⁺. Purity (214 nm): 94.60%; t$_R$=0.86 min.

Following general procedure A, 5-chloro-7-methylisothiazolo[4,5-b]pyridine-3-carboxylic acid (55 mg, 0.22 mmol) and 1-cyclopropyl-2,2,2-trifluoroethanamine hydrochloride afforded 5-chloro-N-(1-cyclopropyl-2,2,2-trifluoroethyl)-7-methylisothiazolo[4,5-b]pyridine-3-carboxamide (55 mg, 69%) LC-MS m/z: 359.0 [M+H]⁺. LC-MS Purity (214 nm): 77.34%; t$_R$=1.62 min.

Following general procedure C, 5-chloro-N-(1-cyclopropyl-2,2,2-trifluoroethyl)-7-methylisothiazolo[4,5-b]pyridine-3-carboxamide (55 mg, 0.157 mmol) and 3-carbamoylphenylboronic acid afforded the title compound (3 mg, 4.4%) as a yellow solid. ¹H NMR (500 MHz, DMSO-d₆) δ 10.30 (d, J=9.5 Hz, 1H), 8.38 (s, 1H), 8.22 (s, 1H), 8.11 (d, J=7.5 Hz, 1H), 8.07 (d, J=7.5 Hz, 1H), 8.00 (s, 1H), 7.78 (t, J=7.5 Hz, 1H), 7.64 (s, 1H), 4.58-4.52 (m, 1H), 2.82 (s, 3H), 1.34-1.30 (m, 1H), 0.72-0.68 (m, 1H), 0.68-0.60 (m, 2H), 0.50-0.45 (m, 1H). LC-MS m/z: 435.1 [M+H]⁺. HPLC: Purity (214 nm): >99%; t$_R$=7.79 min.

5-(Benzo[d]oxazol-4-yl)-N-(1-cyclopropyl-2,2,2-trifluoroethyl)-7-methylisothiazolo[4,5-b]pyridine-3-carboxamide

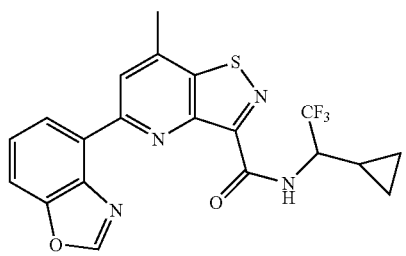 [SMILES: Cc1cc(-c2cccc3ocnc23)nc2c(C(=O)NC(C3CC3)C(F)(F)F)nsc12]

Following general procedure C, methyl 5-chloro-7-methylisothiazolo[4,5-b]pyridine-3-carboxylate (300 mg, 1.24 mmol) and 4-(4,4,5,5-tetramethyl-1,3,2-dioxaborolan-2-yl)benzo[d]oxazole afforded ethyl 5-(benzo[d]oxazol-4-yl)-7-methylisothiazolo[4,5-b]pyridine-3-carboxylate (70 mg, 17%) as a white solid. LC-MS m/z: 326.1 [M+H]⁺. Purity (214 nm): >96%; t$_R$=1.68 min.

A solution of ethyl 5-(benzo[d]oxazol-4-yl)-7-methylisothiazolo[4,5-b]pyridine-3-carboxylate (60 mg, 0.184 mmol) and (Bu₃Sn)₂O (219.4 mg, 0.368 mmol) in 3 mL of toluene was stirred at 120° C. for 24 h, and concentrated in vacuo. The residue was stirred in EA (5 mL) and aqueous NaHCO₃ (10 mL) for 10 minutes. The aqueous phase was separated, washed with EA (5 mL), acidified with 2N HCl to pH=5, and extracted with EA (10 mL×3). The organic phases were washed with brine (5 mL), dried over anhydrous Na₂SO₄, filtered and concentrated in vacuo to afford 5-(benzo[d]oxazol-4-yl)-7-methylisothiazolo[4,5-b]pyridine-3-carboxylic acid as a brown solid (20 mg, 35%). LC-MS m/z: 312.0 [M+H]⁺. Purity (254 nm): >43%; t$_R$=1.27 min.

Following general procedure A, 5-(benzo[d]oxazol-4-yl)-7-methylisothiazolo[4,5-b]pyridine-3-carboxylic acid (15 mg, 0.048 mmol) and 1-cyclopropyl-2,2,2-trifluoroethanamine hydrochloride afforded the title compound (6.6 mg, 24%) as a yellow solid. ¹H NMR (400 MHz, DMSO-d₆) δ 10.27 (d, J=9.2 Hz, 1H), 8.98 (s, 1H), 8.14 (s, 1H), 8.05 (d, J=8.0 Hz, 1H), 7.89 (d, J=8.0 Hz, 1H), 7.73 (t, J=8.0 Hz, 1H), 4.56-4.50 (m, 1H), 2.83 (s, 3H), 1.34-1.28 (m, 1H), 0.72-0.60 (m, 3H), 0.49-0.46 (m, 1H). LC-MS m/z: 433.1 [M+H]⁺. HPLC: Purity (214 nm): >99%; t$_R$=9.29 min.

N-(2-Cyclopropylpropan-2-yl)-5,7-dimethylthieno[3,2-b]pyridine-3-carboxamide

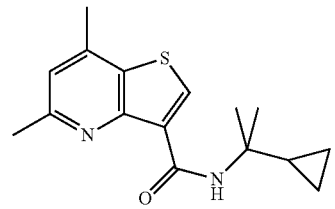 [SMILES: Cc1cc(C)c2scc(C(=O)NC(C)(C)C3CC3)c2n1]

Following general procedure A, 5,7-dimethylthieno[3,2-b]pyridine-3-carboxylic acid (70 mg, 0.34 mmol) and 2-cyclopropylpropan-2-amine afforded the title compound as a yellow solid (33 mg, 74%). ¹H NMR (500 MHz, CDCl₃): δ 10.05 (s, 1H), 8.50 (s, 1H), 6.95 (s, 1H), 2.60 (s, 3H), 2.50 (s, 3H), 1.40 (s, 6H), 1.33-1.30 (m, 1H), 0.47-0.44 (m, 4H). LC-MS m/z: 289.1 [M+H]⁺. HPLC Purity (214 nm): >99%; t$_R$=11.59 min.

N-(1-Cyclopropyl-2,2,2-trifluoroethyl)-5,7-dimethylthieno[3,2-b]pyridine-3-carboxamide

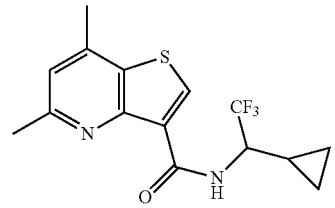 [SMILES: Cc1cc(C)c2scc(C(=O)NC(C3CC3)C(F)(F)F)c2n1]

Following general procedure A, 5,7-dimethylthieno[3,2-b]pyridine-3-carboxylic acid (70 mg, 0.34 mmol) and 1-cyclopropyl-2,2,2-trifluoroethanamine hydrochloride afforded the title compound (23 mg, 210%) as a white solid. ¹H NMR (500 MHz, DMSO-d₆): δ 10.54 (d, J=9.5 Hz, 1H), 8.88 (s, 1H), 7.33 (s, 1H), 7.04 (d, J=7.5 Hz, 1H), 4.60-4.56 (m, 1H), 2.65 (s, 3H), 2.59 (s, 3H), 1.30-1.25 (m, 1H), 0.69-0.58 (m, 2H), 0.52-0.48 (m, 1H), 0.47-0.41 (m, 1H). LC-MS m/z: 329.1 [M+H]⁺. HPLC Purity (214 nm): 98%; t$_R$=11.37 min.

N-(1-Cyclopropyl-2,2,2-trifluoroethyl)-7-methyl-5-(pyridin-3-yl)thieno[3,2-b]pyridine-3-carboxamide

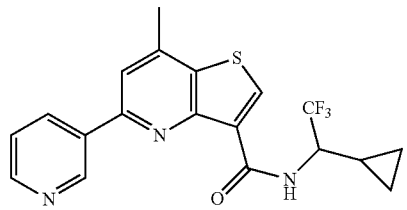 [SMILES: Cc1cc(-c2cccnc2)nc2c(C(=O)NC(C3CC3)C(F)(F)F)csc12]

A mixture of methyl 4-oxotetrahydrothiophene-3-carboxylate (2.3 g, 14.37 mmol) and NH$_2$OH HCl (1.2 g, 17.25 mmol) in MeOH (40 mL) was stirred under reflux for 1 h, quenched with saturated NaHCO$_3$ (200 mL) and extracted with EA (100 mL×3). The combined organic phases were dried over anhydrous Na$_2$SO$_4$, filtered and concentrated in vacuo to afford methyl 4-aminothiophene-3-carboxylate (2.1 g, 93%) as a light yellow oil. LC-MS m/z: 158.0 [M+H]$^+$. $t_R$=1.44 min.

A mixture of methyl 4-aminothiophene-3-carboxylate (157 mg, 1.0 mmol) and 4-methyleneoxetan-2-one (84 mg, 1.0 mmol) in HOAc (2 mL) was stirred at 110° C. for 30 min, and concentrated in vacuo. The residue was purified by silica gel column chromatography to afford methyl 4-(3-oxobutanamido)thiophene-3-carboxylate (80 mg, 33%) as a yellow solid. $^1$H NMR (500 MHz, CDCl$_3$) δ 10.77 (bs, 1H), 8.07 (s, 2H), 3.95 (s, 3H), 3.63 (s, 2H), 2.35 (s, 3H). LC-MS m/z: 242.1 [M+H]$^+$. $t_R$=1.53 min.

A mixture of methyl 4-(3-oxobutanamido)thiophene-3-carboxylate (390 mg, 1.6 mmol) in H$_3$PO$_4$ (6 mL) was stirred at 90° C. overnight, quenched with saturated Na$_2$CO$_3$ (200 mL), and extracted with EA (160 mL×3). The combined organic phases were dried over anhydrous Na$_2$SO$_4$, filtered and concentrated in vacuo to afford methyl 5-hydroxy-7-methylthieno[3,2-b]pyridine-3-carboxylate (300 mg, 84%) as a grey solid. $^1$H NMR (500 MHz, DMSO-d$_6$) δ 10.40 (s, 1H), 8.70 (s, 1H), 6.34 (s, 1H), 3.90 (s, 3H), 2.37 (d, J=1.0 Hz, 3H). LC-MS m/z: 224.1 [M+H]$^+$. $t_R$=1.41 min.

A mixture of methyl 5-hydroxy-7-methylthieno[3,2-b]pyridine-3-carboxylate (600 mg, 2.7 mmol) in POCl$_3$ (10 mL) was stirred at 110° C. for 2 h, poured into crushed ice, and extracted with EA (80 mL×3). The combined organic phases were washed with saturated NaHCO$_3$ (200 mL) and brine (200 mL), dried over anhydrous Na$_2$SO$_4$, and filtered. The filtrate was concentrated in vacuo to afford methyl 5-chloro-7-methylthieno[3,2-b]pyridine-3-carboxylate (510 mg, 78%) as a grey solid. LC-MS m/z: 242.1 [M+H]$^+$. $t_R$=1.71 min.

Following general procedure C, methyl 5-chloro-7-methylthieno[3,2-b]pyridine-3-carboxylate (438 mg, 1.81 mmol) and pyridin-3-ylboronic acid afforded crude methyl 7-methyl-5-(pyridin-3-yl)thieno[3,2-b]pyridine-3-carboxylate (600 mg) as a light yellow solid. LC-MS m/z: 285.1 [M+H]$^+$. $t_R$=1.35 min.

Following general procedure B, crude methyl 7-methyl-5-(pyridin-3-yl)thieno[3,2-b]pyridine-3-carboxylate (572 mg) afforded 7-methyl-5-(pyridin-3-yl)thieno[3,2-b]pyridine-3-carboxylic acid (180 mg, 35% yield over two steps) as a grey green solid. $^1$H NMR (500 MHz, DMSO-d$_6$) δ 12.45 (bs, 1H), 9.36 (s, 1H), 9.00 (s, 1H), 8.69 (s, 1H), 8.52 (d, J=8.0 Hz, 1H), 8.08 (s, 1H), 7.59 (t, J=6.0 Hz, 1H), 2.69 (s, 3H). LC-MS m/z: 271.1 [M+H]$^+$. $t_R$=0.89 min.

Following general procedure A, 7-methyl-5-(pyridin-3-yl)thieno[3,2-b]pyridine-3-carboxylic acid (27 mg, 0.10 mmol) and 1-cyclopropyl-2,2,2-trifluoroethanamine afforded the title compound (20 mg, 34%) as a white solid. $^1$H NMR (500 MHz, CDCl$_3$) δ 10.52 (d, J=9.0 Hz, 1H), 9.27 (d, J=1.5 Hz, 1H), 8.80 (s, 1H), 8.75 (dd, J=4.5 Hz, 1.5 Hz, 1H), 8.35 (dt, J=8.0 Hz, 2.0 Hz, 1H), 7.68 (s, 1H), 7.50 (dd, J=8.0 Hz, 5.0 Hz, 1H), 4.52-4.50 (m, 1H), 2.76 (s, 3H), 1.29-1.24 (m, 1H), 0.76-0.74 (m, 1H), 0.60-0.52 (m, 3H). LC-MS m/z: 392.0 [M+H]$^+$. HPLC: Purity (214 nm): >99%; $t_R$=8.64 min.

(S)—N-(1-Cyclopropylethyl)-7-methyl-5-(pyridin-3-yl)thieno[3,2-b]pyridine-3-carboxamide

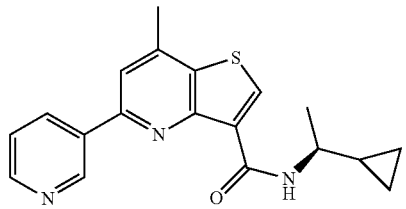 [SMILES: Cc1cc(-c2cccnc2)nc2c(C(=O)N[C@@H](C)C3CC3)csc12]

Following general procedure A, 7-methyl-5-(pyridin-3-yl)thieno[3,2-b]pyridine-3-carboxylic acid (54 mg, 0.20 mmol) and (S)-1-cyclohexylethanamine afforded the title compound (16 mg, 31%) as an off-white solid. $^1$H NMR (500 MHz, DMSO-d$_6$) δ 9.91 (d, J=7.5 Hz, 1H), 9.38 (d, J=2.0 Hz, 1H), 8.86 (s, 1H), 8.71 (dd, J=4.5 Hz, 1.5 Hz, 1H), 8.51 (dt, J=8.0 Hz, 2.0 Hz, 1H), 8.10 (s, 1H), 7.63 (dd, J=8.0 Hz, 5.0 Hz, 1H), 3.63-3.61 (m, 1H), 2.71 (s, 3H), 1.32 (d, J=6.5 Hz, 3H), 1.10-1.08 (m, 1H), 0.56-0.49 (m, 2H), 0.39-0.33 (m, 2H). LC-MS m/z: 338.1 [M+H]$^+$. HPLC: Purity (214 nm): >99%; $t_R$=8.06 min.

5-(3-Carbamoylphenyl)-N-(1-cyclopropyl-2,2,2-trifluoroethyl)-7-methylthieno[3,2-b]pyridine-3-carboxamide

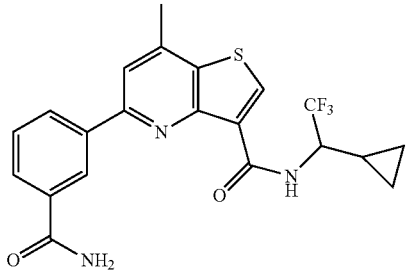 [SMILES: Cc1cc(-c2cccc(C(N)=O)c2)nc2c(C(=O)NC(C3CC3)C(F)(F)F)csc12]

Following general procedure C, methyl 5-chloro-7-methylthieno[3,2-b]pyridine-3-carboxylate (626 mg, 2.6 mmol) and 3-carbamoylphenylboronic acid afforded methyl 5-(3-carbamoylphenyl)-7-methylthieno[3,2-b]pyridine-3-carboxylate (625 mg, 76%) as a grey solid. LC-MS m/z: 327.1 [M+H]$^+$. $t_R$=1.29 min.

Following general procedure B, methyl 5-(3-carbamoylphenyl)-7-methylthieno[3,2-b]pyridine-3-carboxylate (100 mg, 0.3 mmol) afforded 5-(3-carbamoylphenyl)-7-methylthieno[3,2-b]pyridine-3-carboxylic acid (75 mg, 80%) as an off-white solid. LC-MS m/z: 313.1 [M+H]$^+$. $t_R$=0.93 min.

Following general procedure A, 5-(3-carbamoylphenyl)-7-methylthieno[3,2-b]pyridine-3-carboxylic acid (48 mg, 0.15 mmol) and 1-cyclopropyl-2,2,2-trifluoroethanamine hydrochloride afforded the title compound (21 mg, 38%) as a white solid. $^1$H NMR (500 MHz, DMSO-d$_6$) δ 10.57 (d, J=9.0 Hz, 1H), 9.01 (s, 1H), 8.65 (s, 1H), 8.27 (d, J=7.5 Hz, 1H), 8.14 (s, 1H), 8.13 (d, J=7.0 Hz, 1H), 8.00 (d, J=8.0 Hz, 1H), 7.67 (t, J=7.5 Hz, 1H), 7.55 (s, 1H), 4.42-4.38 (m, 1H), 2.74 (s, 3H), 1.51-1.44 (m, 1H), 0.72-0.69 (m, 1H), 0.68-0.60 (m, 2H), 0.40-0.36 (m, 1H). LC-MS m/z: 434.1 [M+H]$^+$. HPLC: Purity (214 nm): >99%; $t_R$=7.96 min.

Example 2—Preparation of Additional Compounds

Additional exemplary compounds were prepared based on general procedures described in Part I below. Exemplary procedures for preparing specific compounds according to the general procedures are described in Part II below.

Part I—General Procedures

General Procedure A: Preparation of Amide Compound by Coupling of a Carboxylic Acid Compound with an Amine Compound To a stirred solution of carboxylic acid compound (1.0 equivalent), HATU (1.5 equivalents), and DIPEA (3.75 equivalents) in DCM or DMF (~4 mL/0.2 mmol) was added the amine (1.25-2.0 equivalents). The reaction mixture was stirred at RT for 4-16 h, and then washed with saturated aqueous $NaHCO_3$ solution (5 mL/0.2 mmol), aqueous citric acid solution (5 mL/0.2 mmol) and brine (5 mL/0.2 mmol). The combined extracts were dried over anhydrous $Na_2SO_4$, filtered and concentrated in vacuo. The crude material was purified by silica gel column chromatography or preparatory HPLC to give the amide compound.

General Procedure B: Conversion of Carboxylic Ester Compound to Carboxylic Acid Compound To a solution of carboxylic ester (1.0 equivalent) in EtOH (5.0 mL/1.0 mmol) and water (0-3.0 mL/1.0 mmol) was added NaOH (2.0-5.0 equivalents) and the mixture was heated at 80° C. for 2 h and then concentrated. To the concentrate, 6N HCl solution was added to adjust the pH to 5-6 and then the mixture was stirred for 10 minutes and subsequently filtered. The resulting solid was collected and dried to give the carboxylic acid compound.

Alternatively, to a solution of carboxylic ester (1.0 equivalent) in THF (5.0 mL/1.0 mmol) was added LiOH (1M solution, 3 equivalents) and the mixture was stirred for 60° C. for 1-2 h and then the pH was adjusted to ~7 with 1 N HCl. The resulting solution was lyophilized to afford the crude carboxylic acid.

General Procedure C: Preparation of Amide Compound from a Carboxylic Acid Compound and an Amine Compound Using Oxalyl Chloride To a solution of carboxylic acid (1.0 equivalent) in DCM (3 mL/0.5 mmol) was added DMF (1 drop) and oxalyl chloride (2.0 equivalents). The solution was stirred at RT for 30 min and concentrated in vacuo. The residue was dissolved in DCM (1 mL/0.5 mmol) followed by the addition of the amine (5.0 equivalents) and triethylamine (2.0 equivalents). The reaction mixture was stirred at RT for 2 hours and diluted with DCM (10 mL/0.5 mmol). The organic solution was washed with $H_2O$ (10 mL/0.5 mmol) and brine (10 mL/0.5 mmol), dried over anhydrous $Na_2SO_4$, and filtered. The filtrate was concentrated in vacuo, and the residue was purified by preparatory HPLC or silica gel chromatography to give the amide.

General Procedure D: Preparation of Coupled Aryl and Heteroaryl Groups Using Suzuki-Catalyzed Coupling Conditions Between an Organoboronic Acid or Ester and an Aryl Halide or Heteroaryl Halide A suspension of heteroaryl chloride (1 equivalent), organoboronic acid or organoboronic ester (1.2 equivalents), $K_3PO_4$ (3.0 equivalents), and $Pd(dppf)Cl_2 \cdot DCM$ (5 mol %) or $Pd_2(dba)_3$ (10 mol %) in DME or 1,4-dioxane (40 mL/mmol) was stirred at 70-100° C. for 2-6 hours under $N_2$. Then, the reaction mixture was concentrated in vacuo and the resulting residue was purified by silica gel column chromatography to afford the coupled ring system.

General Procedure E: Preparation of Coupled Aryl and Heteroaryl Groups Using Buchwald Catalyzed Coupling Conditions Between Organohalides in the Presence of a Tin Reagent A solution of organobromide (1.0 equivalent), organochloride (1.0 equivalent), hexabutylditin (1.0 equivalent), and $Pd(dppf)Cl_2 \cdot DCM$ (10 mol %) or $Pd(t-Bu_3P)_2$ in anhydrous 1,4-dioxane (10 mL/mmol) or DMA (10 mL/mmol) was stirred at 100° C. under $N_2$ overnight, then cooled and the reaction quenched with water (20 mL/mmol). The resulting mixture was extracted with EtOAc (20 mL/mmol×3), the organic phases were separated and dried over anhydrous $Na_2SO_4$ and filtered. The filtrate was concentrated in vacuo, and the resulting residue was purified by silica gel column chromatography or preparative-TLC to afford the coupled ring system.

General Procedure F: Preparation of Coupled Aryl and Heteroaryl Groups Using Buchwald Catalyzed Coupling Conditions Between an Organohalide and Organotin Reagent A solution of organochloride (1.0 equivalent) and organotin reagent (1.0 equivalent) in 1,4-dioxane (20 mL/mmol) was stirred and purged with $N_2$ three times at RT. Then $Pd(dppf)Cl_2 \cdot DCM$ (10 mol %) or $Pd(PPh_3)_2Cl_2$ was quickly added under a $N_2$ atmosphere to the reaction mixture, followed by additional purging with $N_2$ (×3) and then the mixture was stirred at 120° C. overnight. Next, the reaction was cooled to RT and then quenched with water (20 mL/mmol). The resulting mixture was extracted with EA (20 mL/mmol×3), and the organic phases were dried over anhydrous $Na_2SO_4$ and filtered and concentrated in vacuo. The resulting residue was purified by silica gel column chromatography or preparative-TLC to afford the coupled ring system.

General Procedure G: Preparation of Coupled Imidazolidinyl Groups Using Buchwald Catalyzed Coupling Conditions Between an Organohalide and Imidazolidinyl Reagent A solution of organochloride (1.0 equivalent), imidazolidinyl reagent (1.0-2.0 equivalents), $Pd_2(dba)_3$ (10 mol %), x-antphos (20 mol %) and $Cs_2CO_3$ (2.1 equivalents) in dioxane (0.3 mmol/5 mL) was stirred at 110° C. for 2 to 16 h under a $N_2$ atmosphere. The reaction mixture was cooled to RT, quenched with saturated $NH_4Cl$ (20 mL), and extracted with EA (30 mL×3). The combined organic layers were washed with brine (30 mL), dried over anhydrous $Na_2SO_4$ and filtered. The filtrate was concentrated in vacuo, and the residue was purified by silica gel column chromatography to afford the coupled ring system.

Part II—Compounds Prepared Following General Procedures

The following compounds were prepared based on the general procedures described in Part I above.

6-(3-Methoxyphenyl)-8-methyl-N-(1,1,1-trifluorobut-3-yn-2-yl)imidazo[1,2-b]pyridazine-3-carboxamide

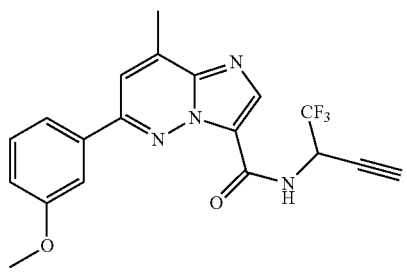 [SMILES: C#CC(NC(=O)c1cnc2c(C)cc(-c3cccc(OC)c3)nn12)C(F)(F)F]

Following general procedure A, 6-(3-methoxyphenyl)-8-methylimidazo[1,2-b]pyridazine-3-carboxylic acid (25 mg, 0.09 mmol) and 1,1,1-trifluorobut-3-yn-2-amine afforded the title compound (4.2 mg, 12%) as a white solid. $^1$H NMR (400 MHz, DMSO-$d_6$) δ 9.50 (d, J=9.6 Hz, 1H), 8.41 (s, 1H), 8.06 (s, 1H), 7.67 (d, J=7.6 Hz, 1H), 7.62 (s, 1H), 7.54 (t, J=8.0 Hz, 1H), 7.18 (dd, J=8.8 Hz, 2.8 Hz, 1H), 6.11-6.06 (m, 1H), 3.90 (d, J=2.4 Hz, 1H), 3.88 (s, 3H), 2.72 (s, 3H). LC-MS m/z: 389.1 [M+H]$^+$. HPLC: Purity (214 nm): 98%; $t_R$=8.51 min.

(R)-6-(Benzo[d]oxazol-5-yl)-N-(1-cyclopropyl-2,2,2-trifluoroethyl)-8-methylimidazo[1,2-b]pyridazine-3-carboxamide

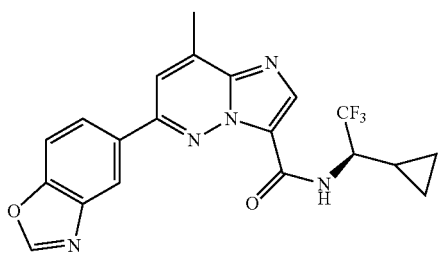 [SMILES: Cc1cc(-c2ccc3ocnc3c2)nn2c(C(=O)N[C@H](C3CC3)C(F)(F)F)cnc12]

Following general procedure A, 6-chloro-8-methylimidazo[1,2-b]pyridazine-3-carboxylic acid (300 mg, 1.42 mmol) and (R)-1-cyclopropyl-2,2,2-trifluoroethanamine hydrochloride afforded (R)-6-chloro-N-(1-cyclopropyl-2,2,2-trifluoroethyl)-8-methylimidazo[1,2-b]pyridazine-3-carboxamide (310 mg, 66%) as a yellow solid. LC-MS m/z: 333.1 [M+H]$^+$. Purity (214 nm): 86%; $t_R$=1.80 min.

Following general procedure D, (R)-6-chloro-N-(1-cyclopropyl-2,2,2-trifluoroethyl)-8-methylimidazo[1,2-b]pyridazine-3-carboxamide (90 mg, 0.27 mmol) and 5-(4,4,5,5-tetramethyl-1,3,2-dioxaborolan-2-yl)benzo[d]oxazole afforded the title compound (44.6 mg, 40%) as a yellow solid. $^1$H NMR (500 MHz, DMSO-$d_6$) δ 9.18 (d, J=9.0 Hz, 1H), 8.90 (s, 1H), 8.52 (d, J=1.5 Hz, 1H), 8.36 (s, 1H), 8.15 (dd, J=9.0 Hz, 2.0 Hz, 1H), 8.11 (d, J=1.0 Hz, 1H), 8.02 (d, J=8.5 Hz, 1H), 4.52-4.44 (m, 1H), 2.73 (s, 3H), 1.31-1.20 (m, 1H), 0.74-0.65 (m, 1H), 0.66-0.60 (m, 2H), 0.44-0.42 (m, 1H). LC-MS m/z: 416.0 [M+H]$^+$. HPLC: Purity (214 nm): >99%; $t_R$=8.01 min.

(S)-6-(Benzo[d]oxazol-5-yl)-N-(1-cyclopropyl-2,2,2-trifluoroethyl)-8-methylimidazo[1,2-b]pyridazine-3-carboxamide

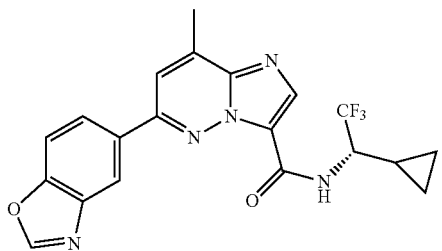 [SMILES: Cc1cc(-c2ccc3ocnc3c2)nn2c(C(=O)N[C@@H](C3CC3)C(F)(F)F)cnc12]

Following general procedure A, 6-chloro-8-methylimidazo[1,2-b]pyridazine-3-carboxylic acid (300 mg, 1.42 mmol) and (S)-1-cyclopropyl-2,2,2-trifluoroethanamine hydrochloride afforded (S)-6-chloro-N-(1-cyclopropyl-2,2,2-trifluoroethyl)-8-methylimidazo[1,2-b]pyridazine-3-carboxamide (300 mg, 65%) as a yellow solid. LC-MS m/z: 333.1 [M+H]$^+$. Purity (214 nm): 86%; $t_R$=1.80 min.

Following general procedure D, (S)-6-chloro-N-(1-cyclopropyl-2,2,2-trifluoroethyl)-8-methylimidazo[1,2-b]pyridazine-3-carboxamide (50 mg, 0.150 mmol) and 5-(4,4,5,5-tetramethyl-1,3,2-dioxaborolan-2-yl)benzo[d]oxazole afforded the title compound (37 mg, 59%) as a yellow solid. $^1$H NMR (500 MHz, MeOD-$d_4$) δ 8.63 (s, 1H), 8.47 (d, J=1.5 Hz, 1H), 8.41 (s, 1H), 8.16 (dd, J=8.5 Hz, 2.0 Hz, 1H), 7.98 (s, 1H), 7.92 (d, J=8.5 Hz, 1H), 4.47-4.43 (m, 1H), 2.82 (s, 3H), 1.34-1.31 (m, 1H), 0.82-0.79 (m, 1H), 0.70-0.62 (m, 2H), 0.53-0.49 (m, 1H). LC-MS m/z: 416.1 [M+H]$^+$. HPLC: Purity (214 nm): >99%; $t_R$=8.03 min.

(R)-6-(Benzo[d]oxazol-5-yl)-8-methyl-N-(1,1,1-trifluoropropan-2-yl)imidazo[1,2-b]pyridazine-3-carboxamide

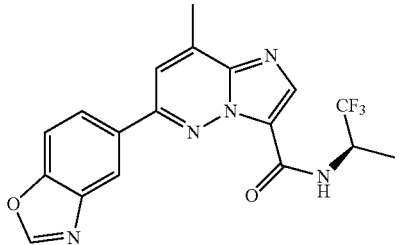 [SMILES: Cc1cc(-c2ccc3ocnc3c2)nn2c(C(=O)N[C@H](C)C(F)(F)F)cnc12]

Following general procedure A, 6-chloro-8-methylimidazo[1,2-b]pyridazine-3-carboxylic acid (250 mg, 1.18 mmol) and (R)-1,1,1-trifluoropropan-2-amine hydrochloride afforded (R)-6-chloro-8-methyl-N-(1,1,1-trifluoropropan-2-yl)imidazo[1,2-b]pyridazine-3-carboxamide (230 mg, 72%) as a yellow solid. LC-MS m/z: 307.0 [M+H]$^+$. LCMS: $t_R$=1.71 min.

Following general procedure D, (R)-6-chloro-8-methyl-N-(1,1,1-trifluoropropan-2-yl)imidazo[1,2-b]pyridazine-3-carboxamide (100 mg, 0.33 mmol) and 5-(4,4,5,5-tetramethyl-1,3,2-dioxaborolan-2-yl)benzo[d]oxazole afforded the title compound (80 mg, 63%) as a white solid. $^1$H NMR (500 MHz, DMSO-$d_6$) δ 9.08 (d, J=8.8 Hz, 1H), 8.90 (s, 1H), 8.52 (s, 1H), 8.35 (s, 1H), 8.15 (d, J=8.4 Hz, 1H), 8.11 (s, 1H), 8.04 (d, J=8.4 Hz, 1H), 5.04-5.02 (m, 1H), 2.72 (s, 3H), 1.48 (d, J=6.8 Hz, 3H). LC-MS m/z: 390.1 [M+H]$^+$. HPLC: Purity (254 nm): 99%; $t_R$=7.59 min.

(S)-6-(Benzo[d]oxazol-5-yl)-8-methyl-N-(1,1,1-trifluoropropan-2-yl)imidazo[1,2-b]pyridazine-3-carboxamide

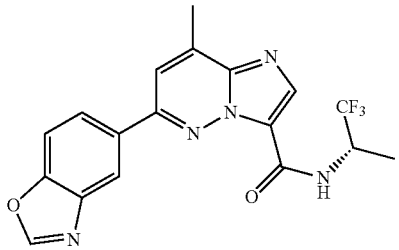 [SMILES: Cc1cc(-c2ccc3ocnc3c2)nn2c(C(=O)N[C@@H](C)C(F)(F)F)cnc12]

Following general procedure A, 6-chloro-8-methylimidazo[1,2-b]pyridazine-3-carboxylic acid (220 mg, 1.05 mmol) and (S)-1,1,1-trifluoropropan-2-amine hydrochloride afforded (S)-6-chloro-8-methyl-N-(1,1,1-trifluoropropan-2-yl)imidazo[1,2-b]pyridazine-3-carboxamide (160 mg, 50%) as a white solid. LC-MS m/z: 307.0 [M+H]$^+$, $t_R$=1.75 min.

Following general procedure D, (S)-6-chloro-8-methyl-N-(1,1,1-trifluoropropan-2-yl)imidazo[1,2-b]pyridazine-3-carboxamide (123 mg, 0.404 mmol) and 5-(4,4,5,5-tetramethyl-1,3,2-dioxaborolan-2-yl)benzo[d]oxazole afforded the title compound (90 mg, 57%) as a white solid. $^1$H NMR (500 MHz, DMSO-d$_6$) δ 9.07 (d, J=9.5 Hz, 1H), 8.90 (s, 1H), 8.52 (s, 1H), 8.35 (s, 1H), 8.16 (dd, J=8.5 Hz, 1.0 Hz, 1H), 8.12 (s, 1H), 8.03 (d, J=8.5 Hz, 1H), 5.04-5.00 (m, 1H), 2.72 (s, 3H), 1.46 (d, J=7.0 Hz, 3H). LC-MS m/z: 390.1 [M+H]$^+$. HPLC: Purity (254 nm): >99%; $t_R$=7.59 min.

(R)-6-(2-Cyano-4-fluorophenyl)-N-(1-cyclopropyl-2,2,2-trifluoroethyl)-8-methylimidazo[1,2-b]pyridazine-3-carboxamide

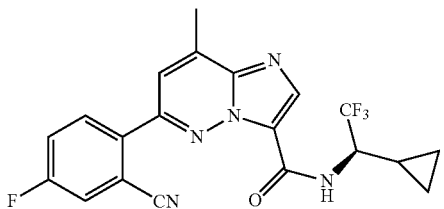 [SMILES: Cc1cc(-c2ccc(F)cc2C#N)nn2c(C(=O)N[C@H](C3CC3)C(F)(F)F)cnc12]

Following general procedure D, (R)-6-chloro-N-(1-cyclopropyl-2,2,2-trifluoroethyl)-8-methylimidazo[1,2-b]pyridazine-3-carboxamide (90 mg, 0.27 mmol) and 2-cyano-4-fluorophenylboronic acid afforded the title compound (19 mg, 17%) as a white solid. $^1$H NMR (500 MHz, MeOD-d$_4$) δ 8.46 (s, 1H), 8.04 (dd, J=8.8 Hz, 4.2 Hz, 1H), 7.89 (dd, J=8.0 Hz, 2.4 Hz, 1H), 7.75 (d, J=1.2 Hz, 1H), 7.72 (td, J=8.4 Hz, 2.4 Hz, 1H), 4.31-4.27 (m, 1H), 2.82 (s, 3H), 1.39-1.34 (m, 1H), 0.77-0.75 (m, 1H), 0.61-0.59 (m, 2H), 0.45-0.43 (m, 1H). LC-MS m/z: 418.1 [M+H]$^+$. HPLC: Purity (254 nm): >99%; $t_R$=8.39 min.

(S)-6-(2-Cyano-4-fluorophenyl)-N-(1-cyclopropyl-2,2,2-trifluoroethyl)-8-methylimidazo[1,2-b]pyridazine-3-carboxamide

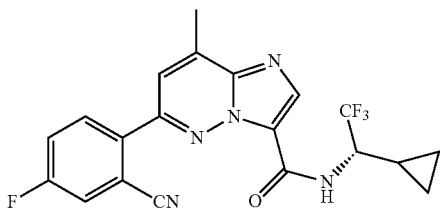 [SMILES: Cc1cc(-c2ccc(F)cc2C#N)nn2c(C(=O)N[C@@H](C3CC3)C(F)(F)F)cnc12]

Following general procedure D, (S)-6-chloro-N-(1-cyclopropyl-2,2,2-trifluoroethyl)-8-methylimidazo[1,2-b]pyridazine-3-carboxamide (80 mg, 0.24 mmol) and 2-cyano-4-fluorophenylboronic acid afforded the title compound (8.2 mg, 8%) as a white solid. $^1$H NMR (500 MHz, DMSO-d$_6$) δ 8.81 (d, J=9.0 Hz, 1H), 8.44 (s, 1H), 8.19 (dd, J=9.0 Hz, 2.0 Hz, 1H), 8.07 (dd, J=9.0 Hz, 5.0 Hz, 1H), 7.89 (td, J=8.5 Hz, 3.0 Hz, 1H), 7.83 (d, J=1.0 Hz, 1H), 4.37-4.33 (m, 1H), 2.74 (d, J=1.0 Hz, 3H), 1.30-1.25 (m, 1H), 0.70-0.61 (m, 2H), 0.53-0.48 (m, 1H), 0.38-0.33 (m, 1H). LC-MS m/z: 418.1 [M+H]$^+$. HPLC: Purity (214 nm): >99%; $t_R$=8.39 min.

(R)-6-(2-Cyano-4-fluorophenyl)-8-methyl-N-(1,1,1-trifluoropropan-2-yl)imidazo[1,2-b]pyridazine-3-carboxamide

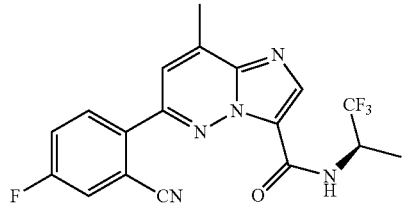 [SMILES: Cc1cc(-c2ccc(F)cc2C#N)nn2c(C(=O)N[C@H](C)C(F)(F)F)cnc12]

Following general procedure D, (R)-6-chloro-8-methyl-N-(1,1,1-trifluoropropan-2-yl)imidazo[1,2-b]pyridazine-3-carboxamide (100 mg, 0.32 mmol) and 2-cyano-4-fluorophenylboronic acid afforded the title compound (14.4 mg, 11%) as a white solid. H NMR (500 MHz, MeOD-d$_4$) δ 8.46 (s, 1H), 8.05 (dd, J=8.8 Hz, 4.8 Hz, 1H), 7.90 (dd, J=8.4 Hz, 2.8 Hz, 1H), 7.75 (d, J=0.8 Hz, 1H), 7.72 (td, J=8.8 Hz, 3.2 Hz, 1H), 5.04-5.00 (m, 1H), 2.81 (d, J=0.8 Hz, 3H), 1.52 (d, J=6.8 Hz, 3H). LC-MS m/z: 392.1 [M+H]$^+$. HPLC: Purity (254 nm): >99%; $t_R$=7.99 min.

(S)-6-(2-Cyano-4-fluorophenyl)-8-methyl-N-(1,1,1-trifluoropropan-2-yl)imidazo[1,2-b]pyridazine-3-carboxamide

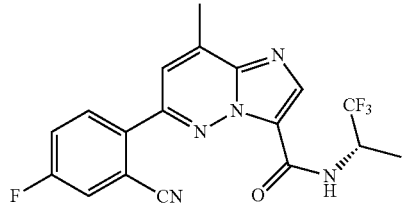 [SMILES: Cc1cc(-c2ccc(F)cc2C#N)nn2c(C(=O)N[C@@H](C)C(F)(F)F)cnc12]

Following general procedure D, (S)-6-chloro-8-methyl-N-(1,1,1-trifluoropropan-2-yl)imidazo[1,2-b]pyridazine-3-carboxamide (76 mg, 0.25 mmol) and 2-cyano-4-fluorophenylboronic acid afforded the title compound (3.8 mg, 4%) as a white solid. $^1$H NMR (500 MHz, DMSO-d$_6$) δ 8.69 (d, J=9.5 Hz, 1H), 8.44 (s, 1H), 8.22 (dd, J=8.5 Hz, 3.0 Hz, 1H), 8.09 (dd, J=8.5 Hz, 5.0 Hz, 1H), 7.90 (id, J=8.5 Hz, 3.0 Hz, 1H), 7.83 (d, J=1.0 Hz, 1H), 5.04-4.99 (m, 1H), 2.74 (d, J=1.0 Hz, 3H), 1.43 (d, J=7.0 Hz, 3H). LC-MS m/z: 392.1 [M+H]$^+$. Purity (214 nm): >99%; $t_R$=1.78 min.

(R)-6-(2-Cyano-4-fluorophenyl)-N-(1-cyclopropylethyl)-8-methylimidazo[1,2-b]pyridazine-3-carboxamide

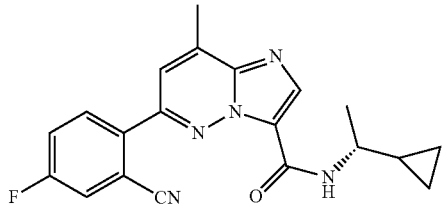 [SMILES: Cc1cc(-c2ccc(F)cc2C#N)nn2c(C(=O)N[C@H](C)C3CC3)cnc12]

Following general procedure A, 6-chloro-8-methylimidazo[1,2-b]pyridazine-3-carboxylic acid (180 mg, 0.85 mmol) and (R)-1-cyclopropylethanamine afforded (R)-6-chloro-N-(1-cyclopropylethyl)-8-methylimidazo[1,2-b]

pyridazine-3-carboxamide (200 mg, 85%) as a yellow solid. LC-MS m/z: 279.1 [M+H]⁺. Purity (214 nm): 94%; $t_R$=1.26 min.

Following general procedure D, (R)-6-chloro-N-(1-cyclopropylethyl)-8-methylimidazo[1,2-b]pyridazine-3-carboxamide (100 mg, 0.33 mmol) and 2-cyano-4-fluorophenylboronic acid afforded the title compound (28.2 mg, 22%) as a white solid. ¹H NMR (500 MHz, DMSO-d₆) δ 8.52 (d, J=8.0 Hz, 1H), 8.34 (s, 1H), 8.22 (dd, J=9.0 Hz, 3.0 Hz, 1H), 8.11 (dd, J=9.0 Hz, 5.5 Hz, 1H), 7.89 (td, J=9.0 Hz, 3.0 Hz, 1H), 7.80 (s, 1H), 3.60-3.52 (m, 1H), 2.73 (s, 3H), 1.28 (d, J=6.5 Hz, 3H), 1.11-1.03 (m, 1H), 0.49-0.41 (m, 1H), 0.40-0.30 (m, 2H), 0.29-0.22 (m, 1H). LC-MS m/z: 364.1 [M+H]⁺. HPLC: Purity (214 nm): >99%; $t_R$=7.93 min.

(R)-6-(5-Cyanofuran-2-yl)-N-(1-cyclopropyl-2,2,2-trifluoroethyl)-8-methylimidazo[1,2-b]pyridazine-3-carboxamide

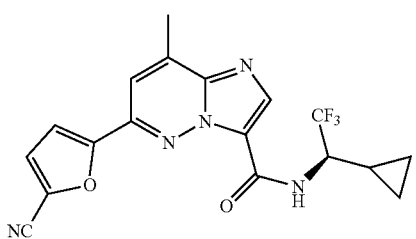 [SMILES: Cc1cc(-c2ccc(C#N)o2)nn2c(C(=O)N[C@H](C3CC3)C(F)(F)F)cnc12]

To a solution of 5-bromofuran-2-carbonitrile (1 g, 10.8 mmol) in 40 mL of anhydrous THF was added n-BuLi (5.6 mL, 14 mmol) at −78° C., followed 30 minutes later by the addition of SnBu₃Cl (2.90 mL, 10.8 mmol). After stirring at RT overnight, the reaction mixture was quenched with saturated NH₄Cl (15 mL), and extracted with EA (50 mL×3). The organic phases were washed with H₂O (50 mL) and brine (50 mL), dried over anhydrous sodium sulfate and filtered. The filtrate was concentrated in vacuo, and the residue was purified by preparative HPLC (MeCN/NH₄HCO₃) to afford 5-(tributylstannyl)furan-2-carbonitrile (1 g, 24%) as a yellow oil. LC-MS m/z: 383.1 [M+H]⁺. $t_R$=2.87 min.

Following general procedure F, (R)-6-chloro-N-(1-cyclopropyl-2,2,2-trifluoroethyl)-8-methylimidazo[1,2-b]pyridazine-3-carboxamide (100 mg, 0.15 mmol) and 5-(tributylstannyl)furan-2-carbonitrile afforded the title compound (5 mg, 6%) as a yellow solid. ¹H NMR (500 MHz, MeOD-d₄) δ 8.43 (s, 1H), 7.90 (s, 1H), 7.59 (d, J=3.5 Hz, 1H), 7.51 (d, J=3.5 Hz, 1H), 4.56-4.52 (m, 1H), 2.79 (s, 3H), 1.37-1.35 (m, 1H), 0.81-0.79 (m, 1H), 0.73-0.71 (m, 1H), 0.62-0.60 (m, 2H). LC-MS m/z: 390.1 [M+H]⁺. HPLC: Purity (214 nm): 97%; $t_R$=8.31 min.

(S)-6-(5-Cyanofuran-2-yl)-N-(1-cyclopropyl-2,2,2-trifluoroethyl)-8-methylimidazo[1,2-b]pyridazine-3-carboxamide

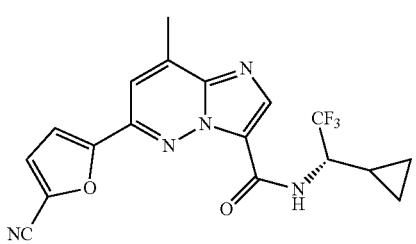 [SMILES: Cc1cc(-c2ccc(C#N)o2)nn2c(C(=O)N[C@@H](C3CC3)C(F)(F)F)cnc12]

Following general procedure F, (S)-6-chloro-N-(1-cyclopropyl-2,2,2-trifluoroethyl)-8-methylimidazo[1,2-b]pyridazine-3-carboxamide (150 mg, 0.45 mmol) and 5-(tributylstannyl)furan-2-carbonitrile afforded the title compound (18 mg, 10%) as a yellow solid. ¹H NMR (400 MHz, DMSO-d₆) δ 9.08 (d, J=9.6 Hz, 1H), 8.40 (s, 1H), 8.00 (s, 1H), 7.89 (d, J=4.0 Hz, 1H), 7.66 (d, J=3.6 Hz, 1H), 4.62-4.55 (m, 1H), 2.70 (s, 3H), 1.32-1.23 (m, 1H), 0.70-0.62 (m, 1H), 0.60-0.55 (m, 1H), 0.53-0.47 (m, 1H). LC-MS m/z: 390.1 [M+H]⁺. HPLC: Purity (214 nm): >99%; $t_R$=8.30 min.

(R)-6-(3-Cyanothiophen-2-yl)-N-(1-cyclopropyl-2,2,2-trifluoroethyl)-8-methylimidazo[1,2-b]pyridazine-3-carboxamide

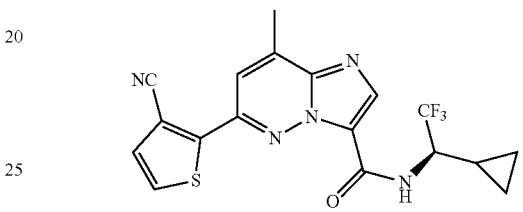

To a solution of 2-bromothiophene-3-carbonitrile (2 g, 10.64 mmol) in anhydrous THF (20 mL) was added n-BuLi (8.5 mL, 21.28 mmol, 2.5M solution in hexane) at −78° C. under N₂. The mixture was stirred at −78° C. for 1 hour, followed by the addition of Bu₃SnCl (750 mg, 2.0 mmol) at −78° C., and stirred at −78° C. for another hour and then warmed to RT. After concentration, the residue was purified by silica gel column chromatography (PE/EA: 10/1) to afford 2-(tributylstannyl)thiophene-3-carbonitrile (4.2 g, 57%) as colorless oil. H NMR (500 MHz, CDCl₃) δ 7.54 (d, J=5.0 Hz, 1H), 7.33 (d, J=5.0 Hz, 1H), 1.62-1.39 (m, 6H), 1.35-1.13 (m, 12H), 0.92-0.70 (m, 9H).

Following general procedure F, (R)-6-chloro-N-(1-cyclopropyl-2,2,2-trifluoroethyl)-8-methylimidazo[1,2-b]pyridazine-3-carboxamide (100 mg, 0.3 mmol) and 2-(tributylstannyl)thiophene-3-carbonitrile afforded the title compound (44 mg, 36%) as a white solid. ¹H NMR (500 MHz, DMSO-d₆) δ 8.79 (d, J=9.0 Hz, 1H), 8.43 (s, 1H), 8.11 (d, J=5.5 Hz, 1H), 7.94 (s, 1H), 7.74 (d, J=5.5 Hz, 1H), 4.38-4.32 (m, 1H), 2.74 (s, 3H), 1.39-1.36 (m, 1H), 0.74-0.65 (m, 2H), 0.59-0.55 (m, 1H), 0.40-0.35 (m, 1H). LC-MS m/z: 406.0 [M+H]⁺. HPLC: Purity (254 nm): >99%. $t_R$=8.45 min.

(S)-6-(3-Cyanothiophen-2-yl)-N-(1-cyclopropyl-2,2,2-trifluoroethyl)-8-methylimidazo[1,2-b]pyridazine-3-carboxamide

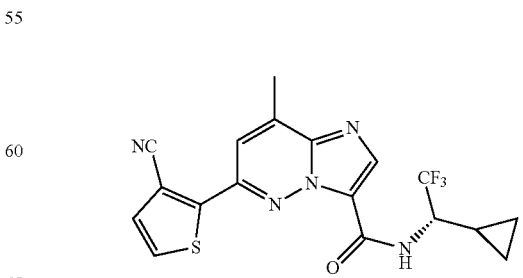

Following general procedure F, (S)-6-chloro-N-(1-cyclopropyl-2,2,2-trifluoroethyl)-8-methylimidazo[1,2-b]

pyridazine-3-carboxamide (100 mg, 0.3 mmol) and 2-(tributylstannyl)thiophene-3-carbonitrile afforded the title compound (12 mg, 9%) as a white solid. $^1$H NMR (500 MHz, DMSO-d$_6$) δ 8.79 (d, J=9.0 Hz, 1H), 8.43 (s, 1H), 8.11 (d, J=5.5 Hz, 1H), 7.94 (s, 1H), 7.74 (d, J=5.5 Hz, 1H), 4.38-4.32 (m, 1H), 2.74 (s, 3H), 1.39-1.36 (m, 1H), 0.74-0.65 (m, 2H), 0.59-0.55 (m, 1H), 0.40-0.35 (m, 1H). LC-MS m/z: 406.0 [M+H]$^+$. HPLC: Purity (254 nm): >99%. $t_R$=8.45 min.

N-(1-Cyclopropyl-2,2,2-trifluoroethyl)-6-(3-isopropyl-2-oxoimidazolidin-1-yl)-8-methylimidazo[1,2-b]pyridazine-3-carboxamide

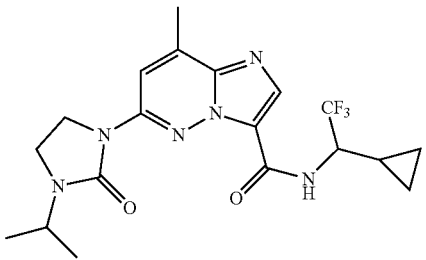 [SMILES: Cc1cc(N2CCN(C(C)C)C2=O)nn2c(C(=O)NC(C3CC3)C(F)(F)F)cnc12]

Following general procedure G, 6-chloro-N-(1-cyclopropyl-2,2,2-trifluoroethyl)-8-methylimidazo[1,2-b]pyridazine-3-carboxamide (60 mg, 0.180 mmol) and 1-isopropylimidazolidin-2-one afforded the title compound (50 mg, 49%) as a yellow solid. $^1$H NMR (500 MHz, MeOD-d$_4$) δ 8.49 (d, J=1.0 Hz, 1H), 8.23 (s, 1H), 4.31-4.23 (m, 2H), 4.11-4.03 (m, 2H), 3.65 (t, J=8.0 Hz, 2H), 2.68 (s, 3H), 1.33-1.30 (m, 1H), 1.27 (d, J=7.0 Hz, 6H), 0.83-0.78 (m, 1H), 0.70-0.63 (m, 2H), 0.50-0.48 (m, 1H). LC-MS m/z: 425.2 [M+H]$^+$. HPLC: Purity (214 nm): >99%; $t_R$=8.31 min.

N-(1-Cyclopropyl-2,2,2-trifluoroethyl)-6-(isoxazol-3-yl)-8-methylimidazo[1,2-b]pyridazine-3-carboxamide

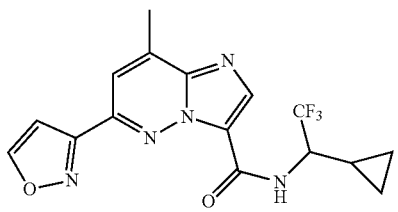 [SMILES: Cc1cc(-c2ccon2)nn2c(C(=O)NC(C3CC3)C(F)(F)F)cnc12]

Following general procedure F, ethyl 6-chloro-8-methylimidazo[1,2-b]pyridazine-3-carboxylate (400 mg, 1.6 mmol) and tributyl(vinyl)stannane afforded ethyl 8-methyl-6-vinylimidazo[1,2-b]pyridazine-3-carboxylate (350 mg, 91%) as a pale white solid. LC-MS m/z: 232.1 [M+H]$^+$. LCMS: Purity (214 nm): 89.2%; $t_R$=1.13 min.

To a solution of ethyl 8-methyl-6-vinylimidazo[1,2-b]pyridazine-3-carboxylate (350 mg, 1.5 mmol) and OsO$_4$ (5 mg, 0.019 mmol) in THF/H$_2$O (10 mL/3 mL) was added NaIO$_4$ (1.28 g, 6 mmol). The resulting mixture was stirred at RT for 12 h, and diluted with water (50 mL). The mixture was extracted with EA (20 mL×3), and the EA layers were washed with brine (15 mL), dried over anhydrous Na$_2$SO$_4$, and filtered. The filtrate was concentrated in vacuo to afford ethyl 6-formyl-8-methylimidazo[1,2-b]pyridazine-3-carboxylate (370 mg, crude) as an oil, which was used directly in the next step. LC-MS m/z: 234.1 [M+H]$^+$. LCMS: Purity (254 nm): 60.2%; $t_R$=1.09 min.

To a solution of ethyl 6-formyl-8-methylimidazo[1,2-b]pyridazine-3-carboxylate (370 mg) in methanol (5 mL) were added hydroxylammonium chloride (354 mg, 4.76 mmol) and Et$_3$N (566 mg, 6.3 mmol). The mixture was stirred at RT for 2 h, and concentrated in vacuo. The resulting residue was purified by silica gel column chromatography (PE/EA: 1/2) to afford ethyl 6-((hydroxyimino)methyl)-8-methylimidazo[1,2-b]pyridazine-3-carboxylate (240 mg, 64% over two steps) as a yellow solid. LC-MS m/z: 249.1 [M+H]$^+$. LCMS: Purity: 90.1%; $t_R$=1.30 min.

To a solution ethyl 6-((hydroxyimino)methyl)-8-methylimidazo[1,2-b]pyridazine-3-carboxylate (190 mg, 0.76 mmol) and ethynyltrimethylsilane (90.2 mg, 0.92 mmol) in MeCN (10 mL) was added CrO$_2$ (332 mg, 4.0 mmol). The reaction mixture was stirred at 80° C. for 2 hours, and filtered through Celite. The filtrate was concentrated in vacuo, and the residue was purified by silica gel column chromatography (PE/EA: 5/1) to afford ethyl 8-methyl-6-(5-(trimethylsilyl)isoxazol-3-yl)imidazo[1,2-b]pyridazine-3-carboxylate (180 mg, 68%) as a yellow solid. LC-MS m/z: 345.1 [M+H]$^+$. LCMS: Purity: 74.2%; $t_R$=1.59 min.

Following general procedure B, ethyl 8-methyl-6-(5-(trimethylsilyl)isoxazol-3-yl)imidazo[1,2-b]pyridazine-3-carboxylate (180 mg, 0.52 mmol) afforded 6-(isoxazol-3-yl)-8-methylimidazo[1,2-b]pyridazine-3-carboxylic acid (45 mg, 35%) as a pale white solid. LC-MS m/z: 267.1 [M+Na]$^+$. LCMS: Purity (254 nm): 79.9%; $t_R$=0.93 min.

Following general procedure A, 6-(isoxazol-3-yl)-8-methylimidazo[1,2-b]pyridazine-3-carboxylic acid (45 mg, 0.18 mmol) and 1-cyclopropyl-2,2,2-trifluoroethanamine hydrochloride afforded the title compound (25 mg, 37%) as a white solid. $^1$H NMR (500 MHz, DMSO-d$_6$) δ 9.25 (d, J=2.0 Hz, 1H), 8.96 (d, J=9.0 Hz, 1H), 8.41 (s, 1H), 7.97 (d, J=1.5 Hz, 1H), 7.06 (d, J=2.0 Hz, 1H), 4.45-4.40 (m, 1H), 2.73 (s, 3H), 1.34-1.32 (m, 1H), 0.70-0.57 (m, 3H), 0.40-0.39 (m, 1H). LC-MS m/z: 366.1 [M+H]$^+$. HPLC: Purity (254 nm): 95%; $t_R$=8.01 min.

6-(6-Chloropyridin-2-yl)-8-methyl-N-(1,1,1-trifluoropropan-2-yl)imidazo[1,2-b]pyridazine-3-carboxamide

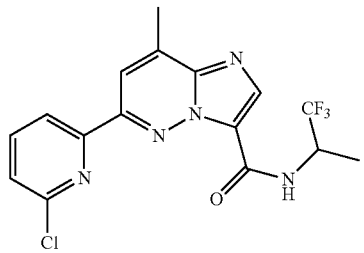 [SMILES: Cc1cc(-c2cccc(Cl)n2)nn2c(C(=O)NC(C)C(F)(F)F)cnc12]

Following general procedure D, 6-chloro-8-methyl-N-(1,1,1-trifluoropropan-2-yl)imidazo[1,2-b]pyridazine-3-carboxamide (90 mg, 0.29 mmol) and 2-chloro-6-(4,4,5,5-tetramethyl-1,3,2-dioxaborolan-2-yl)pyridine afforded the title compound (2.1 mg, 2%) as a white solid. $^1$H NMR (500 MHz, DMSO-d$_6$) δ 9.00 (d, J=9.5 Hz, 1H), 8.40 (s, 1H), 8.23 (d, J=7.0 Hz, 1H), 8.18 (t, J=8.0 Hz, 1H), 8.13 (d, J=1.0 Hz, 1H), 7.75 (d, J=8.0 Hz, 1H), 5.08-4.98 (m, 1H), 2.75 (s, 3H), 1.48 (d, J=7.5 Hz, 3H). LC-MS m/z: 384.1 [M+H]+. HPLC: Purity (214 nm): >99%; t_R=8.71 min.

(R)—N-(1-Cyclopropyl-2,2,2-trifluoroethyl)-8-methyl-6-(3-methylisothiazol-5-yl)imidazo[1,2-b]pyridazine-3-carboxamide

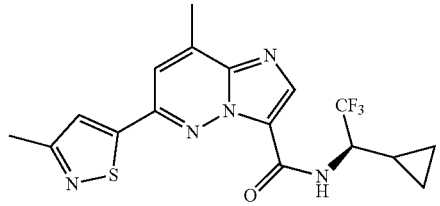 [SMILES: Cc1cc(-c2cc(C)c3ncc(C(=O)N[C@H](C4CC4)C(F)(F)F)n3n2)sn1]

To a solution of 5-bromo-3-methylisothiazole (178 mg, 1.0 mmol) in anhydrous THF (10 mL) was added n-BuLi (2.5 mol/L, 0.48 mL) at −78° C. The mixture was stirred for 1 h followed by the dropwise addition of Bu₃SnCl (326 mg, 1.0 mmol) in anhydrous THF (0.5 mL). The mixture was stirred for 2 h at −78° C., quenched with saturated NH₄Cl (10 mL), and extracted with EA (10 mL×3). The organic phases were dried over anhydrous Na₂SO₄ and filtered. The filtrate was concentrated in vacuo, and the residue was purified by preparative TLC (PE:EA=20:1) to afford 3-methyl-5-(tributylstannyl)isothiazole (190 mg, 49%) as a yellow oil. ¹H NMR (400 MHz, CDCl₃) δ 7.00 (s, 1H), 2.55 (s, 3H), 1.59-1.51 (m, 6H), 1.38-1.28 (m, 6H), 1.13-1.113 (m, 6H), 0.99-0.88 (m, 9H).

Following general procedure F, (R)-6-chloro-N-(1-cyclopropyl-2,2,2-trifluoroethyl)-8-methylimidazo[1,2-b]pyridazine-3-carboxamide (100 mg, 0.301 mmol) and 3-methyl-5-(tributylstannyl)isothiazole afforded the title compound (6 mg, 5%) as a white solid. ¹H NMR (500 MHz, MeOD-d₄) δ 8.42 (s, 1H), 7.93 (d, J=1.5 Hz, 1H), 7.91 (s, 1H), 4.44-4.40 (m, 1H), 2.81 (d, J=0.5 Hz, 3H), 2.60 (s, 3H), 1.39-1.35 (m, 1H), 0.88-0.82 (m, 1H), 0.72-0.63 (m 2H), 0.56-0.51 (m, 1H). LC-MS m/z: 396.1 [M+H]+. HPLC: Purity (214 nm): >99%; t_R=8.49 min.

(S)—N-(1-Cyclopropyl-2,2,2-trifluoroethyl)-8-methyl-6-(3-methylisothiazol-5-yl)imidazo[1,2-b]pyridazine-3-carboxamide

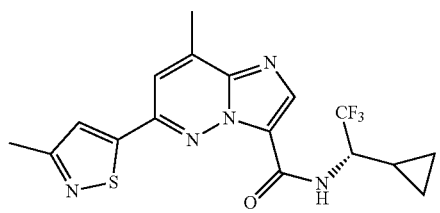 [SMILES: Cc1cc(-c2cc(C)c3ncc(C(=O)N[C@@H](C4CC4)C(F)(F)F)n3n2)sn1]

Following general procedure F, (S)-6-chloro-N-(1-cyclopropyl-2,2,2-trifluoroethyl)-8-methylimidazo[1,2-b]pyridazine-3-carboxamide (100 mg, 0.301 mmol) and 3-methyl-5-(tributylstannyl)isothiazole afforded the title compound (31 mg, 26%) as a white solid. ¹H NMR (500 MHz, MeOD-d₄) δ 8.42 (s, 1H), 7.93 (d, J=1.5 Hz, 1H), 7.91 (s, 1H), 4.44-4.40 (m, 1H), 2.81 (d, J=0.5 Hz, 3H), 2.60 (s, 3H), 1.39-1.35 (m, 1H), 0.88-0.82 (m, 1H), 0.72-0.63 (m 2H), 0.56-0.51 (m, 1H). LC-MS m/z: 396.1 [M+H]+. HPLC: Purity (214 nm): >99%; t_R=8.49 min.

N-(1-Cyclopropyl-2,2,2-trifluoroethyl)-6-(2-fluoropyridin-3-yl)-8-methylimidazo[1,2-b]pyridazine-3-carboxamide

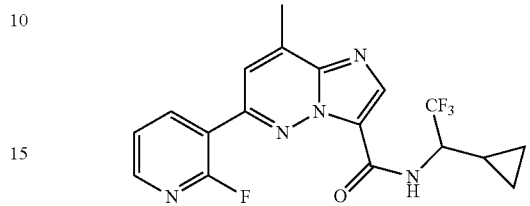

Following general procedure D, 6-chloro-N-(1-cyclopropyl-2,2,2-trifluoroethyl)-8-methylimidazo[1,2-b]pyridazine-3-carboxamide (60 mg, 0.180 mmol) and 2-fluoropyridin-3-ylboronic acid afforded the title compound (15 mg, 16%) as a yellow solid. ¹H NMR (500 MHz, MeOD-d₄) δ 8.50 (td, J=9.5 Hz, 1.5 Hz, 1H), 8.45 (s, 1H), 8.45-8.44 (m, 1H), 7.85 (s, 1H), 7.60 (tt, J=6.5 Hz, 1.0 Hz, 1H), 4.42-4.38 (m, 1H), 2.82 (s, 3H), 1.30-1.26 (m, 1H), 0.84-0.76 (m, 1H), 0.68-0.61 (m, 2H), 0.48-0.45 (m, 1H). LC-MS m/z: 394.0 [M+H]+. HPLC: Purity (214 nm): >99%; t_R=8.01 min.

(R)-6-(5-Chloropyridin-3-yl)-N-(1-cyclopropyl-2,2,2-trifluoroethyl)-8-methylimidazo[1,2-b]pyridazine-3-carboxamide

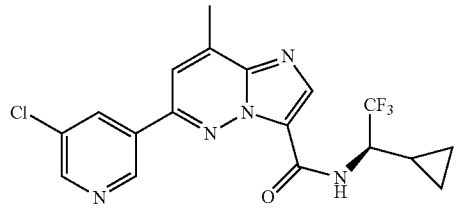 [SMILES: Cc1cc(-c2cncc(Cl)c2)nn2c(C(=O)N[C@H](C3CC3)C(F)(F)F)cnc12]

Following general procedure D, ethyl 6-chloro-8-methylimidazo[1,2-b]pyridazine-3-carboxylate (500 mg, 2.08 mmol) and 5-chloropyridin-3-ylboronic acid afforded ethyl 6-(5-chloropyridin-3-yl)-8-methylimidazo[1,2-b]pyridazine-3-carboxylate (100 mg, 15%) as a white solid. LC-MS m/z: 317.1 [M+H]+. t_R=1.72 min.

Following general procedure B, ethyl 6-(5-chloropyridin-3-yl)-8-methylimidazo[1,2-b]pyridazine-3-carboxylate (100 mg, 0.31 mmol) afforded 6-(5-chloropyridin-3-yl)-8-methylimidazo[1,2-b]pyridazine-3-carboxylic acid (90 mg, 100%) as an off-white solid. LC-MS m/z: 289.0 [M+H]+. t_R=1.19 min.

Following general procedure A, 6-(5-chloropyridin-3-yl)-8-methylimidazo[1,2-b]pyridazine-3-carboxylic acid (90 mg, 0.311 mmol) and (R)-1-cyclopropyl-2,2,2-trifluoroethanamine hydrochloride afforded the title compound (21.8 mg, 17%) as a white solid. ¹H NMR (500 MHz, DMSO-d₆) δ 9.24 (d, J=2.0 Hz, 1H), 9.02 (d, J=9.5 Hz, 1H), 8.85 (d, J=2.5 Hz, 1H), 8.58 (t, J=2.0 Hz, 1H), 8.39 (s, 1H), 8.14 (d, J=1.0 Hz, 1H), 4.48-4.42 (m, 1H), 2.72 (s, 3H), 1.30-1.22 (m, 1H), 0.74-0.56 (m, 3H), 0.44-0.37 (m, 1H). LC-MS m/z: 410.1 [M+H]+. HPLC Purity (214 nm): 99.49%; t_R=8.35 min.

(S)-6-(5-Chloropyridin-3-yl)-N-(1-cyclopropyl-2,2,2-trifluoroethyl)-8-methylimidazo[1,2-b]pyridazine-3-carboxamide

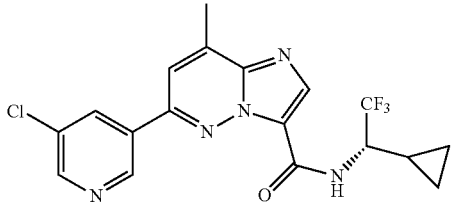 [SMILES: Cc1cc(-c2cncc(Cl)c2)nn2c(C(=O)N[C@@H](C3CC3)C(F)(F)F)cnc12]

Following general procedure A, 6-(5-chloropyridin-3-yl)-8-methylimidazo[1,2-b]pyridazine-3-carboxylic acid (70 mg, 0.24 mmol) and (S)-1-cyclopropyl-2,2,2-trifluoroethanamine hydrochloride afforded the title compound (31.6 mg, 32%) as a white solid. $^1$H NMR (500 MHz, DMSO-$d_6$) δ 9.24 (s, 1H), 9.02 (d, J=9.5 Hz, 1H), 8.85 (d, J=2.5 Hz, 1H), 8.58 (s, 1H), 8.39 (s, 1H), 8.14 (s, 1H), 4.48-4.42 (m, 1H), 2.72 (s, 3H), 1.30-1.22 (m, 1H), 0.74-0.56 (m, 3H), 0.44-0.37 (m, 1H). LC-MS m/z: 410.1 [M+H]$^+$. HPLC Purity (254 nm): 96%; $t_R$=8.35 min.

N-(1-Cyclopropyl-2,2,2-trifluoroethyl)-6-(5-fluoropyridin-3-yl)-8-methylimidazo[1,2-b]pyridazine-3-carboxamide

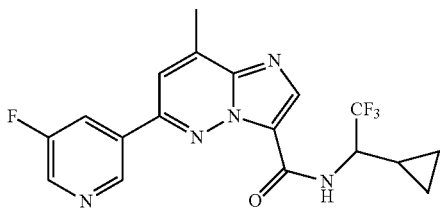 [SMILES: Cc1cc(-c2cncc(F)c2)nn2c(C(=O)NC(C3CC3)C(F)(F)F)cnc12]

Following general procedure D, 6-chloro-N-(1-cyclopropyl-2,2,2-trifluoroethyl)-8-methylimidazo[1,2-b]pyridazine-3-carboxamide (60 mg, 0.180 mmol) and 5-fluoropyridin-3-ylboronic acid afforded the title compound (15 mg, 16%) as a yellow solid. $^1$H NMR (500 MHz, MeOD-$d_4$) δ 9.14 (s, 1H), 8.72 (d, J=3.0 Hz, 1H), 8.44 (s, 1H), 8.34 (dt, J=9.5 Hz, 2.0 Hz, 1H), 7.99 (d, J=1.0 Hz, 1H), 4.46-4.40 (m, 1H), 2.83 (s, 3H), 1.34-1.30 (m, 1H), 0.83-0.80 (m, 1H), 0.69-0.63 (m, 2H), 0.54-0.49 (m, 1H). LC-MS m/z: 394.0 [M+H]$^+$. HPLC: Purity (214 nm): 98.72%; $t_R$=7.91 min.

8-Methyl-6-(2-methylbenzo[d]oxazol-5-yl)-N-(1,1,1-trifluoropropan-2-yl)imidazo[1,2-b]pyridazine-3-carboxamide

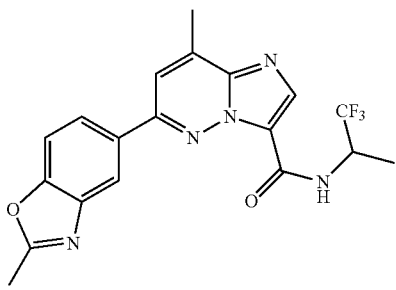 [SMILES: Cc1nc2cc(-c3cc(C)c4ncc(C(=O)NC(C)C(F)(F)F)n4n3)ccc2o1]

Following general procedure D, 6-chloro-8-methyl-N-(1,1,1-trifluoropropan-2-yl)imidazo[1,2-b]pyridazine-3-carboxamide (90 mg, 0.29 mmol) and 2-methyl-5-(4,4,5,5-tetramethyl-1,3,2-dioxaborolan-2-yl)benzo[d]oxazole afforded the title compound (2.1 mg, 2%) as a white solid. $^1$H NMR (500 MHz, DMSO-$d_6$) δ 9.07 (d, J=9.5 Hz, 1H), 8.34 (s, 1H), 8.33 (d, J=4.0 Hz, 1H), 8.05 (s, 1H), 8.04 (d, J=8.5 Hz, 1H), 7.87 (d, J=8.5 Hz, 1H), 5.05-5.00 (m, 1H), 2.71 (s, 3H), 2.67 (s, 3H), 1.47 (d, J=7.0 Hz, 3H). LC-MS m/z: 404.1 [M+H]$^+$. HPLC: Purity (214 nm): 99%; $t_R$=7.93 min.

(R)—N-(1-Cyclopropyl-2,2,2-trifluoroethyl)-6-(3,3-difluoropiperidin-1-yl)-8-methylimidazo[1,2-b]pyridazine-3-carboxamide

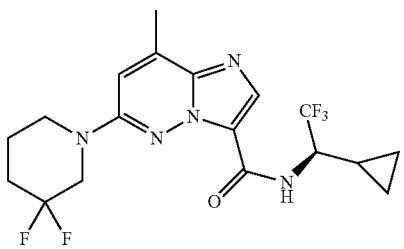 [SMILES: Cc1cc(N2CCCC(F)(F)C2)nn2c(C(=O)N[C@H](C3CC3)C(F)(F)F)cnc12]

To a solution of (R)-6-chloro-N-(1-cyclopropyl-2,2,2-trifluoroethyl)-8-methylimidazo[1,2-b]pyridazine-3-carboxamide (80 mg, 0.24 mmol) in DMF (2 mL) were added 3,3-difluoropiperidine hydrochloride (76 mg, 0.48 mmol), DIPEA (155 mg, 1.2 mmol) and KI (4 mg, 0.024 mmol). The resulting orange mixture was stirred at 150° C. for 4 h under microwave condition. The reaction mixture was purified by preparative HPLC (MeCN/NH$_4$HCO$_3$) and preparative TLC (PE/EA=1/2) to afford the title compound (15.6 mg, 14%) as a white solid. $^1$H NMR (400 MHz, DMSO-$d_6$) δ 9.06 (d, J=9.6 Hz, 1H), 8.06 (s, 1H), 7.46 (s, 1H), 4.40-4.35 (m, 1H), 3.95 (t, J=12.4 Hz, 2H), 3.65 (t, J=5.2 Hz, 2H), 2.54 (s, 3H), 2.20-2.10 (m, 2H), 1.85-1.78 (m, 2H), 1.20-1.15 (m, 1H), 0.72-0.55 (m, 3H), 0.38-0.32 (m, 1H). LC-MS m/z: 418.1 [M+H]$^+$. HPLC Purity (214 nm): 99%; $t_R$=8.25 min.

(S)—N-(1-Cyclopropyl-2,2,2-trifluoroethyl)-6-(3,3-difluoropiperidin-1-yl)-8-methylimidazo[1,2-b]pyridazine-3-carboxamide

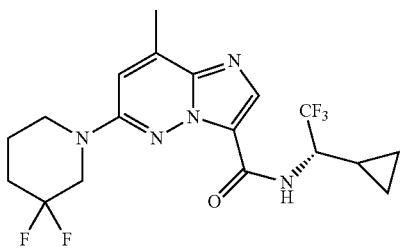 [SMILES: Cc1cc(N2CCCC(F)(F)C2)nn2c(C(=O)N[C@@H](C3CC3)C(F)(F)F)cnc12]

To a solution of (S)-6-chloro-N-(1-cyclopropyl-2,2,2-trifluoroethyl)-8-methylimidazo[1,2-b]pyridazine-3-carboxamide (65 mg, 0.195 mmol) in DMF (2 mL) were added 3,3-difluoropiperidine hydrochloride (62 mg, 0.39 mmol), DIPEA (129 mg, 0.975 mmol) and KI (3 mg, 0.0195 mmol). The resulting orange mixture was stirred at 150° C. for 4 h under microwave condition. The reaction mixture was purified by preparative HPLC (MeCN/NH$_4$HCO$_3$) to afford the title compound (14 mg, 17%) as a white solid. ¹H NMR (500 MHz, DMSO-d₆) δ 9.05 (d, J=9.5 Hz, 1H), 8.06 (s, 1H), 7.45 (d, J=0.5 Hz, 1H), 4.40-4.35 (m, 1H), 3.95 (td, J=12.0 Hz, 3.0 Hz, 2H), 3.65 (t, J=5.0 Hz, 2H), 2.54 (s, 3H), 2.20-2.10 (m, 2H), 1.85-1.78 (m, 2H), 1.20-1.15 (m, 1H), 0.72-0.55 (m, 3H), 0.38-0.32 (m, 1H). LC-MS m/z: 418.1 [M+H]⁺. HPLC Purity (214 nm): 98%; t_R=8.29 min.

6-(2-Cyanophenyl)-N-(1-cyclopropyl-2,2,2-trifluoroethyl)-8-methylimidazo[1,2-b]pyridazine-3-carboxamide

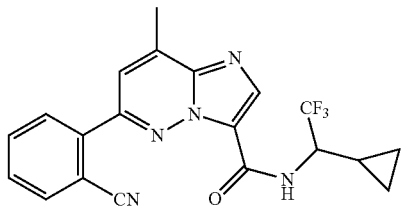 [SMILES: Cc1cc(-c2ccccc2C#N)nn2c(C(=O)NC(C3CC3)C(F)(F)F)cnc12]

Following general procedure D, 6-chloro-N-(1-cyclopropyl-2,2,2-trifluoroethyl)-8-methylimidazo[1,2-b]pyridazine-3-carboxamide (100 mg, 0.301 mmol) and 2-cyanophenyl boronic acid afforded the title compound (30 mg, 25%) as a yellow solid. ¹H NMR (500 MHz, MeOD-d₄) δ 8.48 (s, 1H), 8.04 (d, J=7.5 Hz, 1H), 8.01 (d, J=7.5 Hz, 1H), 7.94 (t, J=6.5 Hz, 1H), 7.79 (t, J=6.5 Hz, 1H), 7.78 (s, 1H), 4.34-4.30 (m, 1H), 2.83 (s, 3H), 1.39-1.36 (m, 1H), 0.78-0.74 (m, 1H), 0.65-0.58 (m, 2H), 0.48-0.44 (m, 1H). LC-MS m/z: 400.0 [M+H]⁺. HPLC: Purity (214 nm): >99%; t_R=8.21 min.

N-(1-Cyclopropyl-2,2,2-trifluoroethyl)-6-(5-fluorofuran-2-yl)-8-methylimidazo[1,2-b]pyridazine-3-carboxamide

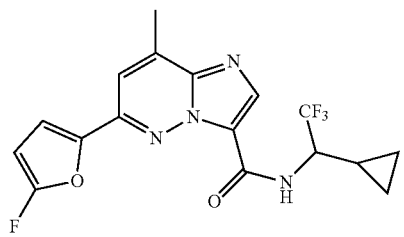 [SMILES: Cc1cc(-c2ccc(F)o2)nn2c(C(=O)NC(C3CC3)C(F)(F)F)cnc12]

Following general procedure F, 6-chloro-N-(1-cyclopropyl-2,2,2-trifluoroethyl)-8-methylimidazo[1,2-b]pyridazine-3-carboxamide (100 mg, 0.30 mmol) and tributyl (5-fluorofuran-2-yl)stannane afforded the title compound (9.4 mg, 8%) as a yellow solid. ¹H NMR (500 MHz, DMSO-d₆) δ 9.14 (d, J=9.5 Hz, 1H), 8.31 (s, 1H), 7.81 (s, 1H), 7.50 (t, J=3.5 Hz, 1H), 6.19 (dd, J=6.0 Hz, 4.0 Hz, 1H), 4.61-4.56 (m, 1H), 2.66 (s, 3H), 1.31-1.20 (m, 1H), 0.70-0.67 (m, 1H), 0.65-0.55 (m, 2H), 0.52-0.48 (m, 1H). LC-MS m/z: 383.1 [M+H]⁺. HPLC: Purity (214 nm): >99%; t_R=8.74 min.

(R)-6-(3-Cyano-5-methylfuran-2-yl)-8-methyl-N-(1,1,1-trifluoropropan-2-yl)imidazo[1,2-b]pyridazine-3-carboxamide

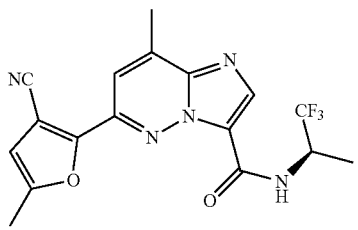 [SMILES: Cc1cc(C#N)c(-c2cc(C)c3ncc(C(=O)N[C@H](C)C(F)(F)F)n3n2)o1]

Following general procedure F, (R)-6-chloro-8-methyl-N-(1,1,1-trifluoropropan-2-yl)imidazo[1,2-b]pyridazine-3-carboxamide (32 mg, 0.10 mmol) and 5-methyl-2-(tributylstannyl)furan-3-carbonitrile afforded the title compound (20 mg, 53%) as a yellow solid. ¹H NMR (400 MHz, DMSO-d₆) δ 8.45 (d, J=8.5 Hz, 1H), 8.44 (s, 1H), 7.80 (s, 1H), 6.95 (s, 1H), 5.08-5.04 (m, 1H), 2.71 (s, 3H), 2.47 (s, 3H), 1.50 (d, J=7.0 Hz, 3H). LC-MS m/z: 378.1 [M+H]⁺. HPLC: Purity (214 nm): 90.8%; t_R=8.27 min.

(S)-6-(3-Cyano-5-methylfuran-2-yl)-8-methyl-N-(1,1,1-trifluoropropan-2-yl)imidazo[1,2-b]pyridazine-3-carboxamide

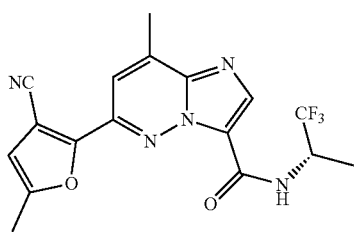 [SMILES: Cc1cc(C#N)c(-c2cc(C)c3ncc(C(=O)N[C@@H](C)C(F)(F)F)n3n2)o1]

Following general procedure F, (S)-6-chloro-8-methyl-N-(1,1,1-trifluoropropan-2-yl)imidazo[1,2-b]pyridazine-3-carboxamide (32 mg, 0.10 mmol) and 5-methyl-2-(tributylstannyl)furan-3-carbonitrile afforded the title compound (19 mg, 50%) as a yellow solid. ¹H NMR (400 MHz, DMSO-d₆) δ 8.45 (d, J=8.5 Hz, 1H), 8.44 (s, 1H), 7.80 (s, 1H), 6.95 (s, 1H), 5.08-5.04 (m, 1H), 2.71 (s, 3H), 2.47 (s, 3H), 1.50 (d, J=7.0 Hz, 3H). LC-MS m/z: 378.1 [M+H]⁺. HPLC: Purity (214 nm): 90.8%; t_R=8.27 min.

(R)—N-(1-Cyclopropyl-2,2,2-trifluoroethyl)-8-methyl-6-(1-methyl-1H-benzo[d]imidazol-5-yl)imidazo[1,2-b]pyridazine-3-carboxamide

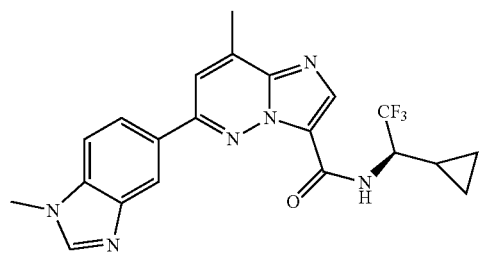 [SMILES: Cc1cc(-c2ccc3c(c2)ncn3C)nn2c(C(=O)N[C@H](C3CC3)C(F)(F)F)cnc12]

Following general procedure D, (R)-6-chloro-N-(1-cyclopropyl-2,2,2-trifluoroethyl)-8-methylimidazo[1,2-b]pyridazine-3-carboxamide (100 mg, 0.3 mmol) and 1-methyl-5-(4,4,5,5-tetramethyl-1,3,2-dioxaborolan-2-yl)-1H-benzo[d]imidazole afforded the title compound (17.5 mg, 14%) as a white solid. $^1$H NMR (500 MHz, DMSO-$d_6$) δ 9.31 (d, J=9.0 Hz, 1H), 8.43 (s, 1H), 8.33 (s, 2H), 8.14 (s, 1H), 8.01 (dd, J=8.5 Hz, 1.0 Hz, 1H), 7.82 (d, J=8.5 Hz, 1H), 4.56-4.46 (m, 1H), 3.92 (s, 3H), 2.72 (s, 3H), 1.30-1.21 (m, 1H), 0.77-0.59 (m, 3H), 0.44-0.40 (m, 1H). LC-MS m/z: 429.1 [M+H]$^+$. HPLC Purity (214 nm): 99.54%; $t_R$=7.29 min.

(S)—N-(1-Cyclopropyl-2,2,2-trifluoroethyl)-8-methyl-6-(1-methyl-1H-benzo[d]imidazol-5-yl)imidazo[1,2-b]pyridazine-3-carboxamide

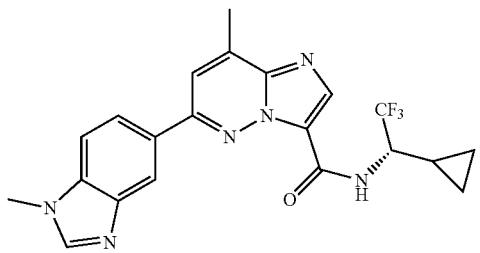 [SMILES: Cc1cc(-c2ccc3c(c2)ncn3C)nn2c(C(=O)N[C@@H](C3CC3)C(F)(F)F)cnc12]

Following general procedure D, (S)-6-chloro-N-(1-cyclopropyl-2,2,2-trifluoroethyl)-8-methylimidazo[1,2-b]pyridazine-3-carboxamide (80 mg, 0.22 mmol) and 1-methyl-5-(4,4,5,5-tetramethyl-1,3,2-dioxaborolan-2-yl)-1H-benzo[d]imidazole afforded the title compound (40 mg, 39%) as a white solid. $^1$H NMR (500 MHz, DMSO-$d_6$) δ 9.31 (d, J=9.0 Hz, 1H), 8.43 (s, 1H), 8.33 (s, 2H), 8.14 (s, 1H), 8.01 (dd, J=8.5 Hz, 1.0 Hz, 1H), 7.82 (d, J=8.5 Hz, 1H), 4.56-4.46 (m, 1H), 3.92 (s, 3H), 2.72 (s, 3H), 1.30-1.21 (m, 1H), 0.77-0.59 (m, 3H), 0.44-0.40 (m, 1H). LC-MS m/z: 429.1 [M+H]$^+$. HPLC Purity (214 nm): 93%; $t_R$=7.30 min.

(R)-6-(5-Methylpyridin-3-yl)-N-(1-cyclopropyl-2,2,2-trifluoroethyl)-8-methylimidazo[1,2-b]pyridazine-3-carboxamide

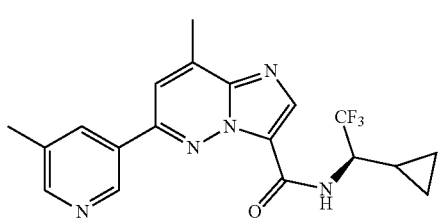 [SMILES: Cc1cncc(-c2cc(C)c3ncc(C(=O)N[C@H](C4CC4)C(F)(F)F)n3n2)c1]

Following general procedure D, (R)-6-chloro-N-(1-cyclopropyl-2,2,2-trifluoroethyl)-8-methylimidazo[1,2-b]pyridazine-3-carboxamide (80 mg, 0.24 mmol), and 5-methylpyridin-3-ylboronic acid afforded the title compound (30 mg, 32%) as a white solid. $^1$H NMR (500 MHz, DMSO-$d_6$) δ 9.092 (d, J=9.0 Hz, 1H), 9.088 (s, 1H), 8.63 (s, 1H), 8.38 (s, 1H), 8.27 (s, 1H), 8.08 (s, 1H), 4.53-4.48 (m, 1H), 2.72 (s, 3H), 2.42 (s, 3H), 1.28-1.24 (m, 1H), 0.73-0.68 (m, 1H), 0.65-0.55 (m, 2H), 0.42-0.37 (m, 1H). LC-MS m/z: 390.1 [M+H]$^+$. HPLC: Purity (214 nm): >99%; $t_R$=7.76 min.

(S)-6-(5-Methylpyridin-3-yl)-N-(1-cyclopropyl-2,2,2-trifluoroethyl)-8-methylimidazo[1,2-b]pyridazine-3-carboxamide

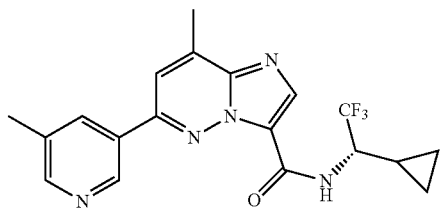 [SMILES: Cc1cncc(-c2cc(C)c3ncc(C(=O)N[C@@H](C4CC4)C(F)(F)F)n3n2)c1]

Following general procedure D, (S)-6-chloro-N-(1-cyclopropyl-2,2,2-trifluoroethyl)-8-methylimidazo[1,2-b]pyridazine-3-carboxamide (80 mg, 0.24 mmol) and 5-methylpyridin-3-ylboronic acid afforded the title compound (21.3 mg, 23%) as a white solid. $^1$H NMR (500 MHz, DMSO-$d_6$) δ 9.092 (d, J=9.0 Hz, 1H), 9.088 (s, 1H), 8.63 (s, 1H), 8.38 (s, 1H), 8.27 (s, 1H), 8.08 (s, 1H), 4.53-4.48 (m, 1H), 2.72 (s, 3H), 2.42 (s, 3H), 1.28-1.24 (m, 1H), 0.73-0.68 (m, 1H), 0.65-0.55 (m, 2H), 0.42-0.37 (m, 1H). LC-MS m/z: 390.1 [M+H]$^+$. HPLC: Purity (214 nm): 96.46%; $t_R$=7.81 min.

(R)-6-(5-Methoxylpyridin-3-yl)-N-(1-cyclopropyl-2,2,2-trifluoroethyl)-8-methylimidazo[1,2-b]pyridazine-3-carboxamide

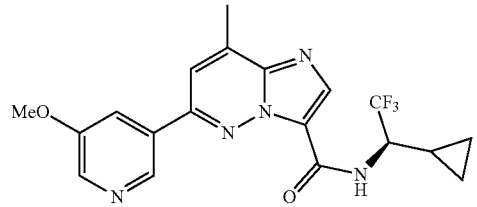

Following general procedure D, (R)-6-chloro-N-(1-cyclopropyl-2,2,2-trifluoroethyl)-8-methylimidazo[1,2-b]pyridazine-3-carboxamide (70 mg, 0.21 mmol) and 3-methoxy-5-(4,4,5,5-tetramethyl-1,3,2-dioxaborolan-2-yl) pyridine afforded the title compound (13 mg, 15%) as a white solid. $^1$H NMR (500 MHz, MeOD-$d_4$) δ 8.82 (d, J=1.5 Hz, 1H), 8.47 (d, J=2.5 Hz, 1H), 8.43 (s, 1H), 8.03 (t, J=2.0 Hz, 1H), 7.97 (d, J=1.0 Hz, 1H), 4.47-4.43 (m, 1H), 4.03 (s, 3H), 2.82 (d, J=1.0 Hz, 3H), 1.31-1.28 (m, 1H), 0.82-0.80 (m, 1H), 0.69-0.61 (m, 2H), 0.53-0.48 (m, 1H). LC-MS m/z: 406.0 [M+H]$^+$. HPLC: Purity (214 nm): 99.20%; $t_R$=7.67 min.

(S)-6-(5-Methoxylpyridin-3-yl)-N-(1-cyclopropyl-2,2,2-trifluoroethyl)-8-methylimidazo[1,2-b]pyridazine-3-carboxamide

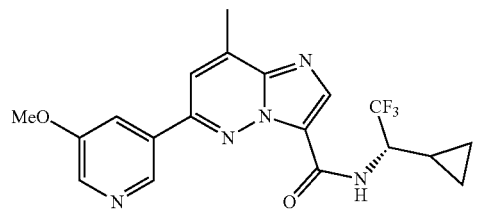 [SMILES: COc1cncc(-c2cc(C)c3ncc(C(=O)N[C@@H](C4CC4)C(F)(F)F)n3n2)c1]

Following general procedure D, (S)-6-chloro-N-(1-cyclopropyl-2,2,2-trifluoroethyl)-8-methylimidazo[1,2-b]pyridazine-3-carboxamide (50 mg, 0.15 mmol) and 5-methoxylpyridin-3-ylboronic acid afforded the title compound (16.3 mg, 27%) as a yellow solid. ¹H NMR (400 MHz, MeOD-d₄) δ 8.82 (s, 1H), 8.46 (s, 1H), 8.42 (s, 1H), 8.02 (s, 1H), 7.96 (s, 1H), 4.46-4.42 (m, 1H), 4.03 (s, 3H), 2.82 (s, 3H), 1.31-1.28 (m, 1H), 0.82-0.78 (m, 1H), 0.66-0.63 (m, 2H), 0.51-0.49 (m, 1H). LC-MS m/z: 406.1 [M+H]⁺. HPLC: Purity (254 nm): 99%; $t_R$=7.69 min.

(R)-6-(6-Methylpyridin-3-yl)-N-(1-cyclopropyl-2,2,2-trifluoroethyl)-8-methylimidazo[1,2-b]pyridazine-3-carboxamide

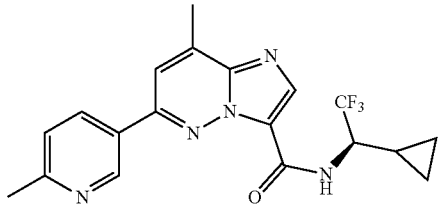 [SMILES: Cc1ccc(-c2cc(C)c3ncc(C(=O)N[C@H](C4CC4)C(F)(F)F)n3n2)cn1]

Following general procedure D, (R)-6-chloro-N-(1-cyclopropyl-2,2,2-trifluoroethyl)-8-methylimidazo[1,2-b]pyridazine-3-carboxamide (70 mg, 0.21 mmol) and 6-methylpyridin-3-ylboronic acid afforded the title compound (34 mg, 41%) as a white solid. ¹H NMR (500 MHz, DMSO-d₆) δ 9.14 (d, J=2.0 Hz, 1H), 9.09 (d, J=9.5 Hz, 1H), 8.36 (s, 1H), 8.32 (dd, J=8.0 Hz, 2.0 Hz, 1H), 8.04 (d, J=1.0 Hz, 1H), 7.52 (d, J=8.0 Hz, 1H), 4.49-4.43 (m, 1H), 2.72 (s, 3H), 2.58 (s, 3H), 1.34-1.21 (m, 1H), 0.77-0.54 (m, 3H), 0.41-0.34 (m, 1H). LC-MS m/z: 390.1 [M+H]⁺. HPLC Purity (214 nm): 99.2%; $t_R$=7.75 min.

(S)-6-(6-Methylpyridin-3-yl)-N-(1-cyclopropyl-2,2,2-trifluoroethyl)-8-methylimidazo[1,2-b]pyridazine-3-carboxamide

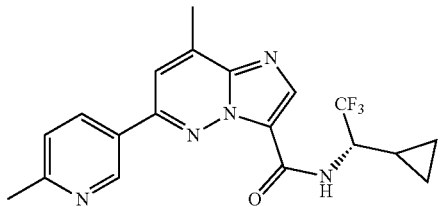 [SMILES: Cc1ccc(-c2cc(C)c3ncc(C(=O)N[C@@H](C4CC4)C(F)(F)F)n3n2)cn1]

Following general procedure D, (S)-6-chloro-N-(1-cyclopropyl-2,2,2-trifluoroethyl)-8-methylimidazo[1,2-b]pyridazine-3-carboxamide (100 mg, 0.30 mmol) and 6-methylpyridin-3-ylboronic acid afforded the title compound (42 mg, 35%) as a yellow solid. ¹H NMR (500 MHz, DMSO-d₆) δ 9.14 (d, J=2.0 Hz, 1H), 9.09 (d, J=9.0 Hz, 1H), 8.36 (s, 1H), 8.32 (dd, J=7.5 Hz, 2.5 Hz, 1H), 8.04 (s, 1H), 7.52 (d, J=8.0 Hz, 1H), 4.52-4.42 (m, 1H), 2.72 (s, 3H), 2.58 (s, 3H), 1.29-1.22 (m, 1H), 0.73-0.67 (m, 1H), 0.65-0.56 (m, 2H), 0.41-0.37 (m, 1H). LC-MS m/z: 390.1 [M+H]⁺. HPLC: Purity (214 nm): >99%; $t_R$=7.73 min.

N—((R)-1-Cyclopropyl-2,2,2-trifluoroethyl)-6-(5-isopropyl-2-oxooxazolidin-3-yl)-8-methylimidazo[1,2-b]pyridazine-3-carboxamide

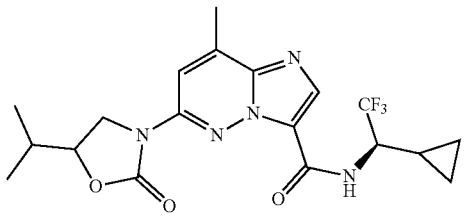 [SMILES: Cc1cc(N2CC(C(C)C)OC2=O)nn2c(C(=O)N[C@H](C3CC3)C(F)(F)F)cnc12]

Following general procedure G, (R)-6-chloro-N-(1-cyclopropyl-2,2,2-trifluoroethyl)-8-methylimidazo[1,2-b]pyridazine-3-carboxamide (80 mg, 0.24 mmol) and 5-isopropyloxazolidin-2-one afforded the title compound (30 mg, 29%) as a white solid. ¹H NMR (500 MHz, DMSO-d₆) δ 8.86 (dd, J=15.0 Hz, 9.5 Hz, 1H), 8.26 (s, 1H), 8.13 (dd, J=8.5 Hz, 1.0 Hz, 1H), 4.56-4.54 (m, 1H), 4.41-4.17 (m, 2H), 4.01-3.85 (m, 1H), 2.66 (s, 3H), 2.02-1.98 (m, 1H), 1.27-1.24 (m, 1H), 1.00 (d, J=6.5 Hz, 3H), 0.93 (dd, J=7.0 Hz, 3.0 Hz, 3H), 0.74-0.60 (m, 2H), 0.60-0.54 (m, 1H), 0.41-0.36 (m, 1H). LC-MS m/z: 426.1 [M+H]⁺. HPLC: Purity (254 nm): >99%; $t_R$=8.59 min.

N—((S)-1-Cyclopropyl-2,2,2-trifluoroethyl)-6-(5-isopropyl-2-oxooxazolidin-3-yl)-8-methylimidazo[1,2-b]pyridazine-3-carboxamide

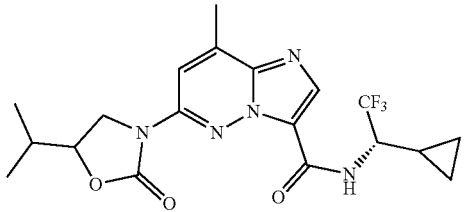 [SMILES: Cc1cc(N2CC(C(C)C)OC2=O)nn2c(C(=O)N[C@@H](C3CC3)C(F)(F)F)cnc12]

Following general procedure G, (S)-6-chloro-N-(1-cyclopropyl-2,2,2-trifluoroethyl)-8-methylimidazo[1,2-b]pyridazine-3-carboxamide (100 mg, 0.3 mmol) and 5-isopropyloxazolidin-2-one afforded the title compound (7 mg, 5%) as a white solid. ¹H NMR (500 MHz, MeOD-d₄) δ 8.34 (dd, J=12.5 Hz, 1H), 8.30 (d, J=2.5 Hz, 1H), 4.57-4.54 (m, 1H), 4.40-4.28 (m, 2H), 4.08-3.95 (m, 1H), 2.73 (s, 3H), 2.07-2.04 (m, 1H), 1.33-1.25 (m, 1H), 1.13 (dd, J=6.5 Hz, 3.5 Hz, 3H), 1.05 (d, J=7.0 Hz, 3H), 0.83-0.81 (m, 1H), 0.66-0.64 (m, 2H), 0.53-0.50 (m, 1H). LC-MS m/z: 426.1 [M+H]⁺. HPLC Purity (214 nm): 95.8%; $t_R$=8.602 min.

(R)—N-(1-Cyclopropyl-2,2,2-trifluoroethyl)-8-methyl-6-(1-methyl-1H-benzo[d]imidazol-6-yl)imidazo[1,2-b]pyridazine-3-carboxamide

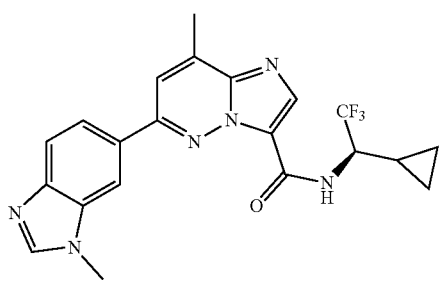 [SMILES: Cc1cc(-c2ccc3ncn(C)c3c2)nn2c(C(=O)N[C@H](C3CC3)C(F)(F)F)cnc12]

Following general procedure D, (R)-6-chloro-N-(1-cyclopropyl-2,2,2-trifluoroethyl)-8-methylimidazo[1,2-b]pyridazine-3-carboxamide (80 mg, 0.24 mmol) and 1-methyl-6-(4,4,5,5-tetramethyl-1,3,2-dioxaborolan-2-yl)-1H-benzo[d]imidazole afforded the title compound (40 mg, 39%) as a yellow solid. $^1$H NMR (500 MHz, DMSO-d$_6$): 9.27 (d, J=9.5 Hz, 1H), 8.37 (s, 1H), 8.36 (s, 1H), 8.31 (d, J=1.0 Hz, 1H), 8.13 (d, J=1.5 Hz, 1H), 7.96 (dd, J=8.5 Hz, 2.0 Hz, 1H), 7.86 (d, J=8.5 Hz, 1H), 4.56-4.52 (m, 1H), 3.94 (s, 3H), 2.74 (s, 3H), 1.34-1.26 (m, 1H), 0.73-0.68 (m, 1H), 0.67-0.56 (m, 2H), 0.45-0.37 (m, 1H). LC-MS m/z: 429.2 [M+H]$^+$. HPLC: Purity (214 nm): >99%; t$_R$=7.14 min.

(S)—N-(1-Cyclopropyl-2,2,2-trifluoroethyl)-8-methyl-6-(1-methyl-1H-benzo[d]imidazol-6-yl)imidazo[1,2-b]pyridazine-3-carboxamide

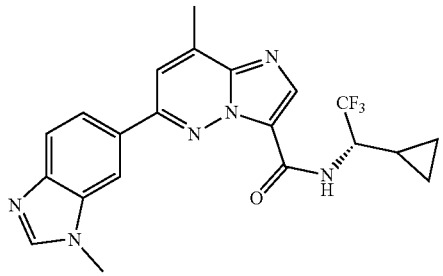 [SMILES: Cc1cc(-c2ccc3ncn(C)c3c2)nn2c(C(=O)N[C@@H](C3CC3)C(F)(F)F)cnc12]

Following general procedure D, (S)-6-chloro-N-(1-cyclopropyl-2,2,2-trifluoroethyl)-8-methylimidazo[1,2-b]pyridazine-3-carboxamide (80 mg, 0.24 mmol) and 1-methyl-6-(4,4,5,5-tetramethyl-1,3,2-dioxaborolan-2-yl)-1H-benzo[d]imidazole afforded the title compound (45 mg, 43%) as a yellow solid. $^1$H NMR (500 MHz, DMSO-d$_6$): 9.27 (d, J=9.5 Hz, 1H), 8.37 (s, 1H), 8.36 (s, 1H), 8.31 (d, J=1.0 Hz, 1H), 8.13 (d, J=1.5 Hz, 1H), 7.96 (dd, J=8.5 Hz, 2.0 Hz, 1H), 7.86 (d, J=8.5 Hz, 1H), 4.56-4.52 (m, 1H), 3.94 (s, 3H), 2.74 (s, 3H), 1.34-1.26 (m, 1H), 0.73-0.68 (m, 1H), 0.67-0.56 (m, 2H), 0.45-0.37 (m, 1H). LC-MS m/z: 429.2 [M+H]$^+$. HPLC: Purity (214 nm): >99%; t$_R$=7.16 min.

(S)-6-(2-Cyano-5-fluorophenyl)-8-methyl-N-(1,1,1-trifluoropropan-2-yl)imidazo[1,2-b]pyridazine-3-carboxamide

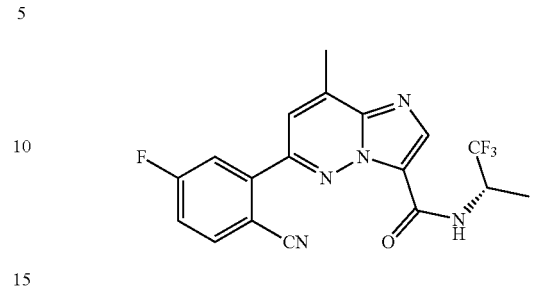

Following general procedure D, (S)-6-chloro-8-methyl-N-(1,1,1-trifluoropropan-2-yl)imidazo[1,2-b]pyridazine-3-carboxamide (70 mg, 0.23 mmol) and (2-cyano-5-fluorophenyl)boronic acid afforded the title compound (4.7 mg, 5%) as a white solid. $^1$H NMR (500 MHz, DMSO-d$_6$) δ 8.67 (d, J=9.0 Hz, 1H), 8.45 (s, 1H), 8.26 (dd, J=8.5 Hz, 5.5 Hz, 1H), 7.97 (dd, J=9.5 Hz, 2.5, 1H), 7.87 (s, 1H), 7.70 (td, J=8.5 Hz, 2.5 Hz, 1H), 5.05-4.99 (m, 1H), 2.73 (s, 3H), 1.43 (d, J=7.0 Hz, 3H). LC-MS m/z: 392.1 [M+H]$^+$. HPLC: Purity (214 nm): >99%; t$_R$=8.18 min.

(S)-6-(2-Cyano-3-fluorophenyl)-8-methyl-N-(1,1,1-trifluoropropan-2-yl)imidazo[1,2-b]pyridazine-3-carboxamide

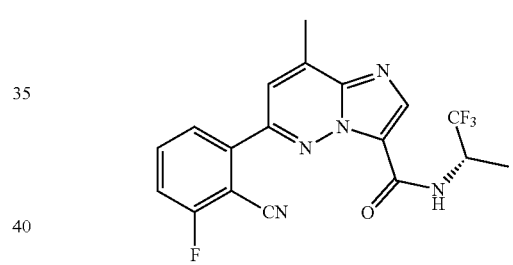

Following general procedure D, (S)-6-chloro-8-methyl-N-(1,1,1-trifluoropropan-2-yl)imidazo[1,2-b]pyridazine-3-carboxamide (61.2 mg, 0.2 mmol) and (2-cyano-3-fluorophenyl)boronic acid afforded the title compound (18 mg, 23%) as a white solid. $^1$H NMR (500 MHz, MeOD-d$_4$) (8.49 (s, 1H), 7.99-7.95 (m, 1H), 7.86 (d, J=8.0 Hz, 1H), 7.79 (s, 1H), 7.66-7.63 (t, J=8.5 Hz, 1H), 5.06-5.03 (m, 1H), 2.83 (s, 3H), 1.54 (d, J=7.5 Hz, 3H). LC-MS m/z: 392.1 [M+H]$^+$. HPLC: Purity (214 nm): >99%; t$_R$=8.15 min.

(S)-6-(2-Cyano-6-fluorophenyl)-8-methyl-N-(1,1,1-trifluoropropan-2-yl)imidazo[1,2-b]pyridazine-3-carboxamide

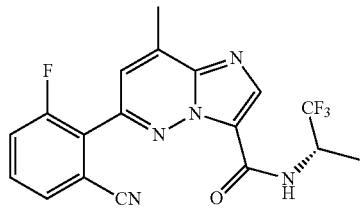 [SMILES: Cc1cc(-c2c(F)cccc2C#N)nn2c(C(=O)N[C@@H](C)C(F)(F)F)cnc12]

To a solution of (S)-6-(2-carbamoyl-6-fluorophenyl)-8-methyl-N-(1,1,1-trifluoropropan-2-yl)imidazo[1,2-b]pyridazine-3-carboxamide (50 mg, 0.30 mmol) in DMF (2 mL) was added SOCl$_2$ (90 mg, 0.90 mmol) dropwise at 0° C. The mixture was stirred at 0° C. for 2 h then diluted with DCM (20 mL), washed with sat. NaHCO$_3$ (10 mL) and brine (10 mL) and dried over anhydrous Na$_2$SO$_4$, filtered and concentrated. The residue was purified by reversed phase HPLC to give the title compound (19.4 mg, 40%) as a white solid. $^1$H NMR (500 MHz, DMSO-d$_6$) δ 8.67 (d, J=9.0 Hz, 1H), 8.46 (s, 1H), 8.04-8.02 (m, 1H), 7.93-7.85 (m, 2H), 7.76 (d, J=1.5 Hz, 1H), 4.99-4.95 (m, 1H), 2.74 (s, 3H), 1.39 (d, J=7.0 Hz 3H). LC-MS m/z: 392.0 [M+H]$^+$. HPLC: Purity (214 nm): >99%; t$_R$=7.85 min.

(S)-6-(2-Cyano-3-fluorophenyl)-N-(1-cyclopropylethyl)-8-methylimidazo[1,2-b]pyridazine-3-carboxamide

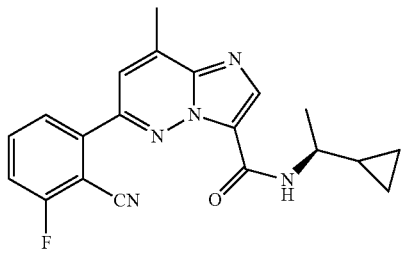 [SMILES: Cc1cc(-c2cccc(F)c2C#N)nn2c(C(=O)N[C@@H](C)C3CC3)cnc12]

Following general procedure D, (S)-6-chloro-N-(1-cyclopropylethyl)-8-methylimidazo[1,2-b]pyridazine-3-carboxamide (70 mg, 0.25 mmol) and (2-cyano-3-fluorophenyl)boronic acid afforded the title compound (26 mg, 29%) as a white solid. $^1$H NMR (500 MHz, DMSO-d$_6$) δ 8.49 (d, J=8.0 Hz, 1H), 8.35 (s, 1H), 8.06-8.01 (m, 1H), 7.93 (d, J=7.5 Hz, 1H), 7.83 (s, 1H), 7.82 (t, J=9.0 Hz, 1H), 3.58-3.55 (m, 1H), 2.74 (s, 3H), 1.28 (d, J=6.5 Hz, 3H), 1.08-1.06 (m, 1H), 0.46-0.44 (m, 1H), 0.38-0.33 (m, 2H), 0.32-0.27 (m, 1H). LC-MS m/z: 364.0 [M+H]$^+$. HPLC: Purity (214 nm): >99%; t$_R$=7.83 min.

(S)-6-(2-Cyano-5-fluorophenyl)-N-(1-cyclopropylethyl)-8-methylimidazo[1,2-b]pyridazine-3-carboxamide

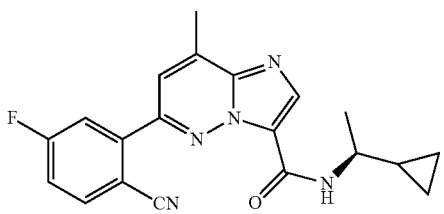 [SMILES: Cc1cc(-c2cc(F)ccc2C#N)nn2c(C(=O)N[C@@H](C)C3CC3)cnc12]

Following general procedure D, (S)-6-chloro-N-(1-cyclopropylethyl)-8-methylimidazo[1,2-b]pyridazine-3-carboxamide (50 mg, 0.18 mmol) and (2-cyano-5-fluorophenyl)boronic acid afforded the title compound (17.2 mg, 24%) as a white solid. $^1$H NMR (500 MHz, DMSO-d$_6$) δ 8.50 (d, J=7.5 Hz, 1H), 8.36 (s, 1H), 8.27 (dd, J=9.0 Hz, 5.5 Hz, 1H), 8.01 (dd, J=9.5 Hz, 2.5 Hz, 1H), 7.85 (d, J=1.0 Hz, 1H), 7.71 (td, J=8.5 Hz, 2.5 Hz, 1H), 3.67-3.50 (m, 1H), 2.73 (s, 3H), 1.28 (d, J=6.5 Hz, 3H), 1.14-1.03 (m, 1H), 0.48-0.43 (m, 1H), 0.40-0.22 (m, 3H). LC-MS m/z: 364.1 [M+H]$^+$. HPLC Purity (214 nm): >99%; t$_R$=8.14 min.

(S)-6-(3-Cyano-5-methylfuran-2-yl)-N-(1-cyclopropylethyl)-8-methylimidazo[1,2-b]pyridazine-3-carboxamide

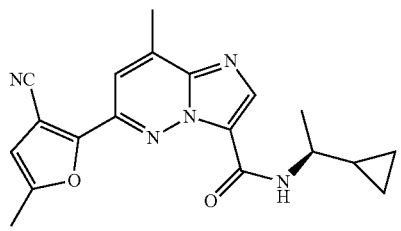 [SMILES: Cc1cc(C#N)c(-c2cc(C)c3ncc(C(=O)N[C@@H](C)C4CC4)n3n2)o1]

A mixture of (S)-6-chloro-N-(1-cyclopropylethyl)-8-methylimidazo[1,2-b]pyridazine-3-carboxamide (28 mg, 0.10 mmol), 5-methyl-2-(tributylstannyl)furan-3-carbonitrile (48 mg, 0.12 mmol), Pd(PPh$_3$)$_4$ (12 mg, 0.01 mmol) and CuBr (1 mg, 0.01 mmol) in dioxane (1 mL) was heated to 100° C. under N$_2$ and stirred for 2 h. The reaction mixture was then cooled to RT, filtered and the filter cake washed with EA/Et$_2$O. The cake was dissolved in MeOH and concentrated and the resulting solid was triturated with DCM/Et$_2$O to give the title compound (8.4 mg, 24%) as a yellow solid. $^1$H NMR (400 MHz, DMSO-d$_6$) δ 8.34-8.33 (m, 1H), 7.78 (s, 1H), 6.95 (s, 1H), 3.54-3.47 (m, 1H), 2.72 (s, 3H), 2.48 (s, 3H), 1.35 (d, J=6.4 Hz, 3H), 1.29-1.23 (m, 1H), 0.51-0.24 (m, 4H). LC-MS m/z: 350.2 [M+H]$^+$. HPLC: Purity (214 nm): >99%; t$_R$=8.34 min.

(R)—N-(1-Cyclopropyl-2,2,2-trifluoroethyl)-2-(3-fluorophenyl)-4-methylimidazo[1,5-b]pyridazine-7-carboxamide

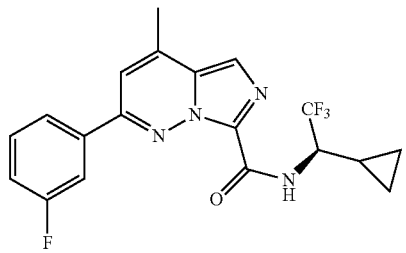 [SMILES: Cc1cc(-c2cccc(F)c2)nn2c(C(=O)N[C@H](C3CC3)C(F)(F)F)ncc12]

Following general procedure A, 2-(3-fluorophenyl)-4-methylimidazo[1,5-b]pyridazine-7-carboxylic acid (80 mg, 0.30 mmol) and (R)-1-cyclopropyl-2,2,2-trifluoroethanamine hydrochloride afforded the title compound (19 mg, 16%) as a white solid. $^1$H NMR (500 MHz, DMSO-d$_6$) δ 9.31 (d, J=9.2 Hz, 1H), 7.98 (d, J=8.0 Hz, 1H), 7.94 (d, J=10.5 Hz, 1H), 7.88 (s, 1H), 7.65 (q, J=7.5 Hz, 1H), 7.60 (s, 1H), 7.44 (td, J=8.5 Hz, 2.0 Hz, 1H), 4.30-4.26 (m, 1H), 2.64 (s, 3H), 1.37-1.33 (m, 1H), 0.72-0.64 (m, 1H), 0.63-0.61 (m, 1H), 0.58-0.55 (m, 1H), 0.38-0.35 (m, 1H). LC-MS m/z: 393.1 [M+H]$^+$. HPLC: Purity (254 nm): >99%; t$_R$=8.83 min.

(S)—N-(1-Cyclopropyl-2,2,2-trifluoroethyl)-2-(3-fluorophenyl)-4-methylimidazo[1,5-b]pyridazine-7-carboxamide

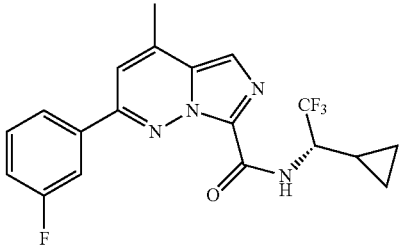

Following general procedure A, 2-(3-fluorophenyl)-4-methylimidazo[1,5-b]pyridazine-7-carboxylic acid (57 mg, 0.21 mmol) and (S)-1-cyclopropyl-2,2,2-trifluoroethanamine hydrochloride afforded the title compound (16 mg, 19%) as a white solid. $^1$H NMR (500 MHz, DMSO-$d_6$) δ 9.31 (d, J=9.5 Hz, 1H), 7.98 (d, J=8.0 Hz, 1H), 7.94 (d, J=10.5 Hz, 1H), 7.88 (s, 1H), 7.65 (dd, J=14.0, 8.0 Hz, 1H), 7.61 (s, 1H), 7.45 (td, J=8.5 Hz, 2.0 Hz, 1H), 4.32-4.24 (m, 1H), 2.64 (s, 3H), 1.38-1.31 (m, 1H), 0.73-0.68 (m, 1H), 0.65-0.60 (m, 1H), 0.58-0.53 (m, 1H), 0.40-0.32 (m, 1H). LC-MS m/z: 393.1 [M+H]$^+$. HPLC Purity (214 nm): >99%; $t_R$=9.01 min.

2-(3-Fluorophenyl)-4-methyl-N-(1,1,1-trifluorobut-3-yn-2-yl)imidazo[1,5-b]pyridazine-7-carboxamide

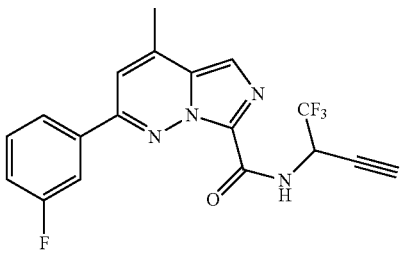 [SMILES: C#CC(NC(=O)c1ncc2c(C)cc(-c3cccc(F)c3)nn12)C(F)(F)F]

Following general procedure A, 2-(3-fluorophenyl)-4-methylimidazo[1,5-b]pyridazine-7-carboxylic acid (100 mg, 0.37 mmol) and 1,1,1-trifluorobut-3-yn-2-amine hydrochloride afforded the title compound (23 mg, 16%) as a white solid. $^1$H NMR (500 MHz, DMSO-$d_6$) δ 9.74 (d, J=9.5 Hz, 1H), 8.00-7.94 (m, 2H), 7.91 (s, 1H), 7.68-7.64 (m, 1H), 7.64 (s, 1H), 7.46 (td, J=8.5 Hz, 2.5 Hz, 1H), 6.02-5.97 (m, 1H), 3.83 (d, J=2.5 Hz, 1H), 2.65 (s, 3H). LC-MS m/z: 377.1 [M+H]$^+$. HPLC: Purity (254 nm): 90%; $t_R$=8.45 min.

2-(3-Methoxyphenyl)-4-methyl-N-(1,1,1-trifluorobut-3-yn-2-yl)imidazo[1,5-b]pyridazine-7-carboxamide

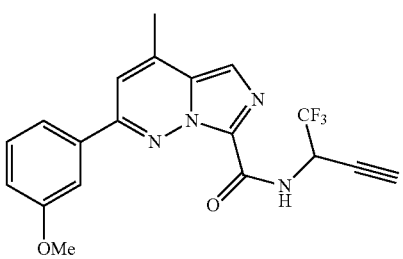 [SMILES: C#CC(NC(=O)c1ncc2c(C)cc(-c3cccc(OC)c3)nn12)C(F)(F)F]

Following general procedure A, 2-(3-methoxyphenyl)-4-methylimidazo[1,5-b]pyridazine-7-carboxylic acid (45 mg, 0.16 mmol) and 1,1,1-trifluorobut-3-yn-2-amine afforded the title compound (26.6 mg, 49%) as a pale yellow solid. $^1$H NMR (400 MHz, DMSO-$d_6$) δ 9.77 (d, J=9.2 Hz, 1H), 7.91 (s, 1H), 7.70 (d, J=8.4 Hz, 1H), 7.65 (s, 1H), 7.64 (d, J=8.0 Hz, 1H), 7.52 (t, J=8.0 Hz, 1H), 7.18 (dd, J=8.4 Hz, 1.6 Hz, 1H), 6.05-6.02 (m, 1H), 3.88 (s, 3H), 3.85 (d, J=2.4 Hz, 1H), 2.65 (s, 3H). LC-MS m/z: 389.0 [M+H]$^+$. HPLC: Purity (214 nm): 97.8%; $t_R$=8.39 min.

(S)-2-(5-Chloropyridin-3-yl)-N-(1-cyclopropyl-2,2,2-trifluoroethyl)-4-methylimidazo[1,5-b]pyridazine-7-carboxamide

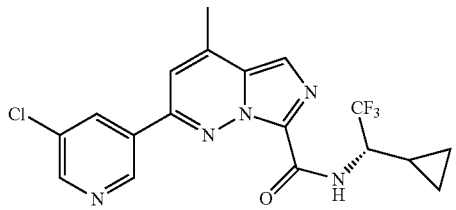 [SMILES: Cc1cc(-c2cncc(Cl)c2)nn2c(C(=O)N[C@@H](C3CC3)C(F)(F)F)ncc12]

A mixture of ZnCN$_2$ (2.34 g, 20.0 mmol), DPPF (554.0 mg, 1.0 mmol), Pd$_2$(dba)$_3$ (457.0 mg, 0.50 mmol) and 6-chloro-5-methylpyridazin-3(2H)-one (1.40 g, 10.0 mmol) in DMF (20 mL) was heated at 100° C. for 5 h. The reaction mixture was diluted with EA/H$_2$O and the organic layer was separated, washed with brine, dried over Na$_2$SO$_4$ and filtered. The filtrate was concentrated in vacuo, and the residue was purified by flash chromatography on silica (PE:EA=1:1) to afford 4-methyl-6-oxo-1,6-dihydropyridazine-3-carbonitrile (1.06 g, 73%) as a white solid. LC-MS m/z: 136.1 [M+H]$^+$. Purity (214 nm): 74%; $t_R$=0.87 min.

To a stirred solution of 4-methyl-6-oxo-1,6-dihydropyridazine-3-carbonitrile (1.06 g, 7.85 mmol) in MeOH (40 ml) at RT was added 5% Pd/C (100 mg) and 6N HCl (2.62 mL, 15.70 mmol) in MeOH (40 mL). The resulting black solution was stirred at RT for 2 h under a H$_2$ atmosphere. The crude reaction mixture was eluted through a short plug of celite (MeOH followed by DCM) and the organic fraction was concentrated to afford 6-(aminomethyl)-5-methylpyridazin-3(2H)-one hydrochloride (790 mg, 58%) as a white solid. LC-MS m/z: 140.2 [M+H]$^+$. Purity (214 nm): 100%; $t_R$=0.45 min.

To a suspension of 6-(aminomethyl)-5-methylpyridazin-3(2H)-one hydrochloride (790 mg, 4.49 mmol) in anhydrous THF (80 mL) at 0° C. was added ethyl 2-chloro-2-oxoacetate (733 mg, 5.39 mmol) followed by NEt$_3$ (3.3 mL, 22.45 mmol). The reaction mixture was slowly warmed to ambient temperature. After 18 h, the mixture was concentrated and the residue was purified by flash chromatography on silica (PE:EA=1:3) to afford ethyl 2-(((4-methyl-6-oxo-1,6-dihydropyridazin-3-yl)methyl)amino)-2-oxoacetate (430 mg, 40%) as a white solid. LC-MS m/z: 240.1 [M+H]$^+$. Purity (214 nm): 85%; $t_R$=1.10 min.

A stirred mixture of ethyl 2-(((4-methyl-6-oxo-1,6-dihydropyridazin-3-yl)methyl)amino)-2-oxoacetate (430 mg, 1.80 mmol) and POCl$_3$ (10 mL) was heated at 100° C. for 3 h. The reaction mixture was cooled to RT and quenched with sat. NaHCO$_3$ (50 mL) at 0° C. The mixture was extracted with DCM (100 mL×3) and the organic layer was washed with brine (50 mL), dried over anhydrous Na$_2$SO$_4$ and filtered. The filtrate was concentrated in vacuo, and the residue was purified by silica gel column chromatography (PE:EA=1:1) to afford ethyl 2-chloro-4-methylimidazo[1,5-b]pyridazine-7-carboxylate (202 mg, 47%) as a yellow solid. LC-MS m/z: 240.1 [M+H]⁺. Purity (214 nm): 100%; $t_R$=1.54 min.

Following general procedure D, ethyl 2-chloro-4-methyl-imidazo[1,5-b]pyridazine-7-carboxylate (190 mg, 0.80 mmol) and (5-chloropyridin-3-yl)boronic acid afforded ethyl 2-(5-chloropyridin-3-yl)-4-methylimidazo[1,5-b]pyridazine-7-carboxylate (70 mg, 30%) as a white solid. LC-MS m/z: 317.0 [M+H]⁺. Purity (214 nm): 96%; $t_R$=1.53 min.

Following general procedure B, ethyl 2-(5-chloropyridin-3-yl)-4-methylimidazo[1,5-b]pyridazine-7-carboxylate (70 mg, 0.22 mmol) afforded 2-(5-chloropyridin-3-yl)-4-methylimidazo[1,5-b]pyridazine-7-carboxylic acid (63 mg, 100%) as a white solid. LC-MS m/z: 289.1 [M+H]⁺. Purity (214 nm): 66%; $t_R$=1.19 min.

Following general procedure A, 2-(5-chloropyridin-3-yl)-4-methylimidazo[1,5-b]pyridazine-7-carboxylic acid (63 mg, 0.22 mmol) and (S)-1-cyclopropyl-2,2,2-trifluoroethanamine hydrochloride afforded the title compound (34 mg, 49%) as a white solid. ¹H NMR (500 MHz, DMSO-d₆) δ 9.28 (d, J=8.0 Hz, 1H), 9.26 (s, 1H), 8.45 (d, J=2.0 Hz, 1H), 8.60 (t, J=2.0 Hz, 1H), 7.91 (s, 1H), 7.69 (s, 1H), 4.27-4.24 (m, 1H), 2.65 (s, 3H), 1.36-1.34 (m, 1H), 0.71-0.70 (m, 1H), 0.64-0.62 (m, 1H), 0.57-0.54 (m, 1H), 0.37-0.32 (m, 1H). LC-MS m/z: 410.1, 412.1 [M+H]⁺. HPLC: Purity (214 nm): 94%; $t_R$=8.30 min.

(S)—N-(1-Cyclopropyl-2,2,2-trifluoroethyl)-4-methyl-2-(3-methylisothiazol-5-yl)imidazo[1,5-b]pyridazine-7-carboxamide

Following general procedure F, ethyl 2-chloro-4-methyl-imidazo[1,5-b]pyridazine-7-carboxylate (100 mg, 0.417 mmol) and 3-methyl-5-(tributylstannyl)isothiazole (325 mg, 0.85 mmol) afforded ethyl 4-methyl-2-(3-methylisothiazol-5-yl)imidazo[1,5-b]pyridazine-7-carboxylate (30 mg, 12%). ¹H NMR (400 MHz, DMSO-d₆) δ 8.01 (s, 1H), 7.91 (s, 1H), 7.57 (d, J=0.8 Hz, 1H), 4.41 (q, J=7.2 Hz, 2H), 2.62 (d, J=0.8 Hz, 3H), 2.52 (s, 3H), 1.41 (t, J=7.2 Hz, 3H). LC-MS m/z: 303.1 [M+H]⁺. $t_R$=1.21 min.

Following general procedure B, ethyl 4-methyl-2-(3-methylisothiazol-5-yl)imidazo[1,5-b]pyridazine-7-carboxylate (30 mg, 0.1 mmol) afforded 4-methyl-2-(3-methylisothiazol-5-yl)imidazo[1,5-b]pyridazine-7-carboxylic acid (27 mg, 99%) as a brown solid. LC-MS (m/z): 275.2 [M+H]⁺, Purity (214 nm): 71%; $t_R$=1.46 min.

Following general procedure A, 4-methyl-2-(3-methylisothiazol-5-yl)imidazo[1,5-b]pyridazine-7-carboxylic acid (27 mg, 0.1 mmol) and (S)-1-cyclopropyl-2,2,2-trifluoroethanamine hydrochloride afforded the title compound (6.4 mg, 16%) as a yellow solid. ¹H NMR (500 MHz, DMSO-d₆) δ 9.19 (d, J=9.0 Hz, 1H), 8.03 (s, 1H), 7.92 (s, 1H), 7.55 (s, 1H), 4.28-4.23 (m, 1H), 2.64 (s, 3H), 2.52 (s, 3H), 1.39-1.34 (m, 1H), 0.76-0.52 (m, 3H), 0.41-0.31 (m, 1H). LC-MS m/z: 396.0 [M+H]⁺. HPLC Purity (214 nm): 97%; $t_R$=8.34 min.

(S)—N-(1-Cyclopropyl-2,2,2-trifluoroethyl)-2-(3-isopropyl-2-oxoimidazolidin-1-yl)-4-methylimidazo[1,5-b]pyridazine-7-carboxamide

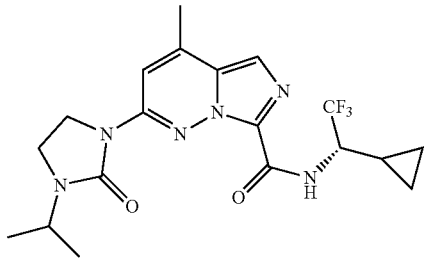 [SMILES: Cc1cc(N2CCN(C(C)C)C2=O)nn2c(C(=O)N[C@@H](C3CC3)C(F)(F)F)ncc12]

Following general procedure B, ethyl 2-chloro-4-methyl-imidazo[1,5-b]pyridazine-7-carboxylate (600 mg, 2.5 mmol) afforded 2-chloro-4-methylimidazo[1,5-b]pyridazine-7-carboxylic acid (530 mg, 100%) as a brown solid. LC-MS (m/z): 212.1 [M+H]⁺, Purity (214 nm): 65%; $t_R$=0.76 min.

Following general procedure A, 2-chloro-4-methylimidazo[1,5-b]pyridazine-7-carboxylic acid (530 mg, 2.5 mmol) and (S)-1-cyclopropyl-2,2,2-trifluoroethanamine hydrochloride afforded (S)-2-chloro-N-(1-cyclopropyl-2,2,2-trifluoroethyl)-4-methylimidazo[1,5-b]pyridazine-7-carboxamide (300 mg, 32%) as a yellow solid. LC-MS (m/z): 333.0 [M+H]⁺, Purity (214 nm): 71%; $t_R$=1.34 min.

Following general procedure G, (S)-2-chloro-N-(1-cyclopropyl-2,2,2-trifluoroethyl)-4-methylimidazo[1,5-b]pyridazine-7-carboxamide (50 mg, 0.15 mmol) and 1-isopropylimidazolidin-2-one afforded the title compound (3.2 mg, 5%) as a white solid. ¹H NMR (500 MHz, CDCl₃) δ 8.74 (d, J=9.5 Hz, 1H), 8.12 (s, 1H), 8.61 (s, 1H), 4.48-4.40 (m, 1H), 4.33-4.27 (m, 1H), 4.09-4.00 (m, 3H), 3.55 (t, J=7.5 Hz, 2H), 2.55 (s, 3H), 2.40 (d, J=6.5 Hz, 6H), 1.16-1.09 (m, 1H), 0.77-0.71 (m, 1H), 0.62-0.53 (m, 3H). LC-MS m/z: 425.0 [M+H]⁺, HPLC: Purity (214 nm): 98%; $t_R$=8.27 min.

(S)-2-(5-Carbamoylfuran-2-yl)-N-(1-cyclopropyl-2,2,2-trifluoroethyl)-4-methylimidazo[1,5-b]pyridazine-7-carboxamide

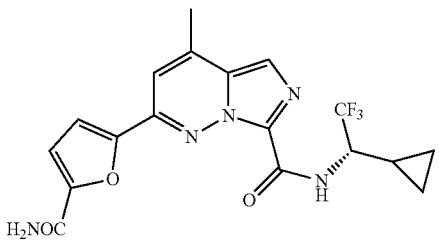 [SMILES: Cc1cc(-c2ccc(C(N)=O)o2)nn2c(C(=O)N[C@@H](C3CC3)C(F)(F)F)ncc12]

Following general procedure F, ethyl 2-chloro-4-methyl-imidazo[1,5-b]pyridazine-7-carboxylate (100 mg, 0.417 mmol) and 5-(tributylstannyl)furan-2-carbonitrile afforded ethyl 2-(5-cyanofuran-2-yl)-4-methylimidazo[1,5-b]pyridazine-7-carboxylate (40 mg, 32%) as a yellow solid. ¹H NMR (500 MHz, MeOD-d₄) δ 7.86 (s, 1H), 7.60-7.52 (m, 2H), 7.44 (d, J=1.0 Hz, 1H), 4.54 (q, J=7.0 Hz, 2H), 2.70 (d, J=1.0 Hz, 3H), 1.50 (t, J=7.0 Hz, 3H). LC-MS m/z: 297.1 [M+H]⁺, t_R=1.22 min.

Following general procedure B, ethyl 2-(5-cyanofuran-2-yl)-4-methylimidazo[1,5-b]pyridazine-7-carboxylate (40 mg, 0.135 mmol) afforded 2-(5-carbamoylfuran-2-yl)-4-methylimidazo[1,5-b]pyridazine-7-carboxylic acid (30 mg, 77%) as a brown solid. LC-MS (m/z): 287.1 [M+H]⁺, Purity (254 nm): 80%, t_R=1.26 min.

Following general procedure A, 2-(5-carbamoylfuran-2-yl)-4-methylimidazo[1,5-b]pyridazine-7-carboxylic acid (30 mg, 0.1 mmol) and (S)-1-cyclopropyl-2,2,2-trifluoroethanamine hydrochloride afforded the title compound (20 mg, 50%) as a yellow solid. ¹H NMR (500 MHz, MeOD-d₄) δ 7.86 (s, 1H), 7.57 (s, 1H), 7.46 (d, J=4.0 Hz, 1H), 7.35 (d, J=3.5 Hz, 1H), 4.44-4.32 (m, 1H), 2.71 (s, 3H), 1.44-1.40 (m, 1H), 0.86-0.80 (m, 1H), 0.74-0.60 (m, 2H), 0.53-0.50 (m, 1H). LC-MS m/z: 408.0 [M+H]⁺. HPLC Purity (214 nm): 94%; t_R=6.76 min.

(S)-2-(5-Cyanofuran-2-yl)-N-(1-cyclopropyl-2,2,2-trifluoroethyl)-4-methylimidazo[1,5-b]pyridazine-7-carboxamide

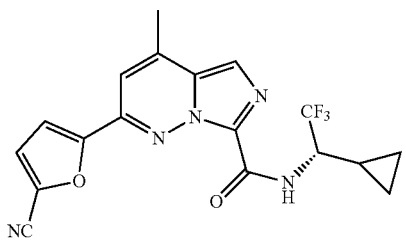 [SMILES: Cc1cc(-c2ccc(C#N)o2)nn2c(C(=O)N[C@@H](C3CC3)C(F)(F)F)ncc12]

To a solution of (S)-2-(5-carbamoylfuran-2-yl)-N-(1-cyclopropyl-2,2,2-trifluoroethyl)-4-methylimidazo[1,5-b]pyridazine-7-carboxamide (10 mg, 0.025 mmol) in DMF (0.5 mL) was added SOCl₂ (7.4 mg, 0.0625 mmol). The mixture was stirred at 0° C. for 1 h, concentrated in vacuo and then purified by preparative HPLC to give the title compound (7.8 mg, 80%) as a yellow solid. ¹H NMR (500 MHz, MeOD-d₄) δ 7.90 (s, 1H), 7.58 (d, J=4.0 Hz, 2H), 7.56 (d, J=3.5 Hz, 2H), 7.44 (d, J=1.0 Hz, 1H), 4.53-4.40 (m, 1H), 2.72 (d, J=1.0 Hz, 3H), 1.40-1.35 (m, 1H), 0.83-0.79 (m, 1H), 0.72-0.69 (m, 1H), 0.69-0.58 (m, 2H). LC-MS m/z: 390.0 [M+H]⁺. HPLC Purity (214 nm): 98%; t_R=8.16 min.

(S)-2-(2-Cyano-4-fluorophenyl)-N-(1-cyclopropylethyl)-4-methylimidazo[1,5-b]pyridazine-7-carboxamide

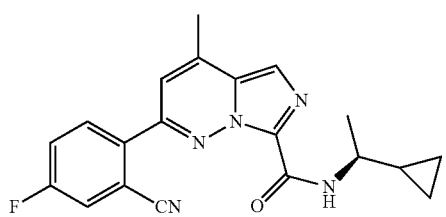 [SMILES: Cc1cc(-c2ccc(F)cc2C#N)nn2c(C(=O)N[C@@H](C)C3CC3)ncc12]

Following general procedure D, ethyl 2-chloro-4-methylimidazo[1,5-b]pyridazine-7-carboxylate (200 mg, 0.84 mmol) and (2-cyano-4-fluorophenyl)boronic acid afforded ethyl 2-(2-cyano-4-fluorophenyl)-4-methylimidazo[1,5-b]pyridazine-7-carboxylate (70 mg, 26%) as a yellow solid. LC-MS m/z: 325.1 (M+1)+. LC-MS Purity (214 nm): 84%; t_R=1.42 min.

Following general procedure B, ethyl 2-(2-cyano-4-fluorophenyl)-4-methylimidazo[1,5-b]pyridazine-7-carboxylate (60 mg, 0.19 mmol) afforded 2-(2-cyano-4-fluorophenyl)-4-methylimidazo[1,5-b]pyridazine-7-carboxylic acid (10 mg, 15%) as a white solid. LC-MS m/z: 297.1 (M+1)¹. LC-MS Purity (254 nm): 59%; t_R=1.03 min.

Following general procedure A, 2-(2-cyano-4-fluorophenyl)-4-methylimidazo[1,5-b]pyridazine-7-carboxylic acid (40 mg, 0.14 mmol) and (S)-1-cyclopropylethan-1-amine afforded the title compound (14.0 mg, 27%) as a white solid. ¹H NMR (500 MHz, DMSO-d₆) δ 8.68 (d, J=8.0 Hz, 1H), 8.18 (dd, J=9.0 Hz, 2.5 Hz, 1H), 8.06 (dd, J=9.0 Hz, 5.0 Hz, 1H), 7.92 (s, 1H), 7.88 (td, J=9.0 Hz, 3.0 Hz, 1H), 7.29 (s, 1H), 3.55-3.51 (m, 1H), 2.65 (s, 3H), 1.27 (d, J=6.5 Hz, 3H), 1.08-1.05 (m, 1H), 0.45-0.43 (m, 1H), 0.36-0.30 (m, 2H), 0.26-0.24 (m, 1H). LC-MS m/z: 363.9 [M+H]⁺. HPLC: Purity (214 nm): >99%; t_R=7.83 min.

(S)-2-(2-Cyano-4-fluorophenyl)-N-(1-cyclopropyl-2,2,2-trifluoroethyl)-4-methylimidazo[1,5-b]pyridazine-7-carboxamide

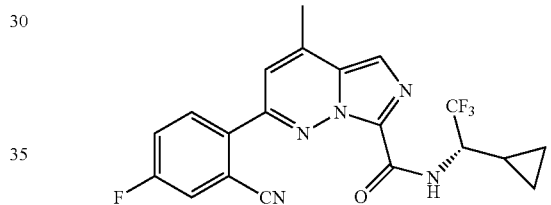

Following general procedure A, 2-(2-cyano-4-fluorophenyl)-4-methylimidazo[1,5-b]pyridazine-7-carboxylic acid (10 mg, 0.034 mmol) and (S)-1-cyclopropyl-2,2,2-trifluoroethanamine hydrochloride afforded the title compound (2.8 mg, 19%) as a yellow solid. ¹H NMR (500 MHz, MeOD-d₄) δ 8.04 (dd, J=8.5 Hz, 5.0 Hz, 1H), 7.96 (s, 1H), 7.88 (dd, J=8.5 Hz, 3.0 Hz, 1H), 7.71 (td, J=8.5 Hz, 3.0 Hz, 1H), 7.31 (d, J=1.0 Hz, 1H), 4.32-4.29 (m, 1H), 2.75 (s, 3H), 1.39-1.34 (m, 1H), 0.79-0.76 (m, 1H), 0.65-0.59 (m, 2H), 0.49-0.46 (m, 1H). LC-MS m/z: 418.1 [M+H]⁺. HPLC: Purity (214 nm): >99%; t_R=8.36 min.

5,7-Dimethyl-N-((1R,4R)-4-(pentyloxy)cyclohexyl)isothiazolo[4,5-b]pyridine-3-carboxamide

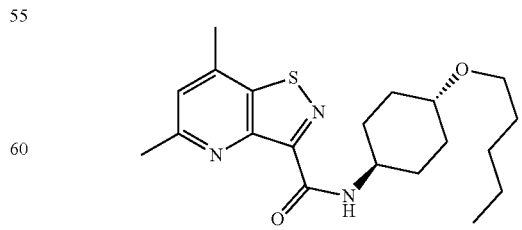

To a solution of 5-bromo-2,4-dimethylpyridine (12 g, 64.5 mmol) in DCM (200 mL) was added m-CPBA (13.2 g, 77.4 mmol) and the solution was stirred at RT overnight. The reaction mixture was partitioned between sat. NaHCO₃ (300 mL) and DCM (200 mL). The organic layer was washed with H₂O (150 mL), brine (150 mL) and dried over anhydrous Na₂SO₄ and concentrated in vacuo to give 5-bromo-2,4-dimethylpyridine 1-oxide (4.0 g, 30%) as a yellow solid. LC-MS m/z: 204.0 [M+H]⁺. LC-MS Purity (214 nm): 98%; $t_R$=0.84 min.

A stirred solution of 5-bromo-2,4-dimethylpyridine 1-oxide (6.0 g, 29.7 mmol), CNSiMe₃ (9.0 g, 89.1 mmol) and TEA (12.0 g, 118.8 mmol) in CH₃CN (60 mL) was refluxed for 20 h. The solution was concentrated and the residue was diluted with H₂O (50 mL). The mixture was extracted with DCM (50 mL×2), washed with brine (100 mL) and the combined organic extracts were dried over anhydrous Na₂SO₄ and concentrated in vacuo. The residue was purified by silica gel chromatography (PE:EA=5:1) to give 3-bromo-4,6-dimethylpicolinonitrile (4.0 g, 60%) as a white solid. LC-MS m/z: 213.0 [M+H]⁺. LC-MS Purity (214 nm): 99%; $t_R$=1.23 min.

To a solution of 3-bromo-4,6-dimethylpicolinonitrile (2.4 g, 11.4 mmol) in DMA (10 mL) was added sodium thiomethoxide (4.0 g, 57.0 mmol) and the reaction mixture was heated to 130° C. and stirred for 1 h. The reaction was quenched with con. HCl (10 mL) at 0° C. and the mixture was stirred at RT overnight. The mixture was concentrated and purified by reversed phase HPLC to give 3,3'-bis(4,6-dimethylpicolinonitrile)disulfide (1.6 g, 43%) as a yellow solid. LC-MS m/z: 327.0 [M+H]⁺. LC-MS Purity (214 nm): 65%; $t_R$=1.41 min.

A mixture of 3,3'-bis(4,6-dimethylpicolinonitrile)disulfide (370 mg, 1.13 mmol) and NaBH₄ (132 mg, 3.47 mmol) in MeCN (20 mL) was stirred at RT overnight. The reaction mixture was acidified with 6N HCl to pH~5 and extracted with EA (20 mL×3). The combined organic phase was dried over anhydrous Na₂SO₄ and concentrated in vacuo to give 3-mercapto-4,6-dimethylpicolinonitrile (256 mg, 69%) as a dark orange solid. LC-MS m/z: 165.1 [M+H]⁺. $t_R$=1.12 min.

A solution of 3-mercapto-4,6-dimethylpicolinonitrile (372 mg, 2.27 mmol) in EA (25 mL) was stirred at 0° C. for 5 min followed by the addition of Br₂ (436 mg, 2.73 mmol). The mixture was stirred at RT for 30 min and then refluxed for 1 h. The reaction was diluted with H₂O (20 mL), extracted with EA (30 mL) and washed with sat. sodium bisulfite (20 mL), dried over anhydrous Na₂SO₄, and concentrated in vacuo to give a residue which was purified by silica gel chromatography (DCM:MeOH=1:0 to 10:1) to give 3-bromo-5,7-dimethylisothiazolo[4,5-b]pyridine (240 mg, 44%) as a white solid. LC-MS m/z: 244.9 [M+H]⁺. $t_R$=1.29 min.

To a solution of 3-bromo-5,7-dimethylisothiazolo[4,5-b]pyridine (180 mg, 0.74 mmol) in a mixture of TEA (0.52 mL, 3.75 mmol) and MeOH (80 mL) was added Pd(dppf)Cl₂·DCM (91 mg, 0.11 mmol). The reaction was heated to 70° C. and stirred for 6 h under 45 atm of CO. Upon completion, the reaction was cooled to RT and the crude product was concentrated in vacuo and purified by reversed phase HPLC to give methyl 5,7-dimethylisothiazolo[4,5-b]pyridine-3-carboxylate (95 mg, 58%) as a white solid. LC-MS m/z: 223.1 [M+H]⁺, Purity (214 nm): 93%; $t_R$=1.09 min.

To a stirred solution of (1R,4R)-4-(pentyloxy)cyclohexan-1-amine (52 mg, 0.28 mmol) in toluene (2 mL) was added AlMe₃ (0.21 mL, 0.42 mmol) at 0° C. The reaction mixture was stirred at RT for 1 h followed by the addition of a solution of methyl 5,7-dimethylisothiazolo[4,5-b]pyridine-3-carboxylate (30 mg, 0.14 mmol) in THF (2 mL). The reaction mixture was heated to 110° C. and stirred for 40 min. Sat. NH₄Cl (10 mL) was then added and the mixture was extracted with EA (20 mL). The organic layer was washed with H₂O (5 mL) and brine (5 mL) and concentrated in vacuo to give a residue which was purified by preparative HPLC to give the title compound (4.2 mg, 8%) as a white solid. ¹H NMR (500 MHz, DMSO-d₆) δ 9.80 (d, J=7.5 Hz, 1H), 7.48 (s, 1H), 7.94-7.85 (m, 1H), 3.94-3.85 (m, 1H), 3.40 (t, J=6.5 Hz, 2H), 3.34-3.33 (m, 1H), 2.69 (s, 3H), 2.64 (s, 3H), 2.04-1.95 (m, 4H), 1.52-1.34 (m, 6H), 1.32-1.25 (m, 4H), 0.88 (t, J=6.5 Hz, 3H). LC-MS m/z: 375.9 [M+H]⁺. HPLC: Purity (214 nm): >99%; $t_R$=10.39 min.

5,7-Dimethyl-N-(1-phenylpropyl)isothiazolo[4,5-b]pyridine-3-carboxamide

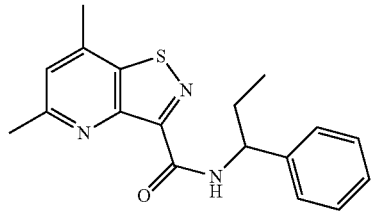 [SMILES: CCC(NC(=O)c1nsc2c(C)cc(C)nc12)c1ccccc1]

To a stirred solution of 1-phenylpropan-1-amine (61 mg, 0.45 mmol) in toluene (2 mL) was added AlMe₃ (0.27 mL, 0.54 mmol) at 0° C. The reaction mixture was stirred at RT for 1 h followed by the addition of a solution of methyl 5,7-dimethylisothiazolo[4,5-b]pyridine-3-carboxylate (40 mg, 0.18 mmol) in THF (2 mL). The reaction mixture was heated to 110° C. and stirred for 40 min. Sat. NH₄Cl (10 mL) was then added and the mixture was extracted with EA (20 mL). The organic layer was washed with H₂O (5 mL), brine (5 mL) and concentrated in vacuo to give a residue which was purified by reversed-phase HPLC to give the title compound (27.5 mg, 47%) as an off white solid. ¹H NMR (500 MHz, DMSO-d₆) δ 10.30 (d, J=8.5 Hz, 1H), 7.50 (s, 1H), 7.45 (d, J=6.5 Hz, 2H), 7.37 (t, J=7.5 Hz, 2H), 7.27 (t, J=7.5 Hz, 1H), 5.06 (q, J=7.5 Hz, 1H), 2.71 (s, 3H), 2.65 (s, 3H), 1.95-1.87 (m, 2H), 0.95 (t, J=7.0 Hz, 3H). LC-MS m/z: 326.2[M+H]⁺. HPLC: Purity (214 nm): 98%; $t_R$=9.27 min.

5,7-Dimethyl-N-(1,2,3,4-tetrahydronaphthalen-1-yl)isothiazolo[4,5-b]pyridine-3-carboxamide

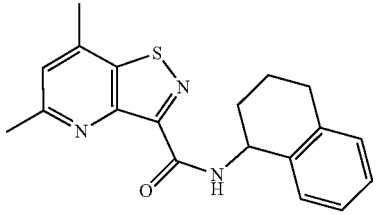 [SMILES: Cc1cc(C)c2snc(C(=O)NC3CCCc4ccccc43)c2n1]

To a stirred solution of 1,2,3,4-tetrahydronaphthalen-1-amine (40 mg, 0.28 mmol) in toluene (2 mL) was added AlMe₃ (0.21 mL, 0.42 mmol) at 0° C. The reaction mixture was stirred at RT for 1 h followed by the addition of a solution of methyl 5,7-dimethylisothiazolo[4,5-b]pyridine-3-carboxylate (30 mg, 0.14 mmol) in THF (2 mL). The reaction mixture was heated to 110° C. and stirred for 40 min. Sat. NH₄Cl (10 mL) was then added and the mixture was extracted with EA (20 mL). The organic layer was washed with H₂O (5 mL), brine (5 mL) and concentrated in vacuo to give a residue which was purified by reversed-phase HPLC to give the title compound (8 mg, 15%) as a white solid. ¹H NMR (500 MHz, DMSO-d₆) δ 10.16 (d, J=9.0 Hz, 1H), 7.45-7.43 (m, 2H), 7.22-7.14 (m, 3H), 5.34-5.28 (m, 3H), 2.90-2.75 (m, 2H), 2.64 (s, 3H), 2.57 (s, 3H), 2.17-2.08 (m, 1H), 1.99-1.86 (m, 3H). LC-MS m/z: 338.0 [M+H]⁺. HPLC: Purity (214 nm): >99%; $t_R$=9.45 min.

N-(2,3-Dihydro-1H-inden-5-yl)-5,7-dimethylisothiazolo[4,5-b]pyridine-3-carboxamide

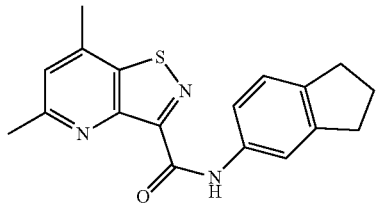 [SMILES: Cc1cc(C)c2snc(C(=O)Nc3ccc4c(c3)CCC4)c2n1]

To a stirred solution of 2,3-dihydro-1H-inden-5-amine (40 mg, 0.28 mmol) in toluene (2 mL) was added AlMe₃ (0.21 mL, 0.42 mmol) at 0° C. The reaction mixture was stirred at RT for 1 h followed by the addition of a solution of methyl 5,7-dimethylisothiazolo[4,5-b]pyridine-3-carboxylate (30 mg, 0.14 mmol) in THF (2 mL). The reaction mixture was heated to 110° C. and stirred for 40 min. Sat. NH₄Cl (10 mL) was then added and the mixture was extracted with EA (20 mL). The organic layer was washed with H₂O (5 mL), brine (5 mL) and concentrated in vacuo to give a residue which was purified by reversed-phase HPLC to give the title compound (5 mg, 10%) as a white solid. ¹H NMR (500 MHz, DMSO-d₆) δ 11.82 (s, 1H), 7.77 (s, 1H), 7.54 (d, J=8.0 Hz, 1H), 7.53 (s, 1H), 7.27 (d, J=7.5 Hz, 1H), 2.91 (t, J=7.0 Hz, 2H), 2.86 (t, J=7.0 Hz, 2H), 2.7 (s, 3H), 2.67 (s, 3H), 2.08-2.02 (m, 2H). LC-MS m/z: 323.9 [M+H]⁺. HPLC: Purity (214 nm): >99%; $t_R$=10.14 min.

5,7-Dimethyl-N-((1R,4R)-4-(pentyloxy)cyclohexyl)furo[3,2-b]pyridine-3-carboxamide

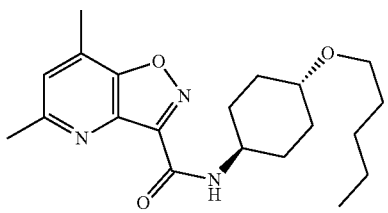 [SMILES: CCCCCO[C@H]1CC[C@H](NC(=O)c2noc3c(C)cc(C)nc23)CC1]

To a solution of 2-bromo-4,6-dimethylpyridin-3-amine (15 g, 75 mmol) in 20% fluoroboric acid (180 mL) was added aq. NaNO₂ (5.7 g, 82.5 mmol, in 30 mL) at 0° C. The mixture was stirred at 0° C. for 30 min and then heated at 110° C. for 30 min. After cooling to RT, the solution was neutralized with sat. NaHCO₃ to pH~7 and extracted with DCM (300 mL). The organic layer was concentrated in vacuo and the residue was purified by silica gel chromatography (PE:EA=1:1) to give 2-bromo-4,6-dimethylpyridin-3-ol (1.7 g, 12%) as a brown solid. LC-MS m/z: 202.0 [M+H]⁺, HPLC: Purity (214 nm): 95%; $t_R$=0.89 min.

A mixture of 2-bromo-4,6-dimethylpyridin-3-ol (1.5 g, 7.46 mmol), ethyl propiolate (730 mg, 7.46 mmol) and 1,4-diazabicyclo[2.2.2]octane (83 mg, 0.75 mmol) in DCM (150 mL) was stirred at RT for 30 min. The reaction mixture was concentrated in vacuo and purified by silica gel chromatography (EA) to give ethyl (E)-3-((2-bromo-4,6-dimethylpyridin-3-yl)oxy)acrylate (1.8 g, 80%) as a white solid. LC-MS m/z: 300.0 [M+H]⁺, HPLC: Purity (214 nm): 95%; $t_R$=1.42 min.

A mixture of ethyl (E)-3-((2-bromo-4,6-dimethylpyridin-3-yl)oxy)acrylate (1.7 g, 5.68 mmol), Pd(PPh₃)₂Cl₂ (400 mg, 0.57 mmol) and KOAc (1.7 g, 17.04 mmol) in DMF (100 mL) under N₂ was stirred at 120° C. for 2 h. The reaction mixture was filtered, concentrated in vacuo and purified by silica gel chromatography (EA) to give ethyl 5,7-dimethylfuro[3,2-b]pyridine-3-carboxylate (500 mg, 40%) as a white solid. LC-MS m/z: 220.0 [M+H]⁺, HPLC: Purity (214 nm): 95%; $t_R$=1.21 min.

Following general procedure B, ethyl 5,7-dimethylfuro[3,2-b]pyridine-3-carboxylate (50 mg, 0.23 mmol) afforded 5,7-dimethylfuro[3,2-b]pyridine-3-carboxylic acid (44 mg, 99%) as a yellow solid. LC-MS m/z: 192.1 [M+H]⁺; $t_R$=0.71 min.

Following general procedure A, 5,7-dimethylfuro[3,2-b]pyridine-3-carboxylic acid (30 mg, 0.16 mmol) and (1R,4R)-4-(pentyloxy)cyclohexan-1-amine afforded the title compound (4.8 mg, 9%) as a yellow solid. ¹H NMR (500 MHz, DMSO-d₆) δ 8.75 (s, 1H), 8.69 (d, J=7.5 Hz, 1H), 7.21 (s, 1H), 3.85-3.83 (m, 1H), 3.39 (1, J=6.5 Hz, 2H), 3.32 (s, 3H), 2.88 (m, 1H), 2.58 (s, 3H), 2.00-1.95 (m, 4H), 1.49-1.45 (m, 2H), 1.42-1.33 (m, 4H), 1.31-1.24 (m, 4H), 0.87 (t, J=7.0 Hz, 3H). LC-MS m/z: 359.1 [M+H]⁺. HPLC: Purity (214 nm)): 95%; $t_R$=11.26 min.

5,7-Dimethyl-N-(1-phenylpropyl)furo[3,2-b]pyridine-3-carboxamide

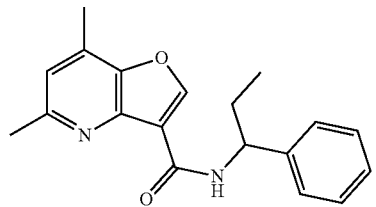 [SMILES: CCC(NC(=O)c1coc2c(C)cc(C)nc12)c1ccccc1]

Following general procedure A, 5,7-dimethylfuro[3,2-b]pyridine-3-carboxylic acid (30 mg, 0.16 mmol) and 1-phenylpropan-1-amine afforded the title compound (4.8 mg, 10%) as a white solid. ¹H NMR (500 MHz, DMSO-d₆) δ 9.27 (d, J=8.0 Hz, 1H), 8.77 (s, 1H), 7.42-7.34 (M, 4H), 7.29-7.25 (m, 2H), 5.03 (q, J=8.0 Hz, 1H), 2.62 (s, 3H), 2.51 (s, 3H), 1.92-1.85 (m, 2H), 0.91 (t, J=7.5 Hz, 3H). LC-MS m/z: 309.1 [M+H]⁺. HPLC: Purity (214 nm): 90%; $t_R$=10.14 min.

5,7-Dimethyl-N-(1,2,3,4-tetrahydronaphthalen-1-yl)furo[3,2-b]pyridine-3-carboxamide

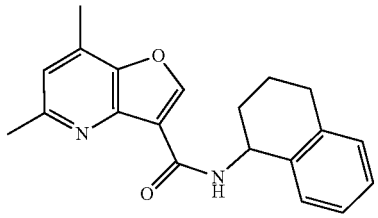 [SMILES: Cc1cc(C)c2occ(C(=O)NC3CCCc4ccccc43)c2n1]

Following general procedure A, 5,7-dimethylfuro[3,2-b]pyridine-3-carboxylic acid (30 mg, 0.16 mmol) and 1,2,3,4-tetrahydronaphthalen-1-amine afforded the title compound (6.6 mg, 12%) as a white solid. $^1$H NMR (500 MHz, DMSO-$d_6$) δ 9.05 (d, J=8.5 Hz, 1H), 8.84 (s, 1H), 7.33 (d, J=7.0 Hz, 1H), 7.21-7.14 (m, 4H), 5.29 (q, J=7.5 Hz, 1H), 2.94-2.73 (m, 1H), 2.47 (s, 3H), 1.15-1.06 (m, 1H), 1.97-1.80 (m, 3H). LC-MS m/z: 321.1 [M+H]$^+$. HPLC: Purity (214 nm): >99%; $t_R$=10.14 min.

N-(2,3-Dihydro-1H-inden-5-yl)-5,7-dimethylfuro[3,2-b]pyridine-3-carboxamide

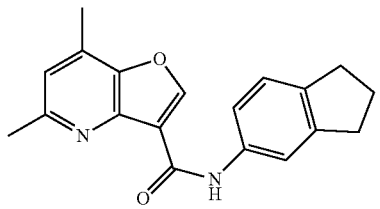 [SMILES: Cc1cc(C)c2occ(C(=O)Nc3ccc4c(c3)CCC4)c2n1]

Following general procedure A, 5,7-dimethylfuro[3,2-b]pyridine-3-carboxylic acid (30 mg, 0.16 mmol) and 2,3-dihydro-1H-inden-5-amine afforded the title compound (9.3 mg, 15%) as a white solid. $^1$H NMR (500 MHz, DMSO-$d_6$) δ 10.75 (s, 1H), 8.92 (s, 1H), 7.68 (s, 1H), 7.47 (d, J=8.0 Hz, 1H), 7.28 (s, 1H), 7.25 (d, J=8.0 Hz, 1H), 2.90 (t, J=7.0 Hz, 2H), 2.85 (t, J=7.0 Hz, 2H), 2.68 (s, 3H), 2.53 (s, 3H), 2.05-2.02 (m, 2H). LC-MS m/z: 307.1 [M+H]$^+$. HPLC: Purity (214 nm)): 95%; $t_R$=10.93 min.

5,7-Dimethyl-N-((1R,4R)-4-(pentyloxy)cyclohexyl)isoxazolo[4,5-b]pyridine-3-carboxamide

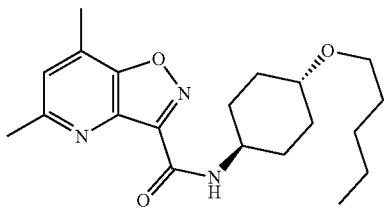 [SMILES: CCCCCO[C@H]1CC[C@H](NC(=O)c2noc3c(C)cc(C)nc23)CC1]

A solution of 4,6-dimethyl-3-nitropyridin-2(1H)-one (9.0 g, 53.5 mmol) in POCl$_3$ (50 mL) was stirred at 100° C. for 5 h and then cooled and concentrated in vacuo to give a residue which was dissolved in DCM (50 mL). Saturated NaHCO$_3$ was added dropwise at 0° C. to pH>7. The organic phase was separated, dried over anhydrous Na$_2$SO$_4$, and filtered. The filtrate was concentrated in vacuo and triturated with PE to afford 2-chloro-4,6-dimethyl-3-nitropyridine (9.0 g, 90%) as a brown solid. LC-MS m/z: 187.1 [M+H]$^+$. Purity (214 nm): 96%; $t_R$=1.76 min.

To a stirred solution of NaH (1.77 g, 44.33 mmol) in THF (60 mL) was added diethyl malonate (12.9 g, 80.6 mmol) at 0° C. and the solution was stirred at RT. After 1 h, a solution of 2-chloro-4,6-dimethyl-3-nitropyridine (7.5 g, 40.3 mmol) in THF (10 mL) was added and the reaction mixture was stirred at 75° C. for 3 d. After cooling to RT sat. NaHCO$_3$ (30 mL) and DCM (50 mL) was added and the organic layer was washed with H$_2$O (10 mL) and brine (10 mL). The combined organic phase was dried over anhydrous Na$_2$SO$_4$, concentrated in vacuo and purified by silica gel chromatography (PE:EA=3:1) to give diethyl 2-(4,6-dimethyl-3-nitropyridin-2-yl)malonate (4.2 g, 33%) as a yellow oil. LC-MS m/z: 311.2 [M+H]$^+$. Purity (214 nm): 88%; $t_R$=1.94 min.

The solution of diethyl 2-(4,6-dimethyl-3-nitropyridin-2-yl)malonate (4.2 g, 13.5 mmol), LiCl (8.53 g, 20.32 mmol) and H$_2$O (487 mg, 2.70 mmol) in DMSO (10 mL) was stirred at 100° C. for 2 d. The reaction mixture was cooled to RT, H$_2$O (20 mL) was added, and the solution extracted with EA (10 mL×5) and washed with brine (10 mL). The combined organic phase was dried over anhydrous Na$_2$SO$_4$, concentrated in vacuo and purified by silica gel chromatography (PE:EA=5:1) to give ethyl 2-(4,6-dimethyl-3-nitropyridin-2-yl)acetate (3.38 g 92%) as a clear oil. LC-MS m/z: 239.2 [M+H]$^+$. Purity (254 nm): 79%; $t_R$=1.83 min.

A solution of NaH (0.57 g, 14.2 mmol) in EtOH (20 mL) was stirred at RT for 30 min followed by the addition of ethyl 2-(4,6-dimethyl-3-nitropyridin-2-yl)acetate (3.38 g, 14.2 mmol) and isopentyl nitrite (0.17 g, 14.2 mmol). The reaction was stirred overnight at RT, then concentrated in vacuo and EA (20 mL) was added. The organic layer was washed with sat. NaHCO$_3$ (20 mL), brine (10 mL), dried over anhydrous Na$_2$SO$_4$, concentrated in vacuo and purified by triturating with diethyl ether (20 mL) to give ethyl 2-(4,6-dimethyl-3-nitropyridin-2-yl)-2-(hydroxyimino)acetate (1.8 g, 47%) as a yellow solid. LC-MS m/z: 268.1 [M+H]$^+$. Purity (214 nm): 97%; $t_R$=1.65 min.

To a stirred solution of ethyl 2-(4,6-dimethyl-3-nitropyridin-2-yl)-2-(hydroxyimino)acetate (1.8 g, 6.74 mmol) in DMF (10 mL) was added NaH (0.27 g, 6.74 mmol) and the solution was stirred at 130° C. for 30 min. The solution was cooled to RT and then EA (50 mL) was added. The organic layer was washed with H$_2$O (10 mL×5), brine (10 mL), dried over Na$_2$SO$_4$, concentrated in vacuo and purified by silica gel chromatography (PE:EA=1:1) to give ethyl 5,7-dimethylisoxazolo[4,5-b]pyridine-3-carboxylate (986 mg, 66%) as a yellow solid. LC-MS m/z: 221.2 [M+H]$^+$. Purity (254 nm): >99%; $t_R$=1.77.

A solution of ethyl 5,7-dimethylisoxazolo[4,5-b]pyridine-3-carboxylate (80 mg, 0.36 mmol), (1R,4R)-4-(pentyloxy)cyclohexan-1-amine (241 mg, 1.09 mmol) and DIPEA (140 mg, 1.09 mmol) in EtOH (3 mL) was stirred at 85° C. for 2 d. The reaction mixture was cooled, concentrated in vacuo and purified by preparative HPLC to give the title compound (43 mg, 33%) as a white solid. $^1$H NMR (400 MHz, DMSO-$d_6$) δ 8.90 (d, J=8.0 Hz, 1H), 7.50 (s, 1H), 3.89-3.82 (m, 1H), 3.40 (t, J=6.8 Hz, 2H), 3.28-3.23 (m, 1H), 2.62 (s, 3H), 2.57 (s, 3H), 1.99-1.95 (m, 4H), 1.51-1.39 (m, 4H), 1.37-1.26 (m, 6H), 0.87 (t, J=6.8 Hz, 3H). LC-MS m/z: 360.3 [M+H]$^+$. HPLC: Purity (214 nm): >99%; $t_R$=10.28 min.

5,7-Dimethyl-N-(1-phenylpropyl)isoxazolo[4,5-b]pyridine-3-carboxamide

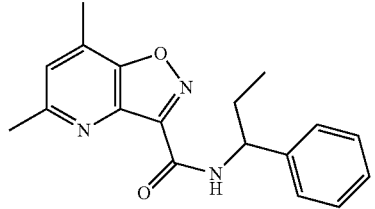 [SMILES: CCC(NC(=O)c1noc2c(C)cc(C)nc12)c1ccccc1]

A solution of ethyl 5,7-dimethylisoxazolo[4,5-b]pyridine-3-carboxylate (100 mg, 0.45 mmol), 1-phenylpropan-1-amine (614 mg, 4.54 mmol) and DIPEA (583 mg, 4.54 mmol in EtOH (2 mL) was stirred at 85° C. overnight. The reaction mixture was cooled, concentrated in vacuo and purified by preparative HPLC to give the title compound (79 mg, 56%) as a white solid. $^1$H NMR (500 MHz, DMSO-$d_6$) δ 9.44 (d, J=8.5 Hz, 1H), 7.51 (d, J=0.5 Hz, 1H), 7.44 (d, J=7.5 Hz, 2H), 7.37 (t, J=7.5 Hz, 2H), 7.28 (t, J=7.5 Hz, 1H), 5.02 (q, 0.1=8.5 Hz, 1H), 2.63 (s, 3H), 2.58 (d, J=1.0 Hz, 3H), 1.91-1.83 (m, 2H), 0.94 (t, J=7.0 Hz, 3H). LC-MS m/z: 310.1 [M+H]$^+$. HPLC: Purity (214 nm): >99%; $t_R$=9.31 min.

5,7-Dimethyl-N-(1,2,3,4-tetrahydronaphthalen-1-yl)isoxazolo[4,5-b]pyridine-3-carboxamide

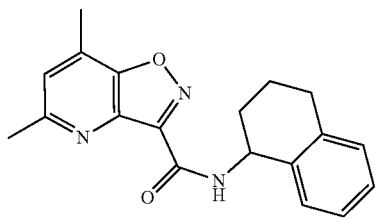 [SMILES: Cc1cc(C)c2onc(C(=O)NC3CCCc4ccccc43)c2n1]

A solution of ethyl 5,7-dimethylisoxazolo[4,5-b]pyridine-3-carboxylate (120 mg, 0.55 mmol) and 1,2,3,4-tetrahydronaphthalen-1-amine (614 mg, 4.36 mmol) in EtOH (3 mL) was stirred at 85° C. for 36 h. The reaction mixture was cooled, concentrated in vacuo and purified by preparative HPLC to give the title compound (112.8 mg, 64%) as a white solid. $^1$H NMR (400 MHz, DMSO-$d_6$) δ 9.32 (d, J=8.4 Hz, 1H), 7.49 (s, 1H), 7.39-7.36 (m, 1H), 7.23-7.13 (m, 3H), 5.33-5.28 (m, 1H), 2.86-2.74 (m, 2H), 2.56 (s, 6H), 2.13-2.08 (m, 1H), 1.97-1.84 (m, 3H). LC-MS m/z: 322.1 [M+H]$^+$. HPLC: Purity (214 nm): >99%; $t_R$=9.43 min.

N-(2,3-Dihydro-1H-inden-5-yl)-5,7-dimethylisoxazolo[4,5-b]pyridine-3-carboxamide

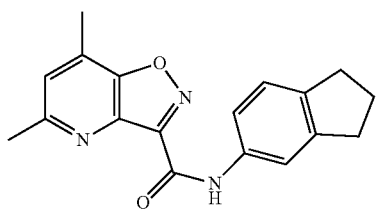 [SMILES: Cc1cc(C)c2onc(C(=O)Nc3ccc4c(c3)CCC4)c2n1]

A solution of 2,3-dihydro-1H-inden-5-amine (60 mg, 0.45 mmol) and n-BuLi (0.18 mL, 0.45 mmol) in THF (2 mL) was stirred at −78° C. for 10 min and then added to a solution of ethyl 5,7-dimethylisoxazolo[4,5-b]pyridine-3-carboxylate (50 mg, 0.23 mmol) in THF (2 mL) at −78° C. The reaction was stirred at −78° C. for 1 h. Then saturated NH$_4$Cl (5 mL) solution was added and the mixture was extracted with DCM (30 mL). The organic layer was washed with H$_2$O (5 mL) and brine (5 mL), concentrated in vacuo and purified by preparative HPLC to give the title compound (21.6 mg, 26%) as a white solid. $^1$H NMR (400 MHz, DMSO-$d_6$) δ 10.90 (s, 1H), 7.70 (s, 1H), 7.54 (s, 1H), 7.50 (d, J=8.4 Hz, 1H), 7.26 (d, J=8.0 Hz, 1H), 2.92-2.84 (m, 4H), 2.66 (s, 3H), 2.61 (s, 3H), 2.08-2.01 (m, 2H). LC-MS m/z: 308.2 [M+H]$^+$. HPLC: Purity (214 nm): >99%; $t_R$=9.99 min.

N-(1-Cyclopropyl-2,2,2-trifluoroethyl)-5,7-dimethylisoxazolo[4,5-b]pyridine-3-carboxamide

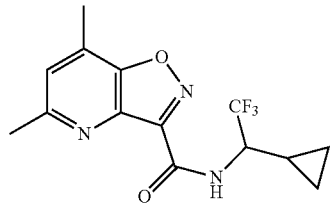 [SMILES: Cc1cc(C)c2onc(C(=O)NC(C3CC3)C(F)(F)F)c2n1]

To a stirred solution of 1-cyclopropyl-2,2,2-trifluoroethanamine hydrochloride (191 mg, 1.09 mmol) in toluene (2 mL) was added AlMe$_3$ (0.68 mL, 1.36 mmol) at 0° C. and the mixture was stirred at RT for 1 h. Then a solution of ethyl 5,7-dimethylisoxazolo[4,5-b]pyridine-3-carboxylate (60 mg, 0.27 mmol) in THF (1 mL) was added and the reaction was stirred at 110° C. for 30 min. Saturated NH$_4$Cl (10 mL) was added and the mixture was extracted with EA (20 mL). The organic layer was washed with H$_2$O (5 mL) and brine (5 mL), concentrated in vacuo and purified by preparative HPLC to give the title compound (37 mg, 37%) as a white solid. $^1$H NMR (500 MHz, DMSO-$d_6$) δ 9.64 (d, J=9.5 Hz, 1H), 7.52 (s, 1H), 4.33 (q, J=8.5 Hz, 1H), 2.63 (s, 3H), 2.59 (s, 3H), 1.30-1.24 (m, 1H), 0.73-0.56 (m, 3H), 0.44-0.39 (m, 1H). LC-MS m/z: 314.2 [M+H]$^+$. HPLC: Purity (214 nm): 97%; $t_R$=8.97 min.

N-(2-Cyclopropylpropan-2-yl)-5,7-dimethylisoxazolo[4,5-b]pyridine-3-carboxamide

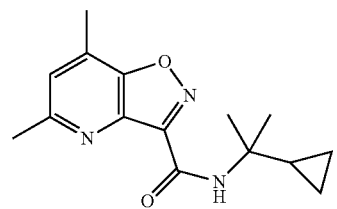 [SMILES: Cc1cc(C)c2onc(C(=O)NC(C)(C)C3CC3)c2n1]

To a stirred solution of 2-cyclopropylpropan-2-amine (67 mg, 0.68 mmol) in toluene (2 mL) was added AlMe$_3$ (0.45 mL, 0.91 mmol) at 0° C. and the mixture was stirred at RT for 1 h. Then a solution of ethyl 5,7-dimethylisoxazolo[4,5-b]pyridine-3-carboxylate (50 mg, 0.23 mmol) in THF (1 mL) was added and the reaction was stirred at 110° C. for 30 min. Saturated NH$_4$Cl (10 mL) solution was added and the mixture was extracted with EA (20 mL). The organic layer was washed with H$_2$O (5 mL) and brine (5 mL), concentrated in vacuo and purified by silica gel chromatography (PE:EA=1:2) to give the title compound (15 mg, 25%) as a white solid. $^1$H NMR (500 MHz, DMSO-$d_6$) δ 8.75 (s, 1H), 7.52 (s, 1H), 2.64 (s, 3H), 2.58 (s, 3H), 1.38 (s, 6H), 1.26-1.23 (m, 1H), 0.48-0.47 (m, 4H). LC-MS m/z: 274.2 [M+H]$^+$. HPLC: Purity (214 nm): 97%; $t_R$=9.26 min.

Example 3—Biological Activity Evaluation

The ability of exemplary compounds to activate glucocerebrosidase (Gcase) was measured. Experimental procedures and results are provided below.

Part I: Assay Procedure

A 484 µL aliquot of a 1.0 mg/mL solution of phosphatidylserine (PS) (Sigma P7769) in chloroform was evaporated under a stream of nitrogen for 1 hour. The lipid film was dissolved over 4 minutes of vigorous vortexing in 40 mL of 176 mM $K_2HPO_4$/50 mM citric acid (pH 4.7) containing 7.5 µL of triton X-100, resulting in a mixed micellar preparation with a composition of 0.32 mM triton and 0.37 mol % PS. 4-Methylumbelliferyl-beta-D-glucopyranoside (ACROS-337025000) was dissolved in the micellar solution to a final concentration of 2 mM for use as the reaction substrate.

Test compounds were diluted to the desired concentrations with dimethylsulfoxide (DMSO) from 10 mM stocks, and 0.41 µL of the DMSO compound mixture was added to 100 µL of micellar solution containing 10 nM GCase and 100 nM saposin C (Enzo ALX-201-262-C050). Pre-incubation was allowed to occur for 30 minutes at room temperature, after which the reaction was initiated by combining 25 µL of substrate solution with 25 µL of compound/GCase/saposin mixture. The reaction proceeded for 15 minutes at room temperature and was stopped by adding 150 µL of 1M glycine, pH 12.5. The endpoint of the reaction was monitored by measuring fluorescence intensity (excitation: 365 nm; emission: 440 nm) on a SpectraMax i3 instrument (Molecular Devices). Test compounds were screened at 1.0 and 0.1 M final concentration, and subsequent 8-point dose response curves were obtained using 3-fold dilutions from a maximum final concentration of 5 µM.

Part II: Results

Gcase activation values for tested compounds are provided in Tables 3 and 4 below, along with cLogP, PSA, and compound solubility in water. The symbol "+" indicates less than 5% Gcase activation; the symbol "++" indicates Gcase activation in the range of 5% up to 20%; and the symbol "+++" indicates Gcase activation greater than 20%. The symbol "N/A" indicates that no data available.

TABLE 3

| Compound Structure | cLogP | PSA | Compound Solubility in Water (µg/mL) | Percent Gcase Activation | |
|---|---|---|---|---|---|
| | | | | 1 µM Test Compound | 0.1 µM Test Compound |
| [structure] | 4.2 | 66.3 | 16.8 | + | + |
| [structure] | 3.9 | 57.1 | 1.5 | ++ | + |
| [structure] | 4.0 | 57.1 | 3.6 | ++ | + |
| [structure] | 3.9 | 57.1 | 14.62 | ++ | + |
| [structure] | 3.4 | 57.1 | 0.7 | ++ | + |

TABLE 3-continued

| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| (structure) | 3.5 | 57.1 | 17.54 | ++ | + |
| (structure) | 3.4 | 57.1 | 15.45 | + | + |
| (structure) | 3.2 | 66.3 | 17.0 | ++ | + |
| (structure) | 2.4 | 78.7 | 1.8 | +++ | + |
| (structure) | 3.7 | 57.1 | 0.9 | +++ | ++ |
| (structure) | 3.8 | 57.1 | 8.8 | +++ | ++ |
| (structure) | 3.6 | 57.1 | 18.8 | +++ | + |

TABLE 3-continued

| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| 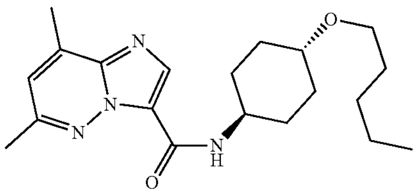 [SMILES: CCCCCO[C@H]1CC[C@H](NC(=O)c2cnc3c(C)cc(C)nn23)CC1] | 3.5 | 66.3 | 3.9 | +++ | ++ |
| 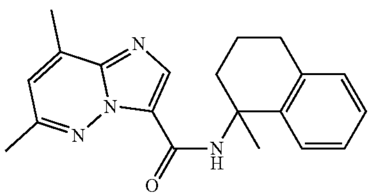 [SMILES: Cc1cc(C)c2ncc(C(=O)NC3(C)CCCc4ccccc43)n2n1] | 4.3 | 57.1 | 7.2 | +++ | ++ |
| 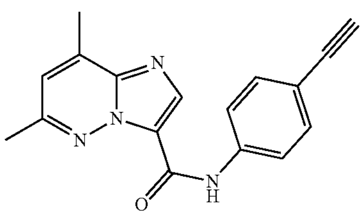 [SMILES: C#Cc1ccc(NC(=O)c2cnc3c(C)cc(C)nn23)cc1] | 2.9 | 57.1 | 0.3 | +++ | ++ |
| 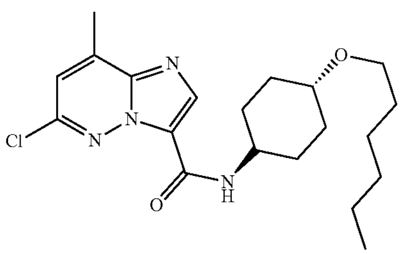 | 4.2 | 66.3 | 3.1 | +++ | ++ |
| 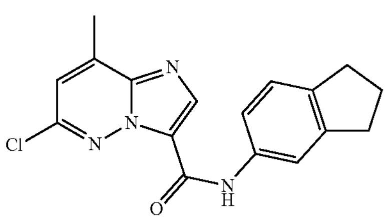 [SMILES: Cc1cc(Cl)nn2c(C(=O)Nc3ccc4c(c3)CCC4)cnc12] | 3.9 | 57.1 | 0.3 | +++ | ++ |
| 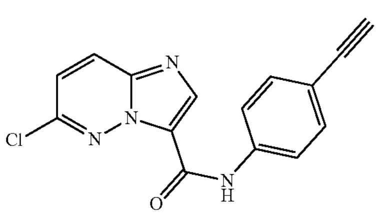 [SMILES: C#Cc1ccc(NC(=O)c2cnc3ccc(Cl)nn23)cc1] | 2.6 | 57.1 | 15.0 | ++ | ++ |
| 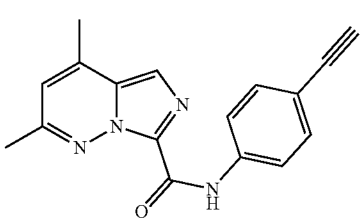 [SMILES: C#Cc1ccc(NC(=O)c2ncc3c(C)cc(C)nn23)cc1] | 3.3 | 57.1 | 1.8 | +++ | + |

TABLE 3-continued

| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| 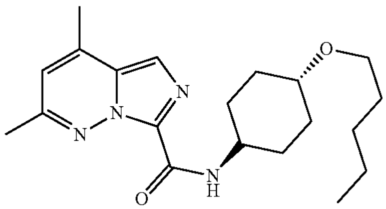 | 3.8 | 68.1 | 23.1 | +++ | ++ |
| | 4.0 | 57.1 | 29.6 | +++ | + |
| 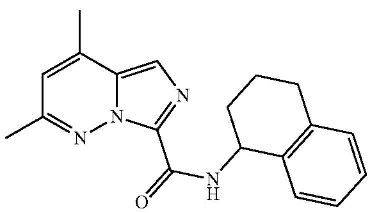 [SMILES: Cc1cc(C)c2cnc(C(=O)NC3CCCc4ccccc43)n2n1] | 4.1 | 57.1 | 38.4 | +++ | ++ |
| | 4.0 | 57.1 | 2.1 | +++ | +++ |
| 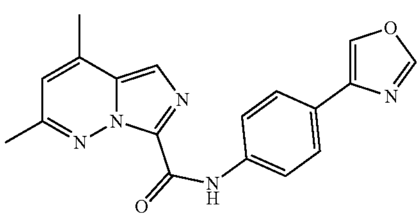 [SMILES: Cc1cc(C)c2cnc(C(=O)Nc3ccc(-c4cocn4)cc3)n2n1] | 2.8 | 78.7 | 0.4 | +++ | + |
| 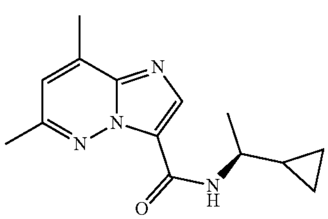 [SMILES: Cc1cc(C)c2ncc(C(=O)N[C@@H](C)C3CC3)n2n1] | 2.1 | 57.1 | N/A | ++ | + |
| 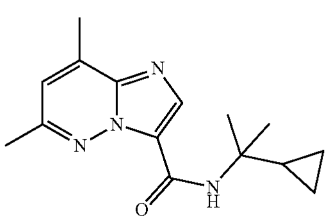 [SMILES: Cc1cc(C)c2ncc(C(=O)NC(C)(C)C3CC3)n2n1] | 2.5 | 57.1 | 27.3 | +++ | ++ |

TABLE 3-continued

| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| 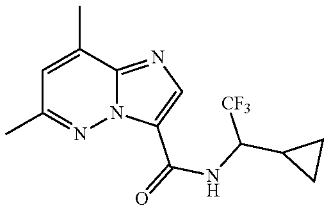 [SMILES: Cc1cc(C)c2ncc(C(=O)NC(C3CC3)C(F)(F)F)n2n1] | 2.4 | 57.1 | N/A | +++ | + |
| | 4.3 | 57.1 | 0.9 | +++ | ++ |
| 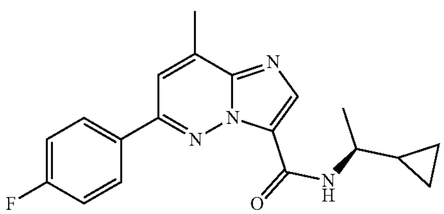 [SMILES: Cc1cc(-c2ccc(F)cc2)nn2c(C(=O)N[C@@H](C)C3CC3)cnc12] | 3.9 | 57.1 | 6.5 | +++ | ++ |
| 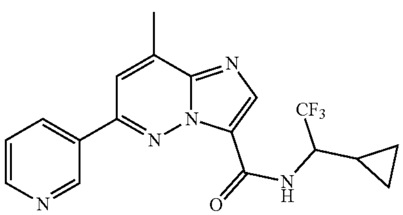 [SMILES: Cc1cc(-c2cccnc2)nn2c(C(=O)NC(C3CC3)C(F)(F)F)cnc12] | 2.5 | 69.4 | N/A | +++ | + |
| | 4.3 | 57.1 | 1.9 | +++ (n = 2) | +++ (n = 2) |
| 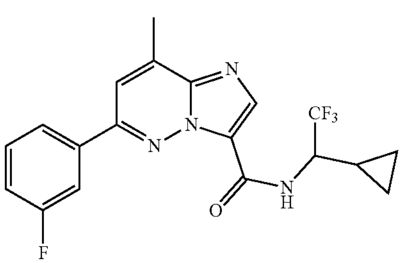 [SMILES: Cc1cc(-c2cccc(F)c2)nn2c(C(=O)NC(C3CC3)C(F)(F)F)cnc12] | 4.2 | 57.1 | 0.03 | +++ (n = 2) | +++ (n = 2) |

TABLE 3-continued
| Compound Structure | cLogP | PSA | Compound Solubility in Water (µg/mL) | Percent Gcase Activation | |
| --- | --- | --- | --- | --- | --- |
| | | | | 1 µM Test Compound | 0.1 µM Test Compound |
| 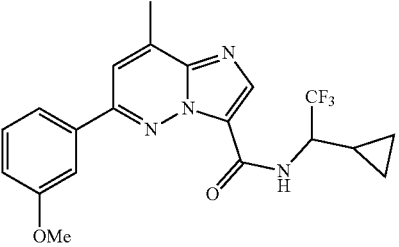 [SMILES: COc1cccc(-c2cc(C)c3ncc(C(=O)NC(C4CC4)C(F)(F)F)n3n2)c1] | 3.9 | 66.3 | 1.4 | +++ | +++ |
| 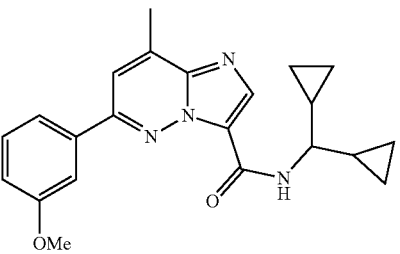 [SMILES: COc1cccc(-c2cc(C)c3ncc(C(=O)NC(C4CC4)C4CC4)n3n2)c1] | 4.1 | 66.3 | 2.7 | +++ (n = 2) | +++ (n = 2) |
| 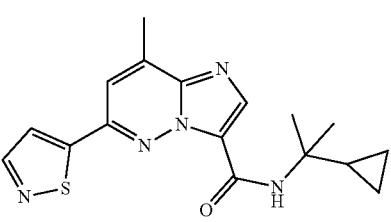 [SMILES: Cc1cc(-c2ccns2)nn2c(C(=O)NC(C)(C)C3CC3)cnc12] | 3.1 | 69.4 | 6.7 | +++ | ++ |
| 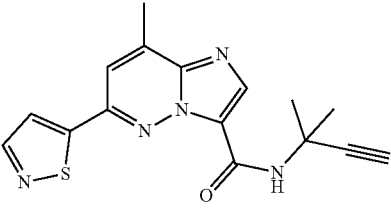 [SMILES: C#CC(C)(C)NC(=O)c1cnc2c(C)cc(-c3ccns3)nn12] | 2.7 | 69.4 | 17.2 | +++ | + |
| 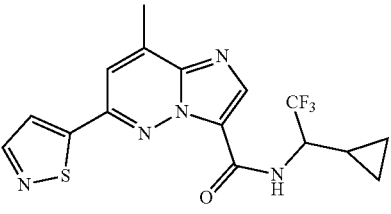 [SMILES: Cc1cc(-c2ccns2)nn2c(C(=O)NC(C3CC3)C(F)(F)F)cnc12] | 2.9 | 69.4 | 0.5 | +++ | ++ |
| 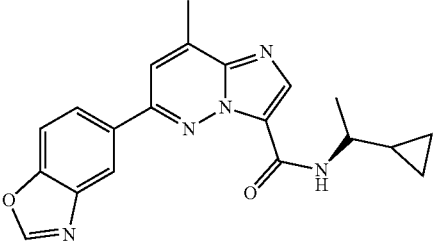 | 3.0 | 78.7 | 1.4 | +++ | +++ |

TABLE 3-continued

| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| (benzoxazole-methyl-imidazopyridazine-CF3-cyclopropyl amide) | 3.3 | 78.7 | 0.2 | +++ | +++ |
| (benzoxazole-methyl-imidazopyridazine-CF3-cyclopropyl amide) | 3.3 | 78.7 | 1.6 | +++ | ++ |
| (methoxypyridine-methyl-imidazopyridazine-CF3-cyclopropyl amide) | 3.5 | 78.7 | 2.2 | +++ | +++ |
| (fluorophenyl-methyl-imidazopyridazine-CF3-methyl amide) | 3.7 | 57.1 | 1.9 | +++ | ++ |
| (benzoxazole-methyl-imidazopyridazine-CF3-cyclopropyl amide) | 3.3 | 78.7 | 0.3 | +++ | ++ |

TABLE 3-continued

| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| | 2.8 | 78.7 | 4.4 | +++ | + |
| | 2.8 | 78.7 | 1.3 | +++ | +++ |
| 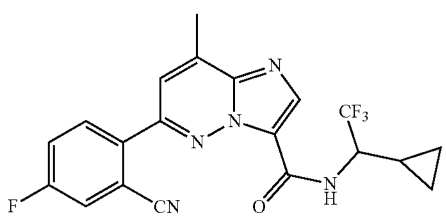 [SMILES: Cc1cc(-c2ccc(F)cc2C#N)nn2c(C(=O)NC(C3CC3)C(F)(F)F)cnc12] | 3.6 | 80.9 | 0.7 | +++ | ++ |
| 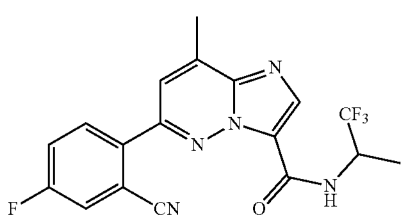 [SMILES: Cc1cc(-c2ccc(F)cc2C#N)nn2c(C(=O)NC(C)C(F)(F)F)cnc12] | 3.1 | 80.9 | 3.9 | +++ | ++ |
| 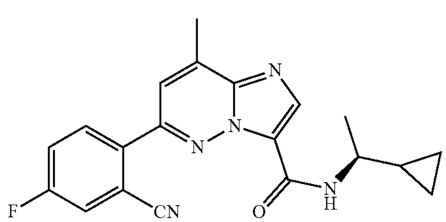 [SMILES: Cc1cc(-c2ccc(F)cc2C#N)nn2c(C(=O)N[C@@H](C)C3CC3)cnc12] | 3.3 | 80.9 | 2.6 | +++ | ++ |
| 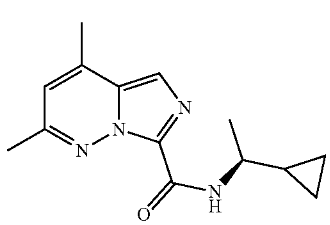 [SMILES: Cc1cc(C)c2cnc(C(=O)N[C@@H](C)C3CC3)n2n1] | 2.5 | 57.1 | N/A | ++ | + |

TABLE 3-continued
| Compound Structure | cLogP | PSA | Water (μg/mL) | 1 μM Test Compound | 0.1 μM Test Compound |
|---|---|---|---|---|---|
| 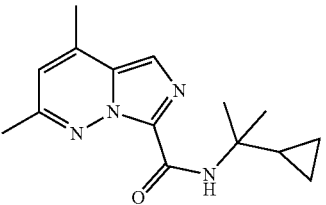 [SMILES: Cc1cc(C)c2cnc(C(=O)NC(C)(C)C3CC3)n2n1] | 2.9 | 57.1 | 24.0 | +++ | + |
| 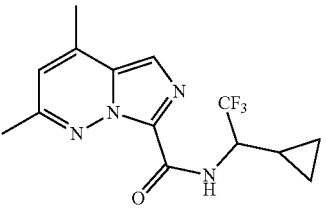 [SMILES: Cc1cc(C)c2cnc(C(=O)NC(C3CC3)C(F)(F)F)n2n1] | 2.8 | 57.1 | N/A | +++ | + |
| 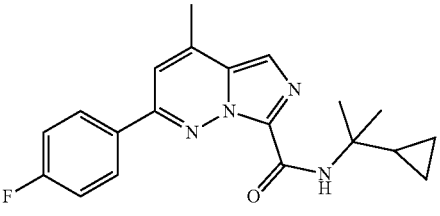 | 4.6 | 57.1 | 1.2 | +++ | +++ |
| 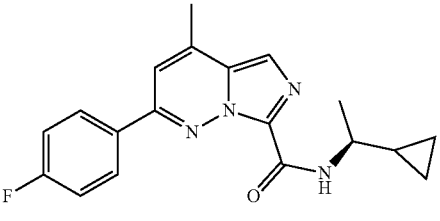 [SMILES: Cc1cc(-c2ccc(F)cc2)nn2c(C(=O)N[C@@H](C)C3CC3)ncc12] | 4.2 | 57.1 | 6.9 | +++ | ++ |
| 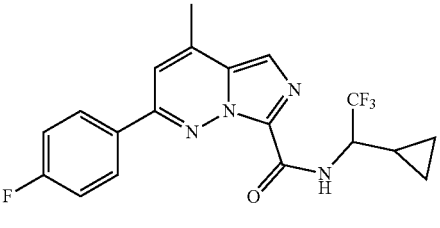 [SMILES: Cc1cc(-c2ccc(F)cc2)nn2c(C(=O)NC(C3CC3)C(F)(F)F)ncc12] | 4.5 | 57.1 | 0.2 | +++ (n = 2) | +++ (n = 2) |
| 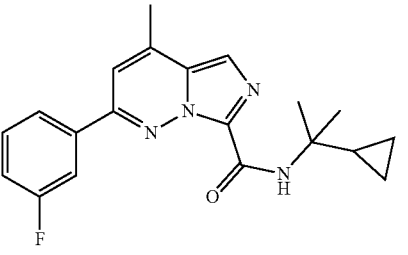 [SMILES: Cc1cc(-c2cccc(F)c2)nn2c(C(=O)NC(C)(C)C3CC3)ncc12] | 4.6 | 57.1 | 8.0 | +++ (n = 2) | +++ (n = 2) |

TABLE 3-continued

| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| (structure) | 4.5 | 57.1 | N/A | N/A | N/A |
| (structure) | 4.3 | 66.3 | N/A | N/A | N/A |
| (structure) | 4.1 | 57.1 | 3.0 | +++ | ++ |
| (structure) | 4.1 | 57.1 | 3.2 | +++ | ++ |
| (structure) | 3.0 | 69.4 | 1.0 | + | + |
| (structure) | 3.3 | 66.2 | 0.3 | ++ | + |

TABLE 3-continued

| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| (structure) | 4.1 | 75.4 | N/A | ++ | + |
| (structure) | 3.5 | 66.2 | 0.7 | ++ | + |
| (structure) | N/A | N/A | N/A | N/A | N/A |
| (structure) | 3.4 | 96.9 | 1.4 | ++ | + |
| (structure) | 4.0 | 75.4 | 1.1 | ++ | + |
| (structure) | 4.0 | 41.5 | N/A | +++ (n = 2) | +++ (n = 2) |

TABLE 3-continued

| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| 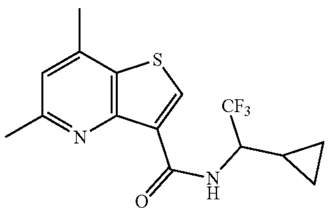 [SMILES: Cc1cc(C)c2scc(C(=O)NC(C3CC3)C(F)(F)F)c2n1] | 3.9 | 41.5 | 0.1 | +++ (n = 2) | +++ (n = 2) |
| 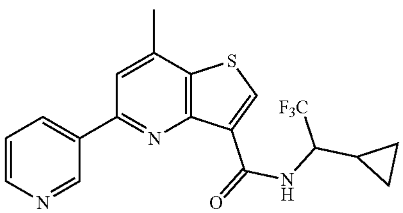 [SMILES: Cc1cc(-c2cccnc2)nc2c(C(=O)NC(C3CC3)C(F)(F)F)csc12] | 4.0 | 53.8 | 0.5 | +++ (n = 2) | +++ (n = 2) |
| 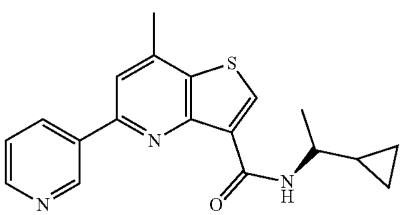 | 3.8 | 53.8 | 1.4 | +++ (n = 2) | +++ (n = 2) |
| 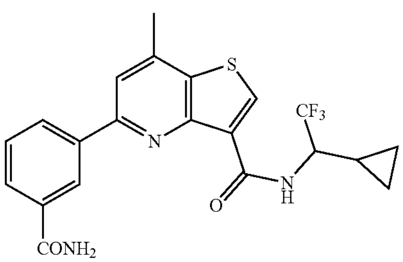 | 4.1 | 84.6 | 0.4 | +++ (n = 2) | +++ (n = 2) |
| 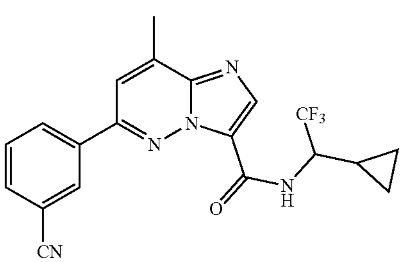 [SMILES: Cc1cc(-c2cccc(C#N)c2)nn2c(C(=O)NC(C3CC3)C(F)(F)F)cnc12] | 3.4 | 80.9 | 0.2 | +++ | +++ |
| 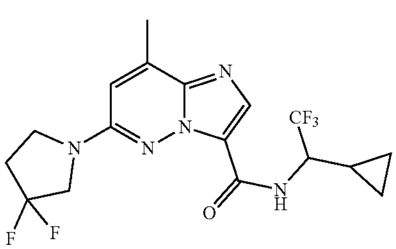 [SMILES: Cc1cc(N2CCC(F)(F)C2)nn2c(C(=O)NC(C3CC3)C(F)(F)F)cnc12] | 2.9 | 60.3 | 8.2 | +++ | +++ |

TABLE 3-continued
| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| 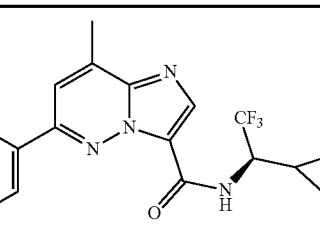 | 2.6 | 90.1 | 0.7 | +++ | +++ |
TABLE 4
| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| 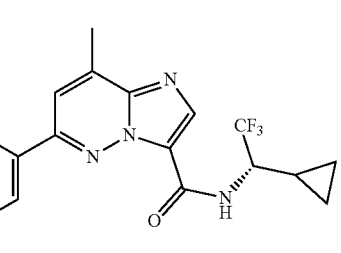 | 3.3 | 78.7 | N/A | +++ | +++ |
| 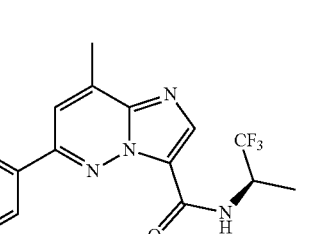 | 3.3 | 78.7 | 0.5 | +++ | +++ |
| 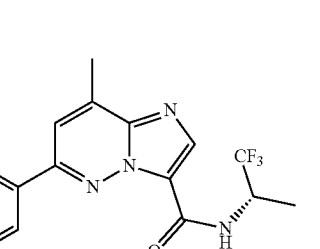 | 2.8 | 78.7 | 1.0 | +++ | ++ |
|  | 2.8 | 78.7 | 1.2 | +++ | +++ |

TABLE 4-continued

| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| | 3.6 | 80.9 | N/A | +++ | ++ |
| | 3.6 | 80.9 | 1.2 | +++ | +++ |
| | 3.1 | 80.9 | 1.9 | ++ | + |
| | 3.1 | 80.9 | 1.9 | +++ | ++ |
| 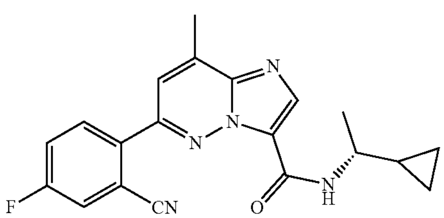 [SMILES: Cc1cc(-c2ccc(F)cc2C#N)nn2c(C(=O)N[C@H](C)C3CC3)cnc12] | 3.3 | 80.9 | 2.3 | +++ | + |
| 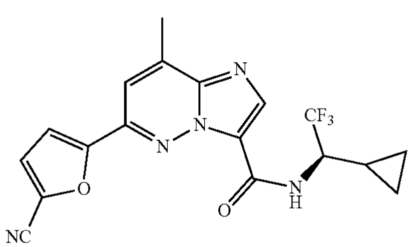 [SMILES: Cc1cc(-c2ccc(C#N)o2)nn2c(C(=O)N[C@H](C3CC3)C(F)(F)F)cnc12] | 2.8 | 90.1 | N/A | +++ | +++ |

TABLE 4-continued
| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| 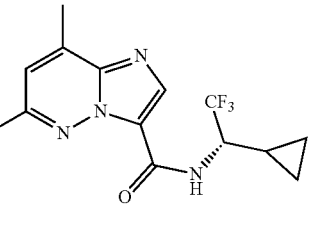 | 2.8 | 90.1 | N/A | +++ | +++ |
| 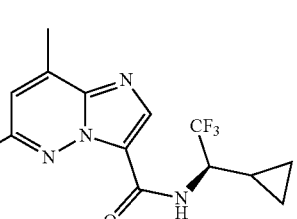 | 3.2 | 80.9 | N/A | +++ | +++ |
| 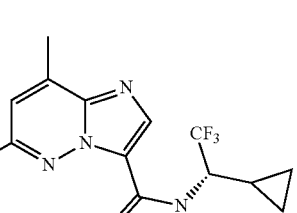 | 3.2 | 80.9 | N/A | +++ | +++ |
| 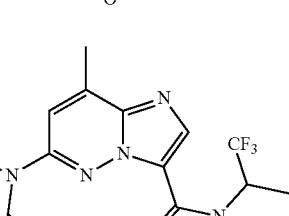 | 2.2 | 80.6 | 18.3 | +++ | ++ |
| 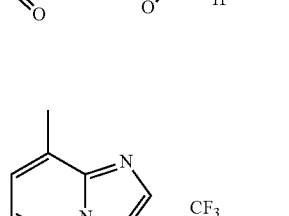 | 2.2 | 78.7 | N/A | +++ | ++ |
| 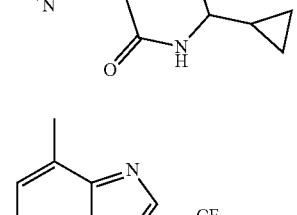 | 3.1 | 69.4 | 3.5 | +++ | ++ |

TABLE 4-continued

| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| | 3.4 | 69.4 | 3.6 | +++ | +++ |
| | 3.4 | 69.4 | N/A | +++ | ++ |
| | 2.7 | 69.4 | N/A | +++ | ++ |
| | 3.3 | 69.4 | 0.3 | +++ | +++ |
| | 3.3 | 69.4 | 0.3 | +++ | +++ |
| | 2.7 | 69.4 | 1.3 | +++ | ++ |

TABLE 4-continued

| Compound Structure | cLogP | PSA | Compound Solubility in Water (µg/mL) | Percent Gcase Activation | |
|---|---|---|---|---|---|
| | | | | 1 µM Test Compound | 0.1 µM Test Compound |
| 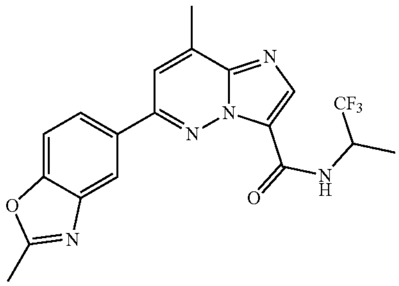 [SMILES: Cc1nc2cc(-c3cc(C)c4ncc(C(=O)NC(C)C(F)(F)F)n4n3)ccc2o1] | 3.1 | 78.7 | 1.5 | +++ | ++ |
| | 3.5 | 60.3 | N/A | +++ | +++ |
| | 3.5 | 60.3 | 1.9 | +++ | +++ |
| 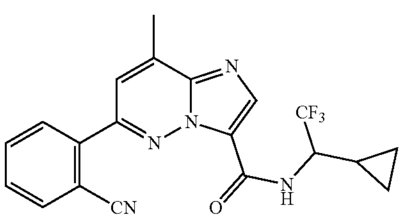 [SMILES: Cc1cc(-c2ccccc2C#N)nn2c(C(=O)NC(C3CC3)C(F)(F)F)cnc12] | 3.4 | 80.9 | 0.1 | +++ | ++ |
| | 3.5 | 66.3 | 0.6 | +++ | +++ |
| 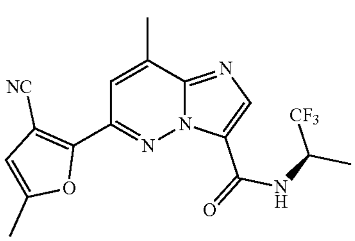 [SMILES: Cc1cc(C#N)c(-c2cc(C)c3ncc(C(=O)N[C@H](C)C(F)(F)F)n3n2)o1] | 2.9 | 90.1 | N/A | +++ | ++ |

TABLE 4-continued

| Compound Structure | cLogP | PSA | Compound Solubility in Water (µg/mL) | Percent Gcase Activation | |
|---|---|---|---|---|---|
| | | | | 1 µM Test Compound | 0.1 µM Test Compound |
| (structure) | 2.9 | 90.1 | 0.1 | +++ | +++ |
| (structure) | 3.4 | 72.7 | N/A | +++ | ++ |
| (structure) | 3.4 | 72.7 | N/A | +++ | ++ |
| (structure) | 3.0 | 69.4 | N/A | +++ | ++ |
| (structure) | 3.0 | 69.4 | N/A | +++ | + |
| (structure) | 2.9 | 78.7 | N/A | +++ | ++ |

TABLE 4-continued

| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| 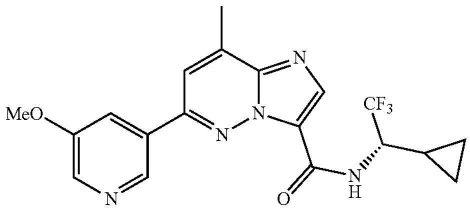 [SMILES: COc1cncc(-c2cc(C)c3ncc(C(=O)N[C@@H](C4CC4)C(F)(F)F)n3n2)c1] | 2.9 | 78.7 | N/A | +++ | ++ |
| | 3.0 | 69.4 | N/A | +++ | ++ |
| | 3.0 | 69.4 | N/A | +++ | + |
| | 2.4 | 88.6 | N/A | +++ | ++ |
| | 2.4 | 88.6 | N/A | +++ | + |
| 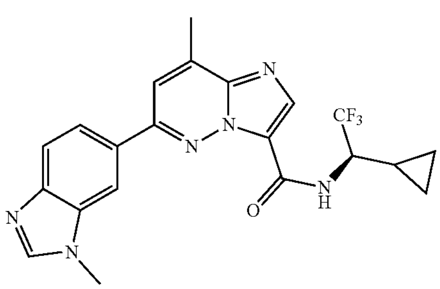 [SMILES: Cc1cc(-c2ccc3ncn(C)c3c2)nn2c(C(=O)N[C@H](C3CC3)C(F)(F)F)cnc12] | 3.4 | 72.7 | 1.0 | +++ | ++ |

TABLE 4-continued

| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| (structure) | 3.4 | 72.7 | N/A | +++ | ++ |
| (structure) | 3.1 | 80.9 | N/A | +++ | ++ |
| (structure) | 3.1 | 80.9 | 1.1 | +++ | ++ |
| (structure) | 3.1 | 80.9 | N/A | +++ | ++ |
| (structure) | 3.3 | 80.9 | 0.5 | +++ | +++ |
| (structure) | 3.3 | 80.9 | N/A | +++ | ++ |

TABLE 4-continued
| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| 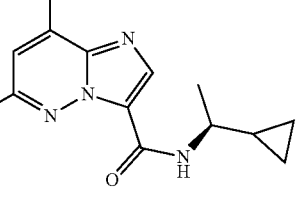 | 3.1 | 90.1 | N/A | +++ | +++ |
| 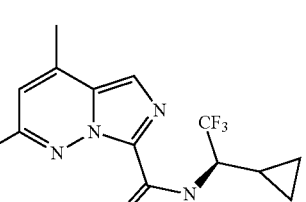 | 4.5 | 57.1 | 0.2 | +++ | +++ |
| 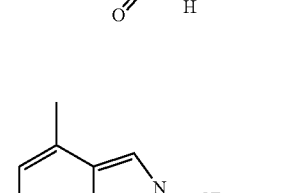 | 4.5 | 57.1 | 0.2 | +++ | +++ |
| 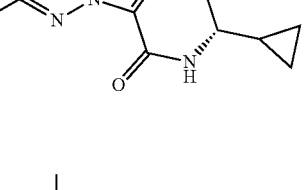 | 4.2 | 57.1 | 0.7 | +++ | +++ |
| 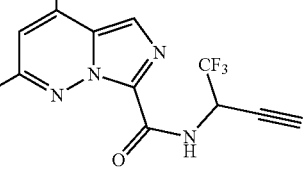 | 3.6 | 69.4 | 0.7 | +++ | ++ |
| 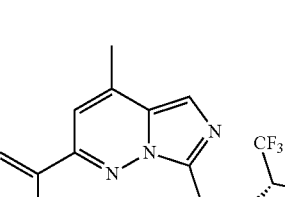 | 3.8 | 69.4 | N/A | +++ | ++ |

TABLE 4-continued

| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| (structure) | 2.5 | 80.6 | N/A | +++ | ++ |
| (structure) | 3.2 | 90.1 | N/A | +++ | ++ |
| (structure) | 3.2 | 90.1 | N/A | +++ | +++ |
| (structure) | 3.6 | 80.9 | N/A | +++ | ++ |
| (structure) | 3.9 | 80.3 | N/A | +++ | ++ |
| (structure) | 4.2 | 63.1 | N/A | +++ | +++ |

TABLE 4-continued
| Compound Structure | cLogP | PSA | Compound Solubility in Water (µg/mL) | Percent Gcase Activation | |
|---|---|---|---|---|---|
| | | | | 1 µM Test Compound | 0.1 µM Test Compound |
| 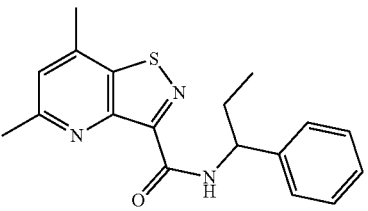 | 4.4 | 53.8 | N/A | +++ | ++ |
| 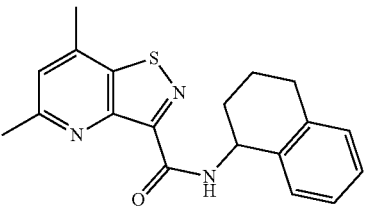 [SMILES: Cc1cc(C)c2snc(C(=O)NC3CCCc4ccccc43)c2n1] | 4.5 | 53.8 | N/A | +++ | +++ |
| 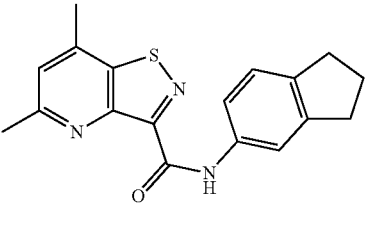 | 4.4 | 53.8 | N/A | +++ | +++ |
| 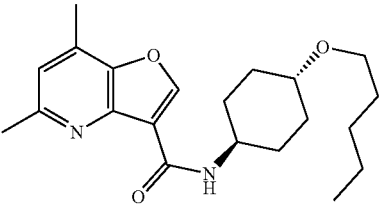 [SMILES: CCCCCO[C@H]1CC[C@H](NC(=O)c2coc3c(C)cc(C)nc23)CC1] | 4.3 | 59.9 | N/A | +++ | ++ |
| 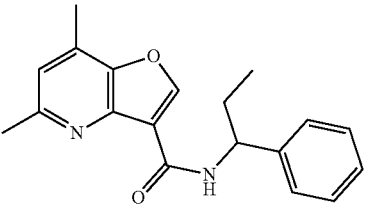 [SMILES: CCC(NC(=O)c1coc2c(C)cc(C)nc12)c1ccccc1] | 4.5 | 50.7 | N/A | +++ | +++ |
| 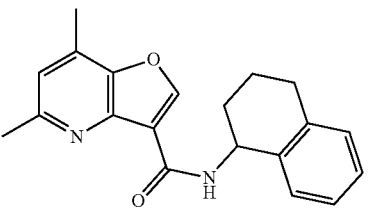 [SMILES: Cc1cc(C)c2occ(C(=O)NC3CCCc4ccccc43)c2n1] | 4.6 | 50.7 | N/A | +++ | +++ |

TABLE 4-continued

| Compound Structure | cLogP | PSA | Compound Solubility in Water (μg/mL) | Percent Gcase Activation | |
| --- | --- | --- | --- | --- | --- |
| | | | | 1 μM Test Compound | 0.1 μM Test Compound |
| (furo[3,2-b]pyridine-3-carboxamide with dimethyl and indanyl) | 4.5 | 50.7 | N/A | +++ | ++ |
| (isoxazolo[4,5-b]pyridine-3-carboxamide with dimethyl and cyclohexyloxy-pentyl) | 4.0 | 72.3 | N/A | +++ | ++ |
| (isoxazolo[4,5-b]pyridine-3-carboxamide with dimethyl and 1-phenylpropyl) | 4.1 | 63.1 | N/A | +++ | ++ |
| (isoxazolo[4,5-b]pyridine-3-carboxamide with dimethyl and tetrahydronaphthyl) | 4.3 | 63.1 | N/A | +++ | ++ |
| (isoxazolo[4,5-b]pyridine-3-carboxamide with dimethyl and indanyl) | 4.1 | 63.1 | N/A | +++ | ++ |
| (isoxazolo[4,5-b]pyridine-3-carboxamide with dimethyl and CF3-cyclopropyl) | 2.9 | 63.1 | N/A | +++ | + |

TABLE 4-continued

| Compound Structure | cLogP | PSA | Compound Solubility in Water (μg/mL) | Percent Gcase Activation | |
|---|---|---|---|---|---|
| | | | | 1 μM Test Compound | 0.1 μM Test Compound |
| 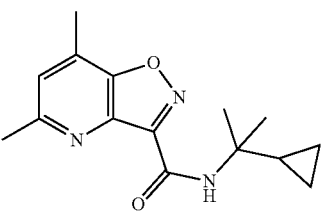 [SMILES: Cc1cc(C)c2onc(C(=O)NC(C)(C)C3CC3)c2n1] | 3.1 | 63.1 | N/A | +++ | ++ |
| 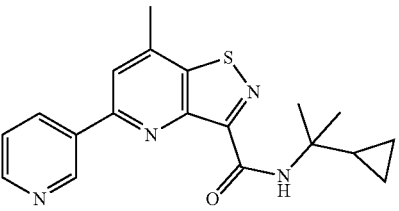 [SMILES: Cc1cc(-c2cccnc2)nc2c(C(=O)NC(C)(C)C3CC3)nsc12] | 3.4 | 66.2 | 0.7 | ++ | + |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:
1. A compound of Formula II:

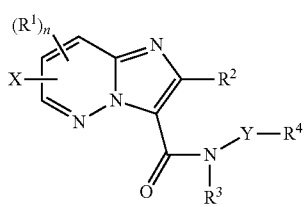

(II)

or a pharmaceutically acceptable salt thereof, wherein:
X is halogen;
$R^1$ represents independently for each occurrence $C_1$-$C_6$ alkyl, halogen, $C_1$-$C_6$ haloalkyl, $C_3$-$C_6$ cycloalkyl, $C_1$-$C_6$ alkoxy, —($C_1$-$C_4$ alkylene)-O—($C_1$-$C_6$ alkyl), —($C_1$-$C_4$ alkylene)-O—($C_3$-$C_6$ cycloalkyl), 3-6 membered heterocyclyl, 6-membered aryl, cyano, or —N($R^5$)$_2$;
$R^2$ is hydrogen, $C_1$-$C_6$ alkyl, halogen, $C_1$-$C_6$ haloalkyl, $C_3$-$C_6$ cycloalkyl, $C_1$-$C_6$ alkoxy, —($C_1$-$C_4$ alkylene)-O—($C_1$-$C_6$ alkyl), —($C_1$-$C_4$ alkylene)-O—($C_3$-$C_6$ cycloalkyl), 3-6 membered heterocyclyl, 6-membered aryl, cyano, or —N($R^5$)$_2$;
$R^3$ is hydrogen, $C_1$-$C_6$ alkyl, or $C_3$-$C_6$ cycloalkyl;
$R^4$ is one of the following:
(a) $C_3$-$C_8$ cycloalkyl substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, —O—($C_3$-$C_6$ cycloalkyl), —O—($C_3$-$C_6$ cycloalkyl), $C_2$-$C_4$ alkynyl, —($C_2$-$C_4$ alkynyl)-$C_1$-$C_6$ alkoxy, and saturated 3-8 membered heterocyclyl;
(b) phenyl that is (i) substituted by $C_2$-$C_4$ alkynyl or —($C_2$-$C_4$ alkynyl)-$C_1$-$C_6$ alkoxy, and (ii) optionally substituted by 1 or 2 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, —O—($C_3$-$C_6$ cycloalkyl), —O—($C_3$-$C_6$ cycloalkyl), heteroaryl, saturated 3-8 membered heterocyclyl, and amino; or
(c) a partially unsaturated 9-10 membered bicyclic carbocyclyl, a partially unsaturated 8-10 membered bicyclic heterocyclyl, a 9-13 membered spiroheterocycloalkyl, or —($C_2$-$C_6$ alkylene)-O-phenyl; each of which is optionally substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, —O—($C_3$-$C_6$ cycloalkyl), —O—($C_3$-$C_6$ cycloalkyl), $C_2$-$C_4$ alkynyl, —($C_2$-$C_4$ alkynyl)-$C_1$-$C_6$ alkoxy, aryl, —O-aryl, heteroaryl, saturated 3-8 membered heterocyclyl, amino, and —$CO_2R^5$;
$R^5$ represents independently for each occurrence hydrogen, $C_1$-$C_6$ alkyl, or $C_3$-$C_6$ cycloalkyl; or two occurrences of $R^5$ attached to the same nitrogen atom are taken together with the nitrogen atom to which they are attached to form a 3-8 membered heterocyclic ring;

Y is a bond, —C(O)—, $C_1$-$C_6$ alkylene, $C_1$-$C_6$ haloalkylene, or $C_3$-$C_6$ cycloalkylene; and n is 0, 1, or 2.

2. The compound of claim 1, wherein $R^1$ is $C_1$-$C_3$ alkyl.

3. The compound of claim 1, wherein X is chloro.

4. The compound of claim 1, wherein $R^2$ is hydrogen.

5. The compound of claim 1, wherein $R^3$ is hydrogen.

6. The compound of claim 1, wherein Y is a bond.

7. The compound of claim 1, wherein Y is $C_1$-$C_6$ alkylene.

8. The compound of claim 1, wherein $R^4$ is $C_3$-$C_8$ cycloalkyl substituted by 1, 2, or 3 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, $C_1$-$C_6$ alkoxy, $C_2$-$C_4$ alkynyl, —($C_2$-$C_4$ alkynyl)-$C_1$-$C_6$ alkoxy, and saturated 3-8 membered heterocyclyl.

9. The compound of claim 1, wherein $R^4$ is a partially unsaturated 9-10 membered bicyclic carbocyclyl optionally substituted by 1, 2, or 3 substituents independently selected from the group consisting of $C_1$-$C_6$ alkyl, halogen, $C_1$-$C_6$ haloalkyl, $C_3$-$C_6$ cycloalkyl, hydroxyl, $C_1$-$C_6$ alkoxy, $C_2$-$C_4$ alkynyl, —($C_2$-$C_4$ alkynyl)-$C_1$-$C_6$ alkoxy, aryl, heteroaryl, and saturated 3-8 membered heterocyclyl.

10. The compound of claim 1, wherein $R^4$ is a partially unsaturated 9-10 membered bicyclic carbocyclyl optionally substituted by $C_1$-$C_6$ alkyl.

11. The compound of claim 1, wherein $R^4$ is phenyl that is (i) substituted by $C_2$-$C_4$ alkynyl or —($C_2$-$C_4$ alkynyl)-$C_1$-$C_6$ alkoxy, and (ii) optionally substituted by 1 or 2 substituents independently selected from the group consisting of $C_1$-$C_8$ alkyl, halogen, $C_1$-$C_6$ haloalkyl, $C_3$-$C_6$ cycloalkyl, —($C_1$-$C_6$ alkylene)-($C_3$-$C_6$ cycloalkyl), hydroxyl, and $C_1$-$C_6$ alkoxy.

12. The compound of claim 1, wherein $R^4$ is phenyl substituted by $C_2$-$C_4$ alkynyl or —($C_2$-$C_4$ alkynyl)-$C_1$-$C_6$ alkoxy.

13. The compound of claim 1, wherein n is 0.

14. A method of treating a disorder selected from the group consisting of Gaucher disease, Parkinson's disease, and Lewy body disease, comprising administering to a patient in need thereof a therapeutically effective amount of a compound of claim 1 to treat the disorder.

15. The method of claim 14, wherein the disorder is Parkinson's disease.

16. The method of claim 14, wherein the disorder is Lewy body disease.

17. A compound selected from the group consisting of

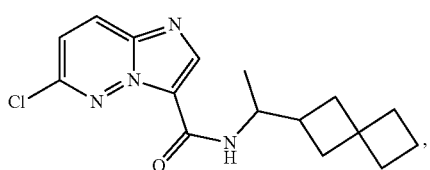

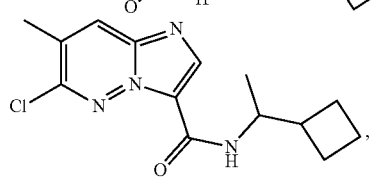

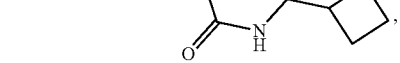

-continued

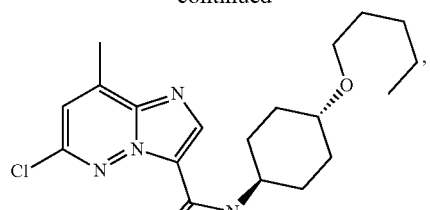

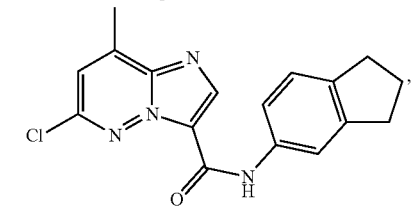

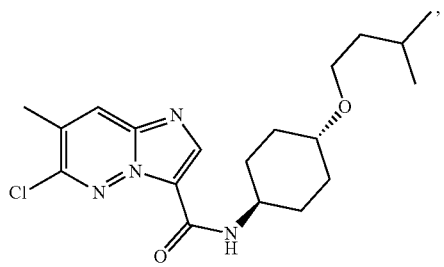

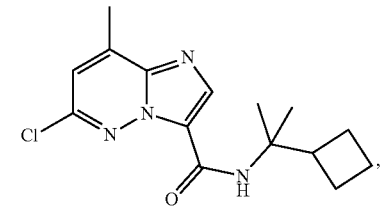

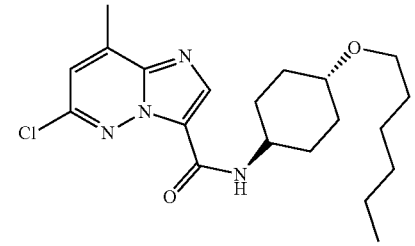

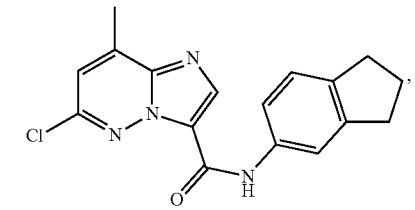

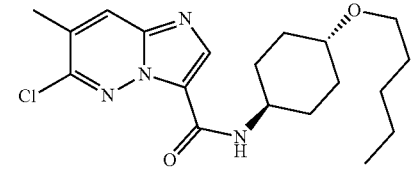

-continued

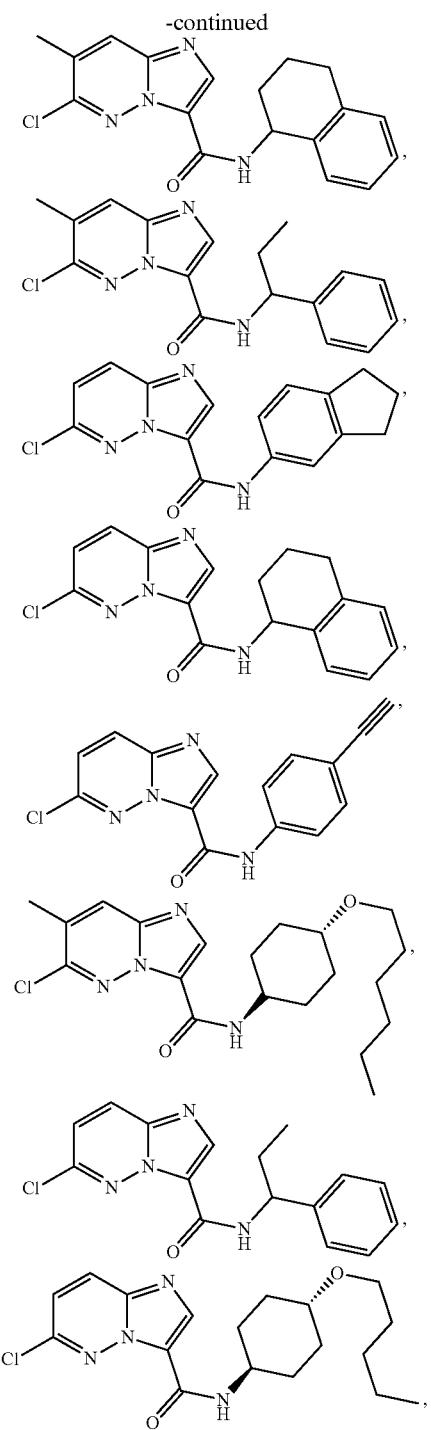

-continued

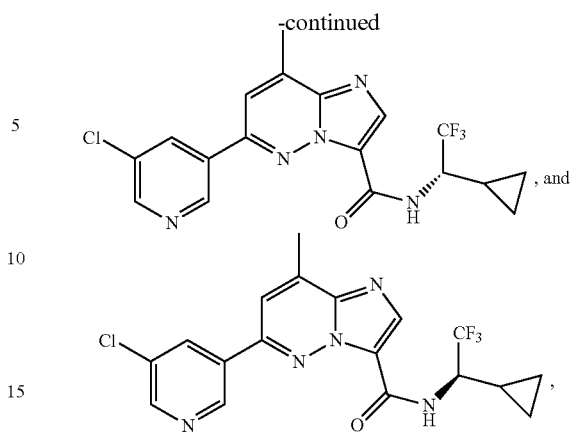

or a pharmaceutically acceptable salt thereof.

18. A method of treating a disorder selected from the group consisting of Gaucher disease, Parkinson's disease, and Lewy body disease in a patient in need thereof, the method comprising administering to the patient a therapeutically effective amount of a compound of claim 17 to treat the disorder.

19. The method of claim 18, wherein the disorder is Parkinson's disease.

20. The method of claim 18, wherein the disorder is Lewy body disease.

21. The compound of claim 17, wherein the compound is

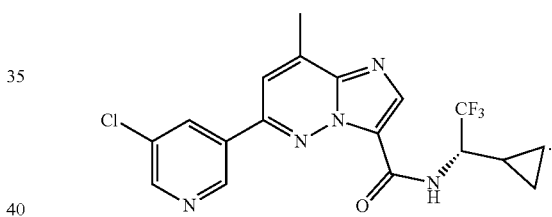

22. The compound of claim 17, wherein the compound is

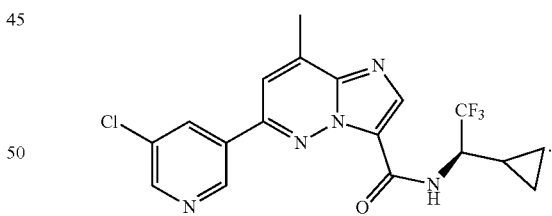

\* \* \* \* \*